(12) United States Patent
Ghosh et al.

(10) Patent No.: US 9,499,558 B2
(45) Date of Patent: *Nov. 22, 2016

(54) COMPOUNDS AND METHODS FOR TREATING HIV

(71) Applicants: Purdue Research Foundation, West Lafayette, IN (US); Hiroaki Mitsuya, Kumamoto (JP)

(72) Inventors: Arun K. Ghosh, West Lafayette, IN (US); Bruno D. Chapsal, Astoria, NY (US); Hiroaki Mitsuya, Kumamoto (JP); Cuthbert D Martyr, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/692,498

(22) Filed: Apr. 21, 2015

(65) Prior Publication Data

US 2015/0225414 A1  Aug. 13, 2015

Related U.S. Application Data

(63) Continuation of application No. 13/929,395, filed on Jun. 27, 2013, now Pat. No. 9,024,038, which is a continuation-in-part of application No. PCT/US2011/067112, filed on Dec. 23, 2011, and a continuation-in-part of application No. PCT/US2011/067160, filed on Dec. 23, 2011.

(60) Provisional application No. 61/427,341, filed on Dec. 27, 2010, provisional application No. 61/427,295, filed on Dec. 27, 2010.

(51) Int. Cl.
*C07D 493/04* (2006.01)

(52) U.S. Cl.
CPC ................................ *C07D 493/04* (2013.01)

(58) Field of Classification Search
USPC .......................................................... 548/159
See application file for complete search history.

(56) References Cited

U.S. PATENT DOCUMENTS

| 9,024,038 B2 | 5/2015 | Ghosh et al. |
| 2005/0267156 A1 | 12/2005 | Surleraux et al. |
| 2013/0289067 A1 | 10/2013 | Ghosh et al. |

FOREIGN PATENT DOCUMENTS

| WO | WO-02083657 A2 | 10/2002 |
| WO | WO-2007147884 A1 | 12/2007 |

OTHER PUBLICATIONS

U.S. Appl. No. 13/929,395, Response to Restriction Requiremet mailed Jun. 16, 2014, 12 pgs.
U.S. Appl. No. 13/929,395, Non Final Office Action mailed Aug. 4, 2014, 17 pgs.
U.S. Appl. No. 13/929,395, Notice of Allowance mailed Jan. 2, 2015, 11 pgs.
U.S. Appl. No. 13/929,395, Restriction Requirement mailed Jun. 16, 2014, 16 pgs.
U.S. Appl. No. 13/929,395, Response filed Oct. 28, 2014 to Non Final Office Action mailed Aug. 4, 2014, 11 pgs.
Surleraux, et al., , Journal of Medicinal Chemistry (2005), 1965-1973.

*Primary Examiner* — Laura L. Stockton
(74) *Attorney, Agent, or Firm* — Schwegman Lundberg & Woessner, P.A.

(57) ABSTRACT

Inhibitors of HIV-1 protease and compositions containing them are described. Use of the inhibitors and compositions containing them to treat HIV, AIDS, and AIDS-related diseases is described.

15 Claims, No Drawings

US 9,499,558 B2

COMPOUNDS AND METHODS FOR TREATING HIV

CROSS-REFERENCE TO RELATED APPLICATIONS

This application is a continuation of U.S. patent application Ser. No. 13/929,395, filed Jun. 27, 2013, which is a continuation-in-part under 35 U.S.C. §365(c) of PCT/US2011/067112, filed Dec. 23, 2011, which claims the benefit of priority under 35 U.S.C. §119 of U.S. Provisional Application Ser. No. 61/427,341 filed on Dec. 27, 2010, the entirety of each of which is incorporated by reference herein and is a continuation-in-part under 35 U.S.C. §365(c) of PCT/US2011/067160, filed Dec. 23, 2011, which claims the benefit of priority under 35 U.S.C. §119 of U.S. Provisional Application Ser. No. 61/427,295 filed on Dec. 27, 2010, the entirety of each of which is incorporated by reference herein.

GOVERNMENT RIGHTS

This invention was made with government support under GM053386 awarded by the National Institutes of Health. The government has certain rights in the invention.

TECHNICAL FIELD

The invention described herein pertains to compounds, to compositions and formulations comprising the compounds, and to methods of use of the compounds and their compositions and formulations for the treatment of diseases, including diseases such as HIV, AIDS, and AIDS-related diseases.

BACKGROUND AND SUMMARY OF THE INVENTION

The AIDS epidemic is one of the most challenging problems in medicine in the 21st century (United Nations. 2004 Report on the global HIV/AIDS Epidemic: 4th global report. New York, U.S.A., 2004). The disclosure of the foregoing is incorporated herein in its entirety by reference. In addition, the entirety of the disclosures of each of the publications cited herein are also incorporated herein by reference. Among many strategies to combat this disease, highly active antiretroviral therapy (HAART) with HIV protease inhibitors (PIs) in combination with reverse transcriptase inhibitors (RTIs) continues to be the first line treatment for control of HIV infection (Sepkowitz, K. A. AIDS—the first 20 years. N. Engl. J. Med. 2001, 344, 1764-1772). This treatment regimen has definitely improved quality of life, enhanced HIV management, and halted the progression of the disease. However, despite these impressive successes, there remain many challenges to treating this devastating disease, including decreasing both the toxicity and complexity of these treatment regimens. In addition, there is a growing population of patients that is developing multi-drug resistant strains of HIV, and there is ample evidence that these strains can be further transmitted (Staszewski et al., Efavirenz plus zidovudine and lamivudine, efavirenz plus indinavir, and indinavir plus zidovudine and lamivudine in the treatment of HIV-1 infection in adults. N. Engl. J. Med. 1999, 341, 1865-1873; Wainberg et al., Public health implications of antiretroviral therapy and HIV drug resistance. J. Am. Med. Assoc. 1998, 279, 1977-1983).

HAART has had a major impact on the AIDS epidemic in industrially advanced nations; however, eradication of human immunodeficiency virus type 1 (HIV 1) appears to be currently unachieved, in part due to the viral reservoirs remaining in blood and infected tissues. The limitation of antiviral therapy of AIDS is also exacerbated by complicated regimens, the development of drug-resistant HIV-1 variants, and a number of inherent adverse effects.

A number of challenges have nonetheless been encountered in bringing about the optimal benefits of the currently available therapeutics of AIDS and HIV-1 infection to individuals receiving HAART (De Clercq 2002. Strategies in the design of antiviral drugs. Nat Rev Drug Discov 1:13-25; Siliciano et al. 2004. A long-term latent reservoir for HIV-1: discovery and clinical implications. J Antimicrob Chemother 54:6-9; Simon, et al. 2003. HIV-1 dynamics in vivo: implications for therapy. Nat Rev Microbiol 1:181-90). They include (i) drug-related toxicities; (ii) partial restoration of immunologic functions once individuals developed AIDS; (iii) development of various cancers as a consequence of survival prolongation; (iv) flame-up of inflammation in individuals receiving HAART or immune re-construction syndrome (IRS); and (v) increased cost of antiviral therapy. Such limitations of HAART are exacerbated by the development of drug-resistant HIV-1 variants (Carr 2003. Toxicity of antiretroviral therapy and implications for drug development. Nat Rev Drug Discov 2:624-34; Fumero et al. 2003. New patterns of HIV-1 resistance during HAART. Clin Microbiol Infect 9:1077-84; Grabar et al. 2006. HIV infection in older patients in the HAART era. J Antimicrob Chemother 57:4-7; Hirsch et al. 2004. Immune reconstitution in HIV-infected patients. Clin Infect Dis 38:1159-66; Little et al. 2002. Antiretroviral-drug resistance among patients recently infected with HIV. N Engl J Med 347:385-94).

Successful antiviral drugs, in theory, exert their virus-specific effects by interacting with viral receptors, virally encoded enzymes, viral structural components, viral genes, or their transcripts without disturbing cellular metabolism or function. However, at present, no antiretroviral drugs or agents are likely to be completely specific for HIV-1 or to be devoid of toxicity or side effects in the therapy of AIDS, which has been an issue because patients with AIDS and its related diseases will have to receive antiretroviral therapy for a long period of time, perhaps for the rest of their lives.

In one embodiment, described herein are novel non-peptidyl compounds and compositions for treating patients in need of relief from HIV, AIDS, and AIDS-related diseases. Also described herein are methods for treating such diseases. In one embodiment, it has been discovered that the non-peptidyl compounds described herein are potent inhibitors of HIV-1 protease. It has also been discovered that these compounds may offer therapeutic benefits to patients suffering from or in need of relief from HIV-1/AIDS.

In another embodiment, described herein is structure-based design of novel HIV-1 protease inhibitors (PI) incorporating a stereochemically defined 4-hexahydro-furopyranol-derived urethanes as the P2-ligand. In one aspect, the inhibitors herein are designed to make extensive interactions including hydrogen bonding with the protein backbone of the HIV-1 protease active site. In another embodiment, the inhibitors described herein appear to show excellent enzyme inhibitory activity and antiviral potency. In one aspect, this antiviral potency may be comparable to that of approved protease inhibitors. In another embodiment, the inhibitors described herein appear to show excellent activity against multi-PI-resistant variants.

In another embodiment, described herein is structure-based design of novel HIV-1 protease inhibitors (PI) incorporating hydrogen bonding residues as the $P_1$ ligand. In one aspect, the inhibitors herein are designed to make extensive interactions including hydrogen bonding with the protein backbone of the HIV-1 protease active site. In another embodiment, the inhibitors described herein appear to show excellent enzyme inhibitory activity and antiviral potency. In one aspect, this antiviral potency may be comparable to that of approved protease inhibitors. In another embodiment, the inhibitors described herein may show excellent activity against multi-PI-resistant variants.

In one illustrative embodiment of the invention, there is provided a compound of the formula (I)

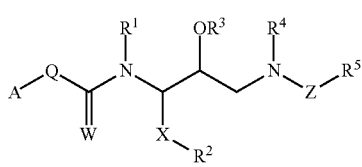

(I)

or a pharmaceutically acceptable salt thereof, wherein

A is cycloheteroalkyl or cycloheteroalkyl-alkyl, each of which is optionally substituted;

Q is oxygen, sulfur, nitrogen, or $C(R^aR^b)$ where each of $R^a$ and $R^b$ is independently selected in each instance from the group consisting of hydrogen, alkyl, and alkoxy;

W is oxygen or sulfur;

$R^1$ is hydrogen, a nitrogen protecting group, or a pro-drug substituent;

X is $C(R^aR^b)_n$, where n is 1, 2, or 3, and each of $R^a$ and $R^b$ is defined as above;

$R^2$ is alkyl, heteroalkyl, cycloalkyl, cycloheteroalkyl, aryl, heteroaryl, arylalkyl, or heteroarylalkyl, each of which is optionally substituted; or $R^2$ is alkyl, heteroalkyl, cycloalkyl, cycloheteroalkyl, aryl, heteroaryl, arylalkyl, or heteroarylalkyl, each of which is substituted, where at least one substituent is a hydrogen bond forming group;

$R^3$ is hydrogen, an oxygen protecting group, a phosphate derivative, or a pro-drug substituent;

$R^4$ is alkyl, haloalkyl, heteroalkyl, cycloalkyl, cycloheteroalkyl, aryl, heteroaryl, arylalkyl, or heteroarylalkyl, each of which is optionally substituted;

Z is C(O), $S(O)_2$, NH, NHC(O), $NHS(O)_2$, C(O)—O, or C(O)—$NR^6$;

$R^5$ is alkyl, heteroalkyl, cycloalkyl, cycloheteroalkyl, aryl, heteroaryl, arylalkyl, or heteroarylalkyl, each of which is optionally substituted; and $R^6$ is hydrogen, alkyl, haloalkyl, heteroalkyl, cycloalkyl, cycloheteroalkyl, aryl, heteroaryl, arylalkyl, or heteroarylalkyl, each of which is optionally substituted; and wherein the compound of formula (I) is other than one in which, together: Q is oxygen, W is oxygen, $R^1$ is hydrogen, X is methylene, $R^2$ is unsubstituted phenyl, $R^3$ is hydrogen or a phosphate derivative, $R^4$ is isobutyl, Z is $S(O)_2$, and $R^5$ is 4-aminophenyl or 4-methoxyphenyl when:

A is a group of the formula

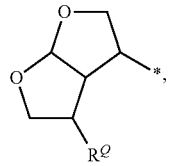

wherein (*) indicates the point of attachment; in which RQ is hydrogen, hydroxy, methoxy or benzyloxy; or A is a group of the formula

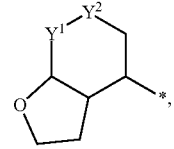

wherein (*) indicates the point of attachment; in which one of $Y^1$ and $Y^2$ is methylene, and the other of $Y^1$ and $Y^2$ is $C(R^eR^f)$ or oxygen; or A is a group of the formula

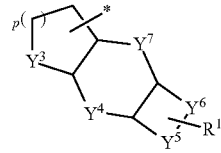

wherein (*) indicates the point of attachment;

p is 1 or 2;

$Y^3$ and $Y^4$ are in each instance independently methylene or oxygen;

$Y^5$ and $Y^6$ are in each instance independently selected from the group consisting of oxygen and alkylene, providing that at least one of $Y^3$ and $Y^4$ is oxygen, and wherein when one of $Y^3$ and $Y^4$ is optionally substituted methylene, at least one of $Y^5$ and $Y^6$ is oxygen, and A does not include a peroxide bond;

$Y^7$ is a bond; and $R^1$ of the group is hydrogen.

Certain embodiments of a compound of a formula (I) are denoted herein as a compound of formula ($I^1$) or a compound of formula ($I^2$). Throughout this specification (*) indicates the point of attachment for a particular radical.

In one illustrative embodiment of the invention, compounds of formula ($I^1$)

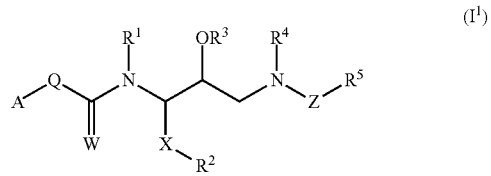

($I^1$)

and pharmaceutically acceptable salts thereof are described herein, wherein

A is cycloheteroalkyl or cycloheteroalkyl-alkyl, each of which is optionally substituted;

Q is oxygen, sulfur, nitrogen, or $C(R^aR^b)$ where each of $R^a$ and $R^b$ is independently selected in each instance from the group consisting of hydrogen, alkyl, and alkoxy;

W is oxygen or sulfur;

$R^1$ is hydrogen, a nitrogen protecting group, or a pro-drug substituent;

X is $C(R^aR^b)_n$, where n is 1, 2, or 3, and each of $R^a$ and $R^b$ is defined as above;

$R^2$ is alkyl, heteroalkyl, cycloalkyl, cycloheteroalkyl, aryl, heteroaryl, arylalkyl, or heteroarylalkyl, each of which is substituted, where at least one substituent is a hydrogen bond forming group;

$R^3$ is hydrogen, an oxygen protecting group, or a pro-drug substituent;

$R^4$ is alkyl, heteroalkyl, cycloalkyl, cycloheteroalkyl, aryl, heteroaryl, arylalkyl, or heteroarylalkyl, each of which is optionally substituted;

Z is C(O), S(O)$_2$, NH, NHC(O), or NHS(O)$_2$; and $R^5$ is alkyl, heteroalkyl, cycloalkyl, cycloheteroalkyl, aryl, heteroaryl, arylalkyl, or heteroarylalkyl, each of which is optionally substituted.

In one illustrative embodiment, the HIV-1 protease inhibitors described herein are compounds of the following formula (I$^2$):

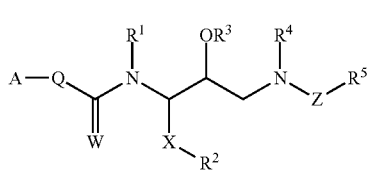

(I$^2$)

and pharmaceutically acceptable salts thereof, wherein

A is the following group, wherein (*) denotes the point of attachment:

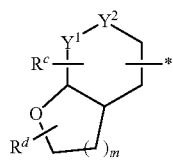

one of $Y^1$ and $Y^2$ is methylene, and the other of $Y^1$ and $Y^2$ is defined as follows:

$Y^1$ is C($R^a R^b$) or oxygen; $Y^2$ is C($R^a R^b$), CHNR$^a$, oxygen, or SO$_2$, where $R^a$ and $R^b$ are independently selected in each instance from hydrogen, alkyl, and alkoxy; m is an integer selected from 0, 1, 2, or 3; and $R^c$ and $R^d$ each represent one or more optional substituents, each of which is independently selected in each instance from hydrogen, alkyl, alkenyl, alkynyl, cycloalkyl, cycloalkylalkyl, aryl, arylalkyl, heterocyclyl, heterocyclylalkyl, heteroaryl, heteroarylalkyl, alkoxy, alkenyloxy, alkynyloxy, cycloalkoxy, cycloalkylalkoxy, aryl, arylalkoxy, heterocyclyloxy, heterocyclylalkoxy, heteroaryloxy, and heteroarylalkoxy, each of which is itself optionally substituted;

Q is oxygen, sulfur, nitrogen, or C($R^a R^b$); where each of $R^a$ and $R^b$ is independently selected in each instance from the group consisting of hydrogen, alkyl, and alkoxy;

W is oxygen or sulfur;

$R^1$ is hydrogen, a nitrogen protecting group, or a pro-drug substituent;

X is C($R^a R^b$)$_n$, where each of $R^a$ and $R^b$ is independently selected in each instance from the group consisting of hydrogen, alkyl, and alkoxy;

$R^2$ is alkyl, heteroalkyl, cycloalkyl, cycloheteroalkyl, aryl, heteroaryl, arylalkyl, or heteroarylalkyl, each of which is optionally substituted;

$R^3$ is hydrogen, an oxygen protecting group, or a pro-drug substituent;

$R^4$ is alkyl, heteroalkyl, cycloalkyl, cycloheteroalkyl, aryl, heteroaryl, arylalkyl, or heteroarylalkyl, each of which is optionally substituted;

Z is C(O), S(O)$_2$, NH, NHC(O), or NHS(O)$_2$; and $R^5$ is alkyl, heteroalkyl, cycloalkyl, cycloheteroalkyl, aryl, heteroaryl, arylalkyl, or heteroarylalkyl, each of which is optionally substituted;

providing that the compound of formula (I$^2$) is not of the formula

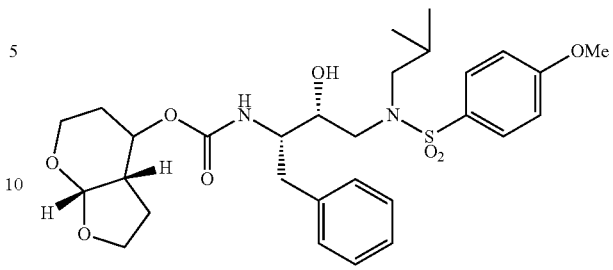

or a pharmaceutically acceptable salt thereof.

In another embodiment, compositions containing one or more of the compounds are also described herein. In one aspect, the compositions include a therapeutically effective amount of the one or more compounds for treating a patient with HIV-1/AIDS. In another embodiment, methods for using the compounds and compositions for treating patients with HIV-1/AIDS are also described herein. In one aspect, the methods include the step of administering one or more of the compounds and/or compositions containing them to a patient with HIV-1/AIDS. In another aspect, the methods include administering a therapeutically effective amount of the one or more compounds and/or compositions described herein for treating patients with HIV-1/AIDS. Another embodiment is the use of the one or more compounds and/or compositions described herein for treating patients with HIV-1/AIDS. In another embodiment, uses of the compounds and compositions in the manufacture of a medicament for treating patients with HIV-1/AIDS are also described herein. In one aspect, the medicaments include a therapeutically effective amount of the one or more compounds and/or compositions for treating a patient with HIV-1/AIDS.

It is appreciated herein that the compounds described herein may be used alone or in combination with other compounds useful for treating HIV/AIDS, including those compounds that may operate by the same or different modes of action. In addition, it is appreciated herein that the compounds described herein may be used in combination with other compounds that are administered to treat other symptoms of HIV/AIDS.

DETAILED DESCRIPTION

Described herein are compounds that exhibit protease inhibition. In one aspect, the compounds described herein exhibit HIV-1 protease inhibition.

In another embodiment, compounds of the following formula (I$^1$) are described herein:

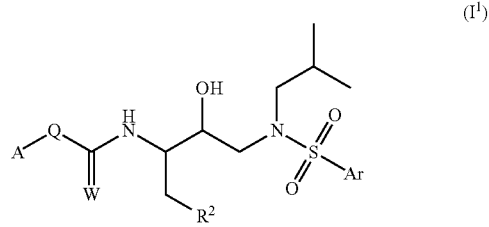

(I$^1$)

wherein A, Q, $R^2$ and Ar are as described in the various embodiments and aspects disclosed herein for a compound of formula (I$^1$).

In one embodiment of a compound of formula (I¹, Ar is aryl or heteroaryl as defined herein. In another embodiment, Ar is selected from the group consisting of 4-methoxyphenyl, 4-(hydroxymethyl)phenyl, a 3-substituted phenyl, a 4-substituted phenyl, an optionally substituted benzisoxazole, an optionally substituted benzoxazole; an optionally substituted benzodioxane or an optionally substituted benzodioxolane, and the like.

In another embodiment, compounds of formula (I¹) having the following relative and/or absolute stereochemistry are described herein:

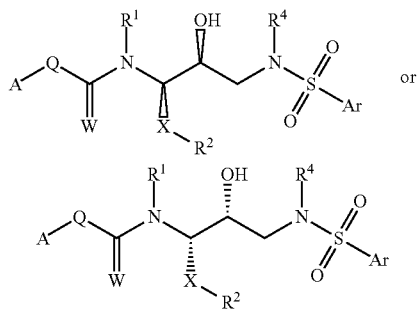

wherein A, Q, W, R¹, X, R², R⁴ and Ar are as described in the various descriptions for a compound of formula (I¹) herein. In one embodiment, Ar is optionally substituted aryl or heteroaryl. In another embodiment, Ar is optionally substituted aryl.

In another embodiment compounds of formula (I¹) of the following formula are described herein:

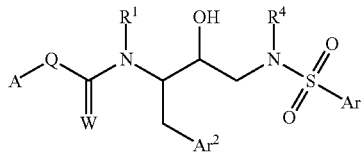

where Ar² is substituted aryl or substituted heteroaryl having one or more of the following illustrative substituents: halo, amino, hydroxy, alkyl, alkenyl, alkoxy, arylalkyl, arylalkyloxy, hydroxyalkyl, hydroxyalkenyl, alkylene dioxy, aminoalkyl, where the amino group may also be substituted with one or two alkyl groups, arylalkylgroups, and/or acylgroups, nitro, acyl and derivatives thereof such as oximes, hydrazones, and the like, cyano, alkylsulfonyl, alkylsulfonylamino, and the like, where at least one substituent is a hydrogen bond forming group, and A, Q, W, R¹, R⁴ and Ar have the meanings described above for a compound of formula (I¹).

In another embodiment compounds of formula (I¹) of the following formula are described herein:

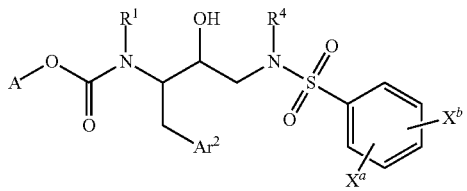

where $X^a$ and $X^b$ are each independently selected from hydrogen, halo, amino, hydroxy, alkyl, alkenyl, alkoxy, arylalkyl, arylalkyloxy, hydroxyalkyl, hydroxyalkenyl, aminoalkyl, where the amino group may also be substituted with one or two alkyl groups, arylalkylgroups, and/or acylgroups, nitro, acyl and derivatives thereof such as oximes, hydrazones, and the like, cyano, alkylsulfonyl, alkylsulfonylamino, and the like, or $X^a$ and $X^b$ together form alkylene dioxy; and A, R¹, Ar², and R⁴ have the meanings described above for a compound of formula (I¹).

In another embodiment, compounds of formula (I¹) of the formula:

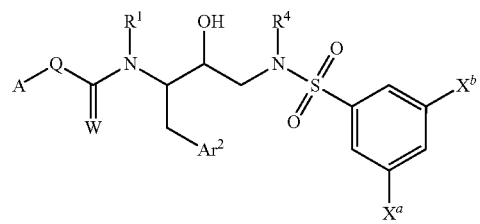

and pharmaceutically acceptable salts thereof are described herein wherein $X^a$ and $X^b$ are independently selected from hydrogen, OH or $OR^{5A}$, where $R^{5A}$ is alkyl, alkylaryl, an oxygen protecting group or a pro-drug substituent; and A, Q, W, R¹, Ar² and R⁴ have the meanings described above for a compound of formula (I¹).

In another embodiment of the compounds of formula (I¹) described herein, R⁴ is alkyl, cycloalkyl, heterocyclyl, heterocyclylalkyl, hydroxy, alkoxy, cycloalkoxy, heterocyclyloxy, heterocyclylalkoxy, amino, mono or dialkylamino, cycloalkylamino, heterocyclylamino, or heterocyclylalkylamino, each of which is optionally substituted. In one aspect, R⁴ is amino substituted alkyl or heterocycyl, or heterocyclylalkyl. In one variation of this aspect, the nitrogen atom of the amino group is mono or disubstituted with alkyl, cycloalkyl, or acyl, or is included in another heterocyclic group such as a pyrrolidinyl, piperidinyl, or piperazinyl group. In another variation of this aspect, the nitrogen atom of the hetetocylclyl group is substituted with alkyl, cycloalkyl, or acyl. In another aspect, R⁴ is optionally substituted alkyl or cycloalkyl, including both linear and branched variations thereof, such as methyl, ethyl, butyl, isobutyl, and the like, and cyclobutyl, cyclopentyl, 3-methyl-cyclopentyl, and the like. In another aspect, R⁴ is optionally substituted heterocyclyl or heterocyclylalkyl, where the heterocyclic portions includes, but is not limited to, tetrahydrofuranyl, azetidinyl, pyrrolidinyl, piperidinyl, morpholinyl, piperazinyl, and the like.

In another illustrative embodiment, compounds of formula (I¹) of formula

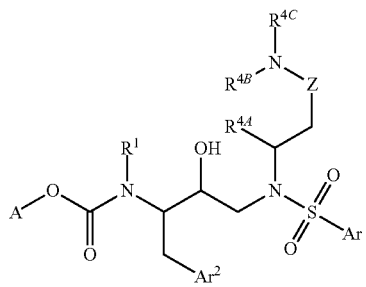

and pharmaceutically acceptable salts thereof are described, wherein

Z is $C(R^cR^d)$ where each of $R^c$ and $R^d$ is independently selected in each instance from the group consisting of hydrogen, alkyl, and arylalkyl; $R^{4A}$, $R^{4B}$ and $R^{4C}$ are independently selected in each instance from the group consisting of hydrogen, alkyl, and arylalkyl, each of which may be optionally substituted, or $R^{4A}$, $R^{4B}$ and the atoms to which they are attached form a ring, and $R^{4C}$ is selected from the group consisting of hydrogen, alkyl, and arylalkyl, each of which may be optionally substituted; and A, $R^1$ and $Ar^2$ have the meanings disclosed above for a compound of formula $(I^1)$.

In another embodiment, compounds of formula $(I^1)$ of the formula:

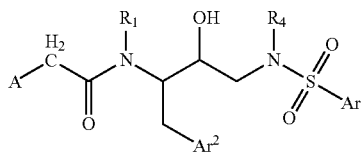

and pharmaceutically acceptable salts thereof are described herein wherein A, $R^1$, $Ar^2$, $R^4$ and Ar have the meanings described above for a compound of formula (O).

In another embodiment, compounds of formula $(I^1)$ are described where in of each of the foregoing formulae and embodiments for a compound of formula $(I^1)$, A is cycloheteroalkyl, which includes monocyclic and polycyclic rings that have at least one nitrogen, oxygen, or sulfur atom, where it is to be understood that the polycyclic rings may be fused and/or Spiro ring systems. Illustratively, monocyclic cycloheteroalkyls include, but are not limited to 5-, 6-, and 7-membered cyclic ethers and diethers, such as tetrahydrofurans, pyrans, 1,3-dioxolanes, 1,3-dixoxanes, 1,4-dioxanes, 1,3-dioxepanes, and the like; pyrrolidines, piperidines, piperazines, and the like; and tetrahydrothiophenes, thiopyrans, including oxidized variations thereof, and the like. Illustratively, polycyclic cycloheteroalkyls include, but are not limited to, the foregoing monocyclic rings fused to each other, or to cycloalkyls, and alternatively the spiro variations thereof. As indicated herein, it is also to be understood that where such fused or spiro ring systems include chiral centers, any and all possible stereoisomers are contemplated to be included herein. In addition, both the pure enantiomers and diastereomers, as well as various mixtures of pure enantiomers and diastereomers are contemplated to be included herein. It is also to be understood that the point of attachment of the cycloheteroalkyl groups described herein may be at any locus of the ring system.

In another illustrative embodiment, compounds of formula $(I^1)$ of formula $(I^{1a})$ or $(I^{1b})$

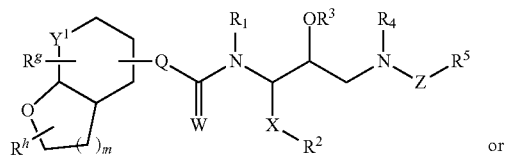

(I$^{1a}$)

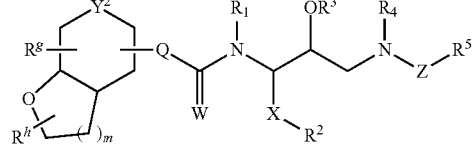

(I$^{1b}$)

and pharmaceutically acceptable salts thereof are described herein, wherein $Y^1$ is $C(R^eR^f)$ or oxygen; $Y^2$ is $C(R^eR^f)$, $CHNR^e$, oxygen, or $SO_2$, where $R^e$ and $R^f$ are independently selected in each instance from hydrogen, alkyl, and alkoxy; m is an integer selected from 0, 1, 2, or 3; and $R^g$ and $R^h$ each represent one or more optional substituents, each of which is independently selected in each instance from hydrogen, alkyl, alkenyl, alkynyl, cycloalkyl, cycloalkylalkyl, aryl, arylalkyl, heterocyclyl, heterocyclylalkyl, heteroaryl, heteroarylalkyl, alkoxy, alkenyloxy, alkynyloxy, cycloalkoxy, cycloalkylalkoxy, aryl, arylalkoxy, heterocyclyloxy, heterocyclylalkoxy, heteroaryloxy, and heteroarylalkoxy, each of which is itself optionally substituted; and Q, W, $R^1$, X, $R^2$, $R^3$, $R^4$, Z and $R^5$ have the meanings described above for a compound of formula $(I^1)$.

In another illustrative embodiment, compounds of formula $(I^1)$ of the formula

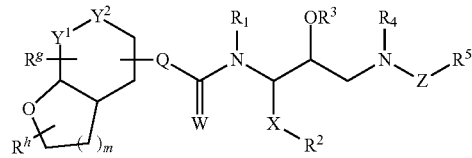

and pharmaceutically acceptable salts thereof are described herein, wherein one of $Y^1$ and $Y^2$ is methylene, and the other of $Y^1$ and $Y^2$ is defined as follows:

$Y^1$ is $C(R^eR^f)$ or oxygen; $Y^2$ is $C(R^eR^f)$, $CHNR^e$, oxygen, or $SO_2$, where $R^e$ and $R^f$ are independently selected in each instance from hydrogen, alkyl, and alkoxy; m is an integer selected from 0, 1, 2, or 3; and $R^g$ and $R^h$ each represent one or more optional substituents, each of which is independently selected in each instance from hydrogen, alkyl, alkenyl, alkynyl, cycloalkyl, cycloalkylalkyl, aryl, arylalkyl, heterocyclyl, heterocyclylalkyl, heteroaryl, heteroarylalkyl, alkoxy, alkenyloxy, alkynyloxy, cycloalkoxy, cycloalkylalkoxy, aryl, arylalkoxy, heterocyclyloxy, heterocyclylalkoxy, heteroaryloxy, and heteroarylalkoxy, each of which is itself optionally substituted; and Q, W, $R^1$, X, $R^2$, $R^3$, $R^4$, Z and $R^5$ have the meanings described above for a compound of formula $(I^1)$.

In another embodiment, compounds of formula $(I^1)$ are described where, in of each of the foregoing formulae and embodiments, $Y^1$ is oxygen; or $Y^1$ is $C(R^eR^f)$, where $R^e$ is hydrogen, and $R^f$ is hydrogen or alkoxy, such as methoxy; or $Y^2$ is oxygen; or $Y^2$ is $C(R^eR^f)$, where $R^e$ is hydrogen, and $R^f$ is hydrogen, such as methoxy.

In another embodiment of a compound of formula $(I^1, A$ is a mono or polycyclic ether. In another embodiment, A is a radical having one of the following structures

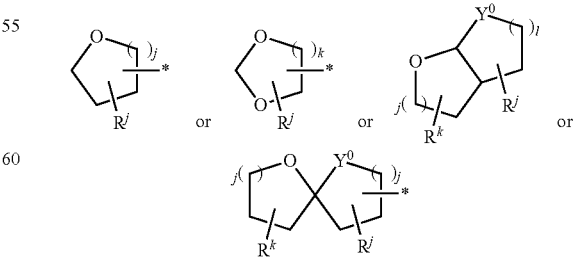

where (*) indicates the point of attachment of the group A; j is an integer that is independently selected in each instance from 0, 1, 2, or 3; k is an integer from 1 to 5; $Y^0$ is $C(R^aR^b)$ or oxygen; each of $R^a$ and $R^b$ is independently selected in each instance from the group consisting of hydrogen, alkyl, and alkoxy; and $R^j$ and $R^k$ each represent one or more optional substituents, each of which is independently selected in each instance from hydrogen, alkyl, alkenyl, alkynyl, cycloalkyl, cycloalkylalkyl, aryl, arylalkyl, heterocyclyl, heterocyclylalkyl, heteroaryl, heteroarylalkyl, alkoxy, alkenyloxy, alkynyloxy, cycloalkoxy, cycloalkylalkoxy, aryl, arylalkoxy, heterocyclyloxy, heterocyclylalkoxy, heteroaryloxy, and heteroarylalkoxy, each of which is itself optionally substituted In one aspect, $R^a$ and $R^b$ are both hydrogen. In another aspect, $R^j$ and $R^k$ are both hydrogen. In another aspect, $R^a$, $R^b$, $R^j$ and $R^k$ are each hydrogen. In another aspect, one or more of $R^j$ and $R^k$ is alkoxy.

It is appreciated that when the integer j is in each case 0 or 1, the ring fusion is syn, whereas when in one instance the integer j is 2 and in the other instance the integer j is 1 or 2, the ring fusion may be syn or anti. It is further appreciated that in each of these relative stereochemical configurations, there are potentially two absolute stereochemical configurations. Unless otherwise indicated by specific reference to a relative or absolute stereochemical configuration, the structures described herein refer both individually to each enantiomer, as well as collectively to all possible mixtures of such enantiomers. It is appreciated that the foregoing cyclic ethers may be optionally substituted with one or more groups $R^a$ and/or $R^b$, each of which is independently selected, and is as described in the various embodiments and aspects disclosed herein for a compound of formula ($I^1$).

In another illustrative embodiment, compounds of formula ($I^1$), and pharmaceutically acceptable salts thereof are described herein, wherein A is of the formula

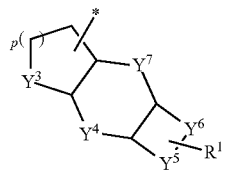

wherein (*) indicates the point of attachment;

p is 1, 2, or 3;

$Y^3$ and $Y^4$ are in each instance independently selected from the group consisting of optionally substituted methylene, oxygen, and amino;

$Y^5$ and $Y^6$ are in each instance independently selected from the group consisting of amino, oxygen, alkylene, and heteroalkylene, providing that at least one of $Y^3$ and $Y^4$ is oxygen, and wherein when one of $Y^3$ and $Y^4$ is optionally substituted methylene, at least one of $Y^5$ and $Y^6$ is oxygen, and A does not include a peroxide bond, a sultanate bond, or a sulfenamide bond;

$Y^7$ is a bond or optionally substituted methylene; and $R^i$ is hydrogen, hydroxyl, carboxylate or derivative thereof, amino or derivative thereof, acyl, sulfonyl or derivative thereof, alkyl, or heteroalkyl.

In another illustrative embodiment, compounds of formula ($I^1$), and pharmaceutically acceptable salts thereof are described herein, wherein A as described above is of the formula

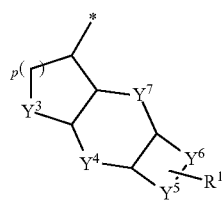

wherein (*) indicates the point of attachment; and p, $Y^3$, $Y^4$, $Y^5$, $Y^6$, $Y^7$, and $R^1$ are each defined as above.

In one embodiment of a compound of formula ($I^1$), for any of the above descriptions of A, $Y^4$ is oxygen. In one embodiment for any of the above descriptions of A, $Y^7$ is a bond. In one embodiment for any of the above descriptions of A, p is 1 or 2. In one embodiment for any of the above descriptions of A, p is 1. In one embodiment for any of the above descriptions of A, $R^1$ is hydrogen. In one embodiment for any of the above descriptions of A, $Y^4$ is oxygen. In one embodiment for any of the above descriptions of A, $Y^5$ or $Y^6$ is oxygen. In one embodiment for any of the above descriptions of A, $Y^4$ and one of $Y^5$ and $Y^6$ are oxygen. In one embodiment for any of the above descriptions of A, $Y^4$ and $Y^5$ are oxygen. In one embodiment for any of the above descriptions of A, each of $Y^3$, $Y^4$ and $Y^5$ is oxygen. In one embodiment for any of the above descriptions of A, $Y^3$ is optionally substituted methylene.

In another embodiment of a compound of formula ($I^1$), A is a radical having one of the following structures

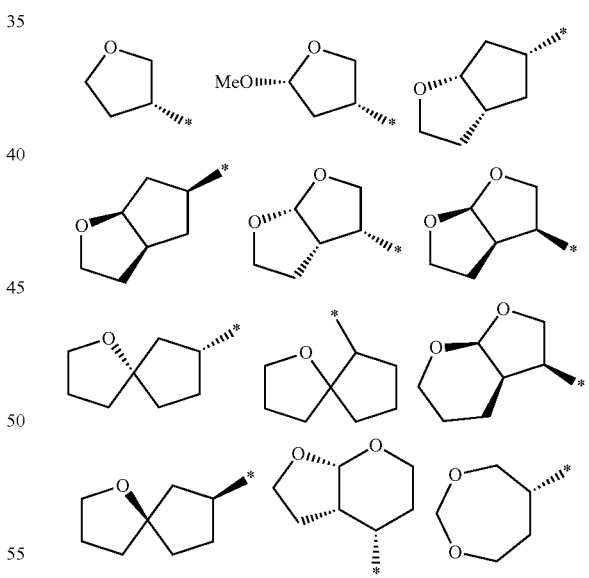

and stereoisomers thereof and mixtures thereof, where (*) indicates the point of attachment of A. It is therefore appreciated that such groups are attached to the group Q, which is oxygen, sulfur, nitrogen, or $C(R^aR^b)$; where each of $R^a$ and $R^b$ is independently selected in each instance, as defined in the various embodiments and aspects disclosed herein for a compound of formula ($I^1$).

In another embodiment of a compound of formula ($I^1$), A is a radical having one of the following structures

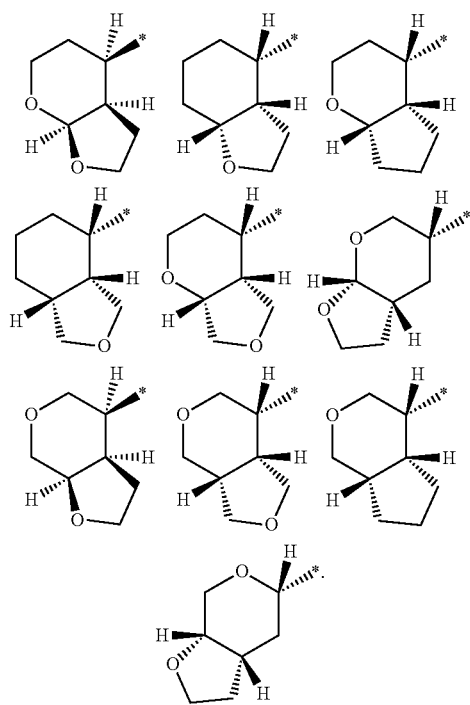

and stereoisomers thereof and mixtures thereof. where (*) indicates the point of attachment of A. It is therefore appreciated that such groups are attached to the group Q, which is oxygen, sulfur, nitrogen, or $C(R^aR^b)$; where each of $R^a$ and $R^b$ is independently selected in each instance, as defined in the various embodiments and aspects disclosed herein.

In another embodiment of a compound of formula ($I^1$), A is a radical having one of the following structures

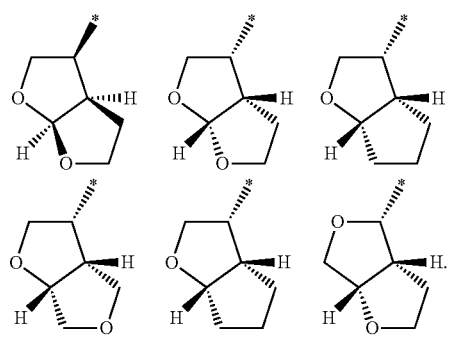

and stereoisomers thereof and mixtures thereof, where (*) indicates the point of attachment of A. It is therefore appreciated that such groups are attached to the group Q, which is oxygen, sulfur, nitrogen, or $C(R^aR^b)$; where each of $R^a$ and $R^b$ is independently selected in each instance, as defined in the various embodiments and aspects disclosed herein.

In another illustrative embodiment of a compound of formula ($I^1$), compounds, and pharmaceutically acceptable salts thereof are described herein, wherein A is of the formula

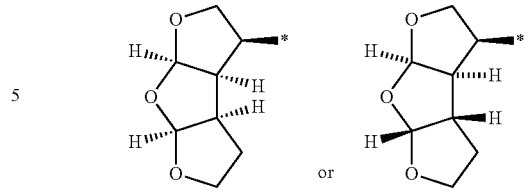

wherein (*) indicates the point of attachment.

In another embodiment of a compound of formula ($I^1$), the group A is cycloheteroalkyl-alkyl of the formula Het-$(CH_2)_q$—; where q is an integer selected from 1, 2, or 3; and Het is optionally substituted cycloheteroalkyl. In another embodiment, Het is oxazolidine, thiazolidine, pyrolidine, piperidine, piperazine, and the like, each of which is optionally substituted, including oxo substituents that form the corresponding oxazolidinones, thiazolidinones, pyrollidinones, piperidinones, piperazinones, and the like.

In any of the foregoing formulae and embodiments of a compound of formula ($I^1$), the following compounds are described wherein:

Q is oxygen; and/or
W is oxygen; and/or
$R^1$ is hydrogen; and/or
$R^3$ is hydrogen; and/or
$R^4$ is a group $CH_2$—K—$R^{4D}$, where K is a bond or $NHCH_2$, and $R^{4D}$ is alkyl, cycloalkyl, cycloheteroalkyl, aryl, or heteroaryl, each of which is optionally substituted; or $R^{4D}$ is isopropyl, furanyl, tetrahydrofuranyl, pyrrolyl, oxazolyl, thiazolyl, isoxazolyl, isothiazolyl, pyrrolidinonyl, oxazolidinonyl, thiazolidinonyl, isoxazolidionyl, or isothiazolidinonyl, each of which is optionally substituted; or $R^4$ is branched alkyl; or $R^4$ is isobutyl; or $R^4$ is lactamylalkyl; or $R^4$ is pyrrolidin-4-on-2-ylalkyl; or $R^4$ is pyrrolidin-4-on-2-ylmethyl; and/or
Z is $SO_2$; or Z is CO; or Z is NH; and/or
$R^5$ is aryl or heteroaryl, each of which is optionally substituted; or $R^5$ is substituted phenyl; or $R^5$ is substituted phenyl, where the substituent is hydroxy or a derivative thereof, amino or a derivative thereof, thio or a derivative thereof, or any of the foregoing where the substituent is covalently attached to the aryl through a group $C(R^xR^y)$; where each of $R^x$ and $R^y$ is independently selected in each instance from the group consisting of hydrogen and alkyl; or $R^x$ and $R^y$ are each hydrogen; and/or
$R^5$ is phenyl substituted with $NH_2$, OH, OMe, $CH_2OH$, and/or $OCH_2O$; or $R^5$ is optionally substituted benzofuran; or $R^5$ is optionally substituted dihydrobenzofuran; or $R^5$ is optionally substituted benzothiopene; or $R^5$ is optionally substituted benzoxazole; or $R^5$ is optionally substituted benzothiazole; or $R^5$ is optionally substituted benzisoxazole; or $R^5$ is optionally substituted benzoisothiazole; and/or
$R^a$ and $R^b$ are each hydrogen; and/or
n is 1.

In another embodiment, compounds of formula ($I^1$) are described where in of each of the foregoing formulae and embodiments, $R^2$ or $Ar^2$ is substituted phenyl.

In another embodiment, compounds of formula ($I^1$) are described where in of each of the foregoing formulae and embodiments, $R^2$ or $Ar^2$ is phenyl substituted with hydroxy or a derivative thereof, amino or a derivative thereof, thio or a derivative thereof, or any of the foregoing where the substituent is covalently attached to the phenyl through a group $C(R^xR^y)$; where each of $R^x$ and $R^y$ is independently selected in each instance from the group consisting of hydrogen and alkyl; or both $R^x$ and $R^y$ are hydrogen.

In another embodiment, compounds of formula ($I^1$) are described where in of each of the foregoing formulae and embodiments, $R^2$ or $Ar^2$ is phenyl substituted with a hydroxy derivative, a thio derivative, or an amino derivative, wherein each of the foregoing, derivatives include those that include a phosphorus-containing group; or $R^2$ or $Ar^2$ is phenyl substituted with OH, alkoxy, SH, alkylthio, $NH_2$, alkylamino, or dialkylamino; or $R^2$ or $Ar^2$ is phenyl substituted with hydroxymethyl, alkoxymethyl, thiomethyl, alkylthiomethyl, $H_2N$-methyl, alkylaminomethyl, or dialkylaminomethyl; or $R^2$ or $Ar^2$ is phenyl substituted with heterocyclylalkyloxy, such as morpholin-1-ylalkyloxy, pyrrolidin-1-ylalkyloxy, or piperidin-1-ylalkyloxy.

In another embodiment, compounds of formula ($I^1$) are described where in of each of the foregoing formulae and embodiments, $R^2$ or $Ar^2$ is capable of forming a hydrogen bond with a group in the S2 site of an HIV protease. In one variation, the group in the S2 site is a glycine, such as Gly-48.

In another embodiment, a compound of formula ($I^1$) having the formula

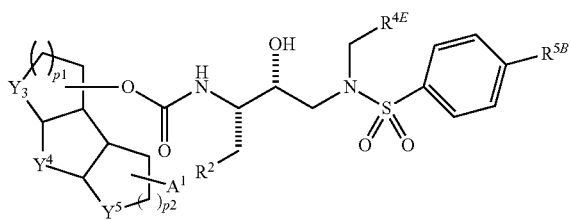

or a pharmaceutically acceptable salt thereof, is described, wherein each of $Y^3$, $Y^4$ and $Y^5$ is oxygen; or
$Y^3$ is methylene and each of $Y^4$ and $Y^5$ is oxygen; or
$Y^4$ is methylene and each of $Y^3$ and $Y^5$ is oxygen; or
$Y^5$ is methylene and each of $Y^3$ and $Y^4$ is oxygen;
each of $p_1$ and $P_2$ is independently 1, 2 or 3;
$A^1$ is selected from the group consisting of hydrogen, hydroxyl or derivative thereof, carboxylate or derivative thereof, amino or derivative thereof, or sulfonyl or derivative thereof, and the like;
$R^2$ has any of the values defined above for $R^2$;
$R^{4E}$ is selected from the group consisting of isopropyl, alkyl, or heteroalkyl, and the like; and
$R^{5B}$ is selected from the group consisting of methoxy, aminomethyl; amino, or heteroalkyl, and the like.

In another embodiment, a compound of formula ($I^1$) having the formula

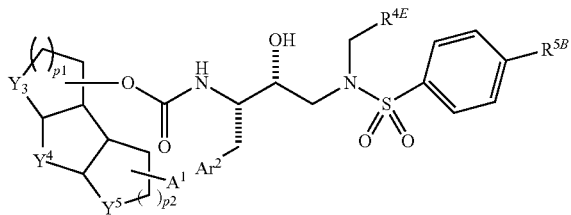

or a pharmaceutically acceptable salt thereof, is described, wherein each of $Y^3$, $Y^4$ and $Y^5$ is oxygen; or
$Y^3$ is methylene and each of $Y^4$ and $Y^5$ is oxygen; or
$Y^4$ is methylene and each of $Y^3$ and $Y^5$ is oxygen; or
$Y^5$ is methylene and each of $Y^3$ and $Y^4$ is oxygen;
each of $p_1$ and $P_2$ is independently 1, 2 or 3;
$A^1$ is selected from the group consisting of hydrogen, hydroxyl or derivative thereof, carboxylate or derivative thereof, amino or derivative thereof, or sulfonyl or derivative thereof, and the like;
$Ar^2$ has any of the values defined above for $Ar^2$;
$R^{4E}$ is selected from the group consisting of isopropyl, alkyl, or heteroalkyl, and the like; and
$R^{5B}$ is selected from the group consisting of methoxy, aminomethyl; amino, or heteroalkyl, and the like.

In another embodiment, a compound of formula ($I^1$) having the formula

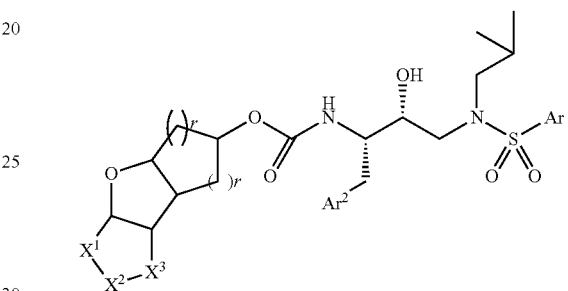

or a pharmaceutically acceptable salt thereof, is described, wherein each of $X^1$, $X^2$ and $X^3$ is methylene; or
$X^1$ is oxygen or $NR^m$ and each of $X^2$ and $X^3$ is methylene; or
each of $X^1$ and $X^2$ is methylene and $X^3$ is oxygen or $NR^m$; or
each of $X^1$ and $X^3$ is methylene and $X^2$ is oxygen or $NR^m$;
$R^m$ is selected from the group consisting of hydrogen, methyl, methylsulfonyl, acetyl or methoxycarbonyl, and the like;
$Ar^2$ has any of the values defined above for $Ar^2$; and
Ar has any of the values defined above for Ar.

In another embodiment, a compound of formula ($I^1$) having the formula

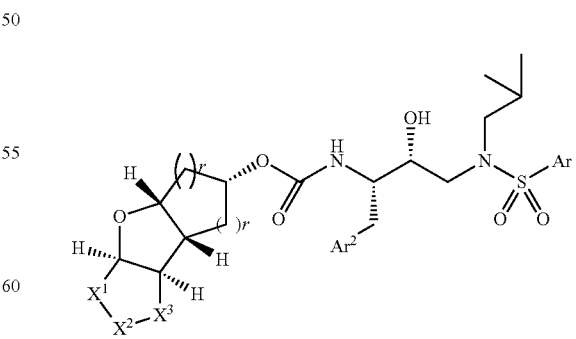

or a pharmaceutically acceptable salt thereof, is described, wherein $X^1$, $X^2$, $X^3$, $R^m$, $Ar^2$, and Ar are as defined above.

In another embodiment, there is provided a compound selected from the group consisting of

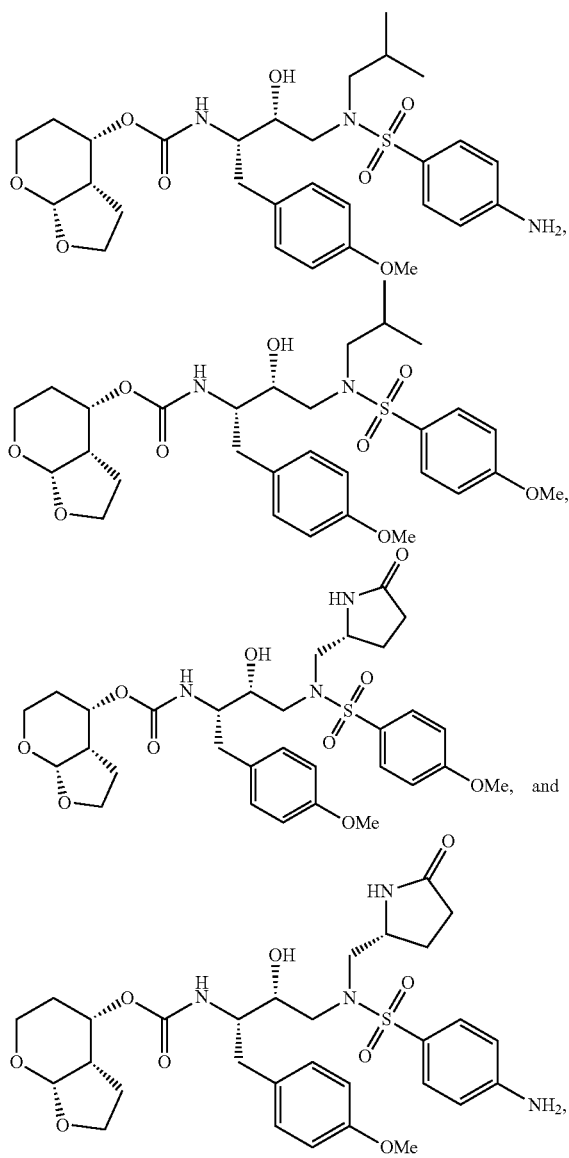

or a pharmaceutically acceptable salt thereof.

In one illustrative embodiment, the compounds described herein have the following formula ($I^2$):

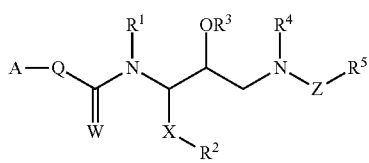

(I²)

and pharmaceutically acceptable salts thereof, wherein

A is the following group, wherein (*) denotes point of attachment:

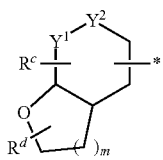

$Y^1$ is $C(R^aR^b)$ or oxygen; $Y^2$ is $C(R^aR^b)$, $CHNR^a$, oxygen, or $SO_2$, where $R^a$ and $R^b$ are independently selected in each instance from hydrogen, alkyl, and alkoxy; m is an integer selected from 0, 1, 2, or 3; and $R^c$ and $R^d$ each represent one or more optional substituents, each of which is independently selected in each instance from hydrogen, alkyl, alkenyl, alkynyl, cycloalkyl, cycloalkylalkyl, aryl, arylalkyl, heterocyclyl, heterocyclylalkyl, heteroaryl, heteroarylalkyl, alkoxy, alkenyloxy, alkynyloxy, cycloalkoxy, cycloalkylalkoxy, aryl, arylalkoxy, heterocyclyloxy, heterocyclylalkoxy, heteroaryloxy, and heteroarylalkoxy, each of which is itself optionally substituted;

Q is oxygen, sulfur, nitrogen, or $C(R^aR^b)$; where each of $R^a$ and $R^b$ is independently selected in each instance from the group consisting of hydrogen, alkyl, and alkoxy;

W is oxygen or sulfur, $R^1$ is hydrogen, a nitrogen protecting group, or a pro-drug substituent;

X is $C(R^aR^b)_n$, where each of $R^a$ and $R^b$ is independently selected in each instance from the group consisting of hydrogen, alkyl, and alkoxy;

$R^2$ is alkyl, heteroalkyl, cycloalkyl, cycloheteroalkyl, aryl, heteroaryl, arylalkyl, or heteroarylalkyl, each of which is optionally substituted;

$R^3$ is hydrogen, an oxygen protecting group, or a pro-drug substituent;

$R^4$ is alkyl, heteroalkyl, cycloalkyl, cycloheteroalkyl, aryl, heteroaryl, arylalkyl, or heteroarylalkyl, each of which is optionally substituted;

Z is $C(O)$, $S(O)_2$, NH, NHC(O), or $NHS(O)_2$; and $R^5$ is alkyl, heteroalkyl, cycloalkyl, cycloheteroalkyl, aryl, heteroaryl, arylalkyl, or heteroarylalkyl, each of which is optionally substituted;

providing that the compound is of formula ($I^2$) not of the formula

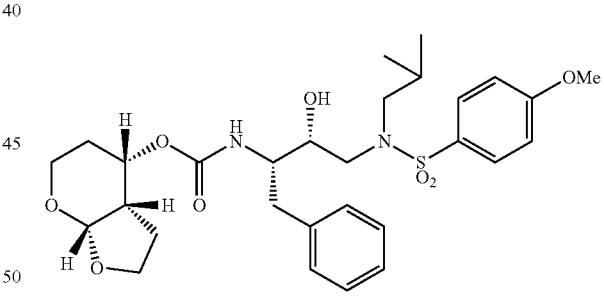

or a pharmaceutically acceptable salts thereof.

In one illustrative embodiment, the compounds of formula ($I^2$) described herein have the following formulae ($I^{2a}$) or ($I^{2b}$):

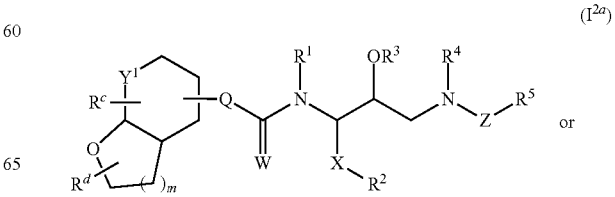

($I^{2a}$)

or

-continued

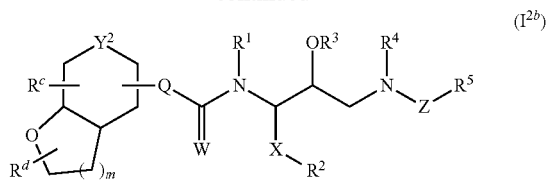
(I²ᵇ)

and pharmaceutically acceptable salts thereof, wherein $Y^1$ is $C(R^aR^b)$ or oxygen; $Y^2$ is $C(R^aR^b)$, $CHNR^a$, oxygen, or $SO_2$, where $R^a$ and $R^b$ are independently selected in each instance from hydrogen, alkyl, and alkoxy; m is an integer selected from 0, 1, 2, or 3; and $R^c$ and $R^d$ each represent one or more optional substituents, each of which is independently selected in each instance from hydrogen, alkyl, alkenyl, alkynyl, cycloalkyl, cycloalkylalkyl, aryl, arylalkyl, heterocyclyl, heterocyclylalkyl, heteroaryl, heteroarylalkyl, alkoxy, alkenyloxy, alkynyloxy, cycloalkoxy, cycloalkylalkoxy, aryl, arylalkoxy, heterocyclyloxy, heterocyclylalkoxy, heteroaryloxy, and heteroarylalkoxy, each of which is itself optionally substituted;

Q is oxygen, sulfur, nitrogen, or $C(R^aR^b)$; where each of $R^a$ and $R^b$ is independently selected in each instance from the group consisting of hydrogen, alkyl, and alkoxy;

W is oxygen or sulfur.

$R^1$ is hydrogen, a nitrogen protecting group, or a pro-drug substituent;

X is $C(R^aR^b)_n$, where each of $R^a$ and $R^b$ is independently selected in each instance from the group consisting of hydrogen, alkyl, and alkoxy;

$R^2$ is alkyl, heteroalkyl, cycloalkyl, cycloheteroalkyl, aryl, heteroaryl, arylalkyl, or heteroarylalkyl, each of which is optionally substituted;

$R^3$ is hydrogen, an oxygen protecting group, or a pro-drug substituent;

$R^4$ is alkyl, heteroalkyl, cycloalkyl, cycloheteroalkyl, aryl, heteroaryl, arylalkyl, or heteroarylalkyl, each of which is optionally substituted;

Z is $C(O)$, $S(O)_2$, NH, NHC(O), or $NHS(O)_2$; and $R^5$ is alkyl, heteroalkyl, cycloalkyl, cycloheteroalkyl, aryl, heteroaryl, arylalkyl, or heteroarylalkyl, each of which is optionally substituted;

providing that the compound of formula (I²) is not of the formula

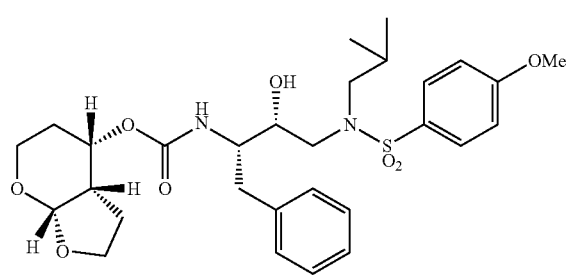 [SMILES: COc1ccc(S(=O)(=O)N(CC(C)C)C[C@@H](O)[C@H](Cc2ccccc2)NC(=O)O[C@H]2CCO[C@H]3OCC[C@H]32)cc1]

or a pharmaceutically acceptable salts thereof.

In other embodiments, described herein are compounds of formulae (I²) above, wherein $R^a$ and $R^b$ are both hydrogen.

In another embodiment, compounds of formula (I²) of the following formula are described herein:

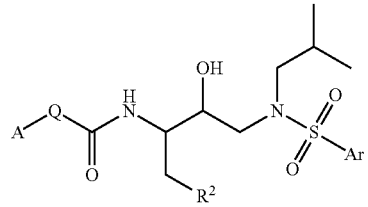

wherein Q and $R^2$ are as described above for a compound of formula (I²); Ar is aryl or heteroaryl, each of which is optionally substituted; or Q, $R^2$ and Ar are as described in the various embodiments and aspects disclosed herein for a compound of formula (I²); and wherein A is selected from the following group, wherein (*) denotes point of attachment:

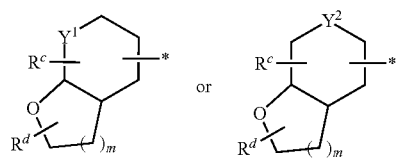

Illustrative non-limiting examples of A for a compound of formula (I²) include the following:

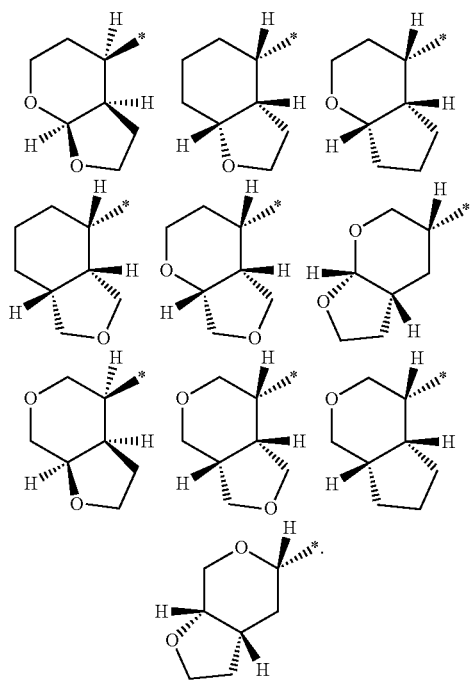

In another embodiment, compounds of formula (I²) having the following relative and/or absolute stereochemistry are described herein:

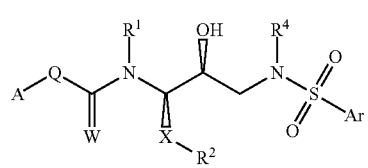

-continued

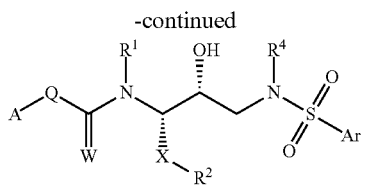

wherein A, Q, W, X, $R^1$, $R^2$, $R^4$, and Ar are as described in the various embodiments and aspects disclosed herein for a compound of formula ($I^2$).

In another embodiment compounds of formula ($I^2$) of the following formula are described herein:

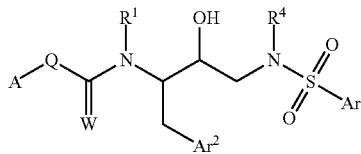

wherein A, Q, W, $R^1$, $R^4$, and Ar are as described in the various embodiments and aspects disclosed herein for a compound of formula ($I^2$), and where $Ar^2$ is substituted aryl or substituted heteroaryl having one or more of the following illustrative substituents; halo, amino, hydroxy, alkyl, alkenyl, alkoxy, arylalkyl, arylalkyloxy, hydroxyalkyl, hydroxyalkenyl, alkylene dioxy, aminoalkyl, where the amino group may also be substituted with one or two alkyl groups, arylalkylgroups, and/or acylgroups, nitro, acyl and derivatives thereof such as oximes, hydrazones, and the like, cyano, alkylsulfonyl, alkylsulfonylamino, and the like and Q, $R^1$, $R^3$ and Ar have the meanings disclosed above for a compound of formula ($I^2$).

In another embodiment compounds of formula ($I^2$) of the following formula are described herein:

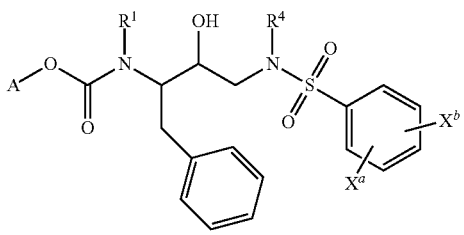

wherein A, $R^1$, and $R^4$ are as described in the various embodiments and aspects disclosed herein for a compound of formula ($I^2$), and where $X^a$ and $X^b$ are each independently selected from halo, amino, hydroxy, alkyl, alkenyl, alkoxy, arylalkyl, arylalkyloxy, hydroxyalkyl, hydroxyalkenyl, alkylene dioxy, aminoalkyl, where the amino group may also be substituted with one or two alkyl groups, arylalkylgroups, and/or acylgroups, nitro, acyl and derivatives thereof such as oximes, hydrazones, and the like, cyano, alkylsulfonyl, alkylsulfonylamino, and the like and $R^1$, $R^3$ and Ar have the meanings disclosed above for a compound of formula ($I^2$).

In another illustrative embodiment of a compound of formula ($I^2$), compounds of the formula:

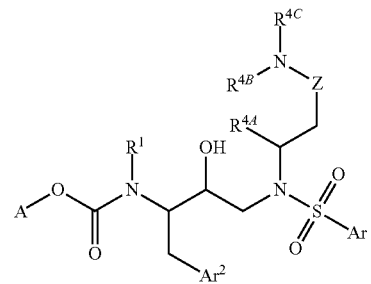

and pharmaceutically acceptable salts thereof are described herein, wherein

Z is C($R^c R^d$) where each of $R^c$ and $R^d$ is independently selected in each instance from the group consisting of hydrogen, alkyl, and arylalkyl; $R^{4A}$, $R^{4B}$ and $R^{4C}$ are independently selected in each instance from the group consisting of hydrogen, alkyl, and arylalkyl, each of which may be optionally substituted, or $R^{4A}$, $R^{4B}$ and the atoms to which they are attached form a ring, and $R^{4C}$ is selected from the group consisting of hydrogen, alkyl, and arylalkyl, each of which may be optionally substituted; and A, $R^1$ and $Ar^2$ have the meanings disclosed above for a compound of formula ($I^2$).

In another embodiment of a compound of formula ($I^2$), compounds of the formula:

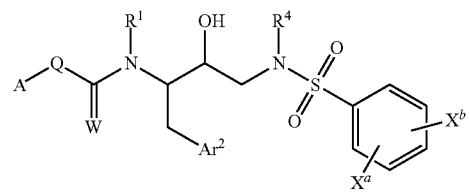

and pharmaceutically acceptable salts thereof are described herein wherein $X^a$ and $X^b$ are independently selected from H, OH or $OR^6$, where $R^6$ is alkyl, alkylaryl, an oxygen protecting group or a pro-drug substituent; and A, Q, W, $R^1$, $Ar^2$ and $R^4$ have the meanings disclosed above for a compound of formula ($I^2$).

In another embodiment of a compound of formula ($I^2$), compounds of the formula:

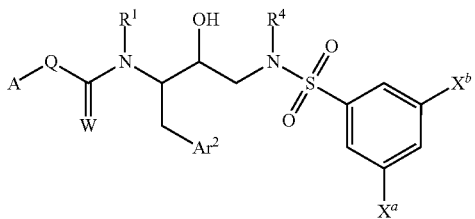

and pharmaceutically acceptable salts thereof are described herein wherein $X^a$ and $X^b$ are independently selected from H, OH or $OR^6$, where $R^6$ is alkyl, alkylaryl, an oxygen protecting group or a pro-drug substituent; and A, Q, W, $R^1$, $Ar^2$ and $R^4$ have the meanings disclosed above for a compound of formula ($I^2$).

In another embodiment of a compound of formula ($I^2$), compounds of the formula:

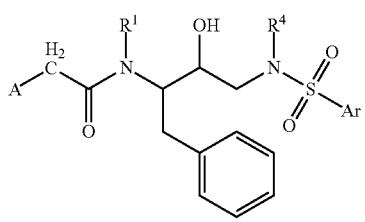

and pharmaceutically acceptable salts thereof are described herein wherein

A, $R^1$, $R^4$ and Ar have the meanings disclosed above for a compound of formula ($I^2$).

In any of the foregoing formulae and embodiments of a compound of formula ($I^2$), the following compounds are described where:

$Y^1$ is oxygen; or $Y^1$ is $C(R^a R^b)$, where $R^a$ is hydrogen, and $R^b$ is hydrogen or alkoxy, such as methoxy; or $Y^2$ is oxygen; or $Y^2$ is $C(R^a R^b)$, where $R^a$ is hydrogen, and $R^b$ is hydrogen or alkoxy, such as methoxy; and/or m is 1; and/or
$R^c$ is hydrogen; and/or
$R^d$ is hydrogen; and/or
Q is oxygen; and/or
W is oxygen; and/or
$R^1$ is hydrogen; and/or
$R^3$ is hydrogen; and/or
$R^4$ is a group $CH_2$—K—$R^{4.4}$, where K is a bond or $NHCH_2$, and $R^{4.4}$ is alkyl, cycloalkyl, cycloheteroalkyl, aryl, or heteroaryl, each of which is optionally substituted; or $R^{4.4}$ is isopropyl, furanyl, tetrahydrofuranyl, pyrrolyl, oxazolyl, thiazolyl, isoxazolyl, isothiazolyl, pyrrolidinonyl, oxazolidinonyl, thiazolidinonyl, isoxazolidinonyl, or isothiazolidinonyl, each of which is optionally substituted; or $R^4$ is branched alkyl; or $R^4$ is isobutyl; or $R^4$ is lactamylalkyl; or $R^4$ is pyrrolidin-4-on-2-ylalkyl; or $R^4$ is pyrrolidin-4-on-2-ylmethyl; and/or Z is $SO_2$; or Z is CO; or Z is NH; and/or
$R^5$ is aryl or heteroaryl, each of which is optionally substituted; or $R^5$ is substituted phenyl; or $R^5$ is substituted phenyl, where the substituent is hydroxy or a derivative thereof, amino or a derivative thereof, thio or a derivative thereof, or any of the foregoing where the substituent is covalently attached to the aryl through a group $C(R^x R^y)$; where each of $R^x$ and $R^y$ is independently selected in each instance from the group consisting of hydrogen and alkyl; or $R^x$ and $R^y$ are each hydrogen; and/or $R^5$ is phenyl substituted with $NH_2$, OH, OMe, $CH_2OH$, and/or $OCH_2O$; or $R^5$ is optionally substituted benzofuran; or $R^5$ is optionally substituted dihydrobenzofuran; or $R^5$ is optionally substituted benzothiopene; or $R^5$ is optionally substituted benzoxazole; or $R^5$ is optionally substituted benzothiazole; or $R^5$ is optionally substituted benzisoxazole; or $R^5$ is optionally substituted benzoisothiazole; and/or $R^a$ and $R^b$ are each hydrogen; and/or
m is 1; and/or
$R^2$ is optionally substituted phenyl.

It is appreciated that when the integer m is 1, the ring fusion is syn, whereas when the integer m is 0.2, or 3, the ring fusion may be syn or anti. It is further appreciated that in each of these relative stereochemical configurations, there are potentially two absolute stereochemical configurations. Unless otherwise indicated by specific reference to a relative or absolute stereochemical configuration, the structures described herein refer both individually to each enantiomer, as well as collectively to all possible mixtures of such enantiomers. It is appreciated that the foregoing cyclic ethers may be optionally substituted with one or more groups $R^a$ and/or $R^b$, each of which is independently selected, and is as described in the various embodiments and aspects disclosed herein.

In another embodiment of the compounds of formula ($I^2$) described herein, the group A is a cyclic ether or another structurally related group, such as is illustratively represented by the following structures

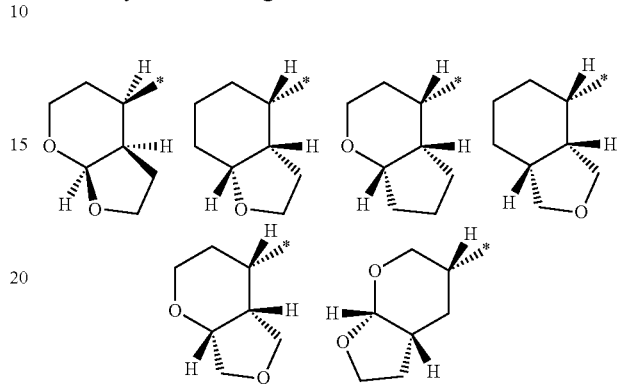

and stereoisomers thereof and mixtures thereof, where (*) indicates the point of attachment of A. It is therefore appreciated that such groups are attached to the group Q, which is oxygen, sulfur, nitrogen, or $C(R^a R^h)$; where each of $R^a$ and $R^h$ is independently selected in each instance, as defined in the various embodiments and aspects disclosed herein.

In another embodiment of the compounds of formula ($I^2$) described herein, $R^3$ is alkyl, cycloalkyl, heterocyclyl, heterocyclylalkyl, hydroxy, alkoxy, cycloalkoxy, heterocycly-loxy, heterocyclylalkoxy, amino, mono or dialkylamino, cycloalkylamino, heterocyclylamino, or heterocyclylalkylamino, each of which is optionally substituted. In one aspect, $R^3$ is amino substituted alkyl or heterocyclyl, or heterocyclylalkyl. In one variation of this aspect, the nitrogen atom of the amino group is mono or disubstituted with alkyl, cycloalkyl, or acyl, or is included in another heterocyclic group such as a pyrrolidinyl, piperidinyl, or piperazinyl group. In another variation of this aspect, the nitrogen atom of the hetetocylclyl group is substituted with alkyl, cycloalkyl, or acyl. In another aspect, $R^3$ is optionally substituted alkyl or cycloalkyl, including both linear and branched variations thereof, such as methyl, ethyl, butyl, isobutyl, and the like, and cyclobutyl, cyclopentyl, 3-methylcyclopentyl, and the like. In another aspect, $R^3$ is optionally substituted heterocyclyl or heterocyclylalkyl, where the heterocyclic portions includes, but is not limited to, tetrahydrofuranyl, azetidinyl, pyrrolidinyl, piperidinyl, morpholinyl, piperazinyl, and the like.

In another embodiment of the compounds of formula ($I^2$) described herein, the group A is a cyclic ether, such as the following structures

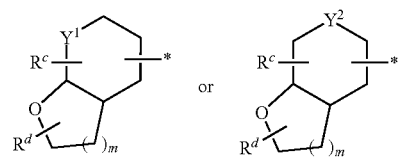

where (*) indicates the point of attachment; m is an integer selected from 0, 1, 2, or 3; $Y^1$ is $C(R^a R^b)$ or oxygen; $Y^2$ is $C(R^aR^b)$, $CHNR^a$, oxygen, or $SO_2$, where $R^a$ and $R^b$ are independently selected in each instance as described herein for the various embodiments and aspects; and $R^c$ and $R^d$ each represent one or more optional substituents, each of which is independently selected in each instance from hydrogen, alkyl, alkenyl, alkynyl, cycloalkyl, cycloalkylalkyl, aryl, arylalkyl, heterocyclyl, heterocyclylalkyl, heteroaryl, heteroarylalkyl, alkoxy, alkenyloxy, alkynyloxy, cycloalkoxy, cycloalkylalkoxy, aryl, arylalkoxy, heterocyclyloxy, heterocyclylalkoxy, heteroaryloxy, and heteroarylalkoxy, each of which is itself optionally substituted. In one aspect, $R^a$ and $R^b$ are both hydrogen. In another aspect, $R^c$ and $R^d$ are both hydrogen. In another aspect, $R^a$, $R^b$, $R^c$, and $R^d$ are each hydrogen. In another aspect, one or more of $R^c$ and $R^d$ is alkoxy.

In another embodiment of the compounds of formula ($I^2$), $R^2$ is alkyl, heteroalkyl, cycloalkyl, cycloheteroalkyl, aryl, heteroaryl, arylalkyl, or heteroarylalkyl, each of which is substituted, where at least one substituent is a hydrogen bond forming group.

In another embodiment of the compounds of formula ($I^2$), $R^a$ and $R^b$ are both hydrogen. In another aspect, $R^c$ and $R^d$ are both hydrogen. In another aspect, $R^a$, $R^b$, $R^c$, and $R^d$ are each hydrogen. In another aspect, one or more of $R^c$ and $R^d$ is alkoxy.

In a further embodiment, there is provided a pharmaceutical composition comprising one or more compounds of any of the preceding descriptions and one or more carriers, diluents, or excipients, or a combination thereof.

In a further embodiment, there is provided a method for treating a patient in need of relieve from an HIV infection, the method comprising the step of administering to a patient in need of relief from the HIV infection a therapeutically effective amount of one or more compounds or compositions of any of the preceding descriptions.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

Illustrative derivatives include, but are not limited to, both those compounds that may be synthetically prepared from the compounds described herein, as well as those compounds that may be prepared in a similar way as those described herein, but differing in the selection of starting materials. For example, described herein are compounds that include various functional groups, such as hydroxy groups, amino groups and carboxylate groups from which derivatives may formed by e.g. acylation and esterification.

It is to be understood that such derivatives may include prodrugs of the compounds described herein, compounds described herein that include one or more protection or protecting groups, including compounds that are used in the preparation of other compounds described herein.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain is cyclic. It is to be understood that cycloalkylalkyl is a subset of cycloalkyl. It is also to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$.

It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylate and derivatives thereof" includes the group $CO_2H$ and salts thereof, and esters and amides thereof, and CN.

As used herein, the term "sulfonyl or a derivative thereof" includes $SO_3H$ and salts thereof, and esters and amides thereof.

As used herein, the term "phosphinyl or a derivative thereof" includes $P(R)O_2H$ and salts thereof, and esters and amides thereof, where R is alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted.

As used herein, the term "phosphonyl or a derivative thereof" includes $PO_3H_2$ and salts thereof, and esters and amides thereof.

"Phosphorous-containing group" includes phosphinyl or a derivative thereof and phosphonyl or a derivative thereof.

A "phosphate derivative" is an organic residue, illustratively an alkyl residue, bearing a $-PO_3H_2$ group and salts thereof, and esters and amides thereof.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical —$(CH_2)_xZ^x$, where x is an integer from 0-6 and $Z^x$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)-alkylcarbonylamino, aminoalkyl, $C_1$-$C_6$ alkylaminoalkyl, ($C_1$-$C_6$ alkyl)($C_1$-$C_6$ alkyl) aminoalkyl, alkylcarbonylaminoalkyl, N—($C_1$-$C_6$ alkyl) alkylcarbonylaminoalkyl, cyano, and nitro; or $Z^x$ is selected from —$CO_2R^4$ and —$CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$)alkoxy, each of which is optionally further substituted with one or more of 1 to 3 halogen atoms; optionally substituted aryl($C_2$-$C_{16}$)alkanoyl and optionally substituted heteroaryl($C_2$-$C_{16}$)alkanoyl, such as the aryl or heteroaryl radical being unsubstituted or substituted by 1 to 3 substituents selected from the group consisting of halogen, ($C_1$-$C_3$)alkyl and ($C_1$-$C_3$)alkoxy, each of which is optionally further substituted with 1 to 3 halogen atoms; and optionally substituted heteroarylalkanyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder, activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21st ed., 2005)). Thus, one embodiment is a pharmaceutical composition comprising one or more compounds of any of the descriptions herein together with a diluent, excipient or carrier.

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like.

Illustrative routes for parenteral administration include intravenous, intraarterial, intraperitoneal, epidural, intraurethral, intrasternal, intramuscular and subcutaneous, as well as any other art recognized route of parenteral administration. Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (generally regarded as safe) compounds.

Examples of emulsifying agents are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE. Examples of chelating agents are sodium EDTA, citric acid, and phosphoric acid. Examples of gel forming agents are CARBOPOL, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN)).

It is appreciated that compounds described herein can exist in unsolvated forms as well as solvated forms, including hydrated forms. It is to be understood that the solvated forms and the unsolvated forms are described herein, either individually or collectively with reference to the compounds and compositions. It is also to be understood that the compounds described herein may exist in multiple amorphous, non-amorphous, partially crystalline, crystalline, and/or other morphological forms. In general, all physical forms are equivalent for the uses contemplated herein and are intended to be included in the methods, uses, compositions, and medicaments described herein. It is also to be understood that the compounds described herein may be present in the form of a salt.

A compound of the invention disclosed herein may be prepared by a route analogous to one previously disclosed for the preparation of protease inhibitors with a similar backbone structure, such as for example WO 2008/133734. In general, the compound may be prepared by acylating the corresponding amine with an acylating agent of formula A-Q-C(W)-L in which L denotes a leaving group. When Q represents NH, the acylating agent may be an isocyanate or isothiocyanate of formula A-N=C=W. Alternatively, a compound of formula A-Q-H is acylated by a compound of formula L-C(W)—NH—R or W=C=N—R in which R represents the remainder of the compound of the invention disclosed herein.

Further preparation and additional illustrative examples are described in copending U.S. provisional application No. 61/379,414, filed Sep. 2, 2010, the disclosure of which is incorporated herein by reference in its entirety.

Embodiments of the invention include those described by the following enumerated clauses:

1. A compound of the formula (I)

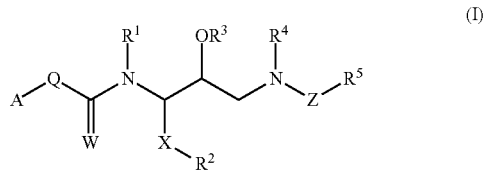

or a pharmaceutically acceptable salt thereof, wherein

A is cycloheteroalkyl or cycloheteroalkyl-alkyl, each of which is optionally substituted;

Q is oxygen, sulfur, nitrogen, or $C(R^a R^b)$ where each of $R^a$ and $R^b$ is independently selected in each instance from the group consisting of hydrogen, alkyl, and alkoxy;

W is oxygen or sulfur;

$R^1$ is hydrogen, a nitrogen protecting group, or a pro-drug substituent;

X is $C(R^a R^b)_n$, where n is 1, 2, or 3, and each of $R^a$ and $R^b$ is defined as above;

$R^2$ is alkyl, heteroalkyl, cycloalkyl, cycloheteroalkyl, aryl, heteroaryl, arylalkyl, or heteroarylalkyl, each of which is optionally substituted; or $R^2$ is alkyl, heteroalkyl, cycloalkyl, cycloheteroalkyl, aryl, heteroaryl, arylalkyl, or heteroarylalkyl, each of which is substituted, where at least one substituent is a hydrogen bond forming group;

$R^3$ is hydrogen, an oxygen protecting group, a phosphate derivative, or a pro-drug substituent;

$R^4$ is alkyl, haloalkyl, heteroalkyl, cycloalkyl, cycloheteroalkyl, aryl, heteroaryl, arylalkyl, or heteroarylalkyl, each of which is optionally substituted;

Z is $C(O)$, $S(O)_2$, NH, NHC(O), $NHS(O)_2$, C(O)—O, or C(O)—$NR^6$;

$R^5$ is alkyl, heteroalkyl, cycloalkyl, cycloheteroalkyl, aryl, heteroaryl, arylalkyl, or heteroarylalkyl, each of which is optionally substituted; and $R^6$ is hydrogen, alkyl, haloalkyl, heteroalkyl, cycloalkyl, cycloheteroalkyl, aryl, heteroaryl, arylalkyl, or heteroarylalkyl, each of which is optionally substituted; and wherein the compound of formula (I) is other than one in which, together: Q is oxygen, W is oxygen, $R^1$ is hydrogen, X is methylene, $R^2$ is unsubstituted phenyl, $R^3$ is hydrogen or a phosphate derivative, $R^4$ is isobutyl, Z is $S(O)_2$, and $R^5$ is 4-aminophenyl or 4-methoxyphenyl when:

A is a group of the formula

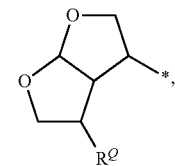

wherein (*) indicates the point of attachment; in which $R^Q$ is hydrogen, hydroxy, methoxy or benzyloxy; or A is a group of the formula

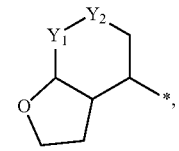

wherein (*) indicates the point of attachment; in which one of $Y^1$ and $Y^2$ is methylene, and the other of $Y^1$ and $Y^2$ is oxygen; or A is a group of the formula

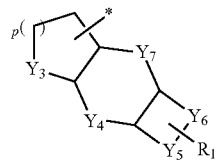

wherein (*) indicates the point of attachment;

p is 1 or 2;

$Y^3$ and $Y^4$ are in each instance independently methylene or oxygen;

$Y^5$ and $Y^6$ are in each instance independently selected from the group consisting of oxygen and alkylene, providing that at least one of $Y^3$ and $Y^4$ is oxygen, and wherein when one of $Y^3$ and $Y^4$ is optionally substituted methylene, at least one of $Y^5$ and $Y^6$ is oxygen, and A does not include a peroxide bond;

$Y^7$ is a bond; and $R^1$ of the group is hydrogen.

2. The compound or salt of clause 1, wherein A is defined as in any of the embodiments herein.

3. The compound or salt of clause 1, wherein A is selected from the group consisting of:

a group of the formula

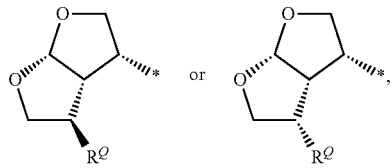

wherein (*) indicates the point of attachment; in which $R^Q$ is hydrogen, hydroxy, alkylamino, alkylcarbonylamino, alkylsulfonylamino, arylsulfonylamino, cycloalkylamino, arylalkylamino, alkoxy, cycloalkoxy, cycloalkylalkoxy, and arylalkoxy, each of which is itself optionally substituted;

a group of the formula

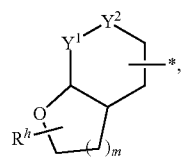

wherein (*) indicates the point of attachment; and wherein one of $Y^1$ and $Y^2$ is methylene, and the other of $Y^1$ and $Y^2$ is oxygen; and $R^h$ represents one or more optional substituents, each of which is independently selected in each instance from hydrogen, hydroxy, alkylamino, cycloalkylamino, arylalkylamino, alkoxy, cycloalkoxy, cycloalkylalkoxy, and arylalkoxy, each of which is itself optionally substituted;

a group of the formula

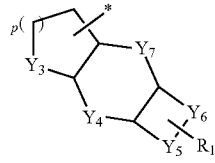

wherein (*) indicates the point of attachment;

p is 1 or 2;

$Y^3$ and $Y^4$ are in each instance independently methylene or oxygen;

$Y^5$ and $Y^6$ are in each instance independently selected from the group consisting of oxygen, nitrogen and alkylene, providing that at least one of $Y^3$ and $Y^4$ is oxygen, and wherein when one of $Y^3$ and $Y^4$ is optionally substituted methylene, at least one of $Y^5$ and $Y^6$ is oxygen, and A does not include a peroxide bond;

$Y^7$ is a bond; and $R^1$ of the group is hydrogen.

4. The compound or salt of clause 3, wherein $R^Q$ is hydrogen, hydroxy, methoxy, benzyloxy or (1-3C)alkylamino.

5. The compound or salt of clause 3, wherein A is

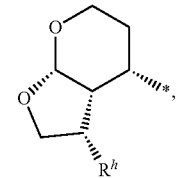

wherein (*) indicates the point of attachment; and $R^h$ represents hydrogen, hydroxy, methoxy, benzyloxy or (1-3C)alkylamino.

6. The compound or salt of clause 1, wherein A is selected from the group consisting of:

A is

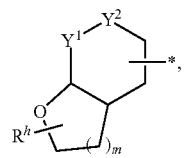

wherein (*) indicates the point of attachment; and wherein one of $Y^1$ and $Y^2$ is methylene, and the other of $Y^1$ and $Y^2$ is defined as follows:

$Y^1$ is $C(R^eR^f)$ or oxygen; $Y^2$ is $C(R^eR^f)$, $CHNR^e$, oxygen, or $SO_2$, where $R^e$ and $R^f$ are independently selected in each instance from hydrogen, alkyl, and alkoxy; m is an integer selected from 0, 1, 2, or 3; and $R^h$ represents one or more optional substituents, each of which is independently selected in each instance from hydrogen, hydroxy, alkylamino, cycloalkylamino, arylalkylamino, alkoxy, cycloalkoxy, cycloalkylalkoxy, and arylalkoxy, each of which is itself optionally substituted;

A is

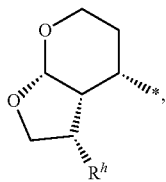

wherein (*) indicates the point of attachment; and $R^h$ represents hydrogen, hydroxy, methoxy, benzyloxy or (1-3C)alkylamino;

7. The compound or salt of clause 1, wherein the compound has the following formula:

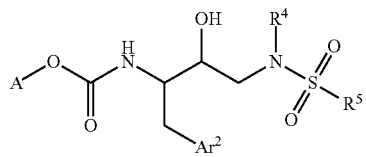

wherein
A is a group of the formula

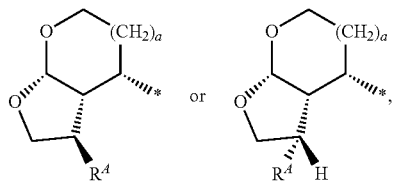

wherein a is 0 or 1; and $R^A$ is hydrogen, hydroxy, amino, $OR^B$, or $NHR^B$ in which $R^B$ is alkyl, alkylcarbonyl, alkylsulfonyl or heteroalkyl or is optionally substituted benzyl or is an optionally substituted 5- or 6-membered aryl or heteroaryl;

$Ar^2$ is phenyl substituted with one or more methoxy, isopropoxy, hydroxymethyl, methoxymethyl, methoxyethyl, fluoro or 2-(morpholino)ethoxy groups;

$R^4$ is isobutyl or 2-fluoro-2-methylpropyl; and $R^5$ is 4-aminophenyl, 4-methoxyphenyl, 4-isopropoxyphenyl, 4-hydroxymethylphenyl; 3-amino-4-methoxyphenyl, 3-amino-4-isopropoxyphenyl, 4-amino-3-fluorophenyl, 3-fluoro-4-methoxyphenyl, 3,4-methylenedioxyphenyl, or a group of the formula

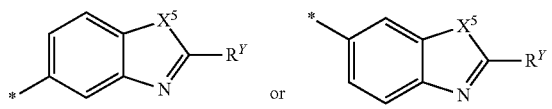

in which $X^5$ is O, S or NH; and $R^Y$ is (1-4C)alkylthio, (1-4C)alkylsulfinyl, (1-4C)alkylsulfonyl or $NHR^X$ or $NR^XR^Z$ and each of $R^X$ and $R^Z$ is independently methyl, isopropyl, cyclopropyl, isobutyl, tert-butyl, cyclohexyl, 4-piperidinyl or 1-cyclopentylpiperidin-4-yl, or the group $NR^XR^Z$ is optionally substituted pyrrolidino, piperidino or piperazino;

or $Ar^2$ is phenyl wherein A is as defined above, and wherein R4 is 2-fluoro-2-methylpropyl and/or R5 is

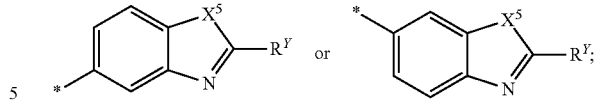

or $Ar^2$ is phenyl wherein a is 1 and $R^A$ is not hydrogen.

8. The compound or salt of clause 7 wherein $Ar^2$ is 3-methoxyphenyl, 4-methoxyphenyl, 3-isopropoxyphenyl, 4-isopropoxyphenyl, 3-hydroxymethylphenyl, 4-hydroxymethylphenyl, 3-methoxymethylphenyl, 4-methoxymethylphenyl, 3-methoxyethylphenyl, 4-methoxyethylphenyl, 3-fluorophenyl, 4-fluorophenyl, 3-[2-(morpholino)ethoxy]phenyl, or 4-[2-(morpholino)ethoxy]phenyl.

9. The compound or salt of clause 7 or 8 wherein $R^B$ is methyl, ethyl or isopropyl.

10. The compound or salt of any of clauses 7-9 wherein $X^5$ is O or S.

11. The compound or salt of any of clauses 7-10, wherein a is 1.

12. The compound or salt of any of clauses 1-11 or 7-11 wherein $R^5$ is

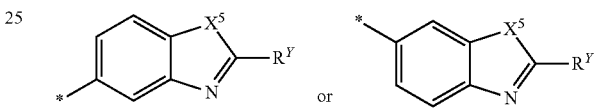

in which $X^5$ is O or S; and $R^Y$ is $NHR^X$ or $NR^XR^Z$ and each of $R^X$ and $R^Z$ is isopropyl or cyclopropyl or the group $NR^XR^Z$ is optionally substituted pyrrolidino, piperidino or piperazino.

14. The compound or salt of any of clauses 1-13 wherein $R^5$ is

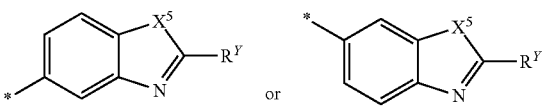

in which $X^5$ is O or S; and $R^Y$ is $NHR^X$; and $R^X$ is isopropyl or cyclopropyl.

101. A compound of the formula ($I^1$)

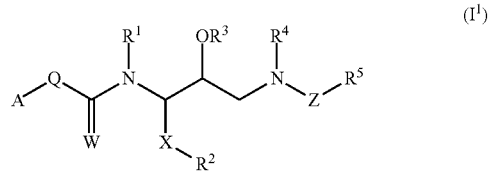

and pharmaceutically acceptable salts thereof, wherein

A is cycloheteroalkyl or cycloheteroalkyl-alkyl, each of which is optionally substituted;

Q is oxygen, sulfur, nitrogen, or $C(R^aR^b)$ where each of $R^a$ and $R^b$ is independently selected in each instance from the group consisting of hydrogen, alkyl, and alkoxy;

W is oxygen or sulfur, $R^1$ is hydrogen, a nitrogen protecting group, or a pro-drug substituent;

X is $C(R^aR^b)_n$, where n is 1, 2, or 3, and each of $R^a$ and $R^b$ is defined as above;

$R^2$ is alkyl, heteroalkyl, cycloalkyl, cycloheteroalkyl, aryl, heteroaryl, arylalkyl, or heteroarylalkyl, each of which is substituted, where at least one substituent is a hydrogen bond forming group;

$R^3$ is hydrogen, an oxygen protecting group, or a pro-drug substituent;

$R^4$ is alkyl, heteroalkyl, cycloalkyl, cycloheteroalkyl, aryl, heteroaryl, arylalkyl, or heteroarylalkyl, each of which is optionally substituted;

Z is C(O), S(O)$_2$, NH, NHC(O), or NHS(O)$_2$; and $R^5$ is alkyl, heteroalkyl, cycloalkyl, cycloheteroalkyl, aryl, heteroaryl, arylalkyl, or heteroarylalkyl, each of which is optionally substituted.

102. The compound or salt of clause 101 which is a compound of formula

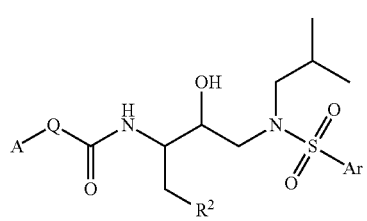

wherein Ar is aryl or heteroaryl, each of which is optionally substituted.

103. The compound or salt of clause 101 or 102 which is a compound having the relative and/or absolute stereochemistry of formula

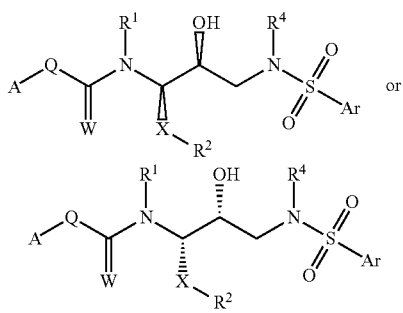

wherein A, Q, W, $R^1$, X, $R^2$, and $R^4$ have any of the values of Clause 1 or Clause 2; and Ar is an optionally substituted aryl or heteroaryl.

104. The compound or salt of any of the preceding clauses 101-103 wherein Ar is 4-methoxyphenyl, 4-(hydroxymethyl)phenyl, a 3-substituted phenyl, a 4-substituted phenyl, an optionally substituted benzisoxazole, an optionally substituted benzoxazole; an optionally substituted benzodioxane or an optionally substituted benzodioxolane.

105. The compound or salt of any of the preceding clauses 101-104 which is a compound having the formula

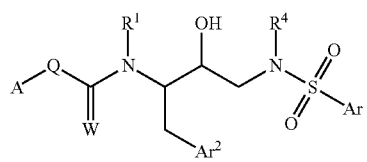

where Ar is aryl or heteroaryl, each of which is optionally substituted; and Ar$^2$ is substituted aryl or substituted heteroaryl having one or more of the following illustrative substituents: halo, amino, hydroxy, alkyl, alkenyl, alkoxy, arylalkyl, arylalkyloxy, hydroxyalkyl, hydroxyalkenyl, alkylene dioxy, aminoalkyl, where the amino group may also be substituted with one or two alkyl groups, arylalkylgroups, and/or acylgroups, nitro, acyl and oxime or hydrazone derivatives thereof, cyano, alkylsulfonyl, and alkylsulfonylamino, where at least one substituent is a hydrogen bond forming group.

106. A compound of any of the preceding clauses 101-105 of the following formula:

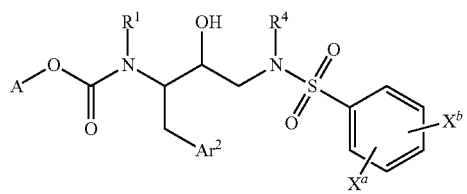

or a pharmaceutically acceptable salt thereof, where $X^a$ and $X^b$ are each independently selected from halo, amino, hydroxy, alkyl, alkenyl, alkoxy, arylalkyl, arylalkyloxy, hydroxyalkyl, hydroxyalkenyl, aminoalkyl, where the amino group may also be substituted with one or two alkyl groups, arylalkylgroups, and/or acylgroups, nitro, acyl and derivatives thereof such as oximes, hydrazones, and the like, cyano, alkylsulfonyl, alkylsulfonylamino; or $X^a$ and $X^b$ together form alkylenedioxy.

107. A compound of any of the preceding clauses 101-106 of the following formula:

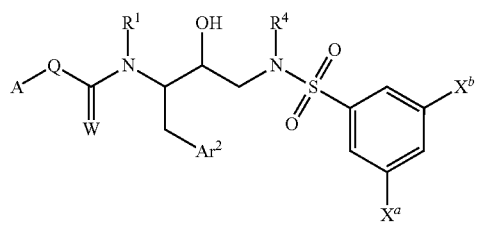

and pharmaceutically acceptable salts thereof, wherein $X^a$ and $X^b$ are independently selected from OH or OR$^{5A}$, where $R^{5A}$ is alkyl, alkylaryl, an oxygen protecting group or a pro-drug substituent; and A, Q, W, $R^1$, Ar$^2$ and $R^4$ have the meanings described in any of the preceding clauses.

108. The compound or salt of any of the preceding clauses 101-107 wherein $R^4$ is alkyl, cycloalkyl, heterocyclyl, heterocyclylalkyl, hydroxy, alkoxy, cycloalkoxy, heterocyclyloxy, heterocyclylalkoxy, amino, mono or dialkylamino, cycloalkylamino, heterocyclylamino, or heterocyclylalkylamino, each of which is optionally substituted.

109. The compound or salt of any of the preceding clauses 101-108 wherein $R^4$ is amino substituted alkyl or heterocycyl, or heterocyclylalkyl.

110. The compound or salt of the preceding clause wherein the nitrogen atom of the amino group is mono or disubstituted with alkyl, cycloalkyl, or acyl, or is included in another heterocyclic group such as a pyrrolidinyl, piperidinyl, or piperazinyl group or the nitrogen atom of the hetetocylclyl group is substituted with alkyl, cycloalkyl, or acyl.

111. The compound or salt of any of the preceding clauses 101-107 wherein $R^4$ is optionally substituted alkyl or cycloalkyl, including both linear and branched variations thereof.

112. The compound or salt of the preceding clause wherein, $R^4$ is methyl, ethyl, butyl, isobutyl, cyclobutyl, cyclopentyl, or 3-methylcyclopentyl.

113. The compound or salt of any of the preceding clauses 101-107 wherein $R^4$ is optionally substituted heterocyclyl or heterocyclylalkyl, where the heterocyclic portions includes, but is not limited to, tetrahydrofuranyl, azetidinyl, pyrrolidinyl, piperidinyl, morpholinyl, or piperazinyl.

114. A compound of any of the preceding clauses 101-113 of the following formula

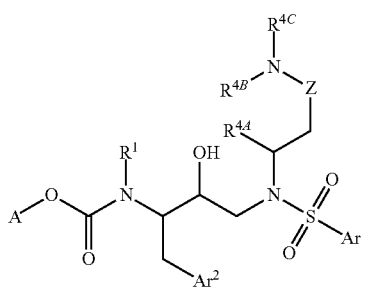

and pharmaceutically acceptable salts thereof, wherein

Z is $C(R^cR^d)$ where each of $R^c$ and $R^d$ is independently selected in each instance from the group consisting of hydrogen, alkyl, and arylalkyl;

$R^{4A}$, $R^{4B}$ and $R^{4C}$ are independently selected in each instance from the group consisting of hydrogen, alkyl, and arylalkyl, each of which may be optionally substituted, or $R^{4A}$, $R^{4B}$ and the atoms to which they are attached form a ring, and $R^{4C}$ is selected from the group consisting of hydrogen, alkyl, and arylalkyl, each of which may be optionally substituted.

115. A compound of any of the preceding clauses 101-113 of the following formula:

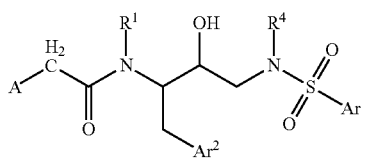

and pharmaceutically acceptable salts thereof.

116. The compound, or pharmaceutically acceptable salt thereof, of any of the preceding clauses 101-115 wherein A is a mono or polycyclic ether.

117. A compound of any of the preceding clauses 101-116 of the following formula:

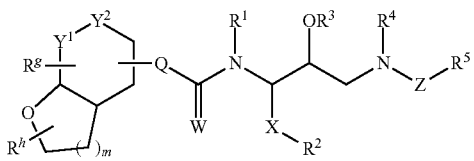

and pharmaceutically acceptable salts thereof, wherein
one of $Y^1$ and $Y^2$ is methylene, and the other of $Y^1$ and $Y^2$ is defined as follows:

$Y^1$ is $C(R^eR^f)$ or oxygen; $Y^2$ is $C(R^eR^f)$, $CHNR^e$, oxygen, or $SO_2$, where $R^e$ and $R^f$ are independently selected in each instance from hydrogen, alkyl, and alkoxy; m is an integer selected from 0, 1, 2, or 3; and $R^g$ and $R^h$ each represent one or more optional substituents, each of which is independently selected in each instance from hydrogen, alkyl, alkenyl, alkynyl, cycloalkyl, cycloalkylalkyl, aryl, arylalkyl, heterocyclyl, heterocyclylalkyl, heteroaryl, heteroarylalkyl, alkoxy, alkenyloxy, alkynyloxy, cycloalkoxy, cycloalkylalkoxy, aryl, arylalkoxy, heterocyclyloxy, heterocyclylalkoxy, heteroaryloxy, and heteroarylalkoxy, each of which is itself optionally substituted.

118. The compound, or pharmaceutically acceptable salt thereof, of the preceding clause 117 wherein $Y^1$ is oxygen; or $Y^1$ is $C(R^eR^f)$, where $R^e$ is hydrogen, and $R^f$ is hydrogen or alkoxy; or $Y^2$ is oxygen; or $Y^2$ is $C(R^eR^f)$, where $R^e$ is hydrogen, and $R^f$ is hydrogen or alkoxy.

119. The compound, or pharmaceutically acceptable salt thereof, of the preceding clause 118 wherein alkoxy is methoxy.

120. The compound, or pharmaceutically acceptable salt thereof, of any of the preceding clauses 101-116 wherein A is a radical having one of the following structures

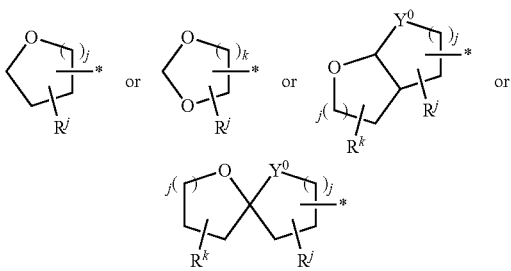

where (*) indicates the point of attachment of the group A; j is an integer that is independently selected in each instance from 0, 1, 2, or 3; k is an integer from 1 to 5; $Y^0$ is $C(R^aR^b)$ or oxygen; each of $R^a$ and $R^b$ is independently selected in each instance from the group consisting of hydrogen, alkyl, and alkoxy; and $R^j$ and $R^k$ each represent one or more optional substituents, each of which is independently selected in each instance from hydrogen, alkyl, alkenyl, alkynyl, cycloalkyl, cycloalkylalkyl, aryl, arylalkyl, heterocyclyl, heterocyclylalkyl, heteroaryl, heteroarylalkyl, alkoxy, alkenyloxy, alkynyloxy, cycloalkoxy, cycloalkylalkoxy, aryl, arylalkoxy, heterocyclyloxy, heterocyclylalkoxy, heteroaryloxy, and heteroarylalkoxy, each of which is itself optionally substituted 121. The compound, or pharmaceutically acceptable salt thereof, of the preceding clause wherein $R^a$ and $R^b$ are both hydrogen; and/or $R^j$ and $R^k$ are both hydrogen; and/or $R^a$, $R^b$, $R^j$ and $R^k$ are each hydrogen; one or more of $R^j$ and $R^k$ is alkoxy.

122. The compound, or pharmaceutically acceptable salt thereof, of any of the preceding clauses 101-116 wherein A is of the formula

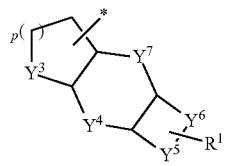

wherein (*) indicates the point of attachment;
p is 1, 2, or 3;
$Y^3$ and $Y^4$ are in each instance independently selected from the group consisting of optionally substituted methylene, oxygen, and amino;

$Y^5$ and $Y^6$ are in each instance independently selected from the group consisting of amino, oxygen, alkylene, and heteroalkylene, providing that at least one of $Y^3$ and $Y^4$ is oxygen, and wherein when one of $Y^3$ and $Y^4$ is optionally substituted methylene, at least one of $Y^5$ and $Y^6$ is oxygen, and A does not include a peroxide bond, a sulfenate bond, or a sulfenamide bond;

$Y^7$ is a bond or optionally substituted methylene; and $R^1$ is hydrogen, hydroxyl, carboxylate or derivative thereof, amino or derivative thereof, acyl, sulfonyl or derivative thereof, alkyl, or heteroalkyl.

123. The compound, or pharmaceutically acceptable salt thereof, of the preceding clause wherein A is of the formula

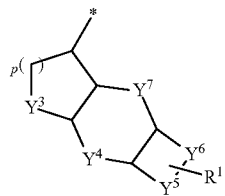

wherein (*) indicates the point of attachment.

124. The compound, or pharmaceutically acceptable salt thereof, of any of the preceding clauses 22 and 23 wherein $Y^4$ is oxygen.

125. The compound, or pharmaceutically acceptable salt thereof, of any of the preceding clauses 122 and 123 wherein $Y^7$ is a bond.

126. The compound, or pharmaceutically acceptable salt thereof, of any of the preceding clauses 122-125 wherein, p is 1 or 2.

127. The compound, or pharmaceutically acceptable salt thereof, of the preceding clause wherein p is 1.

128. The compound, or pharmaceutically acceptable salt thereof, of any of the preceding clauses wherein $R^1$ is hydrogen.

129. The compound, or pharmaceutically acceptable salt thereof, of any of the preceding clauses 122-128 wherein $Y^5$ or $Y^6$ is oxygen.

130. The compound, or pharmaceutically acceptable salt thereof, of any of the preceding clauses 122-129 wherein $Y^4$ and one of $Y^5$ and $Y^6$ are oxygen.

131. The compound, or pharmaceutically acceptable salt thereof, of any of the preceding clauses 122-130 wherein $Y^4$ and $Y^5$ are oxygen.

132. The compound, or pharmaceutically acceptable salt thereof, of any of the preceding clauses 122-131 wherein each of $Y^3$, $Y^4$ and $Y^5$ is oxygen.

133. The compound, or pharmaceutically acceptable salt thereof, of any of the preceding clauses 122-130 wherein $Y^3$ is optionally substituted methylene.

134. The compound, or pharmaceutically acceptable salt thereof, of any of the preceding clauses 101-116 wherein A is a radical having one of the following structures

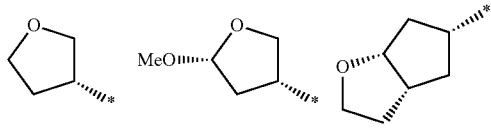

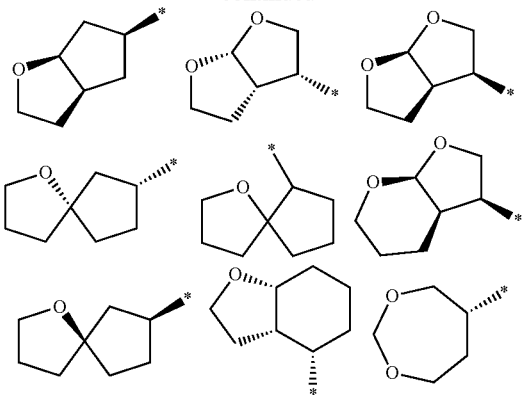

and stereoisomers thereof and mixtures thereof, where (*) indicates the point of attachment.

135. The compound, or pharmaceutically acceptable salt thereof, of any of the preceding clauses 101-120 wherein A is a radical having one of the following structures

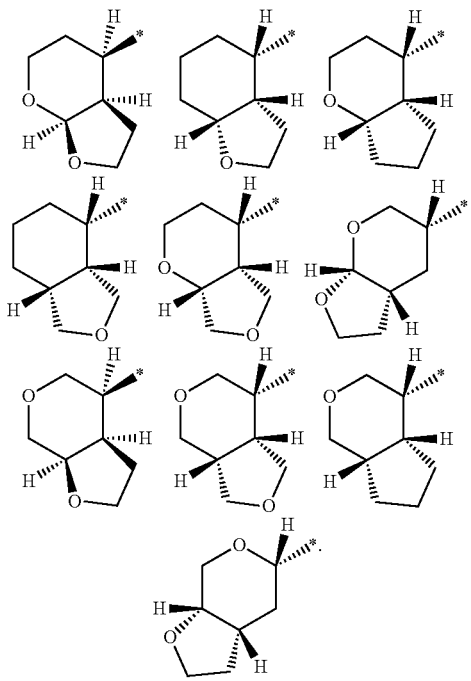

and stereoisomers thereof and mixtures thereof, where (*) indicates the point of attachment.

136. The compound, or pharmaceutically acceptable salt thereof, of any of the preceding clauses 101-120 wherein A is a radical having one of the following structures

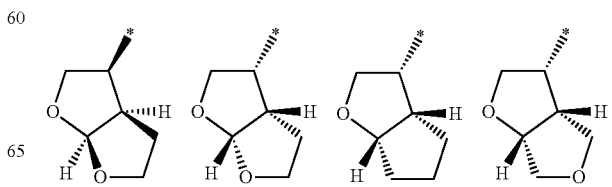

-continued

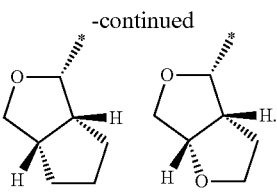

and stereoisomers thereof and mixtures thereof, where (*) indicates the point of attachment.

137. The compound, or pharmaceutically acceptable salt thereof, of any of the preceding clauses 122-133 wherein A is of the formula

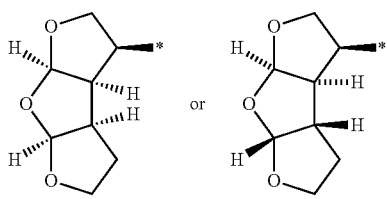 [SMILES: *[C@@H]1CO[C@@H]2O[C@@H]3OCC[C@@H]3[C@@H]21 ; *[C@@H]1CO[C@@H]2O[C@H]3OCC[C@H]3[C@@H]21]

wherein (*) indicates the point of attachment.

138. The compound, or pharmaceutically acceptable salt thereof, of any of the preceding clauses 101-115 wherein the group A is cycloheteroalkyl-alkyl of the formula Het-$(CH_2)_q$—; where q is an integer selected from 1, 2, or 3; and Het is optionally substituted cycloheteroalkyl.

139. The compound, or pharmaceutically acceptable salt thereof, of the preceding clause wherein Het is oxazolidine, thiazolidine, pyrolidine, piperidine, or piperazine, each of which is optionally substituted, including oxo substituents that form the corresponding oxazolidinones, thiazolidinones, pyrollidinones, piperidinones, and piperazinones.

140. The compound of the formula ($I^1$), or pharmaceutically acceptable salt thereof, of any of the preceding clauses wherein:
Q is oxygen; and/or
W is oxygen; and/or
$R^1$ is hydrogen; and/or
$R^3$ is hydrogen; and/or
$R^4$ is a group $CH_2$—K—$R^{4D}$, where K is a bond or $NHCH_2$, and $R^{4D}$ is alkyl, cycloalkyl, cycloheteroalkyl, aryl, or heteroaryl, each of which is optionally substituted; or $R^{4D}$ is isopropyl, furanyl, tetrahydrofuranyl, pyrrolyl, oxazolyl, thiazolyl, isoxazolyl, isothiazolyl, pyrrolidinonyl, oxazolidinonyl, thiazolidinonyl, isoxazolidionyl, or isothiazolidinonyl, each of which is optionally substituted; or $R^4$ is branched alkyl; or $R^4$ is isobutyl; or $R^4$ is lactamylalkyl; or $R^4$ is pyrrolidin-4-on-2-ylalkyl; or $R^4$ is pyrrolidin-4-on-2-ylmethyl; and/or
Z is $SO_2$; or Z is CO; or Z is NH; and/or
$R^5$ is aryl or heteroaryl, each of which is optionally substituted; or $R^5$ is substituted phenyl; or $R^5$ is substituted phenyl, where the substituent is hydroxy or a derivative thereof, amino or a derivative thereof, thio or a derivative thereof, or any of the foregoing where the substituent is covalently attached to the aryl through a group $C(R^xR^y)$; where each of $R^x$ and $R^y$ is independently selected in each instance from the group consisting of hydrogen and alkyl; or $R^x$ and $R^y$ are each hydrogen; and/or
$R^5$ is phenyl substituted with $NH_2$, OH, OMe, $CH_2OH$, and/or $OCH_2O$; or $R^5$ is optionally substituted benzofuran; or $R^5$ is optionally substituted dihydrobenzofuran; or $R^5$ is optionally substituted benzothiopene; or $R^5$ is optionally substituted benzoxazole; or $R^5$ is optionally substituted benzothiazole; or $R^5$ is optionally substituted benzisoxazole; or $R^5$ is optionally substituted benzoisothiazole; and/or
$R^a$ and $R^b$ are each hydrogen; and/or
n is 1.

141. The compound of the formula ($I^1$), or pharmaceutically acceptable salt thereof, of any of the preceding clauses wherein $R^2$ or $Ar^2$ is substituted phenyl.

142. The compound of the formula ($I^1$), or pharmaceutically acceptable salt thereof, of any of the preceding clauses wherein $R^2$ or $Ar^2$ is phenyl substituted with hydroxy or a derivative thereof, amino or a derivative thereof, thio or a derivative thereof, or any of the foregoing where the substituent is covalently attached to the phenyl through a group $C(R^xR^y)$; where each of $R^x$ and $R^y$ is independently selected in each instance from the group consisting of hydrogen and alkyl; or both $R^x$ and $R^y$ are hydrogen.

143. The compound of the formula ($I^1$), or pharmaceutically acceptable salt thereof, of any of the preceding clauses wherein $R^2$ or $Ar^2$ is phenyl substituted with a hydroxy derivative, a thio derivative, or an amino derivative, wherein each of the foregoing, derivatives include those that include a phosphorus-containing group; or $R^2$ or $Ar^2$ is phenyl substituted with OH, alkoxy, SH, alkylthio, $NH_2$, alkylamino, or dialkylamino; or $R^2$ or $Ar^2$ is phenyl substituted with hydroxymethyl, alkoxymethyl, thiomethyl, alkylthiomethyl, $H_2N$-methyl, alkylaminomethyl, or dialkylaminomethyl; or $R^2$ or $Ar^2$ is phenyl substituted with heterocyclylalkyloxy.

144. The compound, or pharmaceutically acceptable salt thereof, of the preceding clause wherein heterocyclylalkyloxy is morpholin-1-ylalkyloxy, pyrrolidin-1-ylalkyloxy, or piperidin-1-ylalkyloxy.

145. The compound of the formula ($I^1$), or pharmaceutically acceptable salt thereof, of any of the preceding clauses wherein $R^2$ or $Ar^2$ is capable of forming a hydrogen bond with a group in the S2 site of an HIV protease.

146. The compound, or pharmaceutically acceptable salt thereof, of the preceding clause wherein the group in the S2 site is a glycine.

147. The compound, or pharmaceutically acceptable salt thereof, of the preceding clause wherein the group in the S2 site is Gly-48.

148. The compound of the formula ($I^1$) of any of the preceding clauses of the following formula:

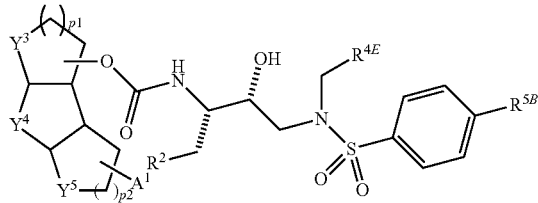

or a pharmaceutically acceptable salt thereof, wherein
each of $Y^3$, $Y^4$ and $Y^5$ is oxygen; or
$Y^3$ is methylene and each of $Y^4$ and $Y^5$ is oxygen; or
$Y^4$ is methylene and each of $Y^3$ and $Y^5$ is oxygen; or
$Y^5$ is methylene and each of $Y^3$ and $Y^4$ is oxygen;
each of $p_1$ and $p_2$ is independently 1, 2 or 3;
$A^1$ is hydrogen, hydroxyl or derivative thereof, carboxylate or derivative thereof, amino or derivative thereof, or sulfonyl or derivative thereof;
$R^{4E}$ is selected from the group consisting of isopropyl, alkyl, or heteroalkyl, and the like; and
$R^{5B}$ is methoxy, aminomethyl; amino, or heteroalkyl.

149. A compound of the formula ($I^1$) of any of the preceding clauses of the following formula:

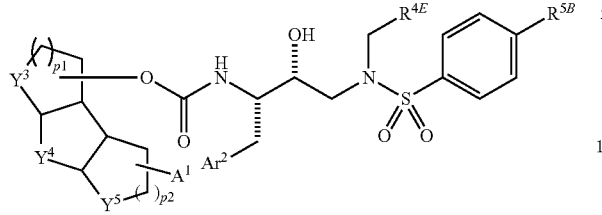

or a pharmaceutically acceptable salt thereof, wherein
each of $Y^3$, $Y^4$ and $Y^5$ is oxygen; or
$Y^3$ is methylene and each of $Y^4$ and $Y^5$ is oxygen; or
$Y^4$ is methylene and each of $Y^3$ and $Y^5$ is oxygen; or
$Y^5$ is methylene and each of $Y^3$ and $Y^4$ is oxygen;
each of $p_1$ and $p_2$ is independently 1, 2 or 3;
$R^t$ is hydrogen, hydroxyl or derivative thereof, carboxylate or derivative thereof, amino or derivative thereof, or sulfonyl or derivative thereof;
$R^{4E}$ is selected from the group consisting of isopropyl, alkyl, or heteroalkyl, and the like; and
$R^{5B}$ is methoxy, aminomethyl; amino, or heteroalkyl.

150. The compound of the formula ($I^1$) of any of the preceding clauses having the formula

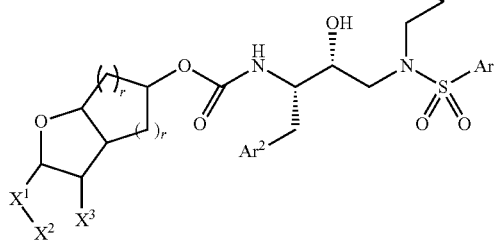

or a pharmaceutically acceptable salt thereof, wherein
each of $X^1$, $X^2$ and $X^3$ is methylene; or
$X^1$ is oxygen or $NR^m$ and each of $X^2$ and $X^3$ is methylene; or
each of $X^1$ and $X^2$ is methylene and $X^3$ is oxygen or $NR^m$; or
each of $X^1$ and $X^3$ is methylene and $X^2$ is oxygen or $NR^m$;
$R^m$ is selected from the group consisting of hydrogen, methyl, methylsulfonyl, acetyl or methoxycarbonyl, and the like.

151. The compound of the preceding clause having the formula

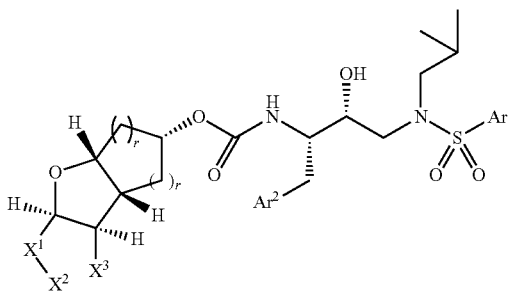

or a pharmaceutically acceptable salt thereof.

152. The compound of clause 101 selected from the group consisting of

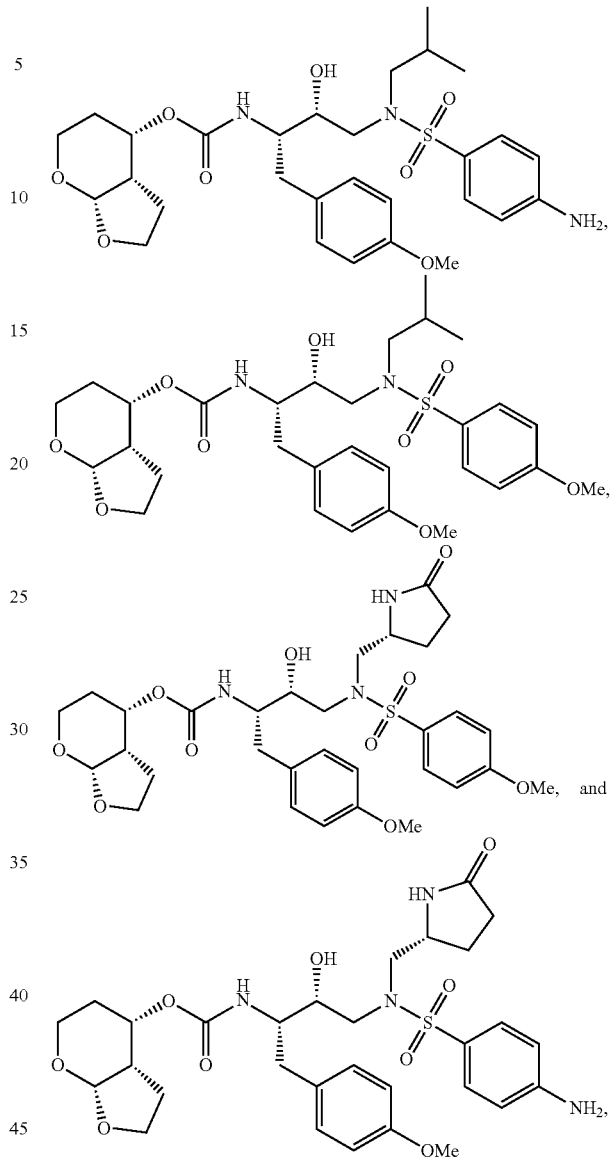

or a pharmaceutically acceptable salt thereof.

153. A pharmaceutical composition comprising one or more compounds of the formula ($I^1$) of any of the preceding clauses and one or more carriers, diluents, or excipients, or a combination thereof.

154. A method for treating a patient in need of relieve from an HIV infection, the method comprising the step of administering to a patient in need of relief from the HIV infection a therapeutically effective amount of one or more compounds of the formula ($I^1$) or compositions of any of the preceding clauses.

201. A compound of the following formula ($I^2$)

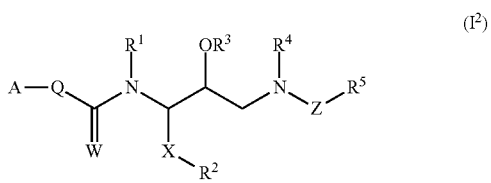

(I²)

and pharmaceutically acceptable salts thereof, wherein

A is the following group, wherein (*) denotes point of attachment:

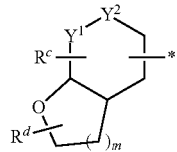

one of $Y^1$ and $Y^2$ is methylene, and the other of $Y^1$ and $Y^2$ is defined as follows:

$Y^1$ is $C(R^a R^b)$ or oxygen; $Y^2$ is $C(R^a R^b)$, $CHNR^a$, oxygen, or $SO_2$, where $R^a$ and $R^b$ are independently selected in each instance from hydrogen, alkyl, and alkoxy; m is an integer selected from 0, 1, 2, or 3; and $R^c$ and $R^d$ each represent one or more optional substituents, each of which is independently selected in each instance from hydrogen, alkyl, alkenyl, alkynyl, cycloalkyl, cycloalkylalkyl, aryl, arylalkyl, heterocyclyl, heterocyclylalkyl, heteroaryl, heteroarylalkyl, alkoxy, alkenyloxy, alkynyloxy, cycloalkoxy, cycloalkylalkoxy, aryl, arylalkoxy, heterocyclyloxy, heterocyclylalkoxy, heteroaryloxy, and heteroarylalkoxy, each of which is itself optionally substituted;

Q is oxygen, sulfur, nitrogen, or $C(R^a R^b)$; where each of $R^a$ and $R^b$ is independently selected in each instance from the group consisting of hydrogen, alkyl, and alkoxy;

W is oxygen or sulfur;

$R^1$ is hydrogen, a nitrogen protecting group, or a pro-drug substituent;

X is $C(R^a R^b)_n$, where each of $R^a$ and $R^b$ is independently selected in each instance from the group consisting of hydrogen, alkyl, and alkoxy;

$R^2$ is alkyl, heteroalkyl, cycloalkyl, cycloheteroalkyl, aryl, heteroaryl, arylalkyl, or heteroarylalkyl, each of which is optionally substituted;

$R^3$ is hydrogen, an oxygen protecting group, or a pro-drug substituent;

$R^4$ is alkyl, heteroalkyl, cycloalkyl, cycloheteroalkyl, aryl, heteroaryl, arylalkyl, or heteroarylalkyl, each of which is optionally substituted;

Z is $C(O)$, $S(O)_2$, NH, NHC(O), or $NHS(O)_2$; and $R^5$ is alkyl, heteroalkyl, cycloalkyl, cycloheteroalkyl, aryl, heteroaryl, arylalkyl, or heteroarylalkyl, each of which is optionally substituted;

providing that the compound is not of the formula

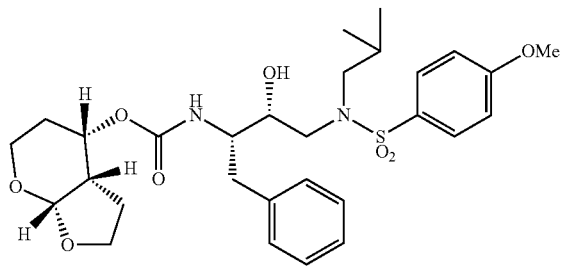 [SMILES: COc1ccc(S(=O)(=O)N(CC(C)C)C[C@@H](O)[C@H](Cc2ccccc2)NC(=O)O[C@H]2CCO[C@H]3OCC[C@H]32)cc1]

or a pharmaceutically acceptable salts thereof.

202. The compound of the preceding clause, wherein $R^a$ and $R^b$ are both hydrogen.

203. The compound of any of the preceding clauses 201-202, where the compound has the formula:

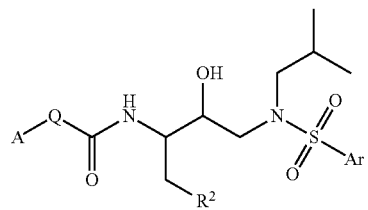

wherein Q and $R^2$ are as described in any of the preceding clauses; Ar is aryl or heteroaryl, each of which is optionally substituted; and wherein A is selected from the following group, wherein (*) denotes point of attachment:

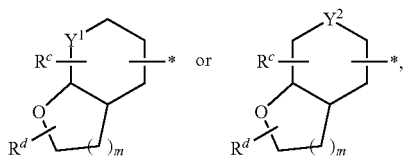

204. The compound of any of the preceding clauses 201-203, wherein A is selected from the following group, wherein (*) denotes point of attachment:

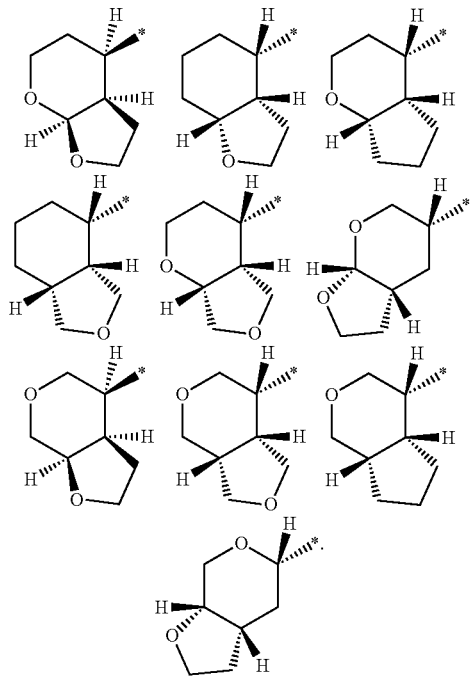

205. The compound of any of the preceding clauses 201-204, wherein the compound has the following relative and/or absolute stereochemistry:

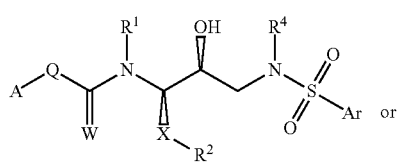

-continued

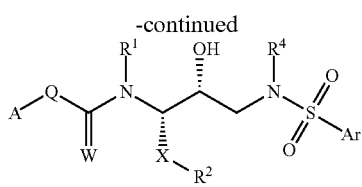

wherein A, Q, W, X, R¹, R², R⁴, and Ar are as described in any of the preceding clauses.

206. The compound of any of the preceding clauses 201-205, wherein the compound has the following formula:

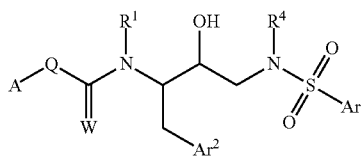

wherein A, Q, W, R¹, R⁴, and Ar are as described in any of the preceding clauses, and where $Ar^2$ is substituted aryl or substituted heteroaryl having one or more of the following illustrative substituents; halo, amino, hydroxy, alkyl, alkenyl, alkoxy, arylalkyl, arylalkyloxy, hydroxyalkyl, hydroxyalkenyl, alkylene dioxy, aminoalkyl, where the amino group may also be substituted with one or two alkyl groups, arylalkylgroups, and/or acylgroups, nitro, acyl and derivatives thereof including oximes, hydrazones, and the like, cyano, alkylsulfonyl, alkylsulfonylamino, and the like.

207. The compound of any of the preceding clauses 201-206, wherein the compound has the following formula:

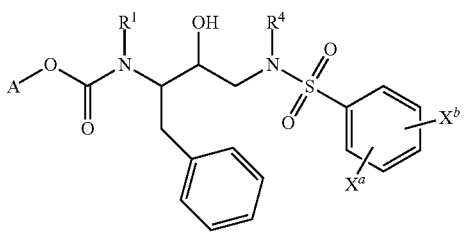

wherein A, R¹, and R⁴ are as described in any of the preceding clauses, and where $X^a$ and $X^b$ are each independently selected from halo, amino, hydroxy, alkyl, alkenyl, alkoxy, arylalkyl, arylalkyloxy, hydroxyalkyl, hydroxyalkenyl, alkylene dioxy, aminoalkyl, where the amino group may also be substituted with one or two alkyl groups, arylalkylgroups, and/or acylgroups, nitro, acyl and derivatives thereof including oximes, hydrazones, and the like, cyano, alkylsulfonyl, alkylsulfonylamino, and the like.

208. The compound of any of the preceding clauses 201-207, wherein the compound has the following formula:

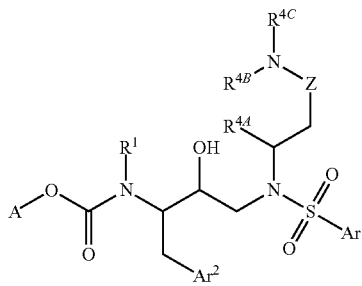

and pharmaceutically acceptable salts thereof, wherein

Z is $C(R^cR^d)$ where each of $R^c$ and $R^d$ is independently selected in each instance from the group consisting of hydrogen, alkyl, and arylalkyl; $R^{4A}$, $R^{4B}$ and $R^{4C}$ are independently selected in each instance from the group consisting of hydrogen, alkyl, and arylalkyl, each of which may be optionally substituted, or $R^{4A}$, $R^{4B}$ and the atoms to which they are attached form a ring, and $R^{4C}$ is selected from the group consisting of hydrogen, alkyl, and arylalkyl, each of which may be optionally substituted; and A, R¹, Ar and $Ar^2$ have the meanings disclosed in any of the preceding clauses.

209. The compound of any of the preceding clauses 201-208, wherein the compound has the following formula:

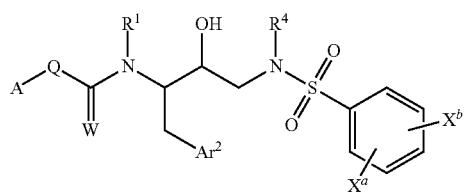

and pharmaceutically acceptable salts thereof wherein $X^a$ and $X^b$ are independently selected from H, OH or $OR^6$, where $R^6$ is alkyl, alkylaryl, an oxygen protecting group or a pro-drug substituent; and A, Q, W, R¹, $Ar^2$ and R⁴ have the meanings disclosed in any of the preceding clauses.

210. The compound of any of the preceding clauses 201-209, wherein the compound has the following formula:

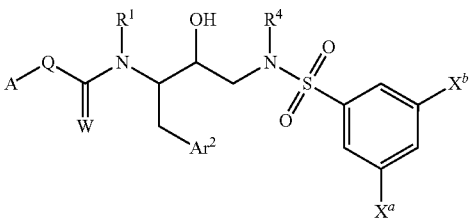

and pharmaceutically acceptable salts thereof wherein $X^a$ and $X^b$ are independently selected from H, OH or $OR^6$, where $R^6$ is alkyl, alkylaryl, an oxygen protecting group or a pro-drug substituent; and A, Q, W, R¹, $Ar^2$ and R⁴ have the meanings disclosed in any of the preceding clauses.

211. The compound of formula ($I^2$) of any of the preceding clauses, wherein the compound has the following formula:

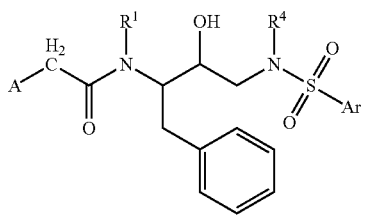

and pharmaceutically acceptable salts thereof wherein

A, R¹, R⁴ and Ar have the meanings disclosed in any of the preceding clauses.

212. The compound formula ($I^2$) of any of the preceding clauses, where:

$Y^1$ is oxygen; or $Y^1$ is $C(R^aR^b)$, where $R^a$ is hydrogen, and $R^b$ is hydrogen or alkoxy, such as methoxy; or $Y^2$ is oxygen;

or $Y^2$ is $C(R^aR^b)$, where $R^a$ is hydrogen, and $R^b$ is hydrogen or alkoxy, such as methoxy; and/or m is 1; and/or $R^c$ is hydrogen; and/or $R^d$ is hydrogen; and/or Q is oxygen; and/or W is oxygen; and/or $R^1$ is hydrogen; and/or $R^3$ is hydrogen; and/or $R^4$ is a group $CH_2$—K—$R^{4A}$, where K is a bond or $NHCH_2$, and $R^{4A}$ is alkyl, cycloalkyl, cycloheteroalkyl, aryl, or heteroaryl, each of which is optionally substituted; or $R^{4A}$ is isopropyl, furanyl, tetrahydrofuranyl, pyrrolyl, oxazolyl, thiazolyl, isoxazolyl, isothiazolyl, pyrrolidinonyl, oxazolidinonyl, thiazolidinonyl, isoxazolidionyl, or isothiazolidionyl, each of which is optionally substituted; or $R^4$ is branched alkyl; or $R^4$ is isobutyl; or $R^4$ is lactamylalkyl; or $R^4$ is pyrrolidin-4-on-2-ylalkyl; or $R^4$ is pyrrolidin-4-on-2-ylmethyl; and/or Z is $SO_2$; or Z is CO; or Z is NH; and/or $R^5$ is aryl or heteroaryl, each of which is optionally substituted; or $R^5$ is substituted phenyl; or $R^5$ is substituted phenyl, where the substituent is hydroxy or a derivative thereof, amino or a derivative thereof, thio or a derivative thereof, or any of the foregoing where the substituent is covalently attached to the aryl through a group $C(R^xR^y)$; where each of $R^x$ and $R^y$ is independently selected in each instance from the group consisting of hydrogen and alkyl; or $R^x$ and $R^y$ are each hydrogen; and/or $R^5$ is phenyl substituted with $NH_2$, OH, OMe, $CH_2OH$, and/or $OCH_2O$; or $R^5$ is optionally substituted benzofuran; or $R^5$ is optionally substituted dihydrobenzofuran; or $R^5$ is optionally substituted benzothiopene; or $R^5$ is optionally substituted benzoxazole; or $R^5$ is optionally substituted benzothiazole; or $R^5$ is optionally substituted benzisoxazole; or $R^5$ is optionally substituted benzoisothiazole; and/or $R^a$ and $R^b$ are each hydrogen; and/or m is 1; and/or $R^2$ is optionally substituted phenyl.

213. The compound formula ($I^2$) of any of the preceding clauses, wherein when the integer m is 1, the ring fusion is syn, or wherein when the integer m is 0, 2, or 3, the ring fusion may be syn or anti; and wherein each of the relative stereochemical configurations may include either or both of the two absolute stereochemical configurations.

214. The compound formula ($I^2$) of any of the preceding clauses, wherein the structures refer both individually to each enantiomer, as well as collectively to all possible mixtures of such enantiomers.

215. The compound of formula ($I^2$) of any of the preceding clauses, wherein the cyclic ethers may be optionally substituted with one or more groups $R^a$ and/or $R^b$, each of which is independently selected, and is as described in any of the preceding clauses.

216. The compound of formula ($I^2$) of any of the preceding clauses, wherein the group A is a cyclic ether or another structurally related group selected from the following structures:

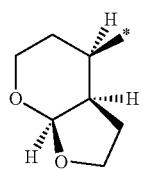 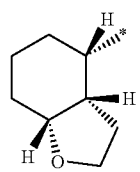 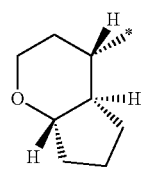

-continued

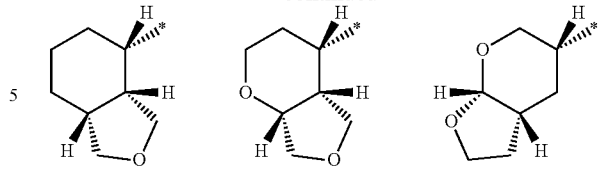

and stereoisomers thereof and mixtures thereof, where (*) indicates the point of attachment of A to the group Q, which is oxygen, sulfur, nitrogen, or $C(R^aR^b)$; where each of $R^a$ and $R^b$ is independently selected in each instance, as defined in any of the preceding clauses.

217. The compound of formula ($I^2$) of any of the preceding clauses, wherein $R^3$ is alkyl, cycloalkyl, heterocyclyl, heterocyclylalkyl, hydroxy, alkoxy, cycloalkoxy, heterocyclyloxy, heterocyclylalkoxy, amino, mono or dialkylamino, cycloalkylamino, heterocyclylamino, or heterocyclylalkylamino, each of which is optionally substituted.

218. The compound of formula ($I^2$) of any of the preceding clauses, wherein $R^3$ is amino substituted alkyl or heterocyclyl, or heterocyclylalkyl.

219. The compound of formula ($I^2$) of any of the preceding clauses, wherein $R^3$ is amino substituted alkyl or heterocyclyl, or heterocyclylalkyl in which the nitrogen atom of the amino group is mono or disubstituted with alkyl, cycloalkyl, or acyl, or is included in another heterocyclic group including a pyrrolidinyl, piperidinyl, or piperazinyl group.

220. The compound of formula ($I^2$) of any of the preceding clauses, wherein $R^3$ is amino substituted alkyl or heterocyclyl, or heterocyclylalkyl in which the nitrogen atom of the hetetocylclyl group is substituted with alkyl, cycloalkyl, or acyl.

221. The compound of formula ($I^2$) of any of the preceding clauses, wherein $R^3$ is optionally substituted alkyl or cycloalkyl, including both linear and branched variations thereof, including methyl, ethyl, butyl, isobutyl, and the like, and cyclobutyl, cyclopentyl, 3-methylcyclopentyl, and the like.

222. The compound of formula ($I^2$) of any of the preceding clauses, wherein $R^3$ is optionally substituted heterocyclyl or heterocyclylalkyl, where the heterocyclic portions includes, but is not limited to, tetrahydrofuranyl, azetidinyl, pyrrolidinyl, piperidinyl, morpholinyl, piperazinyl, and the like.

223. The compound of formula ($I^2$) of any of the preceding clauses, wherein the group A is a cyclic ether, selected from the following structures

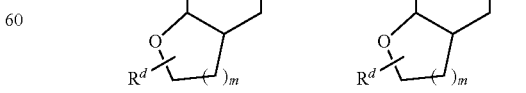

where (*) indicates the point of attachment; m is an integer selected from 0, 1, 2, or 3; $Y^1$ is $C(R^aR^b)$ or oxygen; $Y^2$ is $C(R^aR^b)$, $CHNR^a$, oxygen, or $SO_2$, where $R^a$ and $R^b$ are independently selected in each instance as described above; and $R^c$ and $R^d$ each represent one or more optional substituents, each of which is independently selected in each instance from hydrogen, alkyl, alkenyl, alkynyl, cycloalkyl, cycloalkylalkyl, aryl, arylalkyl, heterocyclyl, heterocyclylalkyl, heteroaryl, heteroarylalkyl, alkoxy, alkenyloxy, alkynyloxy, cycloalkoxy, cycloalkylalkoxy, aryl, arylalkoxy, heterocyclyloxy, heterocyclylalkoxy, heteroaryloxy, and heteroarylalkoxy, each of which is itself optionally substituted.

224. The compound of formula ($I^2$) of any of the preceding clauses, wherein $R^a$ and $R^b$ are both hydrogen.

225. The compound of formula ($I^2$) of any of the preceding clauses, wherein $R^cC$ and $R^d$ are both hydrogen.

226. The compound of formula ($I^2$) of any of the preceding clauses, wherein $R^a$, $R^b$, $R^c$, and $R^d$ are each hydrogen.

227. The compound of formula ($I^2$) of any of the preceding clauses, wherein one or more of $R^c$ and $R^d$ is alkoxy.

228. The compound of formula ($I^2$) of any of the preceding clauses, wherein $R^2$ is alkyl, heteroalkyl, cycloalkyl, cycloheteroalkyl, aryl, heteroaryl, arylalkyl, or heteroarylalkyl, each of which is substituted, where at least one substituent is a hydrogen bond forming group.

229. A pharmaceutical composition comprising one or more compounds of formula ($I^2$) of any of the preceding clauses together with a diluent, excipient or carrier.

230. A method for treating patients with HIV-1/AIDS comprising administering a therapeutically effective amount of the one or more compounds of formula ($I^2$) and/or compositions of any of the preceding clauses.

231. Use of one or more compounds of formula ($I^2$) and/or compositions of any of the preceding clauses for treating patients with HIV-1/AIDS.

232. Use of one or more compounds of formula ($I^2$) and/or compositions of any of the preceding clauses in the manufacture of a medicament for treating patients with HIV-1/AIDS.

233. The compound of any of the preceding clauses, or the compositions, methods, uses, and medicaments of any of the preceding clauses that include the compound, wherein the compound is optically pure, or includes any of a variety of stereoisomeric mixtures, including racemic and other mixtures of enantiomers, other mixtures of diastereomers, and the like; and/or including a single stereochemical configuration at one or more chiral centers, while including mixtures of stereochemical configuration at one or more other chiral centers.

301. The compound or salt of any of the preceeding clauses wherein $R^4$ is 2-fluoro-2-methylpropyl.

302. The compound or salt of any of the preceeding clauses wherein $R^5$ is

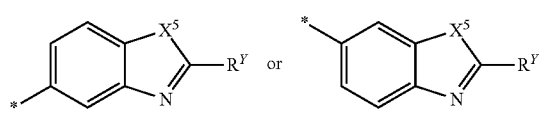

in which $X^5$ is O, S or NH; and $R^Y$ is (1-4C)alkylthio, (1-4C)alkylsulfinyl, (1-4C)alkylsulfonyl or $NHR^X$; and $R^X$ is methyl, isopropyl, cyclopropyl, isobutyl, tert-butyl, cyclohexyl, 4-piperidinyl or 1-cyclopentylpiperidin-4-yl.

303. The compound or salt of the preceeding clause wherein $R^5$ is O or S; and $R^Y$ is $NHR^X$; and $R^X$ is isopropyl or cyclopropyl.

304. The compound of clause 1 selected from the group consisting of

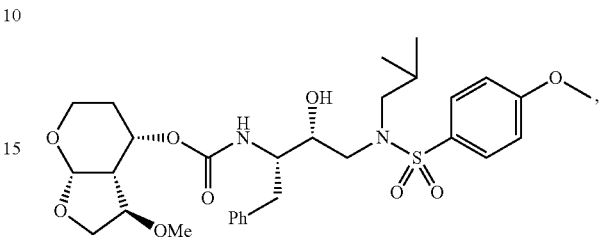

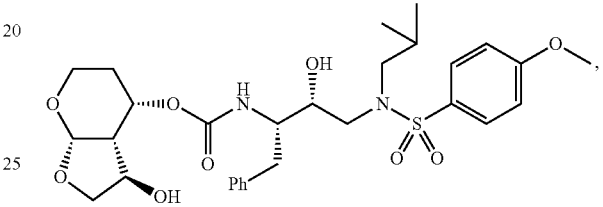

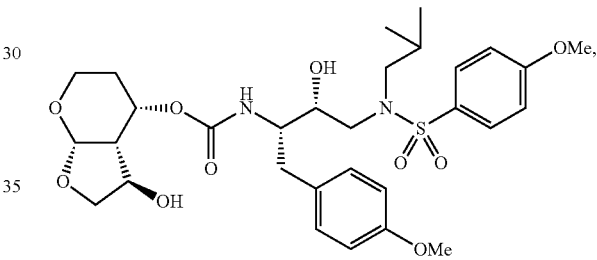

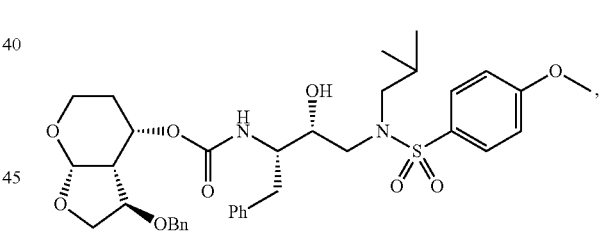

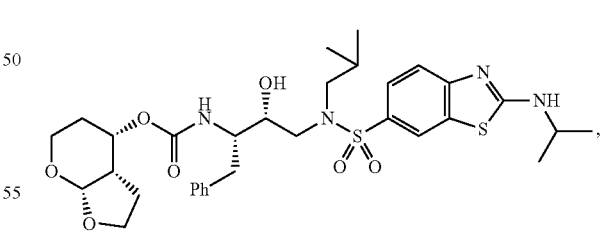

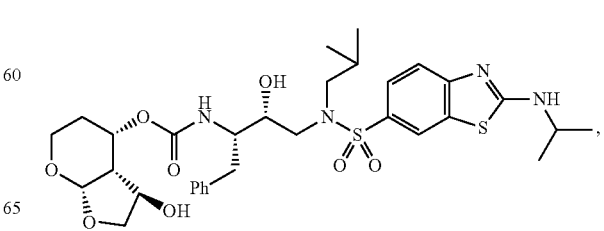

57
-continued
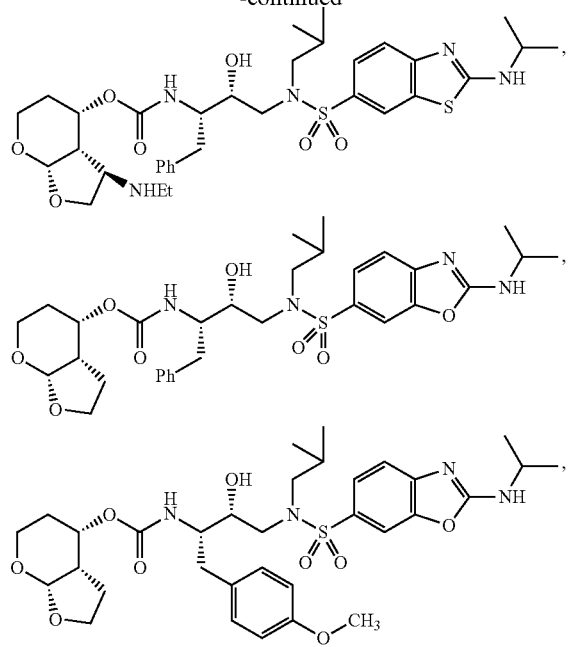
58
-continued
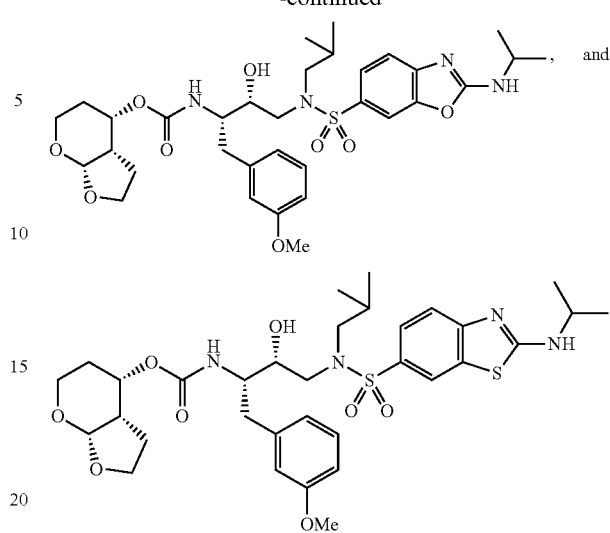
or a pharmaceutically acceptable salt thereof.
305. The compound of clause 1 selected from the group consisting of
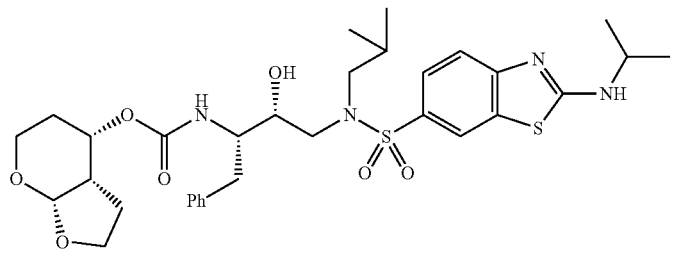
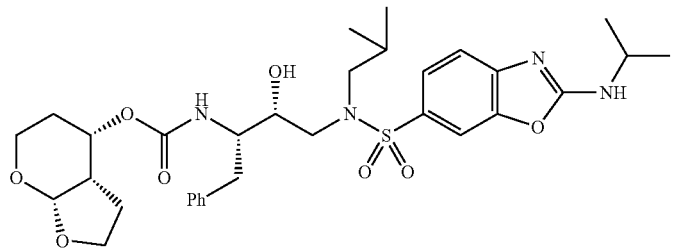
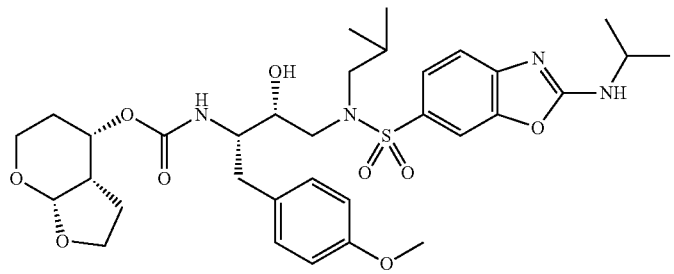

-continued
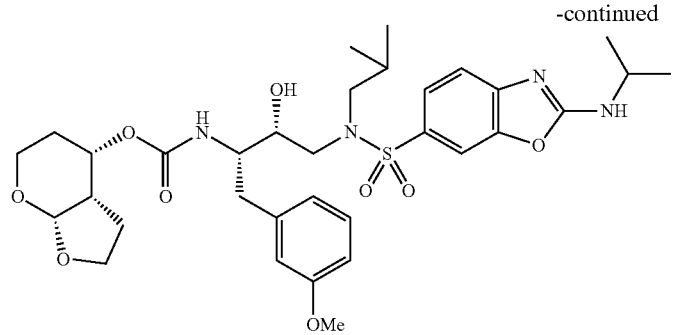
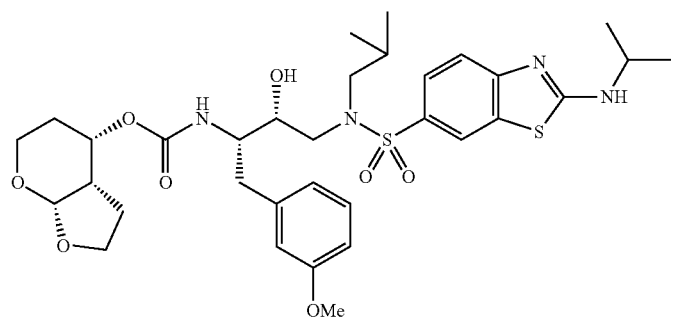
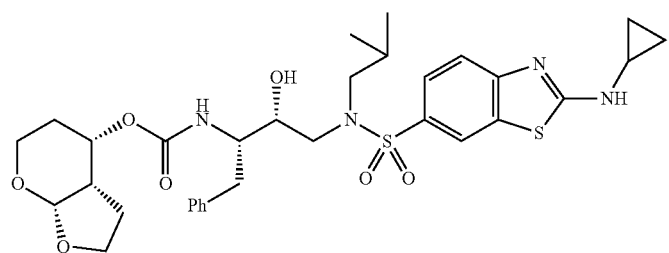
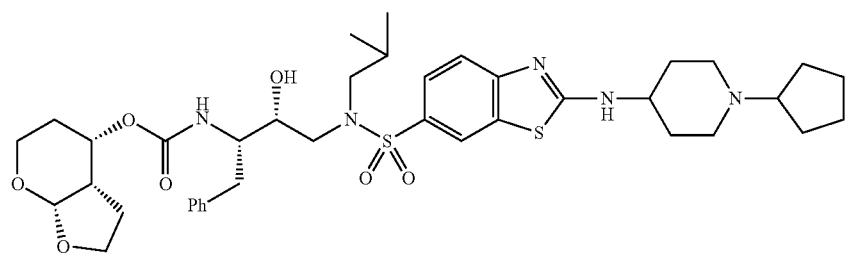
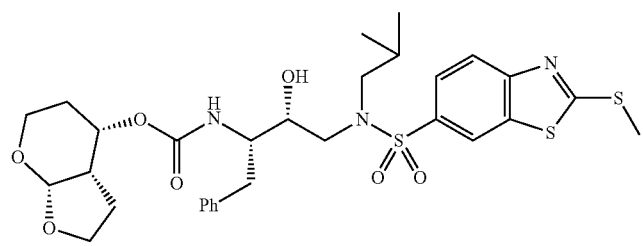
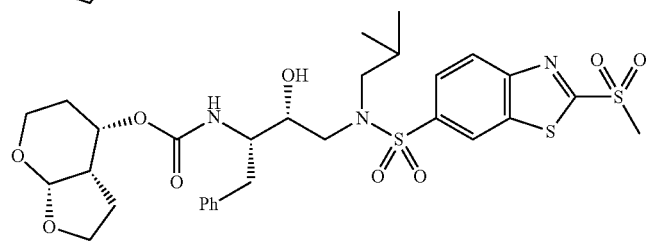

-continued
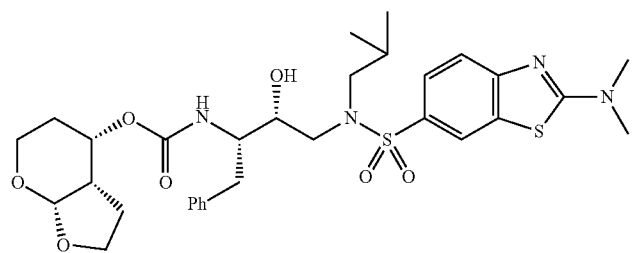
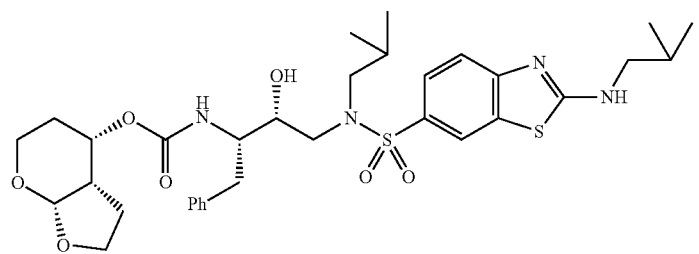
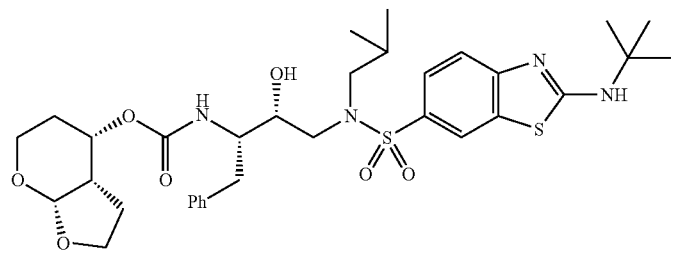
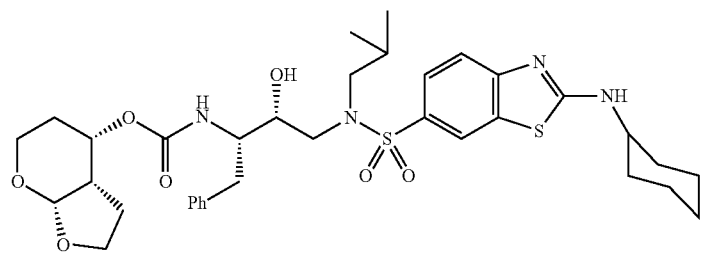
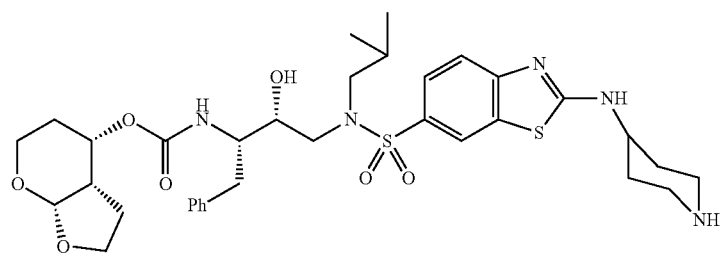
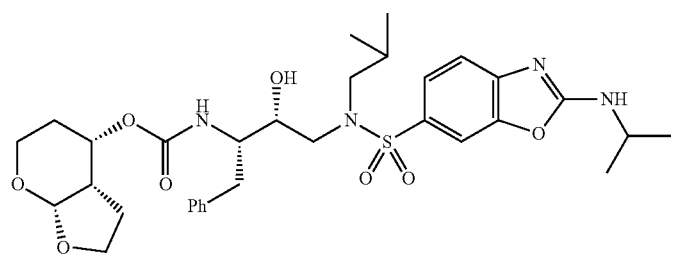

-continued
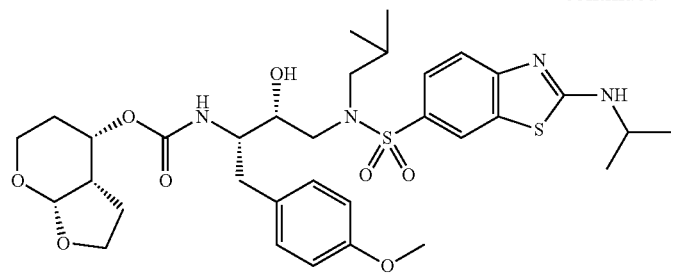
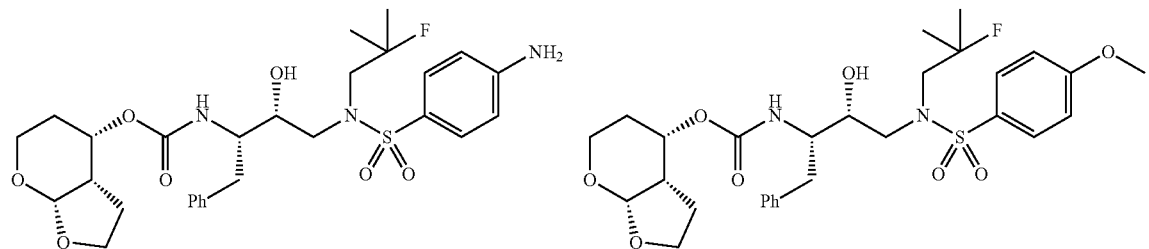
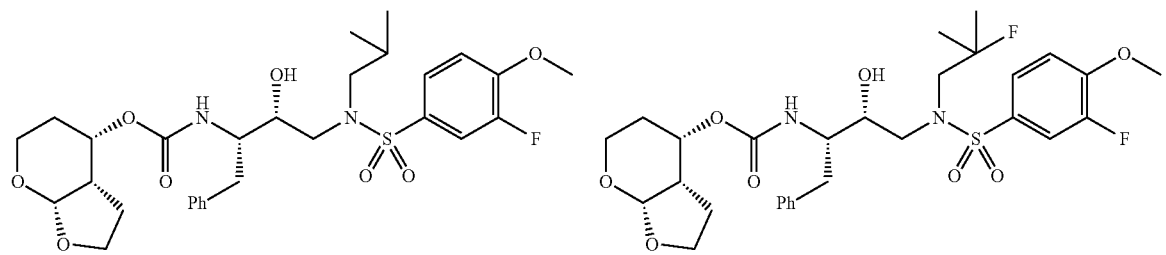
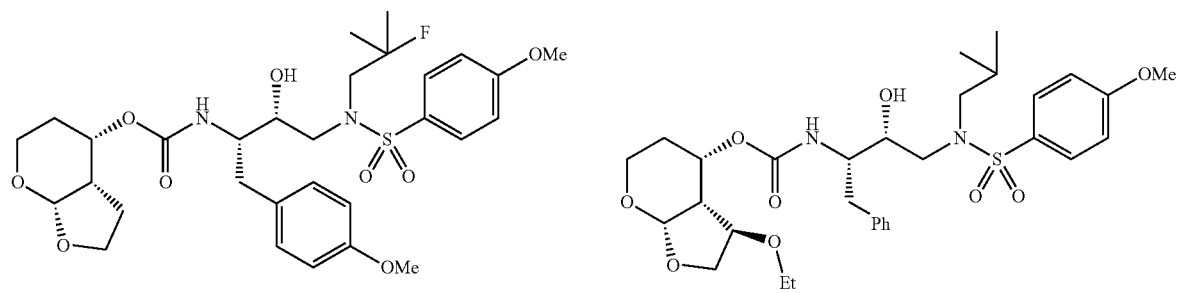
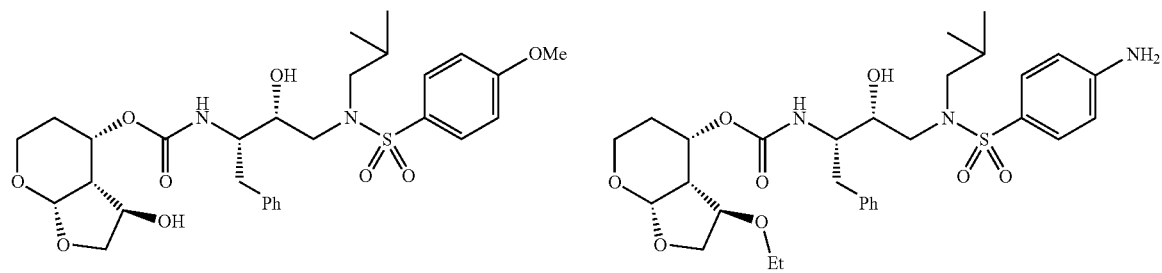
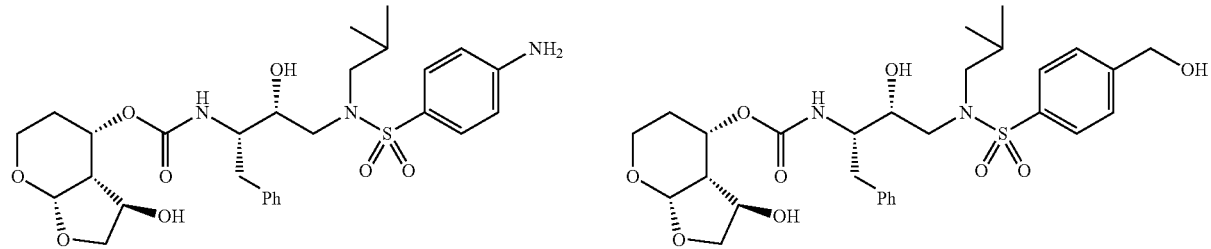

-continued
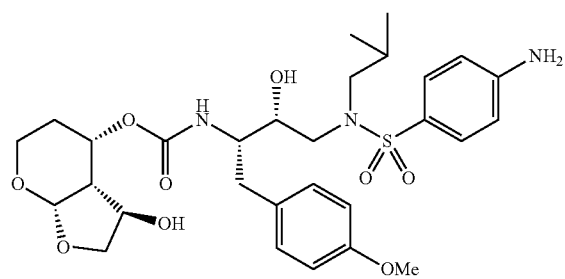
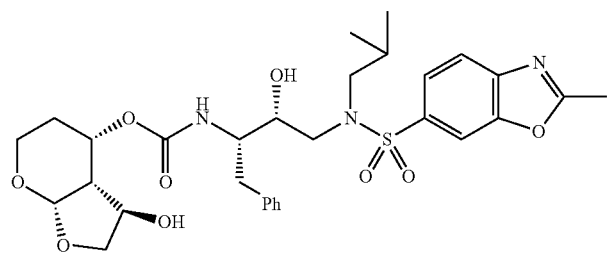
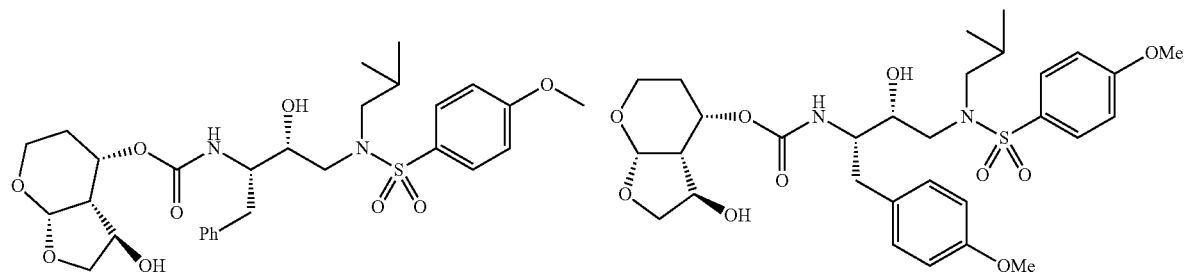
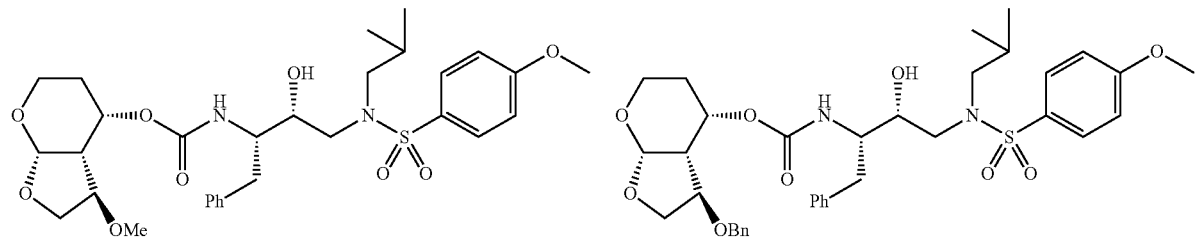
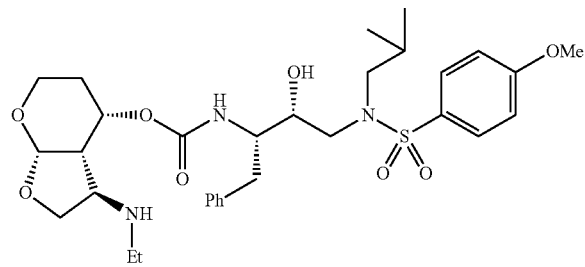
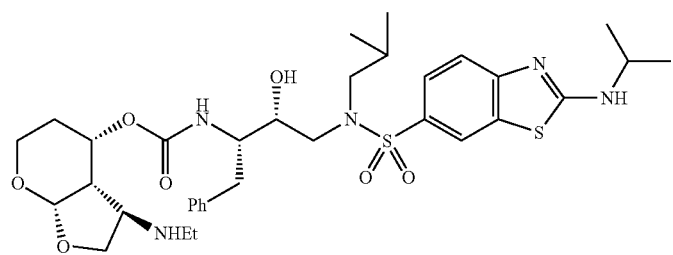

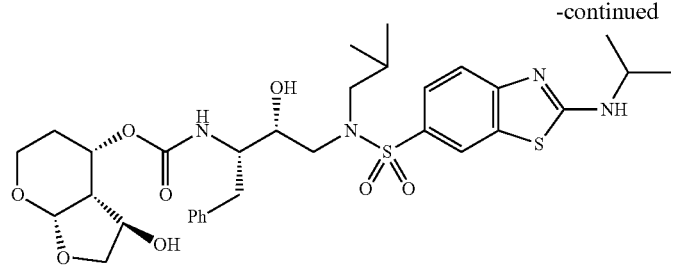

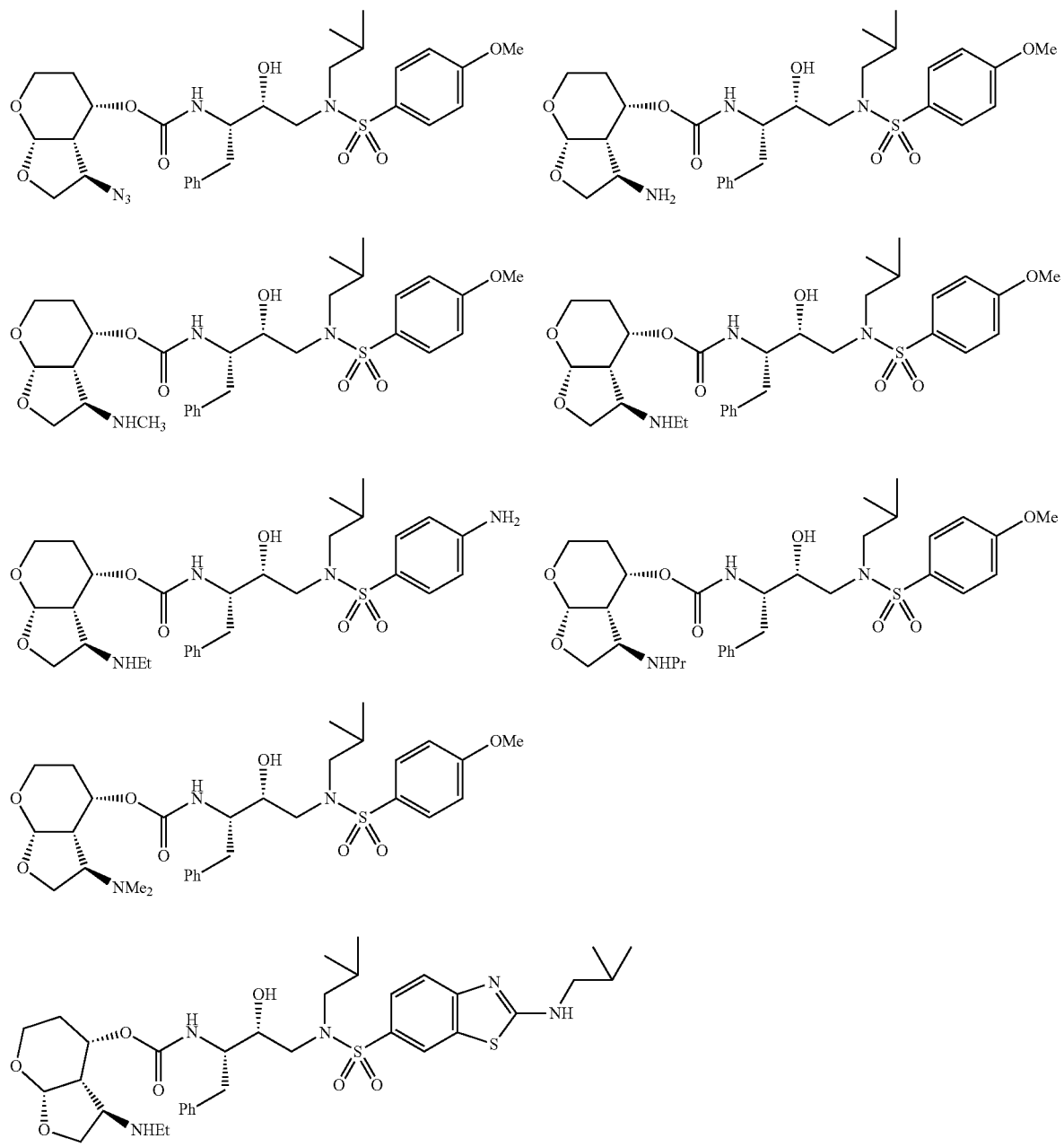

or a pharmaceutically acceptable salt thereof.

The following examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

METHODS AND EXAMPLES A

General Synthesis Example

The synthesis of enantiomerically pure (3aS,4S,7aR)-hexahydro-2H-furo[2,3-b]pyran-4-ol is shown in Scheme 1. It was achieved starting from known enantiomerically pure lactone 4.[27] Lactone 4 was reduced into the corresponding diol using lithium aluminum hydride in 95% yield. Selective monoacetylation at the primary alcohol using AcCl and 2,4,6-collidine at −78° C.,[28] and subsequent silylation of the remaining free hydroxyl furnished intermediate 5 in 86% yield (2 steps). Removal of the acetate group, followed by ozonolysis of the olefin, furnished a bicyclic bis-acetal intermediate. Reduction of the hemiacetal moiety using $Et_3SiH$ and $BF_3$-$Et_2O$ afforded bicyclic intermediate 6 in 55% yield in three steps. Removal of the silyl group with TBAF in THF furnished the desired hexahydrofuropyran-4-ol ligand (−)-7.

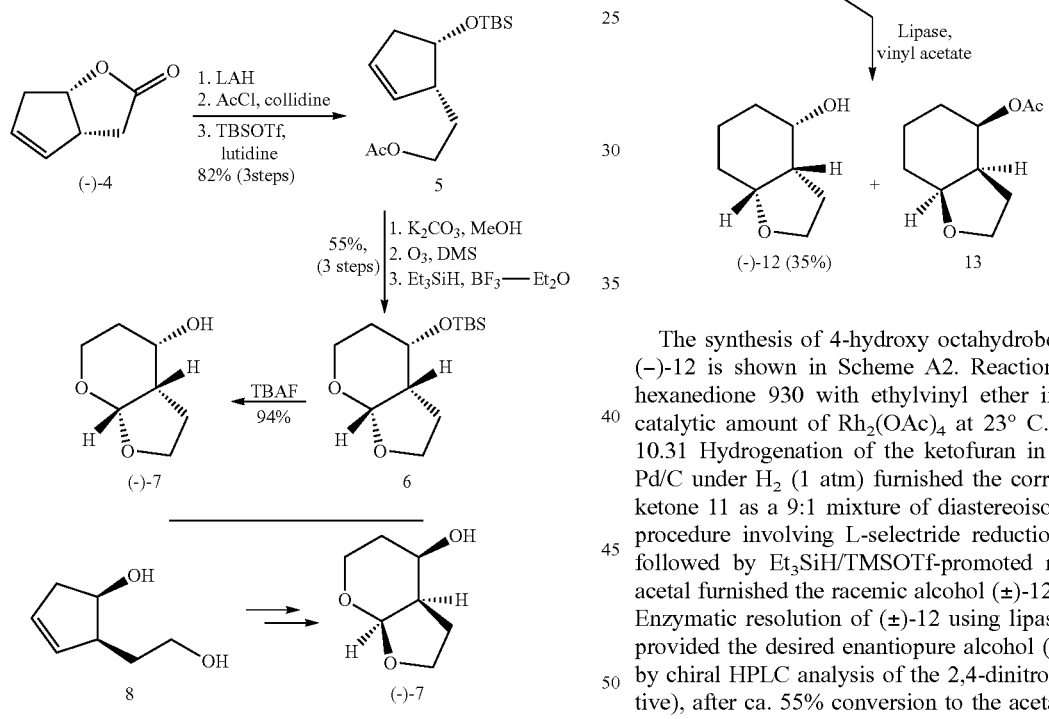

Scheme A1. Synthesis of ligand (−)-7 and its respective enantiomer (+)-7.

To demonstrate the importance of the absolute stereochemistry of the bicyclic structure of ligand (−)-7, its corresponding enantiomer (+)-7 was synthesized starting from intermediate 8 (Scheme 1). Intermediate 8 was synthesized by an enzyme-catalyzed desymmetrization of cyclopentene meso-diacetate followed by a Claisen rearrangement step.[27b,29] The resulting diester was reduced by LAH to provide 8. It was used for the synthesis of (+)-7 and subjected to the same synthetic sequence applied from lactone (−)-4 in the synthesis of (−)-7 (Scheme A1). To examine the importance of each of the two cyclic ether oxygens in the furopyranol ligand (−)-7, the corresponding cyclohexane and cyclopentane derivatives were prepared (Schemes A2 and A3).

Scheme A2. Synthesis of furocyclohexanol $P_2$ ligand (−)12

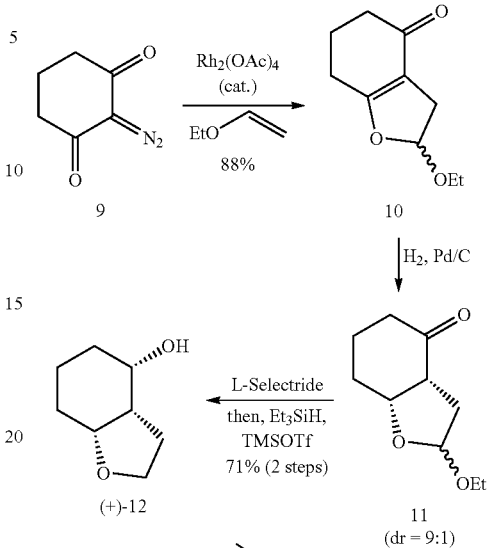

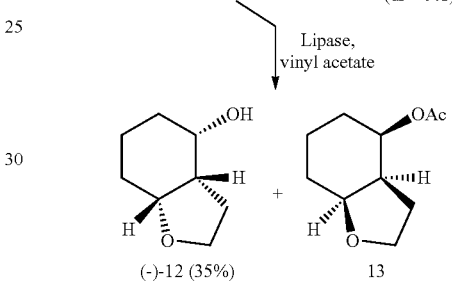

The synthesis of 4-hydroxy octahydrobenzofuran ligand (−)-12 is shown in Scheme A2. Reaction of diazocyclohexanedione 9[30] with ethylvinyl ether in presence of a catalytic amount of $Rh_2(OAc)_4$ at 23° C. gave derivative 10.[31] Hydrogenation of the ketofuran in the presence of Pd/C under $H_2$ (1 atm) furnished the corresponding crude ketone 11 as a 9:1 mixture of diastereoisomers. A one-pot procedure involving L-selectride reduction of the ketone followed by $Et_3SiH$/TMSOTf-promoted reduction of the acetal furnished the racemic alcohol (±)-12 (71% from 10). Enzymatic resolution of (±)-12 using lipase Amano PS-30 provided the desired enantiopure alcohol (−)-12 (98.8% ee by chiral HPLC analysis of the 2,4-dinitrobenzoate derivative), after ca. 55% conversion to the acetate.

Scheme A3. Syntheses of ligands (−)-18 and (−)-19.

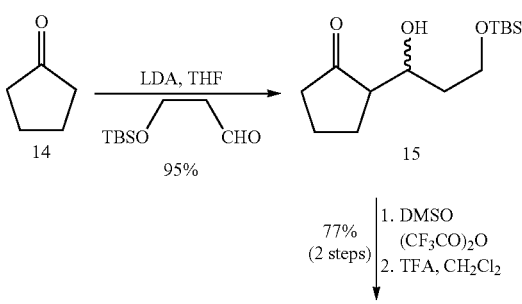

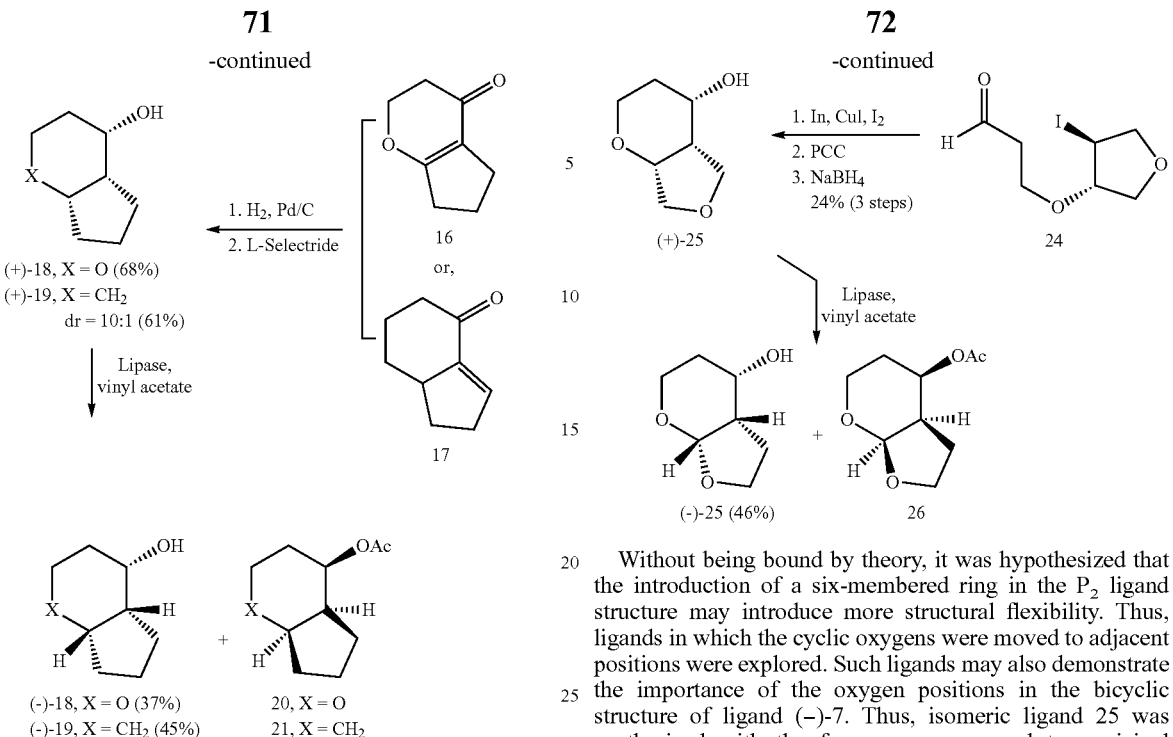

The synthesis of cyclopentapyranol ligand is shown in Scheme A3. Pentanone 14 was treated with LDA then reacted with t-butyldimethylsilyloxypropionaldehyde[32] to furnish intermediate 15 (dr 3:1) in 95% yield. A DMSO-TFAA promoted oxidation of the free hydroxy group followed by TFA-promoted cyclocondensation furnished the bicyclic α,β-unsaturated ketone 16. Hydrogenation in presence of 10% Pd/C followed by L-selectride reduction of the ketone gave racemic alcohol (±)-18 as a single diastereomer in 68% yield over 2 steps. Lipase-catalyzed resolution of the alcohol provided enantiomerically pure alcohol (−)-18. For the synthesis of a P2 ligand devoid of any cyclic oxygen, known tetrahydroindanone 17[33] was similarly hydrogenated in presence of 10% Pd/C to give the corresponding bicyclic ketone. Accordingly, L-selectride-promoted reduction of the ketone provided the corresponding alcohol (dr=10:1, as observed by $^1$H and $^{13}$C NMR). Lipase-mediated resolution of the major cis-alcohol gave the respective chiral ligand (−)-19 (90% ee determined by chiral HPLC).

Without being bound by theory, it was hypothesized that the introduction of a six-membered ring in the $P_2$ ligand structure may introduce more structural flexibility. Thus, ligands in which the cyclic oxygens were moved to adjacent positions were explored. Such ligands may also demonstrate the importance of the oxygen positions in the bicyclic structure of ligand (−)-7. Thus, isomeric ligand 25 was synthesized with the furan oxygen moved to a vicinal position. The synthesis of 4-hydroxyhexahydro-2H-furo[3,4-b]pyran 25 is shown in Scheme 4. Iodoalkoxylation of the 2,5-dihydrofuran 22 using propanediol in the presence of N-iodosuccinimide and catalytic $NH_4OAc$ provided iodoalcohol 23. Swern oxidation gave aldehyde 24 in 86% yield. An intramolecular Barbier-type reaction was then conducted using indium in the presence of copper (I) iodide and iodine, to furnish a mixture of diastereoisomeric alcohols.[34] Oxidation followed by stereoselective reduction using $NaBH_4$ furnished the racemic cis,cis-bicyclic alcohol (±)-25 as the sole product. Lipase-mediated resolution finally gave the enantiomerically pure alcohol 25.

To ascertain the importance of the position of the urethane in (−)-7, hexahydrofuropyran-5-ol ligand 30 was synthesized, as shown in Scheme 5. The free hydroxyl on the pyran ring was moved to the C3 position. The synthesis was accomplished starting from enantiomerically pure bis-THF ligand 27 synthesized by us previously.[35] Dess-Martin oxidation of 27 provided the corresponding ketone. Homologation of the resulting ketone using trimethylsilyldiazomethane in the presence of $AlMe_3$ followed by treatment of the crude mixture with TBAF and acetic acid provided the furanopyranone 29. Stereoselective reduction of ketone 29 using L-selectride furnished alcohol 30 as a mixture of inseparable diastereoisomers (dr=5:1). Both isomers were separated after formation of the corresponding activated mixed carbonate 31g.

Scheme A4. Synthesis of hexahydrofuro[3,4-b]pyran-4-ol ligand 25.

Scheme A5. Synthesis of hexahydrofuro[2,3-b]pyran-5-ol ligand 30

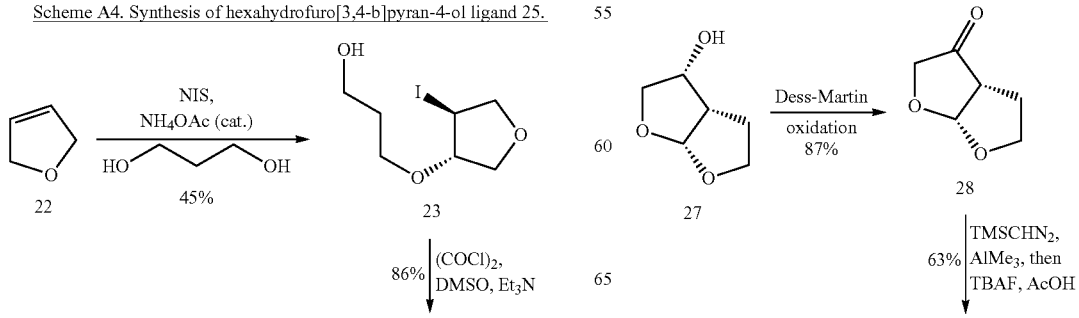

-continued

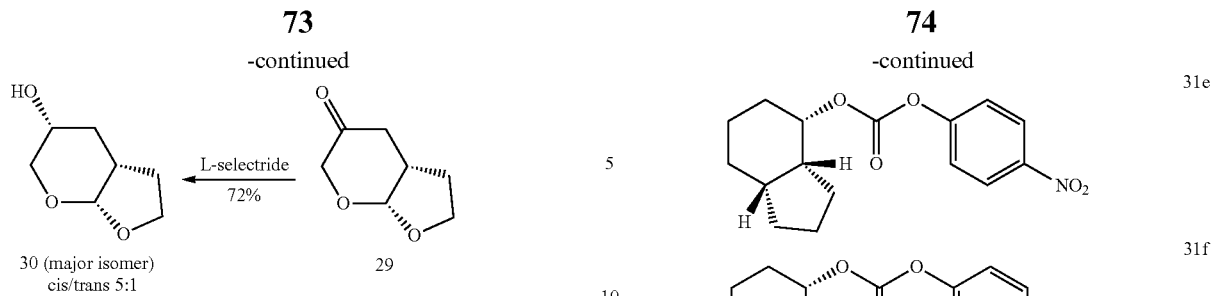

The synthesis of the protease inhibitors was accomplished in a two-step sequence shown in Schemes A6 and A7. Each ligand alcohol synthesized above was reacted with 4-nitrophenyl chloroformate in presence of pyridine to form mixed activated carbonates 31a-g in 70-99% yield. The synthesis of the corresponding protease inhibitors was achieved by coupling the mixed activated carbonates with previously reported hydroxyethylsulfonamide isosteres 32-34 (Scheme 7).[15] The syntheses of various HIV-PI containing the Tp-THF (−)-7, were achieved by respectively treating the Boc-protected isosteres 32-34 with TFA in $CH_2Cl_2$ and subsequently, by coupling the resulting free amine isosteres with activated mixed carbonate 31a in $THF/CH_3CN$ in presence of $Et_3N$. The corresponding inhibitors 35a, 36, and 37 were obtained in good yields (Scheme 7). Inhibitors 35b-g were made in a similar manner.

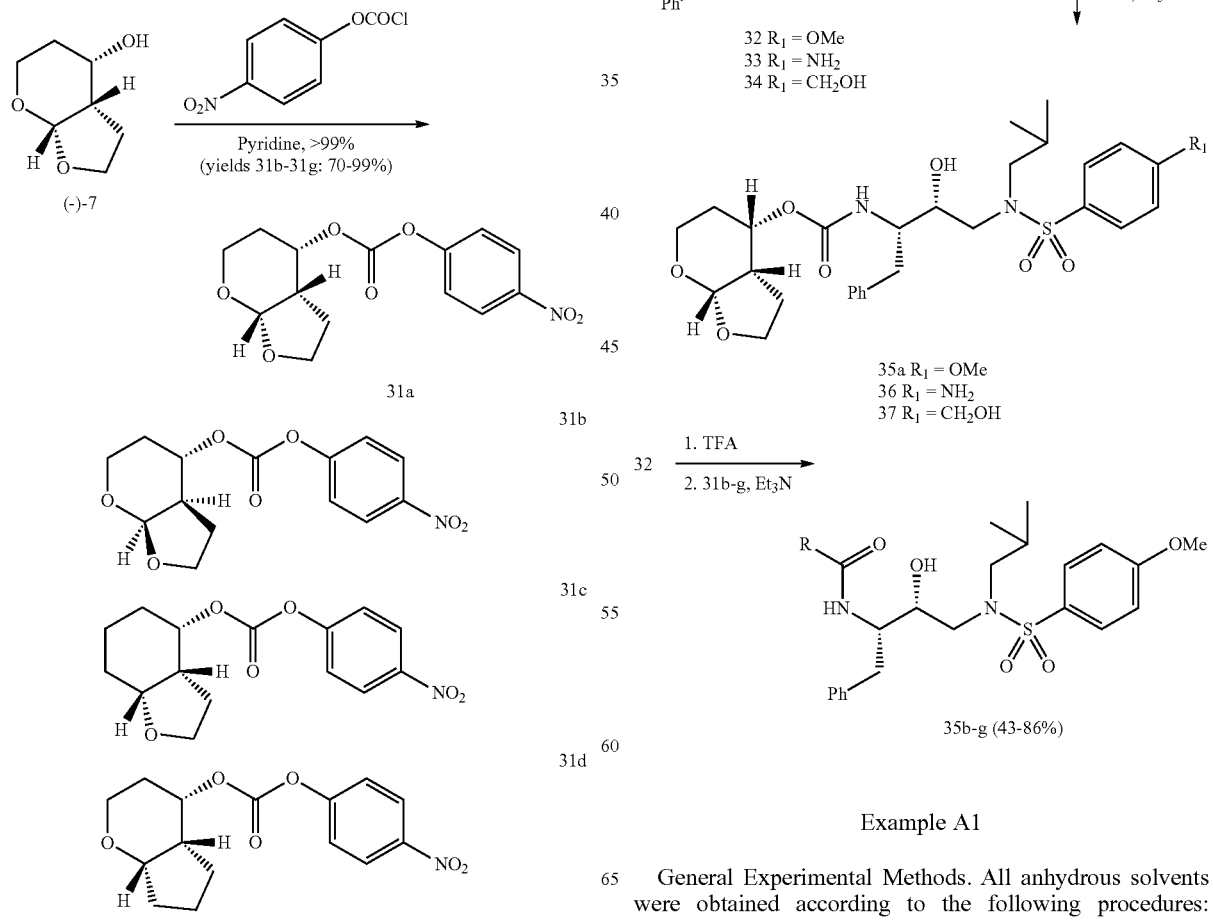

Example A1

General Experimental Methods. All anhydrous solvents were obtained according to the following procedures: diethyl ether and tetrahydrofuran (THF) were distilled from sodium/benzophenone under argon; toluene, methanol, acetonitrile, and dichloromethane from calcium hydride and benzene from sodium. Other solvents were used without purification. All moisture-sensitive reactions were carried out in flame-dried flasks under argon atmosphere. Reactions were monitored by thin layer chromatography (TLC) using Silicycle 60A-$F_{254}$ silica gel pre-coated plates. Flash column chromatography was performed using Silicycle 230-400 mesh silica gel. Yields refer to chromatographically and spectroscopically pure compounds. Optical rotations were recorded on a Perkin Elmer 341 polarimeter. $^1$H NMR and $^{13}$C NMR spectra were recorded on a Varian Inova-300 (300 and 75 MHz), Bruker Avance ARA-400 (400 and 100 MHz) or DRX-500 (500 and 125 MHz). High and low resolution mass spectra were carried out by the Mass Spectroscopy Center at Purdue University. The purity of all test compounds was determined by HRMS and HPLC analysis in the different solvent systems. All test compounds showed ≥95% purity.

Example A2

(1S,2R)-2-[1-(tert-Butyldimethylsilyloxy)-cyclopent-3-en-2-yl]ethyl acetate (5). To a stirred suspension of lithium aluminum hydride (93 mg, 2.45 mmol) in dry $Et_2O$ (6 mL) was added dropwise a solution of (−)-(1S,5R)-2-oxabicyclo[3.3.0]oct-6-en-3-one (4) (150 mg, 1.19 mmol) in $Et_2O$ (4 mL+1 mL rinse) at 0° C. under argon. The reaction mixture was vigorously stirred at this temperature for 1.5 h. Water (0.1 mL) was then carefully added followed by addition of 3M NaOH (0.1 mL) then water (0.3 mL). The solution was stirred until formation of a white precipitate was complete. EtOAc (3 mL) then $Na_2SO_4$ were added and the resulting suspension was filtered out. The amorphous solid was washed several time with EtOAc (5×5 mL). The combined organic layers were dried over $Na_2SO_4$, filtered, and concentrated in vacuo. The crude oil was purified by flash chromatography on silica gel using hexanes/EtOAc (1:1) as the eluent to give the resulting diol (145 mg, 95%) as a colorless oil. TLC: $R_f$=0.28 (hexanes/EtOAc=1:2); $^1$H NMR (CDCl$_3$, 300 MHz) δ 5.74 (m, 1H), 5.56 (m, 1H), 4.48 (dt, J=2.4, 6.6 Hz, 1H), 3.84 (m, 1H), 3.71 (ddd, J=3.6, 8.7, 10.0 Hz, 1H), 2.75 (m, 1H), 2.67 (m, 1H), 2.36 (d, J=17.1 Hz, 1H), 1.98-1.75 (m, 1H).

To a stirred solution of the diol (76 mg, 0.59 mmol) in $CH_2Cl_2$ (3 mL) was added 2,4,6-collidine (1.2 mmol, 155 μL) followed by acetyl chloride (50 μL, 0.71 mmol) at −78° C. under argon. The resulting solution was stirred at this temperature for 5 h at which point additional acetyl chloride (0.25 μL, 0.24 mmol) was added. The solution was stirred for 2 h then sat. aq. $NaHCO_3$ solution was added. The two layers were separated and the aqueous layer was washed with $CH_2Cl_2$ (3×5 mL). The combined organic layer was dried over $Na_2SO_4$, filtered, and concentrated in vacuo. The crude oil was purified by flash chromatography on silica gel using hexanes/EtOAc (6:1 then 4:1) as the eluent to give the monoacetate (88 mg, 87%) as a colorless oil. TLC: $R_f$=0.26 (hexanes/EtOAc=2:1); $^1$H NMR (CDCl$_3$, 300 MHz) δ 5.80-5.72 (m, 1H), 5.64-5.58 (m, 1H), 4.40 (dt, J=2.4, 5.6 Hz, 1H), 4.20 (t, J=7.2 Hz, 2H), 2.74-2.56 (m, 2H), 2.33 (d, J=17.1 Hz, 1H), 2.06 (s, 3H), 2.04-1.88 (m, 1H), 1.87-1.73 (m, 1H); $^{13}$C NMR (CDCl$_3$, 75 MHz) δ 171.1, 132.4, 128.4, 72.7, 63.9, 47.2, 42.1, 26.8, 21.0. HRMS-ESI (m/z): [M+H]$^+$ calcd for $C_9H_{15}O_3$, 171.1021. found 171.1020.

To a stirred solution of the above acetate (54 mg, 0.32 mmol) and 2,6-lutidine (74 μL, 0.63 mmol) in $CH_2Cl_2$ (1 mL) was added tert-butyldimethylsilyltrifluoromethanesulfonate (125 mg, 108 L) at −78° C. under argon. The mixture was stirred for 10 min at which point reaction completion was observed. Sat. aq. $NaHCO_3$ solution (1 mL) and additional $CH_2Cl_2$ (2 mL) were added. The two layers were separated and the aqueous layer was further extracted with $CH_2Cl_2$ (2×2 mL). The combined organic layer was washed with brine, dried ($MgSO_4$), filtered, and concentrated under reduced pressure. The crude oil was purified by column chromatography on silica gel using hexanes/EtOAc (20:1) as the eluent to afford silylated product 5 (90 mg, >99%) as a colorless oil. TLC: $R_f$=0.68 (hexanes/EtOAc=3:1); $^1$H NMR (CDCl$_3$, 300 MHz) δ 5.68 (s, 2H), 4.45 (dt, J=5.1, 6.3 Hz, 1H), 4.14 (t, J=6.9 Hz, 2H), 2.67-2.55 (m, 1H), 2.47 (dd, J=6.9, 15.4 Hz, 1H), 2.23 (dd, J=4.8, 15.4 Hz, 1H), 2.04 (s, 3H), 2.01-1.85 (m, 1H), 1.72-1.56 (m, 1H), 0.88 (s, 9H), 0.06 (s, 6H); $^{13}$C NMR (CDCl$_3$, 75 MHz) δ 171.2, 132.7, 128.4, 73.6, 63.8, 45.9, 41.0, 27.4, 25.8, 21.0, 18.1, −4.6, −5.0.

Example A3

(4S,4aS,7aR)-4-(tert-Butyldimethylsilyloxy)-hexahydrofuro-[2,3-b]pyrane (6). To a stirred solution of 5 (76 mg, 0.27 mmol) in MeOH (2 mL) was added $K_2CO_3$ (37 mg, 0.27 mmol). The solution was stirred at 23° C. for 2 h then sat. aq. $NH_4Cl$ solution (2 mL) was added to the mixture. EtOAc was added and the two layers were separated. The aqueous layer was extracted with EtOAc (4×3 mL). The combined organic layer was washed with brine, dried ($Na_2SO_4$), filtered, and concentrated under reduced pressure. The resulting oil was purified by flash chromatography on silica gel using hexanes/EtOAc (7:1) as the eluent to give the corresponding alcohol (64 mg, 98%) as a colorless oil. This intermediate was used immediately for the subsequent reaction. TLC: R=0.29 (hexanes/EtOAc=5:1); $^1$H NMR (CDCl$_3$, 300 MHz) δ 5.72.5.62 (m, 2H), 4.52 (dt, J=6.0, 6.9 Hz, 1H), 3.74-3.60 (m, 2H), 2.80-2.68 (m, 1H), 2.49 (ddt, J=1.8, 7.2, 16.3 Hz, 1H), 2.34-2.29 (m, 1H), 2.06 (br. s, 1H), 1.90-1.62 (m, 2H); $^{13}$C NMR (CDCl$_3$, 75 MHz) δ 132.9, 128.3, 74.0, 61.1, 46.5, 40.6, 31.2, 25.8, 18.2, −4.7, −5.0.

A stream of ozonized oxygen was bubbled through a solution of the above alcohol (63.8 mg, 0.26 mmol) in $CH_2Cl_2$ (15 mL) at −78° C. until the blue color persisted (5 min). After the solution was flushed with nitrogen, $Me_2S$ (0.5 mL) was added. The solution was warmed to 0° C. and stirred over a 2 h period following which anhydrous $Na_2SO_4$ was added. The solution was left at room temperature overnight then filtered and concentrated in vacuo. The resulting solid was quickly passed through a short column of silica gel using hexanes/EtOAc (3:1) as the eluent to afford the hemiacetal (99 mg) as a white-solid mixture of isomers which was submitted directly to the next step. TLC: $R_f$=0.26 (hexanes/EtOAc=3:1). To an ice-cold solution of the crude diacetal (ca. 0.25 mmol) and $Et_3SiH$ (0.16 mL, 1.0 mmol) in $CH_2Cl_2$ (3 mL) under argon, was slowly added $BF_3$-$Et_2O$ (60 μL, 0.5 mmol). The mixture was stirred at 0° C. for 10 min. Sat. aq. $NaHCO_3$ solution (2 mL) and additional $CH_2Cl_2$ were added. The two phases were separated and the aqueous layer was further extracted with $CH_2Cl_2$ (3×2 mL). The combined organic layer was washed with brine, dried ($MgSO_4$), filtered, and concentrated in vacuo. The crude oil was purified by column chromatography on silica gel using hexanes/EtOAc (7:1) as the eluent to give bicyclic acetal 6 (38 mg, 55% 3 steps) as a amorphous solid. TLC: $R_f$=0.50 (hexanes/EtOAc=3:1); $^1$H NMR (CDCl$_3$, 300 MHz) δ 4.95 (d, J=3.4 Hz, 1H), 4.24-4.08 (m, 2H), 3.92 (dt, J=8.1, 9.1 Hz, 1H), 3.85 (ddd, J=2.0, 4.5, 12.2 Hz, 1H), 3.30 (dt, J=2.0, 12.3 Hz, 1H), 2.39 (m, 1H), 2.07 (tt, J=9.4, 12.0 Hz, 1H), 1.91-1.66 (m, 2H), 1.58-1.48 (m, 1H), 0.89 (s, 9H), 0.07 (s, 3H), 0.067 (s, 3H); $^{13}$C NMR (CDCl$_3$, 75 MHz) δ 101.2, 68.4, 67.8, 61.1, 47.2, 30.3, 25.7, 22.4, 18.2, −4.6, −4.8.

Example A4

(3aS,4S,7aR)-Hexahydro-2H-furo[2,3-b]pyran-4-ol (−)-7. Bicyclic compound 6 (36 mg, 0.139 mmol) was dissolved in THF (1 mL) and tetrabutylammonium fluoride (1M solution THF, 0.21 mL, 0.21 mmol) was added to the solution. The mixture was stirred for 2 h at 23° C. Sat. aq. NH$_4$Cl solution was added (2 mL), followed by EtOAc (2 mL). The two phases were separated and the aqueous layer was further extracted with EtOAc (4×3 mL). The combined organic layer was washed with brine, dried (Na$_2$SO$_4$), filtered, and concentrated in vacuo. The resulting compound was purified by flash chromatography on silica gel using hexanes/EtOAc (1:2 then 1:3) as the eluent to afford pure alcohol (−)-7 (19 mg, 94%) as a amorphous solid. TLC: R$_f$=0.15 (hexanes/EtOAc=1:3); $[α]_D^{23}$-29.6 (c 1.06, CHCl$_3$); $^1$H NMR (CDCl$_3$, 300 MHz) δ 4.99 (d, J=2.7 Hz, 1H), 4.25-4.16 (m, 2H), 3.96 (q, J=7.5 Hz, 1H), 3.90 (ddd, J=2.4, 4.8, 12.3 Hz, 1H), 3.34 (td, J=3.0, 11.7 Hz, 1H), 2.58-2.45 (m, 1H), 2.14-1.98 (m, 1H), 1.96-1.82 (m, 1H), 1.80-1.62 (m, 2H); $^{13}$C NMR (CDCl$_3$, 75 MHz) δ 101.4, 68.4, 67.5, 61.0, 46.3, 29.4, 21.8. HRMS-CI (m/z): [M+H]$^+$ calcd for C$_9$H$_{15}$O$_3$, 127.0759. found 127.0757.

Example A5

(3aR,4R,7aS)-Hexahydro-2H-furo[2,3-b]pyran-4-ol (+)-7. Cyclopentenediol 8 was prepared as described previously.[27b] The same synthetic sequence was the applied on diol as for the synthesis of (−)-7. Ligand (+)-7 was obtained in high enantiomeric purity (99% ee, $[α]_D^{23}$+22.3, c 0.22, CHCl$_3$).

Example A6

2-Ethoxy-2,3,6,7-tetrahydrobenzofuran-4(5H)-one (10). To a stirred solution of 2-diazo-1,3-cyclohexanedione (300 mg, 2.17 mmol) in freshly distilled ethyl vinyl ether (5 mL) was added [Rh$_2$(OAc)$_4$](10 mg, 0.02 mmol). The mixture was stirred at room temperature for 5 h, after which the reaction was diluted with Et$_2$O and few drops of pyridine were added. A red precipitate formed. The solution was filtered on a short pad of silica, flushing with Et$_2$O/THF (4:1) as eluent. After evaporation, the residue was purified by column chromatography on silica gel using hexanes/CH$_2$Cl$_2$/THF (8:1:1) as the eluent to furnish benzofuranone derivative 17 (347 mg, 88%). TLC: R$_f$=0.29 (hexanes/EtOAc=1:1); $^1$H NMR (CDCl$_3$, 400 MHz) δ 5.72 (dd, J=3.3, 7.4 Hz, 1H), 3.88 (m, 1H), 3.62 (m, 1H), 2.92 (ddt, J=2.2, 7.4, 15.8 Hz, 1H), 2.70-2.62 (m, 1H), 2.52-2.37 (m, 2H), 2.33 (t, J=6.5 Hz, 2H), 2.12-1.95 (m, 2H), 1.24 (t, J=7.1 Hz, 3H); $^{13}$C NMR (CDCl$_3$, 100 Hz) δ 195.2, 175.7, 112.3, 108.5, 65.0, 36.3, 32.7, 23.8, 21.5, 14.9.

Example A7

2-Ethoxyhexahydrobenzofuran-4(2H)-one (11). To a solution of the ketone 10 (140 mg, 0.77 mmol) in EtOAc (9 mL) was added 5% Pd/C (128 mg, 60 μmol) and the mixture was stirred under H$_2$ (1 atm) for 1.5 h at room temperature. The mixture was then filtered on Celite and the pad washed with EtOAc. Evaporation of the solvent furnished the corresponding crude ketone 11 as an essentially pure mixture of diastereoisomers (130 mg, dr=9:1). The ketone was directly submitted to the next step without purification. TLC Major isomer: R$_f$=0.35 (hexanes:EtOAc=2:1).

Example A8 cis-Octahydrobenzofuran-4-ol [(±)-12]. A solution of ketone 11 (130 mg, ca. 0.7 mmol) in CH$_2$Cl$_2$ (10 mL) was cooled to −78° C. under Ar. L-Selectride (1M solution, 0.9 mL, 0.9 mmol) was slowly added to the solution over 5 min and the reaction mixture was stirred for 1.5 h at −78° C. Upon complete conversion, Et$_3$SiH (0.6 mL, 437 mg, 3.7 mmol) was added followed by dropwise addition of TMSOTf (380 μL, 466 mg, 2.1 mmol). The solution was stirred for 2.5 h while slowly warming to 0° C. The reaction was quenched by addition of saturated aq. NaHCO$_3$ solution (5 mL). The two phases were separated and the aqueous phase was extracted with Et$_2$O (5×). The combined organic layer was washed with brine, dried (MgSO$_4$), and evaporated under vacuum. The residue was purified by column chromatography on silica gel using hexanes:EtOAc (3:1 to 2:1) as the eluent to yield the desired alcohol (±)-12 (78 mg, 71% over 2 steps) as a colorless oil. TLC: R$_f$=0.25 (hexanes/EtOAc=1:2); $^1$H NMR (CDCl$_3$, 400 MHz) δ 4.01 (dt, J=4.6, 8.8 Hz, 1H), 3.88-3.82 (m, 2H), 3.78 (dt, J=7.1, 8.7 Hz, 1H), 2.31 (m, 1H), 2.12-1.90 (m, 2H), 1.74-1.50 (m, 5H), 1.32-1.22 (m, 1H); $^{13}$C NMR (CDCl$_3$, 100 Hz) δ 77.6, 69.1, 66.7, 43.2, 30.2, 26.9, 25.9, 16.2.

Example A9

(3aS,4S,7aR)-Octahydrobenzofuran-4-ol [(−)-12]. Racemic alcohol 12 (70 mg, 0.5 mmol) was dissolved in THF (5 mL), vinyl acetate (120 μL, 1.25 mmol) was added. Amano lipase PS-30 (30 mg) was added and the resulting suspension was stirred at 15-17° C. After 48 h, 30 mg additional enzyme was added and the mixture was left for additional 48 h until which ca. 54% conv. was reached (NMR and GC). The resulting suspension was diluted with Et$_2$O and filtered on celite, the filter cake rinsed with Et$_2$O. After evaporation of the remaining solvent, the residue was purified by column chromatography using hexanes/EtOAc (5:1, 3:1 then 2:1) as the eluent to yield acetyl furanol 13 (38 mg, 41%) and the desired enantioenriched (−)-hexahydrobenzofuranol (−)-12 (24 mg, 35%). The enantiomeric excess of the 2,4-dinitrobenzoate derivative of (−)-12 was determined to be 98.8% ee by chiral HPLC, Column ChiralPak IA, hexane/isopropanol (90/10 to 50/50, 40 min), 1 mL/min, 35° C., λ=254 nm, R$_t$ Major=16.54 min, R$_t$ minor=37.1 min.

Example A10

2-[3-(tert-Butyldimethylsilyl)oxy)-1-hydroxypropyl]-cyclopentanone (15). A solution of lithium diisopropylamide (14 mmol), freshly prepared by adding nBuLi (1.6 M solution in hexanes, 8.75 mL, 14 mmol) to diisopropylamine (1.97 mL, 1.42 g, 14 mmol) in THF (30 mL) at 0° C. under argon followed by stirring for 30 min, was cooled to −78° C. and cyclopentanone 14 (1.12 mL, 1.07 g, 12.7 mmol) in THF (5 mL) was added dropwise over 10 min. After stirring at −78° C. for 1.5 h, 3-tert-butyldimethylsilyloxypropionaldehyde (1.55 g, 8.2 mmol) in THF (20 mL) was added dropwise over 5 min. The mixture was stirred for an additional 2 h and the reaction was quenched by addition of saturated aqueous NH$_4$Cl solution (10 mL). Following dilution with Et$_2$O, the two phases were separated, and the aqueous phase was extracted with Et$_2$O (2×). The combined organic phase was washed with brine, dried (MgSO$_4$), filtered, and evaporated. The residue was quickly purified by column chromatography on silica gel using hexanes/EtOAc (20:1 to 10:1) as the eluent to give 15 as a 3:1 mixture of diastereoisomers (2.13 g, 95%). Light yellow oil. TLC: R$_f$=0.37 and 0.23 (hexanes/EtOAc=5:1); $^1$H NMR (CDCl$_3$, 400 MHz) δ 4.27 (dt, J=3.1, 9.3 Hz, 0.3H), 4.10 (s, 1H), 3.91 (m, 1H), 3.87 (m, 0.3H), 3.85-3.75 (m, 2.6H), 2.38-2.30 (m, 6.5H), 1.80-1.56 (m, 5.2H), 0.88 (brs, 12H), 0.06 (s, 2H), 0.05 (s, 6H); $^{13}$C NMR (CDCl$_3$, 100 MHz) δ 222.8, 220.4, 70.4, 70.2, 62.6, 60.5, 54.5, 53.9, 39.1, 38.7, 37.0, 36.6, 26.4, 25.9, 25.8, 23.5, 20.7, 20.5, 18.2, −5.5, −5.6; HRMS-CI (m/z): [M−OH]$^+$ calcd for C$_{14}$H$_{27}$O$_2$Si, 255.1780. found 255.1785.

Example A11

2,3,6,7-Tetrahydrocyclopenta[b]pyran-4(5H)-one (16). To a solution of DMSO (425 μL, 468 mg, 6 mmol) in CH$_2$Cl$_2$ (3 mL) was added (CF$_3$CO)$_2$O (406 L, 609 mg, 2.9 mmol) dropwise at −78° C. under argon. The resulting mixture was stirred at that temperature for 45 min then a pre-cooled solution of ketone 15 (272 mg, 1 mmol) in CH$_2$Cl$_2$ (3 mL) was added. The reaction mixture was stirred at −78° C. for 30 min, then at −15° C. for 15 min and cooled back to −78° C. Et$_3$N (1.25 mL, 911 mg, 9 mmol) was added and the mixture was stirred at −78° C. for 45 min. The reaction was quenched by addition of sat. aq. NH$_4$Cl solution and the mixture warmed to room temperature. The two phases were separated and the aqueous phase was extracted with CH$_2$Cl$_2$ (3×) then EtOAc (1×). The combined organic phase was washed with brine, dried (Na$_2$SO$_4$), filtered, and concentrated under reduced pressure. The residue was purified by flash column chromatography using hexanes/EtOAc (20:1 then 15:1 with a few drops of acetic acid) as the eluent to give the corresponding diketone (221 mg, 82%) as a light orange oil. TLC: R$_f$=0.37 (hexanes/EtOAc=10:1); $^1$H NMR (CDCl$_3$, 400 MHz) δ 12.7 (br.s., 1H), 3.90 (t, J=6.2 Hz, 0.66H), 3.89 (t, J=6.5 Hz, 2H), 3.46 (t, J=7.8 Hz, 0.33H), 2.86 (dt, J=3.0, 6.2 Hz, 0.66H), 2.58 (t, J=7.2 Hz, 2H), 2.45 (t, J=6.5 hz, 2H), 2.40 (t, J=7.9 Hz, 2H), 2.31-2.19 (m, 0.66H), 2.10-1.97 (m, 0.66H), 1.95-1.82 (m, 2H), 0.86 (s, 9H), 0.86 (s, 3H), 0.04 (s, 1H), 0.03 (s, 1H), 0.03 (s, 6H); $^{13}$C NMR (CDCl$_3$, 100 MHz) δ 212.9, 206.1, 203.6, 175.4, 110.9, 62.4, 59.6, 58.5, 45.6, 38.7, 37.8, 37.0, 25.7, 25.6, 25.0, 20.6, 20.3, 18.1, −5.6; HRMS-CI (m/z): [M+H]$^+$ calcd for C$_{14}$H$_{26}$O$_3$Si, 271.1729. found 271.1733.

A solution of this diketone (54 mg, 0.2 mmol) was dissolved in CH$_2$Cl$_2$ (2 mL) and cooled to 0° C. under argon. Trifluoroacetic acid (90 μL, 134 mg, 1.2 mmol) was then added dropwise. The mixture was stirred at 0° C. for 30 min then warmed to room temperature and stirred for 4 h. As completion was reached, solid NaHCO$_3$ (ca. 150 mg) was then added and the mixture diluted with EtOAc. After stirring for 10 min, the suspension was filtered on a small celite pad. The solvent was evaporated under reduced pressure and the residue purified by column chromatography on silica gel using hexanes/EtOAc (4:1) as the eluent to furnish α,β-unsaturated ketone 16 (26 mg, 94%) as a colorless oil. TLC: R$_f$=0.23 (hexanes/EtOAc=3:1); $^1$H NMR (CDCl$_3$, 400 MHz) δ 4.49 (t, J=6.9 Hz, 2H), 2.59-2.45 (m, 6H), 1.89 (m, 2H); $^{13}$C NMR (CDCl$_3$, 100 MHz) δ 189.6, 178.5, 114.5, 69.5, 35.4, 32.6, 25.6, 19.0.

Example A12

Octahydrocyclopenta[b]pyran-4-ol [(±)-18]. A solution of α,β-unsaturated ketone 16 (109 mg, 0.79 mmol) in EtOAc (6 mL) was added with 10% Pd/C (50 mg, 0.047 mmol) and carefully placed under H$_2$ (1 atm). The mixture was stirred at room temperature for 12 h. The suspension was then filtered over a Celite pad, the pad washed with EtOAc, and the resulting solution evaporated under reduced pressure. The essentially pure ketone (81 mg) was directly carried out to the next step without further purification. TLC: R$_f$=0.37 (hexanes/EtOAc=3:1); $^1$H NMR (CDCl$_3$, 400 MHz) δ 4.22-4.15 (m, 2H), 3.69 (td, J=2.8, 12.0 Hz, 1H), 2.71 (ddd, J=7.2, 12.3, 15.7 Hz, 1H), 2.48 (dt, J=4.0, 9.0 Hz, 1H), 2.23 (ddt, J=1.4, 2.8, 15.7 Hz, 1H), 2.00-1.80 (m, 5H), 1.71-1.63 (m, 1H); $^{13}$C NMR (CDCl$_3$, 100 MHz) δ 210.2, 82.8, 65.9, 55.1, 38.5, 33.3, 28.4, 22.8.

The ketone was diluted in CH$_2$Cl$_2$ (5 mL) under argon and cooled to −78° C. L-Selectride (1M solution in THF, 0.80 mL, 0.8 mmol) was added dropwise and the resulting mixture was stirred at this temperature for 2 h. Hydrogen peroxide (30% aqueous solution, 3 mL) and 3N NaOH aqueous solution were added and the mixture was warmed to 23° C., and stirred for 5 h. The phases were separated and the aqueous phase extracted with CH$_2$Cl$_2$ (4×). The combined organic phase was washed with brine, dried (Mg$_2$SO$_4$), filtered, and evaporated under reduced pressure. The residue was purified by column chromatography on silica gel using hexanes/EtOAc (4:1 then 1.5:1) as the eluent to yield cis-bicyclic alcohol (−)-18 (77 mg, 68% 2 steps) as a colorless oil. TLC: R$_1$=0.13 (hexanes/EtOAc=2:1); $^1$H NMR (CDCl$_3$, 400 MHz) δ 4.11 (dt, J=5.6, 11.1 Hz, 1H), 3.91 (ddd, J=2.0, 4.5, 11.7 Hz, 1H), 3.84-3.81 (m, 1H), 3.33 (dt, J=2.3, 11.9 Hz, 1H), 2.17-2.08 (m, 1H), 1.92-1.81 (m, 1H), 1.79-1.55 (m, 7H); $^{13}$C NMR (CDCl$_3$, 125 MHz) δ 80.5, 68.3, 65.4, 47.0, 32.6, 29.7, 21.6, 21.3.

Example A13

(4S,4aS,7aS)-Octahydrocyclopenta[b]pyran-4-ol ((−)-18). Racemic alcohol (±)-18 (68 mg, 0.48 mmol) was dissolved in THF (5 mL) and vinyl acetate (225 μL, 2.4 mmol) was added. Amano lipase PS-30 (30 mg) was added and the resulting suspension was stirred at 15-20° C. The mixture was left stirring for >48 h until around 50% conversion was reached (as seen by NMR). The resulting suspension was diluted with Et$_2$O and filtered on celite, the filter cake rinsed with Et$_2$O. After evaporation of the remaining solvent, the residue was purified by column chromatography using hexanes/EtOAc (5:1, 3:1 then 1.5:1) to yield the desired enantioenriched pyranol (−)-18 (25 mg, 37%). [α]$_D^{20}$ 47.5 (c 1.32, CHCl$_3$). An enantiopurity of 94.1% ee for the alcohol was measured by chiral HPLC analysis of the corresponding activated carbonate 31d: Column ChiralPak IA, 0.7 mL/min, Hexanes/IPA (98:2 to 85:15, from 0 to 45 min), λ=210 nm, T=30° C., R$_t$ minor=22.4 min, R$_t$ Major=23.3 min.

Example A14

(±)-endo-cis-Bicyclo[4.3.0]nonan-2-ol [(±)-19]. Enone 17$^{33}$ (106 mg, 0.77 mol) was dissolved in THF (10 mL), the flask was purged with argon. Pd/C 10% (60 mg, 0.06 mmol) was added to the solution and the resulting suspension was stirred under hydrogen (1 atm). TLC monitoring first shows isomerization of the enone, through migration of the olefin to the internal position, followed by slow formation of the reduced cis-product. After 12 h, the solution was filtered on a pad of celite and the solvent removed in vacuo. The residue was purified by flash column chromatography on silica gel using hexanes/EtOAc (30:1 to 10:1) to give the reduced ketone (98 mg, 92%). TLC: R$_f$=0.65 (hexanes/EtOAc=5:1); $^1$H NMR (CDCl$_3$, 400 MHz) δ 2.62-2.54 (m, 1H), 2.48-2.38 (m, 1H), 2.38-2.23 (m, 2H), 2.08-1.98 (m, 1H), 1.94-1.30 (m, 9H); $^{13}$C NMR (CDCl$_3$, 100 MHz) δ 214.6, 53.1, 42.9, 39.6, 31.0, 27.2, 26.6, 23.8, 23.0. A solution of the ketone (135 mg, 0.98 mmol) in CH$_2$Cl$_2$ (3 mL) was cooled to −78° C. under argon. L-Selectride (1M solution THF, 1.2 mL) was added dropwise to the solution and the reaction mixture was stirred at −78° C. for 1 h. Hydrogen peroxide solution (30% solution, 1.5 mL) then NaOH (3M solution, 1.5 mL) were added and the reaction was warmed to 23° C., and stirred for 1 h. After dilution with water (2 mL) then addition of Na$_2$SO$_3$ saturated aqueous solution (3 mL), the aqueous phase was successively extracted with CH$_2$Cl$_2$ (4×). The combined organic phase was dried (Na$_2$SO$_4$), filtered, and evaporated in vacuo. The residue was purified by column chromatography on silica gel using hexanes/EtOAc (6:1) to yield racemic alcohol (±)-19 (92 mg, 66%) as a colorless oil. TLC: R$_f$=0.25 (hexanes/EtOAc=5:1); $^1$H NMR (CDCl$_3$, 500 MHz) δ 3.96 (m, 1H), 2.26-2.17 (m, 1H), 1.93 (m, 1H), 1.79-1.53 (m, 7H), 1.47-1.15 (5H), 0.96 (dq, J=3.3, 13.0 Hz, 1H); $^{13}$C NMR (CDCl$_3$, 125 MHz) δ 71.6, 46.4, 40.1, 31.5, 29.5, 27.0, 23.9, 21.4, 21.2; HRMS-EI (m/z): [M−OH]$^−$ calcd for C$_9$H$_{15}$, 122.1096. found 122.1097.

Example A15

(−)-(1R,2S,6R)-Bicyclo[4.3.0]nonan-2-ol [(−)-19]. Racemic 19 (86 mg, 0.62 mmol) was dissolved in THF (5 mL), vinyl acetate (0.5 mL) was added. Amano lipase PS-30 (60 mg) was added and the resulting suspension was stirred at 23° C. until 50% conv. was reached (NMR) in ca. 6 h. The resulting suspension was diluted with Et$_2$O and filtered on celite, the filter cake rinsed with Et$_2$O. After evaporation of the remaining solvent, the residue was purified by column chromatography using hexanes/EtOAc (8:1, 6:1 then 4:1) to yield acetate 21 and the desired enantioenriched (−)-indanol (−)-19 (38.5 mg, 45% yield). [α]$_D^{20}$ −28.3° (c 1.02, CHCl$_3$), ([α]f lit. −27.2° (c 1.0, CHCl$_3$).$^{38}$ The enantiomeric excess of the 2,4-dinitrobenzoate derivative was determined to be 89.9% ee by chiral HPLC, Column ChiralPak IA, hexane/isopropanol (100/0 to 90/10, 15 min; 90/10 to 80/20, 15 min), 1 mL/min, R$_t$ minor=16.58 min, R$_t$ Major=19.5 min.

Example A16

3-((4-Iodotetrahydrofuran-3-yl)oxy)propan-1-ol (23). To a solution of freshly distilled 2,5-dihydrofuran (700 mg, 0.740 mL, 10 mmol), in a mixture of dry 1,3-propanediol/dimethoxyethane (1:1, 5 mL) at 0° C. under argon, were successively added NH$_4$OAc (77 mg, 1 mmol), followed by N-iodosuccinimide (11 mmol, 2.47 g). The mixture was warmed to 23° C. and stirred for 12 h protected from light. The reaction was quenched by addition of sat. aq. Na$_2$SO$_3$ then diluted with water. The mixture was extracted with Et$_2$O/EtOAc (1:1). The combined organic phase was dried (Na$_2$SO$_4$), filtered, and evaporated under reduced pressure. The residue was purified by flash column chromatography on silica gel using hexanes/EtOAc (4:1, 3:1 then 2.5:1) to give iodoalcohol 23 (1.2 g, 45%) as a pale yellow oil. TLC: R$_f$=0.3 (hexanes/EtOAc=1:1); $^1$H NMR (CDCl$_3$, 400 MHz) δ 4.33 (m, 1H), 4.29-4.19 (m, 3H), 4.04 (dd, J=2.2, 9.8 Hz, 1H), 3.79 (dd, J=1.5, 9.8 Hz, 1H), 3.76-3.69 (m, 3H), 3.60 (m, 1H), 1.81 (m, 2H); $^{13}$C NMR (CDCl$_3$, 100 MHz) δ 88.2, 76.1, 71.8, 67.9, 60.6, 32.3, 23.4.

Example A17

3-((4-Iodotetrahydrofuran-3-yl)oxy)propanal (24). Oxalyl chloride (580 mg, 392 L, 4.6 mmol) was diluted in CH$_2$Cl$_2$ (12 mL) under argon and the solution was cooled to −78° C. Dry DMSO (715 mg, 650 μL, 9.15 mmol) in CH$_2$Cl$_2$ (3 mL) was added to the cold solution dropwise and the mixture was stirred for 30 min. A solution of alcohol 23 (500 mg, 1.83 mmol) in CH$_2$Cl$_2$ (4 mL) was then added slowly, and the mixture was kept stirring for an additional hour at −78° C. Et$_3$N (1.3 g, 1.8 mL, 12.8 mmol) was then introduced, the white suspension was stirred at −78° C. for 20 min and slowly warmed to rt. A 0.5 M phosphate buffer solution pH 5.5 (20 mL) was added, the two phases were separated and the resulting aqueous phase was extracted with Et$_2$O (4×). The combined organic phase was dried (MgSO$_4$), filtered, and evaporated. The residue was purified by flash column chromatography using hexanes/EtOAc (6:1 to 4:1) to yield the desired aldehyde 24 (433 mg, 86%) as a light yellow oil. TLC: R$_f$=0.76 (hexanes/EtOAc=1:1); $^1$H NMR (CDCl$_3$, 300 MHz) δ 9.77 (t, J=1.3 Hz, 1H), 4.35 (m, 1H), 4.30-4.19 (m, 3H), 4.04 (dd, J=2.3, 9.8 Hz, 1H), 3.92 (ddd, J=5.3, 6.7, 9.5 Hz, 1H), 3.77 (dd, J=1.7, 10.1 Hz, 1H), 3.75 (ddd, J=5.2, 6.2, 9.5 Hz, 1H), 2.69 (m, 2H); $^{13}$C NMR (CDCl$_3$, 75 MHz) δ 200.1, 88.3, 76.1, 71.8, 63.1, 43.7, 23.3.

Example A18

Hexahydro-2H-furo[3,4-b]pyran-4-ol ((±)-25). To a solution of aldehyde 24 (100 mg, 0.37 mmol) in DME (10 mL) was successively added indium (60 mg, 0.55 mmol), CuI (48 mg, 0.25 mmol), and a catalytic amount of iodine (10 mg, 0.037 mmol). After stirring the suspension for 5 min, water (4 mL) was added and the mixture was stirred at room temperature for 4 h. The suspension was filtered on a celite pad, washing the pad with THF. The solvent was reduced under vacuum and the resulting aqueous phase acidified with 1M HCl and saturated with NaCl. The aqueous phase was extracted with EtOAc and the combined organic phase was dried over MgSO$_4$. After filtration, and evaporation, the crude was purified by flash column chromatography on silica gel using hexanes/EtOAc (1:1 to 1:5) to provide the bicyclic alcohol (±)-25 (25 mg, 47%) as a mixture of diastereoisomers. TLC: R$_f$=0.28 (EtOAc 100%). Pyridinium chlorochromate (74 mg, 0.346 mmol) was added to a suspension of flame-dried 4 Å MS in CH$_2$Cl$_2$ (2 mL) at room temperature under argon. A solution of the above alcohol (25 mg, 0.173 mmol) in CH$_2$Cl$_2$ (1.5 mL) was transferred to the suspension at 0° C. and the solution was stirred for 1 h at 0° C. The reaction was quenched by addition of isopropanol and the mixture was filtered on a silica pad flushing with Et$_2$O. After evaporation of the solvent, the corresponding ketone thus obtained was used directly to the next step. TLC: R$_f$=0.45 (hexanes/EtOAc=1:1); The ketone was re-dissolved in EtOH (1.5 mL), the solution was cooled to −20° C. and NaBH$_4$ (25 mg, 0.66 mmol) was added at once. After stirring at this temperature for 30 min, the reaction was quenched by addition of sat. aq. NH$_4$Cl solution (1.5 mL). The solution was extracted with EtOAc and the combined organic phase dried (Na$_2$SO$_4$), filtered, and evaporated. The corresponding racemic alcohol (±)-25 was purified by flash column chromatography using hexanes/EtOAc (1:1 to 1:5) as the eluent. Colorless oil (12 mg, 50% 2 steps). TLC: R$_f$=0.25 (100% EtOAc). $^1$H NMR (CDCl$_3$, 300 MHz) δ 4.26 (m, 1H), 4.05 (t, J=3.0 Hz, 1H), 4.04-3.95 (m, 3H), 3.94-3.85 (m, 2H), 3.40 (dt, J=2.5, 11.8 Hz, 1H), 2.60 (m, 1H), 1.94 (d, J=4.0 Hz, 1H), 1.80 (ddt, J=4.6, 11.5, 12.5 Hz, 1H), 1.74 (m, 1H); $^{13}$C NMR (CDCl$_3$, 75 MHz) δ 78.3, 74.5, 67.1, 66.4, 65.0, 45.5, 30.0.

To a solution of racemic (±)-25 (10 mg, 0.07 mmol) in dry THF (1 mL) under an argon atmosphere, was added vinyl acetate (60 mg, 65 µL, 0.7 mmol) followed by addition of Immobilized Amano Lipase PS-30 (10 mg) on Celite-545. The mixture was stirred at 15-20° C. for 2 days until >50% conversion could be observed by NMR of aliquots. The resulting suspension was diluted in Et$_2$O and filtered on a small celite pad. The solvents were evaporated and the residue purified by flash chromatography using hexanes/EtOAc (1:1 to 1:5) as the eluent to give enantiomeric alcohol 25 (4.6 mg, 46%) as a colorless oil. An enantiopurity of >99.5% ee for the alcohol was measured by analysis of the corresponding activated carbonate 31f on chiral HPLC (Column ChiralPak IC, hexane/isopropanol 52:48, 1 mL/min, λ=215 nm, T=24° C., R$_t$ minor=14.4 min, R$_t$ Major=15.5 min).

Example A19

(3aR,6aR)-Tetrahydrofuro[2,3-b]furan-3(2H)-one (28). Enantiomerically pure (3R,3aS,6aR)-hexahydrofuro[2,3-b]furan-3-ol (bis-THF) 27 (85 mg, 0.65 mmol) was diluted in dry CH$_2$Cl$_2$ (6 mL) under argon, the solution was cooled to 0° C. and anhydrous Na$_2$HPO$_4$ (52 mg, 0.36 mol) was added. Dess-Martin periodinane (360 mg, 0.85 mmol) was added at once at 0° C. and the resulting suspension warmed to 23° C. and stirred for 3 h. The reaction was then quenched by successive addition of sat. aq. NaHCO$_3$ and sat. aq. Na$_2$SO$_3$ solutions (1.5+1.5 mL). The phases were separated and the aqueous phase was extracted with CH$_2$Cl$_2$ then EtOAc. The combined organic phases were dried (Na$_2$SO$_4$), filtered on a small pad of silica gel, and evaporated to dryness. The residue was purified by column chromatography on silica gel using hexanes/EtOAc (3:1) to furnish ketone 28 (73 mg, 87%) as a white crystalline solid. TLC: R$_f$=0.57 (hexanes/EtOAc=1:1); Spectral data corresponded to those previously reported in the literature.[35]

Example A20

(3aS,7aR)-Tetrahydro-2H-furo[2,3-b]pyran-5(3H)-one (29). AlMe$_3$ (25% w/w hexanes, 250 µL, 0.6 mmol) was diluted in dry CH$_2$Cl$_2$ (5 mL) under argon and the solution was cooled to −78° C. A solution of ketone 28 (64 mg, 0.5 mmol) in dry CH$_2$Cl$_2$ (5 mL) was slowly added dropwise. After 10 min, TMSCHN$_2$ (2 M solution in Et$_2$O, 275 µL, 0.55 mmol) was added. The reaction was stirred for 2 h while warmed to −30° C. Saturated Rochelle's salts solution (5 mL) was added and the mixture was stirred for 1 h. The phases were separated, the aqueous phase extracted with CH$_2$Cl$_2$, and the combined organic phase was dried (MgSO$_4$). The solution was filtered on a small silica gel pad, flushing with Et$_2$O, and the collected organic phase evaporated. A crude mixture of the desired ketone along with α-silylated derivatives and isomers was then obtained. The mixture was re-dissolved in THF (5 mL). AcOH (6 drops) and TBAF (0.5 mL, 0.5 mmol) were successively added. The resulting mixture was stirred at 23° C. for 3 h and evaporated to dryness. The residue was purified by flash column chromatography on silica gel using hexanes/EtOAc (5:1) as the eluent to give ketone 29 (45 mg, 63%). TLC: R$_f$=0.35 (hexanes/EtOAc=2:1); $^1$H NMR (CDCl$_3$, 400 MHz) δ 5.49 (d, J=6.8 Hz, 1H), 4.11 (d, J=18.2 Hz, 1H), 4.10 (m, 1H), 3.92 (d, J=18.2 Hz, 1H), 3.74 (dt, J=6.5, 8.9 Hz, 1H), 2.85 (m, 1H), 2.71 (d, J=6.3, 15.6 Hz, 1H), 2.48 (m, J=3.9, 15.6 Hz, 1H), 2.15 (m, 1H), 1.55 (ddt, J=7.7, 8.9, 12.7 Hz, 1H); $^{13}$C NMR (CDCl$_3$, 100 MHz) δ 210.7, 100.9, 67.5, 67.1, 39.2, 36.2, 31.3.

Example A21

(3aS,5R,7aR)-Hexahydro-2H-furo[2,3-b]pyran-5-ol (30). A solution of the ketone 29 (25 mg, 0.173 mmol) dissolved in CH$_2$Cl$_2$ (5 mL) was cooled to −78° C. under argon. L-Selectride (1M in THF, 200 µL, 0.2 mmol) was added dropwise. The solution was stirred at this temperature for 3 h and quenched by addition of sat. aq. NH$_4$Cl solution. The aqueous phase was extracted with EtOAc, the combined organic extract was dried (Na$_2$SO$_4$), filtered, and evaporated. The crude was purified by column chromatography on silica gel using hexanes/EtOAc (2:1, 1:1, then 1:2) to yield alcohol 30 as a 5:1 mixture of diastereoisomers (18 mg, cis major). The stereoisomers were separated in the subsequent synthesis of the mixed activated carbonate 31g. TLC: R$_f$=0.25 (hexanes/EtOAc=1:2); $^1$H NMR (CDCl$_3$, 300 MHz) δ 5.08 (d, J=3.8 Hz, 0.2H), 5.05 (d, J=3.3 Hz, 1H), 4.16-4.11 (m, 1.2H), 3.95-3.84 (m, 1.6H), 3.81-3.70 (m, 2H), 3.63 (m, 1H), 3.27 (dd, J=7.9, 11.2 Hz, 0.2H), 2.35-1.70 (m, 6H).

Example A22

(3aS,4S,7aR)-Hexahydro-2H-furo[2,3-b]pyran-4-yl (4-nitrophenyl)carbonate (31a). Furopyranol ligand (−)-7 (9 mg, 0.063 mmol) was diluted in CH$_2$Cl$_2$ (0.5 mL) under argon. The solution was cooled to 0° C. and dry pyridine (17 µL, ca. 0.21 mmol) was added 4-nitrophenyl chloroformate (24 mg, 0.12 mmol) was added at once to the solution upon which a white precipitate formed. The reaction was stirred for 2 h while warming to rt. Upon completion, the mixture was concentrated reduced pressure and the residue was purified by column chromatography on silica gel using hexanes/EtOAc (6:1 then 3:1) as the eluent to give the corresponding activated carbonate 31a (18 mg, >99%). TLC: R$_f$=0.25 (hexanes/EtOAc=3:1); $^1$H NMR (CDCl$_3$, 300 MHz) δ 8.29 (d, J=8.7 Hz, 2H), 7.39 (d, J=8.7 Hz, 2H), 5.30-5.19 (m, 1H), 5.07 (d, J=2.7 Hz, 1H), 4.28 (dt, J=3 Hz, 1H), 4.04-3.95 (m, 2H), 3.47-3.37 (m, 1H), 2.80-2.68 (m, 1H), 2.30-2.10 (m, 1H), 2.05-1.90 (m, 3H); $^{13}$C NMR (CDCl$_3$, 75 MHz) δ 155.3, 151.7, 145.4, 125.3, 121.7, 101.1, 75.4, 68.5, 60.5, 43.2, 25.8, 22.5.

Example A23

(3aR,4R,7aS)-Hexahydro-2H-furo[2,3-b]pyran-4-yl (4-nitrophenyl) carbonate (31b). The title compound was obtained from (+)-7 as described for (−)-7 in 86% yield after purification on column chromatography on silica gel using hexanes/EtOAc (6:1 then 3:1). Spectral data were consistent with those recorded for 31a.

Example A24

(3aR,4S,7aR)-Octahydrobenzofuran-4-yl (4-nitrophenyl) carbonate (31c). The title compound was obtained from (−)-12 as described for (−)-7 in 83% yield after purification by column chromatography on silica gel using hexanes/EtOAc (8:1 to 6:1). TLC: R$_f$=0.7 (hexanes/EtOAc=3:1); $^1$H NMR (CDCl$_3$, 400 MHz) δ 8.28 (d, J=9.2 Hz, 2H), 7.39 (d, J=9.2 Hz, 2H), 5.07 (m, 1H), 4.13-4.05 (m, 2H), 3.90 (q, J=8.2 Hz, 1H), 2.72 (m, 1H), 2.10-2.00 (m, 2H), 1.90-1.68 (m, 4H), 1.55-1.45 (m, 1H), 1.34-1.23 (m, 1H); C NMR (CDCl$_3$, 100 MHz) δ 155.4, 151.9, 145.2, 125.2, 121.7, 77.7, 77.1, 66.5, 41.2, 27.0, 26.2, 25.4, 18.0.

Example A25

((4S,4aR,7aS)-Octahydrocyclopenta[b]pyran-4-yl) (4-nitrophenyl) carbonate (31d). The title compound was obtained from (−)-18 as described for (−)-7 in 85% yield after purification by column chromatography on silica gel using hexanes/CH$_2$Cl$_2$/THF (4:1:0 then 4:1:0.1) as the eluent. TLC: R$_f$=0.31 (hexanes/EtOAc=1:1); $^1$H NMR (CDCl$_3$, 400 MHz) δ 8.28 (d, J=9.1 Hz, 2H), 7.38 (d, J=9.1 Hz, 2H), 5.21 (m, 1H), 4.00 (ddd, J=1.8, 4.7, 12.0 Hz, 1H), 3.93 (dt, J=2.5, 2.7 Hz, 1H), 3.43 (dt, J=2.1, 12.0 Hz, 1H), 2.36 (m, 1H), 2.04-1.82 (m, 4H), 1.82-1.62 (m, 4H); $^{13}$C NMR (CDCl$_3$, 100 MHz) δ 155.5, 151.9, 145.3, 125.3, 121.8, 80.7, 77.3, 65.0, 43.7, 32.6, 26.3, 22.3, 21.7.

Example A26

(3aR,4S,7aR)-Octahydro-1H-inden-4-yl (4-nitrophenyl) carbonate (31e). The title compound was obtained from (−)-19 as described for (−)-7 in 90% yield after purification by column chromatography on silica gel using hexanes/EtOAc (20:1 to 10:1) as the eluent. $^1$H NMR (CDCl$_3$, 400 MHz) δ 8.27 (d, J=9.1 Hz, 2H), 7.38 (d, J=9.1 Hz, 2H), 5.05 (m, 1H), 2.41 (m, 1H), 2.05 (m, 1H), 1.98-1.24 (m, 11H), 1.05 (dq, J=3.4, 12.7 Hz, 1H); $^{13}$C NMR (CDCl$_3$, 100 MHz) δ 155.7, 151.9, 145.2, 125.2, 121.8, 80.7, 42.8, 40.2, 31.3, 26.6, 25.7, 23.4, 22.4, 21.3.

Example A27

(4S,4aS,7aR)-Hexahydro-2H-furo[3,4-b]pyran-4-yl (4-nitrophenyl)carbonate (31f). The title was obtained from (−)-25 as described for (−)-7 in >99% yield following column chromatography purification on silica gel using hexanes/EtOAc (3:1 then 2:1) as the eluent. $^1$H NMR (CDCl$_3$, 400 MHz) δ 8.29 (d, J=9.1 Hz, 2H), 7.38 (d, J=9.1 Hz, 2H), 5.32 (m, 1H), 4.20-3.88 (m, 6H), 3.50 (m, 1H), 2.81 (m, 1H), 2.10-1.90 (m, 2H).

Example A28

[(3aS,5R,7aR)-Hexahydro-2H-furo[2,3-b]pyran-5-yl]-(4-nitrophenyl)carbonate (31g). The title compound was obtained from 30 as described for (−)-7 in 70% yield. Purified and separated from the 5-epi diastereoisomer following flash column chromatography on silica gel using hexanes/EtOAc (3:1, 2:1, then 1:1) as the eluent. Amorphous solid (70% from a 5:1 mixture of diastereoisomers). TLC: R$_f$=0.16 (hexanes/EtOAc=2:1); $^1$H NMR(C$_6$D$_6$, 800 MHz) δ 7.64 (d, J=9.0 Hz, 2H), 6.69 (d, J=9.0 Hz, 2H), 4.76 d, J=3.6 Hz, 1H), 4.35 (m, 1H), 4.02 (dt, J=3.8, 8.6 Hz, 1H), 3.94 (dt, J=2.8, 13.0 Hz, 1H), 3.60 (q, J=8.0 Hz, 1H), 3.12 (dd, J=2.0, 13.0 Hz), 2.04 (m, 1H), 1.67 (dq, J=3.1, 15.1 Hz, 1H), 1.50 (m, 1H), 1.46-1.38 (m, 2H); $^{13}$C NMR (C$_6$D6, 200 MHz) δ 154.9, 151.9, 145.2, 124.9, 121.2, 100.7, 72.0, 67.4, 63.8, 35.9, 27.9, 27.3.

Example A29

(3aS,4S,7aR)-Hexahydro-2H-furo[2,3-b]pyran-4-yl-(2S,3R)-4-(N-isobutyl-4-methoxyphenyl sulfonamido)-3-hydroxy-1-phenylbutan-2-yl carbamate (35a). Sulfonamide isostere 32 (42 mg, 0.08 mmol) was dissolved in a 30% TFA solution in CH$_2$Cl$_2$ (3 mL), the solution was stirred at 23° C. for 2 h after which the solvent was evaporated under reduced pressure. The corresponding Boc-deprotected intermediate (0.08 mmol) was then diluted in dry acetonitrile (0.8 mL) at 0° C. under argon and Et$_3$N (0.3 mL, 2 mmol) was added. A solution of activated carbonate 31a (18.6 mg, 0.06 mmol) in acetonitrile or THF (0.5 mL) was then added to the mixture. The reaction was stirred at 23° C. until completion was reached (2-3 days). The solution was then evaporated in vacuo and the resulting residue purified by flash chromatography on silica gel using hexanes/EtOAc (2:1 then 1:1) as the eluent to afford the inhibitor 35a as a amorphous solid (19.8 mg, 55%). TLC R$_f$=0.35 (hexanes/EtOAc=1:1); $^1$H NMR (CDCl$_3$, 300 MHz) δ 7.71 (d, J=8.9 Hz, 2H), 7.33-7.17 (m, 5H), 6.97 (d, J=8.9 Hz, 2H), 5.05-4.90 (m, 1H), 4.93 (d, J=3.6 Hz, 1H), 4.84 (d, J=8.4 Hz, 1H), 4.15 (dt, J=2.4, 9.0 Hz, 1H), 3.87 (s, 3H), 3.98-3.76 (m, 4H), 3.31 (t, J=11.7 Hz, 1H), 3.22-2.90 (m, 4H), 2.90-2.78 (m, 2H), 2.48-2.32 (m, 1H), 1.96-1.25 (m, 5H), 0.92 (d, J=6.6 Hz, 3H), 0.87 (d, J=6.6 Hz, 3H); $^{13}$C NMR (CDCl$_3$, 75 MHz) δ 163.1, 155.5, 137.6, 129.8, 129.4, 128.4, 126.5, 114.3, 101.1, 72.9, 70.2, 68.5, 60.9, 58.9, 55.7, 54.9, 53.8, 43.5, 35.6, 27.3, 26.2, 22.3, 20.2, 19.9. HRMS-ESI (m/z): [M+Na]$^+$ calcd for C$_{29}$H$_{40}$N$_2$O$_8$NaS, 599.2403. found 599.2406.

Example A30

(3aS,4S,7aR)-Hexahydro-2H-furo[2,3-b]pyran-4-yl (2S,3R)-4-(4-amino-N-isobutylphenylsulfonamido)-3-hydroxy-1-phenylbutan-2-yl carbamate (36). The title compound was obtained from 31a and sulfonamide isostere 33 as described for inhibitor 35a, in 64% yield following purification by flash-chromatography using CHCl$_3$/2% MeOH as the eluent. TLC: R$_f$=0.45 (hexanes/EtOAc=1:3); $^1$H NMR (CDCl$_3$, 300 MHz) δ 7.55 (d, J=8.7 Hz, 2H), 7.32-7.16 (m, 5H), 6.67 (d, J=8.7 Hz, 2H), 4.97 (m, 1H), 4.93 (d, J=3.4 Hz, 1H), 4.85 (d, J=8.7 Hz, 1H), 4.20-4.11 (m, 3H), 3.92-3.80 (m, 5H), 3.31 (dt, J=2.2, 11.9 Hz, 1H), 3.15 (dd, J=8.1, 15.2 Hz, 1H), 3.05 (dd, J=4.2, 14.1 Hz, 1H), 3.01-2.80 (m, 3H), 2.75 (dd, J=6.6, 13.4 Hz, 1H), 2.40 (m, 1H), 1.97-1.60 (m, 4H), 1.46 (m, 1H), 0.92 (d, J=6.6 Hz, 3H), 0.87 (d, J=6.6 Hz, 3H); $^{13}$C NMR (CDCl$_3$, 100 MHz) δ 155.5, 150.7, 137.7, 129.5, 129.5, 128.4, 126.5, 126.2, 114.1, 101.1, 72.8, 70.1, 68.5, 60.8, 58.9, 54.8, 53.8, 43.4, 35.5, 27.3, 26.2, 22.2, 20.2, 19.9; HRMS-ESI (m/z): [M+Na]$^+$ calcd for C$_{29}$H$_{39}$N$_3$O$_7$NaS, 584.2406. found 584.2402.

Example A31

(3aS,4S,7aR)-Hexahydro-2H-furo[2,3-b]pyran-4-yl (2S,3R)-3-hydroxy-4-(4-(hydroxymethyl)-N-isobutylphenylsulfonamido)-1-phenylbutan-2-yl carbamate (37). The title compound was obtained from 31a and sulfonamide isostere 34 as described for inhibitor 35a in 72% yield following purification by flash-chromatography on silica gel using CHCl$_3$/2% MeOH as the eluent. Amorphous solid. TLC: R$_f$=0.23 (hexanes/EtOAc=1:2); $^1$H NMR (CDCl$_3$, 400 MHz) δ 7.76 (d, J=8.1 Hz, 2H), 7.52 (d, J=8.1 Hz, 2H), 7.32-7.17 (m, 5H), 4.96 (m, 1H), 4.93 (d, J=3.2 Hz, 1H), 4.85 (d, J=8.5 Hz, 1H), 4.80 (s, 2H), 4.15 (t, J=8.5 Hz, 1H), 3.92-3.80 (m, 4H), 3.70 (s, 1H), 3.31 (t, J=11.6 Hz, 1H), 3.16 (dd, J=8.0, 15.0 Hz, 1H), 3.10-2.95 (m, 3H), 2.88-2.76 (m, 2H), 2.41 (m, 1H), 2.04 (m, 1H), 1.95-1.78 (m, 2H), 1.76-1.56 (m, 2H), 1.47 (m, 1H), 0.93 (d, J=6.6 Hz, 3H), 0.88 (d, J=6.6 Hz, 1H); $^{13}$C NMR (CDCl$_3$, 100 MHz) δ 155.6, 146.2, 137.6, 137.1, 129.4 128.5, 127.6, 127.1, 126.5, 101.1, 72.8, 70.2, 68.4, 64.2, 60.8, 58.8, 54.9, 53.7, 43.4, 35.5, 27.3, 26.2, 22.2, 20.1, 19.9; HRMS-ESI (m/z): [M+Na]$^+$ calcd for C$_{29}$H$_{40}$N$_2$O$_8$NaS, 599.2403. found 599.2414.

Example A32

(3aR,4R,7aS)-Hexahydro-2H-furo[2,3-b]pyran-4-yl ((2S,3R)-3-hydroxy-4-(N-isobutyl-4-methoxyphenylsulfonamido)-1-phenylbutan-2-yl)carbamate (35b). The title compound was obtained from 31b and sulfonamide isostere 32 in 65% yield as described for inhibitor 35a, following purification by column chromatography on silica gel using hexanes/EtOAc (3:1 then 1.5:1) as the eluent. White amorphous solid. TLC: $R_f$=0.44 (hexanes/EtOAc=1:1); $^1$H NMR (CDCl$_3$, 400 MHz) δ 7.70 (d, J=8.9 Hz, 2H), 7.31-7.26 (m, 2H), 7.25-7.20 (m, 3H), 6.98 (d, J=8.9 Hz, 2H), 5.00 (m, 1H), 4.97 (d, J=2.7 Hz, 1H), 4.88 (d, J=8.0 Hz, 1H), 4.17 (t, J=7.7 Hz, 1H), 3.99-3.72 (m, 6H), 3.87 (s, 3H), 3.31 (dt, J=1.9, 12.0 Hz, 1H), 3.13 (dd, J=8.4, 15.0 Hz, 1H), 3.08-2.84 (m, 4H), 2.79 (dd, J=6.7, 13.4 Hz, 1H), 2.53 (m, 1H), 2.00 (m, 1H), 1.83 (m, 1H), 1.73 (m, 1H), 1.68-1.54 (m, 2H); $^{13}$C NMR (CDCl$_3$, 100 MHz) δ 163.1, 155.7, 137.7, 129.8, 129.5, 128.5, 126.5, 114.3, 101.2, 72.6, 70.2, 68.4, 60.8, 58.7, 55.6, 55.1, 53.7, 43.6, 35.3, 27.3, 26.2, 22.5, 20.1, 19.9; HRMS-ESI (m/z): [M+Na]$^+$ calcd for C$_{29}$H$_{40}$N$_2$O$_8$NaS, 599.2403. found 599.2407.

Example A33

(3aR,4S,7aR)-Octahydrobenzofuran-4-yl (2S,3R)-3-hydroxy-4-(N-isobutyl-4-methoxyphenylsulfonamido)-1-phenylbutan-2-yl carbamate (35c). The title compound was obtained from 31c and sulfonamide isostere 32 in 75% yield as described for inhibitor 35a, following purification by column chromatography on silica gel using hexanes/EtOAc (3:1 then 2.5:1) as the eluent. TLC: $R_f$=0.39 (hexanes/EtOAc=1:1); $^1$H NMR (CDCl$_3$, 400 MHz) δ 7.72 (d, J=8.9 Hz, 2H), 7.311-7.16 (m, 5H), 6.98 (d, J=8.9 Hz, 2H), 4.83 (m, 2H), 3.95-3.75 (m, 5H), 3.87 (s, 3H), 3.68 (q, J=8.1 Hz, 1H), 3.14 (dd, J=8.4, 15.2 Hz, 1H), 3.08 (dd, J=4.1, 14.1 Hz, 1H), 3.05-2.99 (m, 1H), 2.96 (dd, J=8.4, 13.4 Hz, 1H), 2.87-2.75 (m, 2H), 2.35 (m, 1H), 1.83 (m, 1H), 1.70-1.40 (m, 7H), 1.20 (m, 1H), 0.92 (d, J=6.6 Hz, 3H), 0.87 (d, J=6.6 Hz, 3H); $^{13}$C NMR (CDCl$_3$, 100 MHz) δ 163.0, 156.1, 137.7, 129.7, 129.5, 129.4, 128.4, 126.4, 114.3, 73.0, 71.8, 66.6, 58.8, 55.6, 54.7, 53.7, 41.2, 35.6, 27.3, 27.2, 27.0, 25.7, 20.1, 19.9, 17.7; HRMS-ESI (m/z): [M+Na]$^+$ calcd for C$_{30}$H$_{42}$N$_2$O$_7$NaS, 597.2610. found 597.2621.

Example A34

(4S,4aR,7aS)-Octahydrocyclopenta[b]pyran-4-yl ((2S,3R)-3-hydroxy-4-(N-isobutyl-4-methoxyphenylsulfonamido)-1-phenylbutan-2-yl)carbamate (35d). The title compound was obtained from 31d and sulfonamide isostere 32 in 81% yield as described for inhibitor 35a, following purification by column chromatography on silica gel using hexanes/EtOAc (3:1 then 2.5:1) as the eluent. TLC: $R_f$=0.58 (hexanes/EtOAc=1:1); $^1$H NMR (CDCl$_3$, 400 MHz) δ 7.70 (d, J=8.9 Hz, 2H), 7.30-7.17 (m, 5H), 6.96 (d, J=8.9 Hz, 2H), 4.94 (m, 1H), 4.81 (d, J=8.1 Hz, 1H), 3.86 (s, 3H), 3.90-3.76 (m, 4H), 3.33 (t, J=11.9 Hz, 1H), 3.13 (dd, AB, J=8.3, 15.0 Hz, 1H), 3.08-2.91 (m, 3H), 2.85 (m, 1H), 2.79 (dd, J=6.8, 13.5 Hz, 1H), 2.04 (m, 1H), 1.81 (m, 2H), 1.76-1.64 (m, 3H), 1.64-1.49 (m, 3H), 0.90 (d, J=6.6 Hz, 3H), 0.86 (d, J=6.6 Hz, 3H); $^{13}$C NMR (CDCl$_3$, 100 MHz) δ 163.0, 156.0, 137.7, 129.8, 129.4, 128.4, 126.4, 114.3, 80.5, 72.7, 71.7, 65.2, 58.7, 55.6, 54.8, 53.7, 44.1, 35.6, 32.5, 27.2, 26.6, 22.0, 21.6, 20.1, 19.8; HRMS-ESI (m/z): [M+Na]$^+$ calcd for C$_{30}$H$_{42}$N$_2$O$_7$S, 597.2610. found 597.2612.

Example A35

(3aR,4S,7aR)-Octahydro-1H-inden-4-yl-(2S,3R)-3-hydroxy-4-(N-isobutyl-4-methoxyphenylsulfonamido)-1-phenylbutan-2-yl carbamate (35e). The title compound was obtained from 31e and sulfonamide isostere 32 as described for inhibitor 35a. Following preliminary purification by flash-chromatography using hexanes/CH$_2$Cl$_2$:THF (8:1:1) as the eluent, the inhibitor was obtained as a mixture of unseparable isomeric compounds. Compound 35e was derivatized into the corresponding N,O-isopropylidene compound by treatment of 35e (20 mg) with 2,2-dimethoxypropane (0.1 mL) and a catalytic amount of pTSA (1.5 mg) in dry CH$_2$Cl$_2$ (1 mL) for 8 h at 23° C. After neutralization with Et$_3$N, the organic phase was evaporated to dryness. Following a quick silica gel column (hexanes/EtOAc=8:1), the resulting inhibitor was purified by HPLC: Preparative HPLC column Sunfire$^{PM}$ Prep C18 OBD, 30×100 mm, Eluent: MeOH/H$_2$O 85:15 (30 min) then 90:10 (15 min), flow 15 mL·min$^{-1}$, R$_t$=42 min. The isopropylidene derivative was then obtained as a colorless oil (24 mg). The product was then taken into MeOH (2 mL), pTSA.H$_2$O (36 mmol, 1.5 mg) was added and the resulting solution was refluxed for 6 h. After neutralization with a few drops of Et$_3$N, the solution was evaporated and the residue purified by column chromatography on silica gel using hexanes/CH$_2$Cl$_2$/HF (8:1:1) to give inhibitor 35e (15 mg, 43% from 31e). TLC: $R_f$=0.35 (hexanes/EtOAc=5:1); $^1$H NMR (CDCl$_3$, 400 MHz) δ 7.71 (d, J=8.9 Hz, 2H), 7.32-7.18 (m, 5H), 6.97 (d, J=8.9 Hz, 2H), 4.79 (m, 1H), 4.70 (d. J=8.1 Hz, 1H), 3.90 (m, 1H), 3.87 (s, 3H), 3.81 (m, 1H), 3.18-3.02 (m, 3H), 2.98-2.82 (m, 2H), 2.78 (dd, J=6.6, 13.2 Hz, 1H), 2.10 (m, 1H), 1.90 (m, 1H), 1.82 (m, 1H), 1.74-1.19 (m, 11H), 0.95 (m, 1H), 0.90 (d, J=6.6 Hz, 3H), 0.86 (d, J=6.6 Hz, 3H); $^{13}$C NMR (CDCl$_3$, 100 MHz) δ 163.0, 156.4, 137.7, 129.9, 129.5, 129.4, 128.5, 126.4, 114.3, 74.9, 72.8, 58.8, 55.6, 54.8, 53.8, 43.1, 39.9, 35.7, 31.3, 27.2, 26.9, 26.1, 23.5, 22.2, 21.3, 20.1, 19.9; HRMS-ESI (m/z): [M+Na]$^+$ calcd for C$_{31}$H$_{44}$N$_2$O$_6$NaS, 595.2818. found 595.2816.

Example A36

(4S,4aS,7aR)-Hexahydro-2H-furo[3,4-b]pyran-4-yl ((2S,3R)-3-hydroxy-4-(N-isobutyl-4-methoxyphenylsulfonamido)-1-phenylbutan-2-yl)carbamate (35f). The title compound was obtained from 31f and sulfonamide isostere 32 in 75% yield as described for inhibitor 35a, following purification by column chromatography using hexanes/EtOAc (3:1 then 2.5:1) as the eluent. TLC: $R_f$=0.24 (hexanes/EtOAc=1:1); $^1$H NMR (CDCl$_3$, 800 MHz) δ 7.70 (d, J=8.8 Hz, 2H), 7.30 (m, 2H), 7.24-7.20 (m, 3H), 6.97 (d, J=8.8 Hz, 2H), 5.05 (m, 1H), 4.83 (d, J=8.5 Hz, 1H), 4.03 (t, J=3.2 Hz, 1H), 3.96 (m, 1H), 3.87 (s, 3H), 3.87 (s, 3H), 3.88-3.81 (m, 5H), 3.62 (t, J=8.3 Hz, 1H), 3.39 (t, J=11.5 Hz, 1H), 3.14 (dd, J=8.4, 15.0 Hz, 1H), 3.02 (dd, J=4.0, 14.1 Hz, 1H), 2.99-2.94 (m, 2H), 2.84 (dd, J=8.7, 14.1 Hz, 1H), 2.77 (dd, J=6.6, 13.4 Hz, 1H), 2.51 (m, 1H), 1.81 (m, 1H), 1.78 (dq, J=4.5, 12.4 Hz, 1H), 1.71 (dd, J=5.4, 12.4 Hz, 1H), 0.91 (d J=6.6 Hz, 3H), 0.87 (d, J=6.6 Hz, 3H); $^{13}$C NMR (CDCl$_3$, 200 MHz) δ 163.0, 155.5, 137.5, 129.6, 129.45, 129.38, 128.5, 126.6, 114.3, 78.4, 74.4, 72.6, 70.0, 66.1, 64.9, 58.8, 55.6, 54.9, 53.7, 42.7, 35.4, 27.2, 26.9, 20.1, 19.8; HRMS-ESI (m/z): [M+Na]$^+$ calcd for C$_{29}$H$_{40}$N$_2$O$_8$S, 599.2403. found 599.2397.

Example A37

(3aS,5R,7aR)-Hexahydro-2H-furo[2,3-b]pyran-5-yl ((2S,3R)-3-hydroxy-4-(N-isobutyl-4-methoxyphenylsulfonamido)-1-phenylbutan-2-yl)carbamate (35g). The title compound was obtained from 31g and sulfonamide isostere 32 in 86% yield as described for inhibitor 35a, following purification by column chromatography on silica gel using hexanes/EtOAc (gradient 3:1 to 1.5:1) as the eluent. TLC: $R_f$=0.33 (hexanes/EtOAc=1:1); $^1$H NMR (CDCl$_3$, 400 MHz) δ 7.72 (d, J=8.9 Hz, 2H), 7.32-7.26 (m, 2H), 7.25-7.17

(m, 3H), 6.98 (d, J=8.9 Hz, 2H), 4.98 (d, J=3.5 Hz, 1H), 4.89 (d, J=8.7 Hz, 1H), 4.54 (m, 1H), 4.11 (dt, J=3.5, 8.3 Hz, 1H), 3.87 (s, 3H), 3.90-3.77 (m, 4H), 3.74 (m, 1H), 3.56 (d, J=12.7 Hz, 1H), 3.12 (dd, J=8.5, 15.1 Hz, 1H), 3.09-2.91 (m, 3H), 2.84 (dd, J=8.5, 14.1 Hz, 1H), 2.79 (dd, J=6.8, 13.4 Hz, 1H), 2.08 (m, 1H), 2.04-1.93 (m, 2H), 1.90-1.76 (m, 3H), 0.91 (d, J=6.6 Hz, 3H), 0.87 (d, J=6.6 Hz, 3H); $^{13}$C NMR (CDCl$_3$, 100 MHz) δ 163.4, 155.7, 137.6, 129.7, 129.5, 128.5, 126.5, 114.4, 101.0, 72.5, 68.0, 67.1, 65.4, 58.8, 55.6, 54.9, 53.8, 36.2, 35.8, 28.3, 27.8, 27.2, 20.1, 19.9; HRMS-ESI (m/z): [M+Na]$^+$ calcd for $C_{29}H_{40}N_2O_8NaS$, 599.2403. found 599.2397.

EXAMPLE

As mentioned above, and without being bound by theory, preliminary modeling suggested that a hexahydrofuropyranol (−)-7 ligand may interact with backbone atoms and residues in the protease S2-site. All inhibitors in Table 1 were evaluated in enzyme inhibitory assays following a protocol described by Toth and Marshall.[36] Inhibitors that showed potent $K_i$ values, were further evaluated through in vitro antiviral assays. As can be seen, inhibitor 35a, with Tp-THF (−)-7 exhibited an enzyme $K_1$ value of 2.7 μM. Antiviral activity of 35a and other inhibitors were determined in MT-2 human-T-lymphoid cells exposed to HIV-$1_{LAI}$.[19] As shown, 35a seems to show antiviral potency (IC$_{50}$=0.5 nM), comparable to PIs 1a and 1b. The bicyclic ring stereochemistry of the P$_2$ ligand appears to be important, as inhibitor 35b, with enantiomeric ligand (+)-7, seems to display a significant reduction in enzyme inhibitory potency (>20-fold increase in $K_i$) as well as antiviral activity (ID$_{50}$=19 nM).

TABLE 1

Enzymatic Inhibitory and Antiviral Activity of Compounds 35a-g, 36, and 37.

| Entry | Inhibitor | $K_i$ (nM) | IC$_{50}$ (μM)$^a$ |
|---|---|---|---|
| 1 | 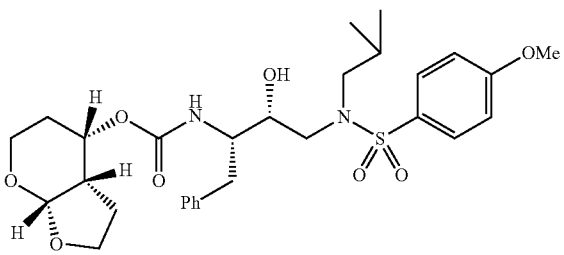<br>35a | 0.0027 | 0.0005 |
| 2 | 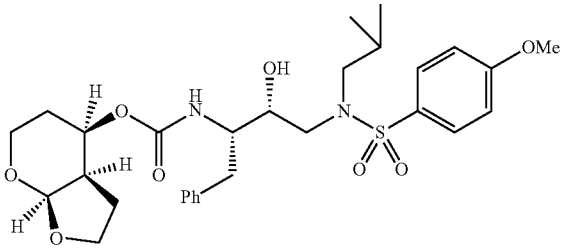<br>35b | 0.068 | 0.019 |
| 3 | 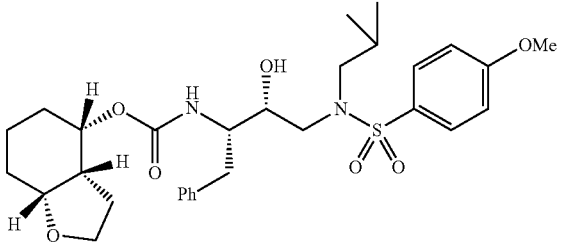<br>35c | 0.005 | 0.008 |

TABLE 1-continued

Enzymatic Inhibitory and Antiviral Activity of Compounds 35a-g, 36, and 37.

| Entry | Inhibitor | $K_i$ (nM) | $IC_{50}$ (μM)[a] |
|---|---|---|---|
| 4 | 35d | 1.43 | — |
| 5 | 35e | 9 | >1 μM |
| 6 | 35f | 5.3 | >1 μM |
| 7 | 35g | 0.11 | — |
| 8 | 36 | 0.010 | 0.0065 |

TABLE 1-continued

Enzymatic Inhibitory and Antiviral Activity of Compounds 35a-g, 36, and 37.

| Entry | Inhibitor | $K_i$ (nM) | $IC_{50}$ (μM)[a] |
|---|---|---|---|
| 9 | 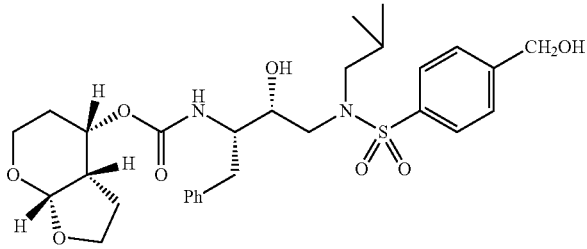 37 | 0.085 | 0.0045 |

[a]Values are means of at least two experiments.
[b]Human T-lymphoid (MT-2) cells (2 × 10³) were exposed to 100 TCID$_{50}$s of HIV-1$_{LAI}$ and cultured in the presence of each PI, and IC$_{50}$ values were determined using the MTT assay. The IC$_{50}$ values of amprenavir (APV), saquinavir (SQV), and indinavir (IDV) were 0.03 μM, 0.015 μM, and 0.03 μM, respectively.

To probe the importance of the cyclic ether oxygens in the bicyclic structure of (−)-7, inhibitors 35c-e were synthesized and evaluated. As shown, inhibitor 35c, with a cyclohexane ring in place of the tetrahydropyran ring, only displayed a 2-fold reduction in $K_i$-values but a 16-fold decrease in antiviral activity compared to inhibitor 35a. A more dramatic loss of enzymatic potency was observed with compound 35d with a cyclopentane ring in place of a THF ring in the P2 ligand. The $K_i$ value dropped to 1.43 nM. Inhibitor 35e, which lacks both cyclic ether oxygens, displayed even lower $K_i$ and no appreciable antiviral activity. Without being bound by theory, those results may indicate an important role of both cyclic ether oxygens in ligand (−)-7. Furthermore, the difference of activity observed between 35a and 35c, may suggest that the O7 oxygen on the THF-ring of (−)-7 exerts a stronger interaction with the enzyme compared to the pyran oxygen. Inhibitor 35f, in which the THF-oxygen of the P$_2$ ligand is located at a vicinal position, also exhibited a substantial loss of potency (i.e. $K_i$=5.3 nM) and no antiviral activity. These results seem to corroborate previous observations with the bis-THF ligand in PIs 1-2. The THF-oxygen in (−)-7 likely has a stronger hydrogen bonding interaction with the Asp29 backbone NH, and may form a weak hydrogen bond with Asp30, in the S$_2$ subsite of the HIV protease. The position of the urethane oxygen on the bicyclic ligand in inhibitor 35g has been investigated. This has resulted in a substantial loss of protease inhibitory activity. Furthermore, the potency enhancing effect of the 7p-THF ligand with various hydroxyethyl sulfonamide isosteres to give inhibitor 36 and 37 was examined. The 4-methoxy sulfonamide derivative 35a appears to be the most potent inhibitor in the series comparable to inhibitor 2. However, the 4-amino derivative 36 exhibited very comparable enzyme inhibitory and antiviral potency similar to 1a.

Inhibitor 35a was examined for its activity against a panel of multidrug-resistant HIV-1 variants and compared it with that of other clinically available PIs including 1a. The results are shown in Table 2. All inhibitors seem to show high antiviral activity against an HIV-1 clinical strain isolated from a drug-naïve patient (wild-type).[19] Compound 35a appears to display the most potent activity with an IC$_{50}$ of 1.9 nM. When tested against multidrug-resistant HIV-1 virus, compound 35a seems to have retained high activity to all variants with IC$_{50}$ values ranging from 2.6-27.5 nM. In contrast, other inhibitors, except 1a, seem to exhibit loss of activity. Interestingly, 1a and 35a seem to show similar fold-change of IC$_{50}$ against most multidrug-resistant HIV strains. The results may indicate that 35a is highly active against multidrug-resistant HIV-1 variants. This inhibitor outperformed the clinically available PIs with high antiviral activity and seems to compare well with 1a, which currently stands as the leading PI for the treatment of drug-resistant HIV infection.

TABLE 2

Comparison of the antiviral activity of 35a and other PIs against multidrug resistant clinical isolates in PHA-PBMs cells

| | EC$_{50}$ (μM) | | | |
|---|---|---|---|---|
| Virus | 35a | ATV | LPV | DRV |
| HIV-1$_{ERS104pre}$ (X4) | 0.0019 ± 0.0015 | 0.0027 ± 0.0006 | 0.031 ± 0.004 | 0.004 ± 0.001 |
| HIV-1$_{MDR/B}$ (X4) | 0.0145 ± 0.0001 (8) | 0.470 ± 0.007 (174) | >1 (>32) | 0.034 ± 0.008 (9) |
| HIV-1$_{MDR/C}$ (X4) | 0.0037 ± 0.0018 (2) | 0.039 ± 0.003 (14) | 0.437 ± 0.004 (14) | 0.009 ± 0.005 (2) |
| HIV-1$_{MDR/G}$ (X4) | 0.0026 ± 0.0004 (1) | 0.019 ± 0.008 (7) | 0.181 ± 0.023 (6) | 0.026 ± 0.009 (7) |
| HIV-1$_{MDR/TM}$ (X4) | 0.0275 ± 0.0055 (14) | 0.075 ± 0.003 (28) | 0.423 ± 0.082 (14) | 0.022 ± 0.015 (6) |

TABLE 2-continued

Comparison of the antiviral activity of 35a and other PIs against multidrug resistant clinical isolates in PHA-PBMs cells

| Virus | EC$_{50}$ (µM) | | | |
|---|---|---|---|---|
| | 35a | ATV | LPV | DRV |
| HIV-1$_{MDR/MM}$ (R5) | 0.0050 ± 0.0023 (3) | 0.205 ± 0.024 (76) | 0.762 ± 0.115 (25) | 0.017 ± 0.005 (4) |
| HIV-1$_{MDR/ISL}$ (R5) | 0.0275 ± 0.0009 (14) | 0.293 ± 0.099 (109) | >1 (>32) | 0.023 ± 0.005 (6) |

The amino acid substitutions identified in the protease-encoding region of HIV-1$_{ERS104pre}$, HIV-1$_B$, HTV-1$_C$, HIV-1$_G$, HIV-1$_{TM}$, HIV-1$_{MM}$, HIV-1$_{ISL}$ compared to the consensus type B sequence cited from the Los Alamos database include L63P; L10I, K14R, L33I, M36I, M46I, F53I, K55R, I62V, L63P, A71V, G73S, V82A, L90M, I93L; L10I, I15V, K20R, L24I, M36I, M46L, I54V, I62V, L63P, K70Q, V82A, L89M; L10I, V11I, T12E, I15V, L19I, R41K, M46L, L63P, A71T, V82A, L90M; L10I, K14R, R41K, M46L, I54V, L63P, A71V, V82A, L90M; I93L; L10I, K43T, M46L, I54V, L63P, A71V, V82A, L90M, Q92K; and L10I, L24I, I33F, E35D, M36I, N37S, M46L, I54V, R57K, I62V, L63P, A71V, G73S, V82A, respectively.
IIIV-1$_{ERS104pre}$ served as a source of wild-type IIIV-1.
The EC$_{50}$ values were determined by using PHA-PBMs as target cells and the inhibition of p24 Gag protein production by each drug was used as an endpoint.
The numbers in parentheses represent the fold changes of EC$_{50}$ values for each isolate compared to the EC$_{50}$ values for wild-type HIV-1$_{ERS104pre}$. All assays were conducted in duplicate, and the data shown represent mean values (±1 standard deviations) derived from the results of two or three independent experiments.

In order to obtain molecular insights into the enzyme-inhibitor interactions of 35a in the protease active site, an active model of 35a was created. Inhibitor 35a was modeled starting from the X-ray crystal structure of 1b. The conformation of 35a was optimized using the MMFF94 force field,[37] as implemented in Molecular Operating Environment (version 2009.10, Chemical Computing Group, Montreal). The modeled structure maintains the important binding interactions (hydroxyl group with Asp25 and Asp25' carboxylates; cyclic ether oxygens with Asp29 and Asp30 backbone NH groups; methoxy oxygen with the Asp30' backbone NH bond; carbonyl oxygen and sulfonamide oxygen with a water molecule binding to Ile50 and Ile50') that are observed in the crystal structure of 1b-bound HIV-1 protease.

Thus, in one embodiment, described herein is structure-based design of novel HIV-1 protease inhibitors incorporating a stereochemically defined 4-hexahydrofuropyranol-derived urethanes as the P2-ligand. In one aspect, the inhibitors were designed to make extensive interactions including hydrogen bonding with the protein backbone of the HIV-1 protease active site. In another embodiment, described herein are inhibitors that appear to show excellent enzyme inhibitory activity and antiviral potency. In one aspect, this antiviral potency may be comparable to that of approved protease inhibitors. In another embodiment, the inhibitors described herein appear to show excellent activity against multi-PI-resistant variants. In another embodiment, structure activity studies are described herein, which may indicate that the stereochemistry of the Tp-THF ligand and position of its oxygens may be important to the ligand's high enzyme affinity. Without being bound by theory, it seems from the data herein that both oxygens of the hexahydro-Tp-THF ligand appear to interact with the Asp29 and Asp30 backbone NH's similar to the bis-THF ligand oxygens, and that the extra methylene unit in the Tp-THF ligand appears to fill in the hydrophobic pocket in the S2-site more effectively in comparison with the bis-THF in 1a.

While certain embodiments of the present invention have been described and/or exemplified above, it is contemplated that considerable variation and modification thereof are possible. Accordingly, the present invention is not limited to the particular embodiments described and/or exemplified herein.

The following publications, and each additional publication cited herein, are incorporated herein by reference in their entirety.

1. Conway, B. HAART in Treatment-experienced Patients in the 21st Century: the Audacity of Hope. *Future Virol.* 2009, 4, 39-41.
2. Bartlett, J. A.; DeMasi, R.; Quinn, J.; Moxham, C.; Rousseau, F. Overview on the Effectiveness of Triple Combination Therapy in Antiretroviral-naive HIV-1 Infected Adults. *AIDS* 2001, 15, 1369-1377.
3. Walensky, R. P.; Paltiel, A. D.; Losina, E.; Mercincavage, L. M.; Schackman, B. R.; Sax, P. E.; Weinstein, M. C.; Freedberg, K. A. The Survival Benefits of AIDS Treatment in the United States. *J. Infec. Dis.* 2006, 194, 11-19.
4. Sepkowitz, K. A. AIDS—The First 20 Years. *N. Engl. J. Med.* 2001, 344, 1764-1772.
5. Palella, F. J. Jr.; Delaney, K. M.; Moorman, A. C.; Loveless, M. O.; Fuhrer, J.; Satten, G. A.; Aschman, D. J.; Holmberg, S. D. Declining Morbidity and Mortality among Patients with Advanced Human Immunodeficiency Virus Infection. *N. Engl. J. Med.* 1998, 338, 853-860.
6. De Clercq, E. Anti-HIV drugs: 25 compounds approved within 25 years after the discovery of HIV. *Int. J. Antimicrob. Agents.* 2009, 307-320.
7. Pillay, D.; Bhaskaran, K.; Jurriaans, S.; Prins, M.; Masquelier, B.; Dabis, F.; Gifford, R.; Nielsen, C.; Pedersen, C.; Balotta, C.; Rezza, G.; Ortiz, M.; de Mendoza, C.; Kucherer, C.; Poggensee, G.; Gill, J.; Porter, K. The Impact of Transmitted Drug Resistance on the Natural History of HIV Infection and Response to First-line Therapy. *AIDS* 2006, 20, 21-28.
8. Grabar, S.; Pradier, C.; Le Corfec, E.; Lancar, R.; Allavena, C.; Bentata, M.; Berlureau, P.; Dupont, C.; Fabbro-Peray, P.; Poizot-Martin, I.; Costagliola, D. Factors Associated with Clinical and Virological Failure in Patients Receiving a Triple Therapy Including a Protease Inhibitor. *AIDS* 2000, 14, 141-149.
9. Little, S. J.; Holte, S.; Routy, J. P.; Daar, E. S.; Markowitz, M.; Collier, A. C.; Koup, R. A.; Mellors, J. W.; Connick, E.; Conway, B.; Kilby, M.; Wang, L.; Whitcomb, J. M.; Hellmann, N. S.; Richman, D. D. Antiretroviral-drug Resistance among Patients Recently Infected with HIV. *N. Engl. J. Med.* 2002, 347, 385-394.
10. Grant, R. M.; Hecht, F. M.; Warmerdam, M.; Liu, L.; Liegler, T.; Petropoulos, C. J.; Hellmann, N. S.; Chesney, M.; Busch, M. P.; Kahn, J. O. Time Trends in Primary HIV-1 Drug Resistance among Recently Infected Persons. *J. Am. Med. Assoc.* 2002, 288, 181-188.
11. Hue, S.; Gifford, R. J.; Dunn, D.; Fernhill, E.; Pillay, D. On behalf of the UK Collaborative group on HIV Drug Resistance. Demonstration of Sustained Drug-Resistant Human Immunodeficiency Virus Type 1 Lineages Circulating among Treatment-Naive Individuals. *J. Virol.* 2009, 83, 2645-2654.

12. Lucas, G. M. Antiretroviral Adherence, Drug resistance, Viral Fitness and HIV Disease Progression: a Tangled Web is Woven. *J. Antimicrob. Chemother.* 2005, 55, 413-416.
13. Spaltenstein, A.; Kazmierski, W. M.; Miller, J. F.; Samano, V. Discovery of Next Generation Inhibitors of HIV Protease. *Curr. Top. Med. Chem.* 2005, 5, 1589-1607.
14. Ghosh, A. K.; Sridhar, P. R.; Kumaragurubaran, N.; Koh, Y.; Weber, I. T.; Mitsuya, H. Bis-Tetrahydrofuran: A Privileged Ligand for Darunavir and a New Generation of HIV-Protease Inhibitors That Combat Drug-Resistance. *ChemMedChem* 2006, 1, 939-950.
15. Ghosh, A. K.; Sridhar, P. R.; Leshchenko, S.; Hussain, A. K.; Li, J.; Kovalevsky, A. Yu.; Walters, D. E.; Wedekind, J. E.; Grum-Tokars, V.; Das, D.; Koh, Y.; Maeda, K.; Gatanaga, H.; Weber, I. T.; Mitsuya, H. Structure-based Design of Novel HIV-1 Protease Inhibitors to Combat Drug Resistance. *J. Med. Chem.* 2006, 49, 5252-5261.
16. Ghosh, A. K.; Xu, C.-X.; Rao, K. V.; Baldridge, A.; Agniswamy, J.; Wang, Y.-F.; Weber, I. T.; Aoki, M.; Miguel, S. G. P.; Amano, M.; Mitsuya, H. Probing multidrug-resistance/protein-ligand interaction with new oxatricyclic designed ligands in HIV-1 Protease inhibitors. *ChemMedChem* 2010, 5, 1850-1854.
17. FDA approves Darunavir on Jun. 23, 2006: FDA approved new HIV treatment for patients who do not respond to existing drugs. Please see http://www.fda.gov/bbs/topics/NEWS/2006/NEW01395.html.
18. On Oct. 21, 2008, FDA granted traditional approval to Prezista (darunavir), co-administered with ritonavir and with other antiretroviral agents, for the treatment of HIV-1 infection in treatment-experienced adult patients. In addition to the traditional approval, a new dosing regimen for treatment-naïve adult patients was approved.
19. Koh, Y.; Nakata, H.; Maeda, K.; Ogata, H.; Bilcer, G.; Devasamudram, T.; Kincaid, J. F.; Boross, P.; Wang, Y.-F.; Tie, Y.; Volarath, P.; Gaddis, L.; Harrison, R. W.; Weber, I. T.; Ghosh, A. K.; Mitsuya, H. Novel bis-Tetrahydrofuranylurethane-Containing Nonpeptidic Protease Inhibitor (PI) UIC-94017 (TMC114) with Potent Activity against Multi-PI-Resistant Human Immunodeficiency Virus In Vitro. *Antimicrob. Agents Chemother.* 2003, 47, 3123-3129.
20. De Meyer, S.; Azijn, H.; Surleraux, D.; Jochmans, D.; Tahri, A.; Pauwels, R.; Wigerinck, P.; de Bethune, M.-P. TMC114, a Novel Human Immunodeficiency Virus Type 1 Protease Inhibitor Active against Protease Inhibitor-Resistant Viruses, Including a Broad Range of Clinical Isolates. *Antimicrob. Agents Chemother.* 2005, 49, 2314-2321.
21. Lefebvre, E.; Schiffer, C. A. Resilience to Resistance of HIV-1 Protease Inhibitors: Profile of darunavir. *AIDS Rev.* 2008, 10, 131-142.
22. Ghosh, A. K.; Chapsal, B. D.; Weber, I. T.; Mitsuya, H. Design of HIV Protease Inhibitors Targeting Protein Backbone: An Effective Strategy for Combating Drug Resistance. *Acc. Chem. Res.* 2008, 41, 78-86.
23. Tie, Y.; Boross, P. I.; Wang. Y.-F.; Gaddis, L.; Hussain, A. K.; Leshchenko, S.; Ghosh, A. K.; Louis, J. M.; Harrison, R. W.; Weber, I. T. High Resolution Crystal Structures of HIV-1 Protease with a Potent Non-Peptide Inhibitor (UIC-94017) Active against Multi-Drug-Resistant Clinical Strains. *J. Mol. Biol.* 2004, 338, 341-352.
24. King, N. M.; Prabu-Jeyabalan, M.; Nalivaika, E. A.; Wigerinck, P.; de Bethune, M.-P.; Schiffer, C. A. Structural and Thermodynamic Basis for the Binding of TMC114 a Next-Generation Human Immunodeficiency Virus Type 1 Protease Inhibitor. *J. Virol.* 2004, 78, 12012-12021.
25. Kovalevsky, A. Y.; Liu, F.; Leshchenko, S.; Ghosh, A. K.; Louis, J. M.; Harrison, R. W.; Weber, I. T. Ultra-High Resolution Crystal Structure of HIV-1 Protease Mutant Reveals Two Binding Sites for Clinical Inhibitor TMC114. *J. Mol. Biol.* 2006, 363, 161-173.
26. Amano, M.; Koh, Y.; Das, D.; Li, J.; Leschenko, S.; Wang, Y.-F.; Boross, P. I.; Weber, I. T.; Ghosh, A. K.; Mitsuya, H. A Novel Bis-Tetrahydrofuranylurethane-Containing Nonpeptidic Protease Inhibitor (PT), GRL-98065, Is Potent against Multi-PT-Resistant Human Immunodeficiency Virus In Vitro. *Antimicrob. Agents Chemother.* 2007, 51, 2143-2155.
27. (a) Nakashima, H.; Masayuki, S.; Taniguchi, T.; Ogasawara, K. Chiral Preparation of Polyoxygenated Cyclopentanoids. *Synthesis* 2000, 6, 817-823. (b) Laumen, K.; Schneider, M. P. A Facile Chemoenzymatic Route to Optically Pure Building Blocks for Cyclopentanoid Natural Products. *J. Chem. Soc., Chem. Commun.* 1986, 1298-1299.
28. Ishihara, K.; Kurihara, H.; Yamamoto, H. An Extremely Simple, Convenient, and Selective Method for Acylating Primary Alcohols in the Presence of Secondary Alcohols. *J. Org. Chem.* 1993, 58, 3791-3793.
29. Nara, M.; Terashima, S.; Yamada, S. Stereochemical Studies—LVII Synthesis of Optically Active Compounds by the Novel Use of Meso-Compounds-1. Efficient Synthesis of Two Structural Types of Optically Pure Prostaglandin Intermediates. *Tetrahedron* 1980, 36, 3161-3170.
30. Moriarty, R. M.; Bailey, B. R. III.; Prakash, O.; Prakash, I. Capture of Electron-Deficient Species with Aryl Halides. New Syntheses of Hypervalent Iodonium Ylides. *J. Am. Chem. Soc.* 1985, 107, 1375-1378.
31. Müller, P.; Allenbach, Y. F.; Bernardinelli, G. On the Enantioselectivity of Transition Metal-Catalyzed 1,3-Cycloadditions of 2-Diazocyclohexane-1,3-diones. *Helv. Chim. Acta* 2003, 86, 3164-3178.
32. Ferrie, L.; Reymond, S.; Capdevielle, P.; Cossy, J. Formal Chemoselective Synthesis of Leucascandrolide A. *Org. Lett.* 2007, 9, 2461-2464.
33. Tsantali, G. G.; Takakis, I. M. Expeditious Copper-Catalyzed Conjugate 1,4-Addition of Bromo[2-(1,3-dioxolan-2-yl)ethyl]magnesium to, -Cycloalkenones and Subsequent Tranformations. *J. Org. Chem.* 2003, 68, 6455-6458.
34. Shen, Z.-L.; Geo, G.-L.; Loh, T.-P. Indium-Copper and Indium-Silver Mediated Barbier Grignard Type Alkylation Reaction of Aldehydes using Unactivated Alkyl Halides in Water. *J. Org. Chem.* 2008, 73, 3922-3924.
35. Ghosh, A. K.; Leschenko, S.; Noetzel, M. Stereoselective Photochemical 1,3-Dioxolane Addition to 5-Alkoxymethyl-2(5H)-furanone: Synthesis of Bis-Tetrahydrofuranyl Ligand for HIV Protease Inhibitor UIC-94017 (TMC-114). *J. Org. Chem.* 2004, 69, 7822-7829.
36. Toth, M. V.; Marshall, G. R. A Simple Continuous Fluorometric Assay for HIV Protease. *Int. J. Pept. Protein Res.* 1990, 36, 544-550.
37. Halgren, T. A. MMFF VII. Characterization of MMFF94, MMFF94s, and Other Widely Available Force Fields for Conformational Energies and for Intermolecular-Interaction Energies and Geometries. *J. Comput. Chem.* 1999, 20, 730-748.
38. Hodgson, D. M.; Lee, G. P.; Marriot, R. E.; Thompson, A. J.; Wisedale, R.; Witherington, J. Isomerisations of Cycloalkene- and Bicycloalkene-derived Achiral Epoxides by Enantioselective α-deprotonation. *J. Chem. Soc. Perkin Trans.* 1, 1998, 2151-2161.

Examples Table 2
The scoring in the biological screens is as follows:
| HIV-1 Inhibitory Potency | | | |
|---|---|---|---|
| $K_i$: | | $IC_{50}$: | |
| >10 nM | – | >1000 nM | – |
| <10 nM | + | <1000 nM | + |
| <1 nM | ++ | <100 nM | ++ |
| <0.1 nM | +++ | <10 nM | +++ |
| | | <1 nM | +++ |
| Ex. No. | Inhibitor | $K_i$ | $IC_{50}{}^a$ |
|---|---|---|---|
| 1 | 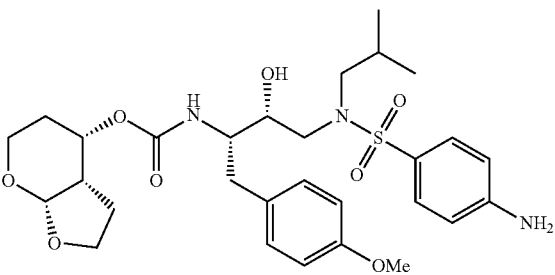 [SMILES: COc1ccc(C[C@H](NC(=O)O[C@H]2CCO[C@H]3OCC[C@H]32)[C@H](O)CN(CC(C)C)S(=O)(=O)c2ccc(N)cc2)cc1] | ++ | +++ |
| 2 | 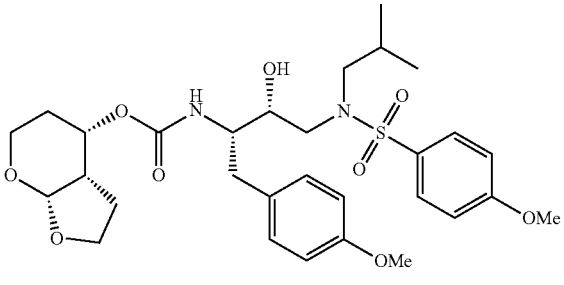 [SMILES: COc1ccc(C[C@H](NC(=O)O[C@H]2CCO[C@H]3OCC[C@H]32)[C@H](O)CN(CC(C)C)S(=O)(=O)c2ccc(OC)cc2)cc1] | +++ | ++++ |
| 3 | 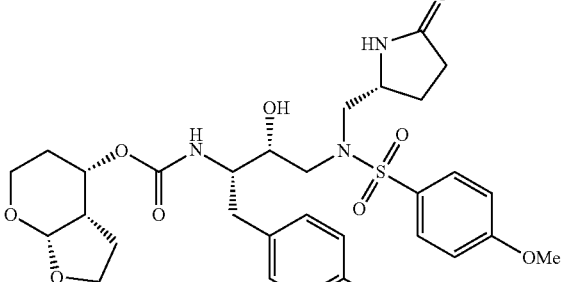 | +++ | + |
| 4 | 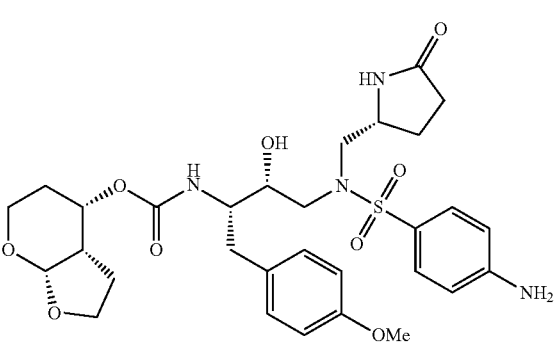 [SMILES: COc1ccc(C[C@H](NC(=O)O[C@H]2CCO[C@H]3OCC[C@H]32)[C@H](O)CN(C[C@H]2CCC(=O)N2)S(=O)(=O)c2ccc(N)cc2)cc1] | + | – |
[a] Values are means of at least two experiments. The $IC_{50}$ values of amprenavir (APV), saquinavir (SQV), and indinavir (IDV) were 0.03 μM, 0.015 μM, and 0.03 μM, respectively.

Further examples of general preparations of the inhibitors of the invention are described as follows:

Scheme 1: Synthesis of key Tp-THF intermediate

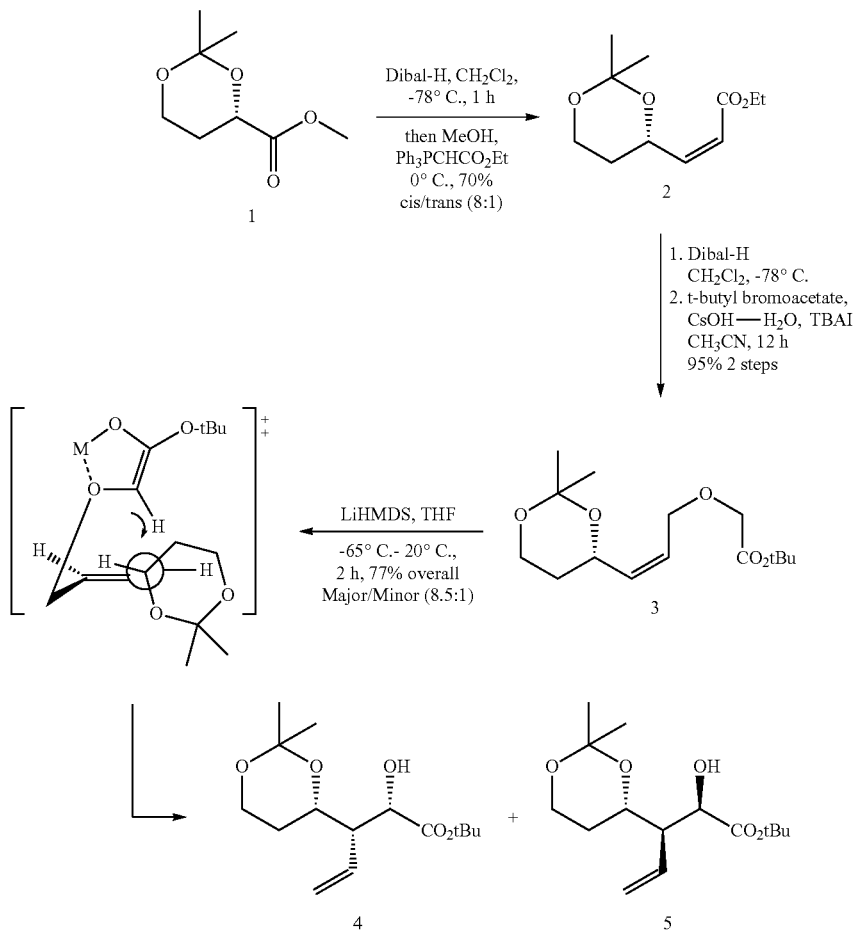

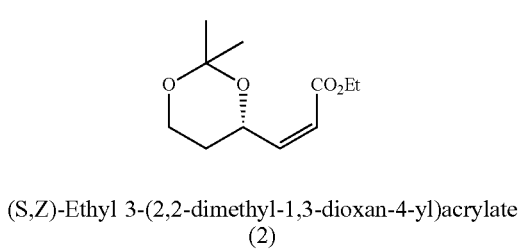

(S,Z)-Ethyl 3-(2,2-dimethyl-1,3-dioxan-4-yl)acrylate (2)

To a solution of (S)-methyl 2,2-dimethyl-1,3-dioxane-4-carboxylate (1) (3.0 g, 17.2 mmol) in $CH_2Cl_2$ (100 mL) at −78° C. was added Dibal-H (1M in $CH_2C2$, 19.0 mL). The solution was allowed to warm slowly to −50° C. over 1 h. Upon completion, methanol (100 mL) was added to the reaction followed by $Ph_3PCHCO_2Et$ (4.20 g, 12.1 mmol) and the reaction was allowed to stir for 1 h at 0° C. The reaction was concentrated under vacuum and the solid was washed with $CH_2Cl_2$ (3×20 mL) and concentrated under vacuum. The crude mixture was purified on silica gel using 5-10% ethyl acetate/hexanes. The desired product was obtained as a separable mixture of cis/trans (8:1) isomers (2.6 g, 70% yield). Cis-2: $R_f$=0.38 (10% ethyl acetate/hexanes). $[\alpha]_{23}^D$=−12.5 (c 1.01, $CHCl_3$). $^1H$ NMR (300 MHz, Chloroform-d) δ 6.17 (dd, J=11.4 Hz, 7.1 Hz, 1H), 5.76 (d, J=11.7 Hz, 1H), 5.52 (q, J=7.1 Hz, 1H), 4.24-4.10 (q, J=7.5 Hz, 2H), 4.10-3.97 (m, 1H), 3.90-3.76 (d, J=16 Hz, 1H), 1.67-1.61 (m, 2H), 1.50 (s, 3H), 1.39 (s, 3H), 1.28 (t, J=7.1 Hz, 3H). $^{13}C$ NMR (75 MHz, $CDCl_3$) δ 165.7, 149.7, 119.2, 98.3, 66.8, 60.2, 59.5, 30.0, 29.4, 19.3, 14.2. trans-2: $R_f$=0.20 (10% ethyl acetate/hexanes). $^1H$ NMR (400 MHz, Chloroform-d) δ 6.86 (dd, J=15.7 Hz, 7.1 Hz, 1H), 6.04 (d, J=11.8 Hz, 1H), 4.27-4.08 (q, J=7.5 Hz, 2H), 4.01 (ddt, J=14.9 Hz, 8.3 Hz, 2.7 Hz, 1H), 3.90-3.76 (m, 1H), 3.76-3.59 (m, 1H), 1.82-1.60 (m, 1H), 1.60-1.50 (m, 1H), 1.48 (s, 3H), 1.41 (s, 3H), 1.28 (t, J=7.1 Hz, 3H). $^{13}C$ NMR (101 MHz, $CDCl_3$) δ 166.4, 147.0, 120.3, 108.6, 98.5, 67.8, 60.3, 59.5, 30.4, 29.7, 19.0, 14.1.

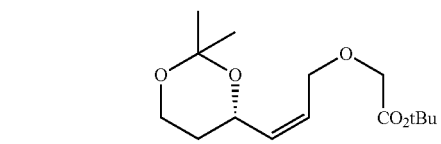 [SMILES: CC(C)(C)OC(=O)COC/C=C\[C@@H]1CCOC(C)(C)O1]

(S,Z)-t-butyl 2-(3-(2,2-dimethyl-1,3-dioxan-4-yl)allyloxy)acetate (3)

Diisobutyl aluminum hydride (1M in $CH_2Cl_2$, 27.5 mL, 27.5 mmol,) was slowly added to a cold solution (−78° C.)

of 2 (12.0 g, 56.0 mmol) in dichloromethane (200 mL). The solution was allowed to stir for 15 min at −78° C. A saturated solution of Rochelle's salt (50 mL) was added and the reaction mixture was warmed to room temperature. The reaction was stirred until both layers were clear. The organic layer was separated and the aqueous layer was extracted with dichloromethane (3×15 mL). The organic layers were combined, washed with brine and dried over MgSO$_4$. The solid was filtered out and the organic layer was concentrated under vacuum. The crude mixture was purified on silica gel using 20% ethyl acetate/hexanes to obtain the desired allyl alcohol (9.4 g, 98% yield) as a colorless oil. R$_f$=0.27 (40% ethyl acetate/hexanes). $^1$H NMR (300 MHz, Chloroform-d) δ 5.78-5.74 (m, 1H), 5.50 (ddt, J=11.2 Hz, 7.0 Hz, 1.3 Hz, 1H), 4.78-4.62 (m, 1H), 4.24 (dd, J=12.9 Hz, 7.0 Hz, 1H), 4.20-4.08 (m, 1H), 4.00 (td, J=12.2 Hz, 2.8 Hz, 1H), 3.83 (ddd, J=11.8 Hz, 5.4 Hz, 1.5 Hz, 1H), 2.47-2.27 (m, 1H), 1.86-1.63 (m, 1H), 1.55 (s, 3H), 1.48-1.45 (m, 1H), 1.39 (s, 3H). $^{13}$C NMR (75 MHz, CDC$_3$) δ 132.3, 131.5, 98.5, 65.7, 59.6, 58.8, 31.2, 29.9, 19.1

To a round bottom flask charged with activated molecular sieves (6.0 g) was added a solution of substrate, (S,Z)-3-(2,2-dimethyl-1,3-dioxan-4-yl)prop-2-en-1-ol (9.0 g, 52.0 mmol) in acetonitrile (150 mL), followed by t-butylbromoacetate (9.90 mL, 67.2 mmol), tetrabutylammonium iodide (2.0 g, 5.2 mmol) and cesium hydroxide monohydrate (13.1 g, 78.0 mmol) at room temperature. The reaction was allowed to stir for 6 h. The solid was filtered out and the solvent was concentrated under vacuum; the residue was purified by flash column chromatography (5% ethyl acetate/hexanes) to afford 3 (14.4 g, 97% yield) as a colorless oil. R$_f$=0.57 (30% ethyl acetate/hexanes). [α]$_{23}^D$=+22.9 (c 1.29, CHCl$_3$) $^1$H NMR (300 MHz, Chloroform-d) δ 5.72-5.51 (m, 2H), 4.77-4.65 (m, 1H), 4.26-4.09 (m, 2H), 4.01 (dd, J=17.3, 2.6 Hz, 1H), 3.93 (d, J=3.6 Hz, 2H) 3.82 (ddd, J=11.8 Hz, 5.4 Hz, 1.4 Hz, 1H), 1.79-1.65 (m, 1H), 1.48 (s, 3H), 1.46 (s, 10H), 1.37 (s, 3H). $^{13}$C NMR (75 MHz, CDCl$_3$) δ 169.5, 134.1, 127.7, 98.3, 81.5, 67.6, 66.8, 65.5, 59.5, 31.1, 29.9, 28.0, 19.1.

(2S,3S)-t-Butyl 3-((S)-2,2-dimethyl-1,3-dioxan-4-yl)-2-hydroxypent-4-enoate (4)

A solution of LiHMDS (84.0 mL 1.0 M in THF, 84.0 mmol) was added to a cold solution (−60° C.) of 3 (12.0 g, 42.0 mmol) in THF (250 mL) (LiHMDS was added at a rate that did not exceed −50° C.). The reaction mixture was allowed to warm slowly to −20° C. over 2 h. The reaction was quenched with saturated ammonium chloride (10 mL) extracted with ethyl acetate (3×20 mL) after warming to room temperature. The organic layers were combined washed with brine, dry over anhydrous MgSO$_4$ and reduce under vacuum. The residue was purified with a 5-10% gradient of ethyl acetate/hexanes. The desired 4 (9.0 g, 77% yield, 8.5:1 mixture of diastereomers) was obtained as a colorless oil. R$_f$=0.30 (20% ethyl acetate/hexanes). [α]$_{23}^D$=+ 5.8 (c 1.02, CHCl$_3$); $^1$H NMR (300 MHz, Chloroform-d) δ 5.86-5.74 (m, 1H), 5.26-5.01 (dd, J=12.1 Hz, 2H), 4.23 (t, J=4.23 Hz, 1H), 4.12 (m, 1H), 3.99 (td, J=11.9 Hz, 2.8 Hz, 1H), 3.86 (dd, J=11.1 Hz, 4.9 Hz, 1H), 3.15 (d, J=4.2 Hz, 1H), 2.48-2.45 (m, 1H), 1.90-1.64 (m, 1H), 1.45 (d, J=4.7 Hz, 13H), 1.35 (s, 3H). $^{13}$C NMR (75 MHz, CDCl$_3$) δ 172.8, 133.1, 119.3, 98.5, 82.5, 71.0, 69.3, 59.8, 52.2, 29.8, 28.6, 28.1, 19.2.

5

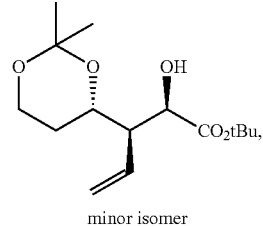

minor isomer

R$_f$=0.37 (20% ethyl acetate/hexanes) [α]$^{23}$=−17.5 (c 1.8, CHCl$_1$H NMR (300 MHz, Chloroform-d) δ 5.69-5.51 (m, 1H), 5.20-5.04 (m, 2H), 4.46 (dd, J=5.1 Hz, 2.2 Hz, 1H), 4.08-3.80 (m, 3H), 2.94 (d, J=5.2 Hz, 1H), 2.40 (td, J=9.8 Hz, 2.2 Hz, 1H), 1.53-1.34 (m, 17H). $^{13}$C NMR (75 MHz, CDCl$_3$) δ 174.1, 132.1, 119.9, 98.6, 82.4, 69.0, 67.0, 60.1, 53.9, 30.0, 29.9 28.1, 19.2.

Scheme 3: Synthesis of substituted Tp-THF analogues

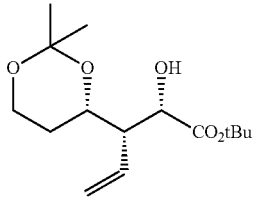 [SMILES: C=C[C@H]([C@@H]1CCOC(C)(C)O1)[C@H](O)C(=O)OC(C)(C)C]

4

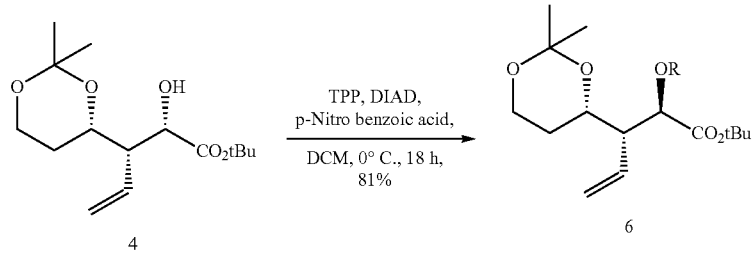

6

R = p-Nitrobenzoate

1. K$_2$CO$_3$/MeOH, 0° C., 1 h, 98%
2. MeI, NaH, THF, 0° C.-23° C., or BnBr, TBAI, NaH, THF, 0° C. -rt, 2 h,

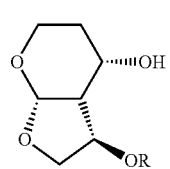
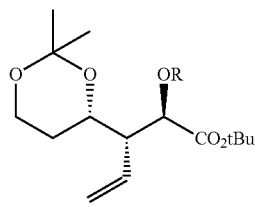

9 R = Me, 70% yield
10 R = Bn, 63% yield

1. LAH, THF, 0° C., 1 h
2. O₃, DMS, then, THF, p-TsOH

7 R = Me, 96% yield
8 R = Bn, 88% yield

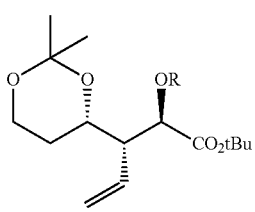

R = p-nitrobenzoate (2R,3R)-1-t-Butoxy-3-((S)-2,2-dimethyl-1,3-dioxan-4-yl)-1-oxopent-4-en-2-yl-4-nitro-benzoate (6)

Into a cold (0° C.) solution of 4 (0.15 g, 0.52 mmol) in THF (10 mL) was added triphenylphosphine (0.55 g, 2.1 mmol) p-nitrophenylbenzoic acid (0.35 g, 2.1 mmol) and diethyl azodicarboxylate (0.95 μL, 2.1 mmol). The reaction was allowed to stir 36 h. The reaction was diluted with ethyl acetate (10 mL) and quenched with a saturated solution of sodium bicarbonate (10 mL). The reaction was extracted with ethyl acetate (3×15 ml). The organic layers were combined, washed with brine and dried over anhydrous sodium sulfate. The solvent was concentrated under vacuum and the crude mixture was purified on silica gel using 5% ethyl acetate/hexanes to obtain 6 (0.21 g, 91%) as a pale yellow solid. $R_f$=0.36 (10% ethyl acetate/hexanes). $[α]_{23}^D$=−0.27 (c 1.1, CHCl₃). ¹H NMR (300 MHz, Chloroform-d) δ 8.36-8.21 (m, 4H), 5.86 (dt, J=17.2 Hz, 10.0 Hz, 1H), 5.32-5.09 (m, 2H), 4.24 (dt, J=11.8 Hz, 2.7 Hz, 1H), 3.97 (td, J=12.0 Hz, 2.8 Hz, 1H), 3.89-3.73 (m, 1H), 2.65 (td, J=9.5 Hz, 2.9 Hz, 1H), 1.93-1.74 (m, 1H), 1.44 (s, 9H), 1.34 (s, 3H), 1.27 (s, 3H). ¹³C NMR (75 MHz, CDCl₃) δ 168.3, 163.8, 150.68, 134.9, 132.3, 130.8, 123.6, 120.4, 98.4, 82.8, 73.6, 66.6, 59.7, 50.9, 29.6, 28.4, 28.0, 18.8.

mmol). The reaction was allowed to stir for 0.5 h. The reaction was quenched with a saturated ammonium chloride (5.0 mL) and the methanol was removed under vacuum. The solution was extracted with ethyl acetate (3×10 mL) and the combined organic layer was combined, washed with brine and dried over anhydrous sodium sulfate. The solvent was removed under vacuum and the residue was purified on silica gel using 10% ethyl acetate/hexanes to obtain the free secondary alcohol (0.28 mg, 99% yield) as a white solid. $R_f$=0.38 (30% ethyl acetate/hexanes). $[α]_{23}^D$=−21.6 (c 1.1, CHCl₃). ¹H NMR (400 MHz, Chloroform-d) δ 5.92 (dt, J=17.2 Hz, 10.0 Hz, 1H), 5.29-5.03 (m, 2H), 4.22 (dt, J=11.8 Hz, 2.8 Hz, 1H), 4.11 (dd, J=8.9 Hz, 6.2 Hz, 1H), 3.95 (td, J=12.1 Hz, 2.8 Hz, 1H), 3.80 (ddd, J=11.7, 5.4, 1.6 Hz, 1H), 3.28 (d, J=9.1 Hz, 1H), 2.32-2.27 (m, 1H), 1.85-1.74 (m, 1H), 1.46 (s, 9H), 1.44 (s, 3H), 1.35 (s, 3H), 1.19 (d, J=13.0 Hz, 1H). ¹³C NMR (100 MHz, CDCl₃) δ 173.1, 134.1, 118.8, 98.5, 82.1, 73.0, 68.6, 59.7, 52.5, 29.7, 28.4, 28.1, 18.9

To a cold (0° C.) solution of (2R,3S)-t-Butyl 3-((S)-2,2-dimethyl-1,3-dioxan-4-yl)-2-hydroxypent-4-enoate (0.12 g, 0.40 mmol) in THF (5 mL) was added sodium hydride (20.0 mg, 0.8 mmol) followed by methyl iodide (50.0 μL, 0.80 mmol). The reaction was allowed to stir for 2 h at 23° C. then quenched with saturated ammonium chloride (5 mL). The reaction mixture was extracted with ethyl acetate (3×10 mL). The organic layers were combined, washed with brine and dried over anhydrous sodium sulfate. The solvent was reduced under vacuum and the residue was purified on silica gel to obtain 7 (0.12 g, 96% yield) as a colorless oil. $R_f$=0.54 (20% ethyl acetate/hexanes). ¹H NMR (300 MHz, Chloroform-d) δ 5.74 (dt, J=17.2 Hz, 10.1 Hz, 1H), 5.22-4.93 (m, 2H), 4.29 (d, J=11.9 Hz, 1H), 3.95 (td, J=12.0 Hz, 2.8 Hz, 1H), 3.83-3.73 (m, 2H), 3.35 (s, 3H), 2.26 (td, J=9.9 Hz, 2.2 Hz, 1H), 1.79-1.71 (m, 1H), 1.43 (s, 9H), 1.41 (s, 3H), 1.35 (s, 3H), 1.19-1.07 (m, 1H). ¹³C NMR (75 MHz, CDCl₃) δ 171.3, 132.9, 119.8, 98.2, 81.5, 80.5, 65.9, 60.0, 58.1, 52.3, 29.8, 28.4, 28.1, 19.1.

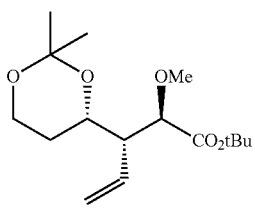 [SMILES: C=C[C@H]([C@@H]1CCOC(C)(C)O1)[C@@H](OC)C(=O)OC(C)(C)C]

(2R,3R)-t-Butyl 3-((S)-2,2-dimethyl-1,3-dioxan-4-yl)-2-methoxypent-4-enoate (7)

To a cold (0° C.) solution of 6 (0.42 g, 0.96 mmol) in methanol was added potassium carbonate (0.16 g, 1.16

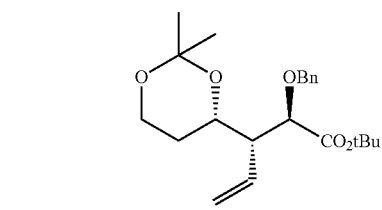 [SMILES: C=C[C@H]([C@@H]1CCOC(C)(C)O1)[C@@H](OCc1ccccc1)C(=O)OC(C)(C)C]

(2R,3R)-t-Butyl 2-(benzyloxy)-3-((S)-2,2-dimethyl-1,3-dioxan-4-yl)pent-4-enoate (8)

Follow the procedure outlined above for compound 7.88% yield. $R_f$=0.70 (20% ethyl acetate/hexanes). ¹H NMR (300 MHz, Chloroform-d) δ 7.43-7.27 (m, 5H), 5.76 (dt, J=17.2 Hz, 10.1 Hz, 1H), 5.24-4.94 (m, 2H), 4.58 (d, J=11.3 Hz, 1H), 4.48-4.28 (m, 2H), 3.99-3.89 (m, 2H), 3.86-3.70 (m, 1H), 2.37 (td, J=10.0 Hz, 2.1 Hz, 1H), 1.82-1.68 (m, 1H), 1.44 (s, 9H), 1.37 (s, 3H), 1.33 (s, 3H) 1.15 (d, J=12.9, 1H). $^{13}$C NMR (75 MHz, CDCl$_3$) δ 171.2, 137.4, 132.8, 128.3, 127.9, 119.9, 98.2, 81.4, 78.4, 72.5, 65.8, 59.9, 52.4, 29.8, 28.3, 28.1, 19.1.

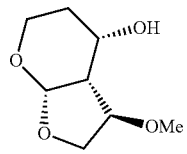 [SMILES: CO[C@H]1CO[C@@H]2OCC[C@H](O)[C@@H]21]

(3R,3aS,4S,7aS)-3-Methoxyhexahydro-2H-furo[2,3-b]pyran-4-ol (9)

To a cold (0° C.) solution of 7 (0.14 mg, 0.47 mmol) in THF (5 mL) was added lithium aluminum hydride (41.0 mg, 1.03 mmol). The reaction was allowed to stir for 1 h at 23° C. after which the reaction was cooled to 0° C. and quenched by adding excess ethyl acetate, 1N NaOH (0.5 mL), H$_2$O (0.5 mL). After a white precipitate formed magnesium sulfate was added and stirred for 15 min. The reaction mixture was filtered and concentrated under vacuum.

The crude mixture was taken up in CHCl$_3$/MeOH (4:1) and a stream of O$_3$ was bubble through the solution at −78° C. until a blue color persisted. Argon was bubbled through the blue solution until the solution became clear. Dimethyl sulfide (0.13 mL, 5.0 eq) was added to the reaction and the mixture was warmed to room temperature and stirred an additional 3 h. To the reaction mixture was added p-TsOH (10 mol %) the mixture was stirred for 18 h at room temperature. The reaction was carefully concentrated and the residue was purified on silica gel (20% ether/hexanes to 50% ether/hexanes) to afford 9.45% yield 2 steps. Rf=0.20 (70% ethyl acetate/hexanes). $^1$H NMR (300 MHz, Chloroform-d) δ 5.06 (d, J=3.8 Hz, 1H), 4.38-4.22 (m, 2H), 4.21-4.13 (m, 1H), 3.94-3.86 (m, 3H), 3.33 (s, 3H), 2.53-2.47 (m, 2H), 1.92-1.76 (m, 1H), 1.76-1.54 (m, 1H). $^{13}$C NMR (75 MHz, CDCl$_3$) δ 101.4, 78.9, 72.2, 66.3, 60.5, 57.9, 51.1, 30.2.

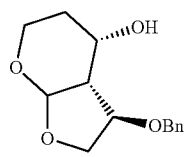

(3R,3aS,4S,7aS)-3-(Benzyloxy)hexahydro-2H-furo[2,3-b]pyran-4-ol (10)

Follow the 2 step procedure outlined above for the formation of the desired P2-ligand. 88% yield. [α]23D=+ 45.0 (c 1.1, CHCl3); Rf=0.22 (60% ethyl acetate/hexanes). 1H NMR (300 MHz, Chloroform-d) δ 7.47-7.18 (m, 5H), 5.05 (d, J=3.7 Hz, 1H), 4.51 (d, J=1.6 Hz, 1H), 4.49-4.36 (m, 1H), 4.26 (dd, J=9.0 Hz, 6.8 Hz, 1H), 4.21-4.06 (m, 1H), 3.93-3.85 (m, 2H), 3.31 (td, J=11.8 Hz, 2.4 Hz, 1H), 2.66-2.54 (m, 1H), 2.49 (bs, 1H), 1.93-1.75 (m, 1H), 1.75- 1.47 (m, 1H). $^{13}$C NMR (75 MHz, CDCl$_3$) δ 137.4, 128.5, 128.0, 128.0, 101.3, 72.7, 72.5, 66.4, 60.6, 51.2, 30.1.

Scheme 4: Synthesis of substituted Tp-THF analogues

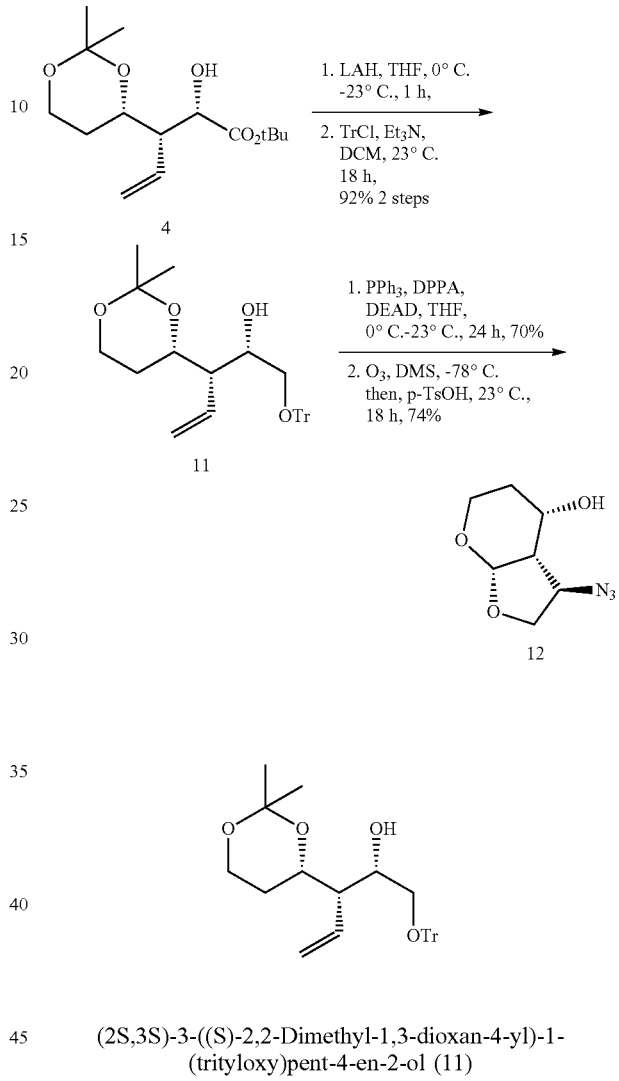

(2S,3S)-3-((S)-2,2-Dimethyl-1,3-dioxan-4-yl)-1-(trityloxy)pent-4-en-2-ol (11)

To a cold (0° C.) solution of 4 (1.50 g, 5.30 mmol) in THF (30 mL) was added lithium aluminum hydride (0.45 g, 11.7 mmol). The reaction was allowed to stir for 1 h at 23° C. after which the reaction was cooled to 0° C. and quenched by adding excess ethyl acetate, 1N NaOH (0.5 mL), H$_2$O (0.5 mL). After a white precipitate formed magnesium sulfate was added and stirred for 15 min. The reaction mixture was filtered and concentrated under vacuum.

The crude 1,2-diol was dissolved in CH$_2$Cl$_2$ (20.0 mL). to that mixture was added triethyl amine (1.6 mL, 11.1 mmol) and triphenylmethyl chloride (1.6 g, 5.83 mmol). The reaction was allowed to stir for 24 h. Upon completion the reaction was concentrated under vacuum and purified on silica gel to obtain 11. (2.20 g, 92% yield) as a white solid. R$_f$=0.30 (20% ethyl acetate/hexanes). [α]$_{23}$D=−1.86 (c 1.5, CHCl$_3$). $^1$H NMR (400 MHz, Chloroform-d) δ 7.48-7.39 (m, 6H), 7.35-7.18 (m, 10H), 5.85 (dt, J=17.4 Hz, 10.1 Hz, 1H), 5.16 (dd, J=10.3 Hz, 2.1 Hz, 1H), 4.99 (dd, J=17.3 Hz, 2.1 Hz, 1H), 4.17-3.98 (m, 2H), 3.93 (td, J=12.1 Hz, 2.7 Hz, 1H), 3.79 (dd, J=11.2 Hz, 4.8 Hz, 1H), 3.21-3.06 (m, 2H), 3.04 (d, J=1.1 Hz, 1H), 2.30 (dt, J=9.8 Hz, 3.3 Hz, 1H), 1.80 (dd, J=12.5 Hz, 5.3 Hz, 1H), 1.30 (d, J=5.5 Hz, 6H), 1.29-1.15 (m, 1H). $^{13}$C NMR (100 MHz, CDCl$_3$) δ 144.0, 128.7, 127.8, 127.0, 119.8, 98.2, 86.5, 73.0, 71.2, 64.9, 59.8, 50.9, 29.8, 28.7, 19.0.

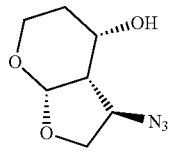 [SMILES: [N-]=[N+]=N[C@H]1CO[C@@H]2OCC[C@H](O)[C@@H]21]

(3R,3aS,4S,7aS)-3-Azidohexahydro-2H-furo[2,3-b]pyran-4-ol (12)

To a solution of 11 (2.2 g, 4.80 mmol) in THF (50.0 mL) at 0° C. was added triphenyl phosphine (5.0 g, 19.2 mmol), diethylazodicarboxylate (3.3 g, 19.2 mmol), Diphenylphosphoryl azide (2.5 g, 9.6 mmol) sequentially. The reaction mixture was stirred at room temperature for 24 h after which it was concentrated under vacuum and purified on silica gel to get the desired azide (1.6 g, 70% yield). R$_f$=0.35 (10% ethyl acetate/hexanes). [α]$_{23}$$^D$=+16.3 (c 1.6, CHCl$_3$). $^1$H NMR (400 MHz, Chloroform-d) δ 7.56-7.39 (m, 6H), 7.38-7.13 (m, 10H), 5.48 (dt, J=17.3 Hz, 10.1 Hz, 1H), 4.96 (dd, J=10.3 Hz, 1.9 Hz, 1H), 4.84 (dd, J=17.3 Hz, 1.8 Hz, 1H), 4.30 (dt, J=11.9 Hz, 2.4 Hz, 1H), 3.98 (td, J=12.1 Hz, 2.7 Hz, 1H), 3.88-3.71 (m, 1H), 3.69-3.64 (m, 1H), 3.38 (dd, J=10.1 Hz, 2.6 Hz, 1H), 3.07 (dd, J=10.0 Hz, 7.9 Hz, 1H), 1.98 (td, J=10.2 Hz, 2.2 Hz, 1H), 1.81-1.59 (m, 1H), 1.49 (s, 3H), 1.35 (s, 3H), 1.20-1.03 (m, 1H). $^{13}$C NMR (100 MHz, CDCl$_3$) δ 143.8, 133.6, 128.6, 127.8, 127.0, 119.6, 98.4, 87.0, 67.2, 65.4, 62.3, 59.9, 50.5, 29.7, 28.4, 18.9.

(S)-4-((3S,4R)-4-azido-5-(trityloxy)pent-1-en-3-yl)-2,2-dimethyl-1,3-dioxane (0.08 g, 0.17 mmol) was taken up in CH$_2$C3/MeOH (20 ml, 4:1) and a stream of O$_3$ was bubble through the solution at −78° C. until a blue color persisted. Argon was bubbled through the blue solution until the solution became clear. Dimethyl sulfide (0.5 mL) was added to the reaction and the mixture was warmed to room temperature and stirred an additional 3 h. To the reaction mixture was added p-TsOH (10 mol %) the mixture was stirred for 18 h at room temperature. The reaction was carefully concentrated and the residue was purified on silica gel (20% ether/hexanes to 50% ether/hexanes) to afford 12, (23.0 mg, 74% yield) as a white solid. R$_f$=0.33 (50% ethyl acetate/hexanes). [α]$_{23}$$^D$=−20.4 (c 1.0, CHCl$_3$). $^1$H NMR (400 MHz, Chloroform-d) δ 5.07 (d, J=3.7 Hz, 1H), 4.42-4.27 (m, 2H), 4.21 (dt, J=10.9 Hz, 5.7 Hz, 1H), 3.90 (ddd, J=12.2 Hz, 4.3 Hz, 2.3 Hz, 1H), 3.83-3.71 (m, 1H), 3.32 (td, J=12.0 Hz, 2.0 Hz, 1H), 2.63-2.45 (m, 2H), 1.79 (ddd, J=13.2 Hz, 3.8 Hz, 1.6 Hz, 1H), 1.69 (td, J=11.6 Hz, 4.5 Hz, 1H). $^{13}$C NMR (100 MHz, CDCl$_3$) δ 101.7, 72.3, 65.5, 60.8, 59.0, 52.01, 29.8.

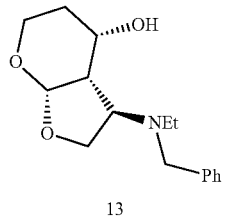

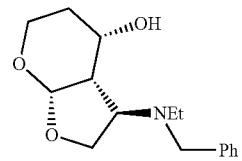

(3R,3aS,4S,7aS)-3-(Benzyl(ethyl)amino)hexahydro-2H-furo[2,3-b]pyran-4-ol (13)

(3R,3aS,4S,7aS)-3-azidohexahydro-2H-furo[2,3-b]pyran-4-ol was dissolved in a solution methanol and placed under argon. 10% Palladium on carbon (10 mol %) was added and the mixture was stirred under a hydrogen balloon for 1 h. Upon completion the reaction was filtered through a plug of silica. The solvent was removed under vacuum and the product was used without further purification.

The crude amino alcohol obtained from the previous step was dissolved in methanol and treated with benzaldehyde (1.0 eq) and sodium triacetoxyborohydride (1.2 eq). The reaction was allowed to stir for 18 h (or until the starting material was consumed). The acetaldehyde (1.5 eq) was added followed by additional sodium triacetoxyborohydride (1.5 eq) and the reaction was allowed to continue for an additional 12 h to give the desired dialkylated amino-Tp-THF ligand. 81% yield. R$_f$=0.34 (5% MeOH/DCM). [α]$_{23}$$^D$=+74.6 (c 1.23, CHCl$_3$). $^1$H NMR (400 MHz, Chloroform-d) δ 7.48-7.12 (m, 5H), 4.91 (d, J=3.6 Hz, 1H), 4.16 (q, J=11.3 Hz, 1H), 4.09-4.04 (m, 2H), 4.03-3.86 (m, 2H), 3.85-3.75 (m, 1H), 3.33 (d, J=13.3 Hz, 1H), 3.23 (td, J=12.4 Hz, 1.6 Hz, 1H), 2.80 (dq, J=14.7 Hz, 7.4 Hz, 1H), 2.66-2.63 (m, 1H), 2.43 (dq, J=13.6 Hz, 6.9 Hz, 1H), 1.76 (dd, J=13.3 Hz, 5.6 Hz, 1H), 1.57-1.42 (m, 1H), 1.12 (t, J=7.1 Hz, 3H). $^{13}$C NMR (100 MHz, CDCl$_3$) δ 137.7, 128.9, 128.6, 127.5, 100.4, 67.9, 64.1, 61.2, 57.9, 54.3, 44.1, 43.9, 30.6, 13.0.

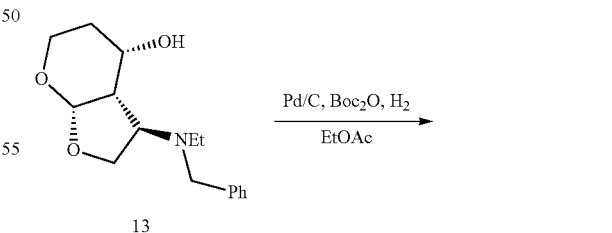

Scheme V: Synthesis of amine substituted Tp-THF ligands

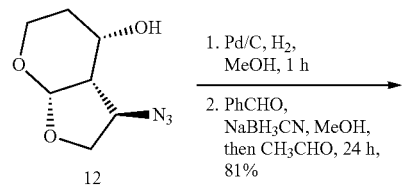

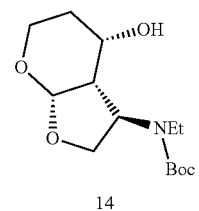

t-Butyl ethyl((3R,3aS,4S,7aS)-4-hydroxyhexahydro-2H-furo[2,3-b]pyran-3-yl)carbamate (14)

To a solution of compound 13 and 10% Pd/C in ethyl acetate was added Boc anhydride (2.0 eq). The mixture was placed under an atmosphere of H₂ for 24 h. 81% yield. ¹H NMR (400 MHz, Chloroform-d) δ 5.10 (d, J=3.5 Hz, 1H), 4.89-4.84 (m, 1H), 4.28 (t, J=9.6 Hz, 1H), 3.93-3.87 (m, 3H), 3.72 (bs, 1H), 3.34-3.21 (m, 2H), 3.08-2.99 (m, 1H), 2.46 (bs, 1H), 1.86-1.82 (m, 1H), 1.78-1.69 (m, 1H), 1.47 (s, 9H), 1.21 (t, J=7.0 Hz, 3H).

General Procedure for the Preparation of Activated Carbonates from Polycyclic P2-Ligands Scheme V: Synthesis of activated Tp-THF ligands

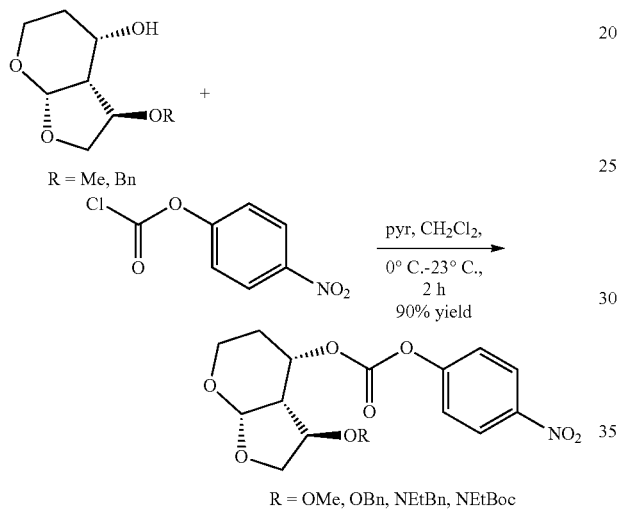

To a solution of the desired Tp-THF alcohol in dry CH₂Cl₂ was added pyridine (2.30 eq). The resulting mixture was cooled to 0° C. under argon and 4-nitrophenylchloroformate (2.20 eq) was added in one portion. The resulting mixture was stirred at 0° C. until completion. The reaction mixture was evaporated to dryness and the residue was purified by flash column chromatography on silica gel using a gradient of 20-40% ethyl acetate/hexanes to afford the desired mixed carbonate.

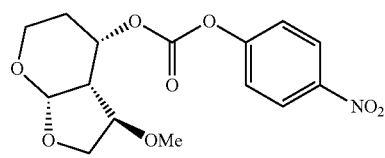 [SMILES: CO[C@H]1CO[C@@H]2OCC[C@H](OC(=O)Oc3ccc([N+](=O)[O-])cc3)[C@@H]21]

(3R,3aR,4S,7aS)-3-Methoxyhexahydro-2H-furo[2,3-b]pyran-4-yl 4-nitrophenyl carbonate (15a)

Follow the general procedure outlined above for the activation of the desired P₂-ligand. 90% yield. R_f=0.29 (40% ethyl acetate/hexanes). ¹H NMR (300 MHz, Chloroform-d) δ 8.27 (d, J=9.1 Hz, 2H), 7.38 (d, J=9.3 Hz, 2H), 5.22-4.97 (m, 2H), 4.36 (dd, J=9.0 Hz, 6.8 Hz, 1H), 4.27-4.22 (m, 1H), 4.07-3.84 (m, 2H), 3.51-3.34 (m, 1H), 3.34 (s, 3H), 2.96-2.91 (m, 1H), 2.06-1.79 (m, 2H). ¹³C NMR (75 MHz, CDCl₃) δ 155.5, 151.5, 145.4, 125.3, 121.7, 101.4, 79.2, 73.7, 72.6, 60.1, 58.0, 48.2, 26.9.

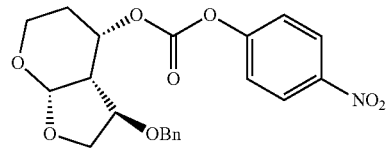 [SMILES: O=C(Oc1ccc([N+](=O)[O-])cc1)O[C@H]1CCO[C@H]2OC[C@H](OCc3ccccc3)[C@H]21]

(3R,3aR,4S,7aS)-3-(Benzyloxy)hexahydro-2H-furo[2,3-b]pyran-4-yl 4-nitrophenyl carbonate (15b)

Follow the general procedure outlined above for the activation of the desired P₂-ligand. 87% yield. R_f=0.35 (40% ethyl acetate/hexanes). ¹H NMR (300 MHz, Chloroform-d) δ 8.11 (d, J=7.1 Hz, 2H), 7.44-7.16 (m, 5H), 7.04 (d, J=7.1 Hz, 2H), 5.27-5.07 (m, 2H), 4.59-4.42 (m, 3H), 4.33 (dd, J=9.1 Hz, 6.9 Hz, 1H), 4.03-3.96 (m, 2H), 3.44-3.36 (m, 1H), 3.09-3.04 (m, 1H), 2.04-1.91 (m, 2H). ¹³C NMR (75 MHz, CDCl₃) δ 155.2, 151.5, 145.1, 137.4, 128.3, 127.9, 125.0, 121.6, 101.3, 77.3, 73.8, 72.9, 60.2, 48.3, 26.8.

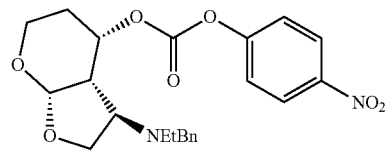

(3R,3aS,4S,7aS)-3-(Benzyl(ethyl)amino)hexahydro-2H-furo[2,3-b]pyran-4-yl 4-nitrophenyl carbonate (15c)

To a solution of the corresponding ligand amino Tp-THF in dry CH₂Cl₂ was added pyridine (2.30 eq). The resulting mixture was cooled to 0° C. under argon and 4-nitrophenylchloroformate (2.20 eq) was added in one portion. The resulting mixture was stirred at 23° C. until the consumption of the alcohol. The reaction mixture was concentrated and the residue was purified by flash column chromatography on silica gel using a gradient of 20-40% ethyl acetate/hexanes to afford the desired ligand-activated carbonate. 77% yield. R_f=0.6 (30% ethyl acetate/hexanes). ¹H NMR (400 MHz, Chloroform-d) δ 8.23 (d, J=9.2 Hz, 2H), 7.32-7.14 (m, 7H), 5.24-5.19 (m, 1H), 5.17 (d, J=3.9 Hz, 1H), 4.08-3.98 (m, 2H), 3.97 (t, J=3.6 Hz, 1H), 3.87 (d, J=4.5 Hz, 1H), 3.75 (d, J=13.7 Hz, 1H), 3.49-3.36 (m, 2H), 3.03-2.98 (m, 1H), 2.62 (p, J=7.2 Hz, 1H), 2.52-2.39 (p, J=6.8 Hz, 1H), 1.98-1.85 (m, 2H), 1.01 (t, J=7.1 Hz, 3H). ¹³C NMR (100 MHz, CDCl₃) δ 155.4, 151.6, 145.3, 139.1, 131.0, 129.1, 128.1, 127.0, 125.2, 121.9, 101.1, 74.6, 66.1, 60.3, 59.1, 53.1, 45.8, 44.5, 26.9, 12.5.

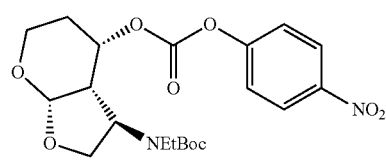

t-Butyl ethyl((3R,3aS,4S,7aS)-4-((4-nitrophenoxy)carbonyloxy)hexahydro-2H-furo[2,3-b]-pyran-3-yl)carbamate (15d)

The mixed carbonate above was obtained following the general procedure outlined above. ¹H NMR (400 MHz, Chloroform-d) δ 8.28 (d, J=9.1 Hz, 2H), 7.38 (d, J=8.7 Hz, 2H), 5.21-5.13 (m, 2H), 4.31 (t, J=8.9 Hz, 1H), 4.03 (dd, J=12.3, 2.6 Hz, 1H), 3.97-3.83 (m, 1H), 3.59-3.22 (m, 3H), 3.07 (bs, 1H), 2.17-2.01 (m, 1H), 2.01-1.89 (m, 1H), 1.46 (s, 9H), 1.18 (bs, 3H).

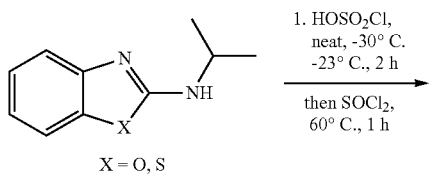

15e: The above mixed carbonate was obtained following the general procedure outlined in J. Med. Chem., 2011, 54, 622-634.

Synthesis of Aryl Sulfonyl Chlorides

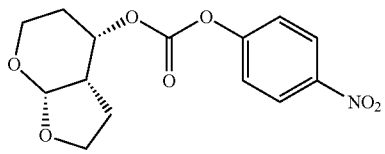 [SMILES: O=C(Oc1ccc([N+](=O)[O-])cc1)O[C@H]1CCO[C@H]2OCC[C@H]21]

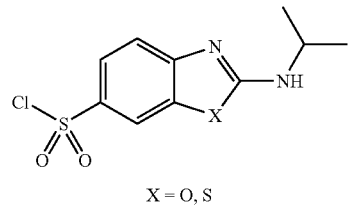

N-isopropylbenzo[d]oxazol-2-amine or N-isopropylbenzo[d]thiazol-2-amine were treated with chlorosulfonic acid (5.0 eq) at −30° C. The reaction was warmed to 23° C. and stirred at that temperature for 3 h. Thionyl chloride (2.0 eq) was added and the reaction was heated to 60° C. for 1 hr. The reaction was cooled to 0° C., diluted with ethyl acetate and washed with water. The organic layer was dried over sodium sulfate and concentrated under vacuum. The residue was dissolved in ethyl acetate and washed with a solution of saturated sodium bicarbonate. The crude sulfonyl chloride was used without further purification (85-90% yield).

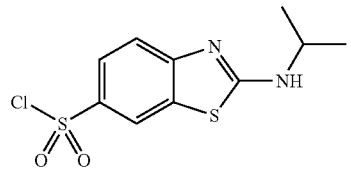 [SMILES: CC(C)Nc1nc2ccc(S(=O)(=O)Cl)cc2s1]

(16a): ¹H NMR (400 MHz, Chloroform-d) δ 8.25 (s, 1H), 7.94 (d, J=8.7 Hz, 1H), 7.61 (d, J=8.7 Hz, 1H), 3.90 (bs, 1H), 1.38 (d, J=6.4 Hz, 6H).

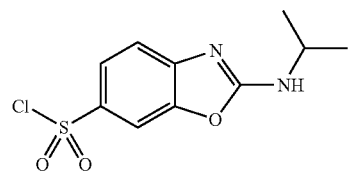 [SMILES: CC(C)Nc1nc2ccc(S(=O)(=O)Cl)cc2o1]

(16b): ¹H NMR (400 MHz, Chloroform-d) δ 7.92 (d, J=1.9 Hz, 1H), 7.89 (s, 3H), 5.63 (s, 1H), 4.17-4.10 (m, 1H), 1.38 (d, J=6.5 Hz, 6H).

Synthesis of the Hydroxyethyl Amine Isosteres

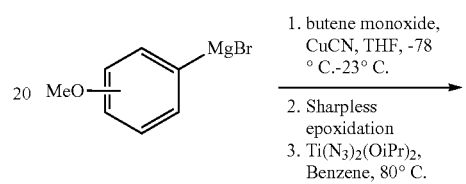

The above azido diols were obtained following the general procedure outlined by Ghosh et al. (J. Med. Chem. 1993, 36, 2300-2310). 50% yield over 3 steps.

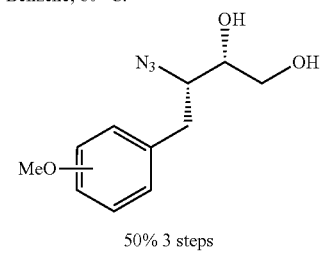

(17a): ¹H NMR (400 MHz, Chloroform-d) δ 7.18 (d, J=8.5 Hz, 2H), 6.87 (d, J=8.4 Hz, 2H), 3.81-3.78 (s, 3H), 3.78-3.76 (m, 1H), 3.76-3.70 (m, 1H), 3.69-3.63 (m, 2H), 2.98 (dd, J=14.2, 3.6 Hz, 1H), 2.79-2.70 (m, 3H).

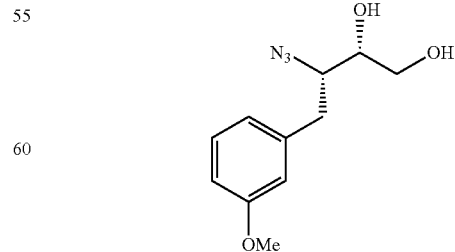

(17b): ¹H NMR (400 MHz, Chloroform-d) δ 7.23 (t, J=7.7 Hz, 1H), 6.91-6.75 (m, 3H), 3.81-3.78 (s, 3H), 3.78-3.76 (m, 1H), 3.76-3.70 (m, 1H), 3.69-3.63 (m, 2H), 2.98 (dd, J=14.2, 3.6 Hz, 1H), 2.79-2.70 (m, 3H).

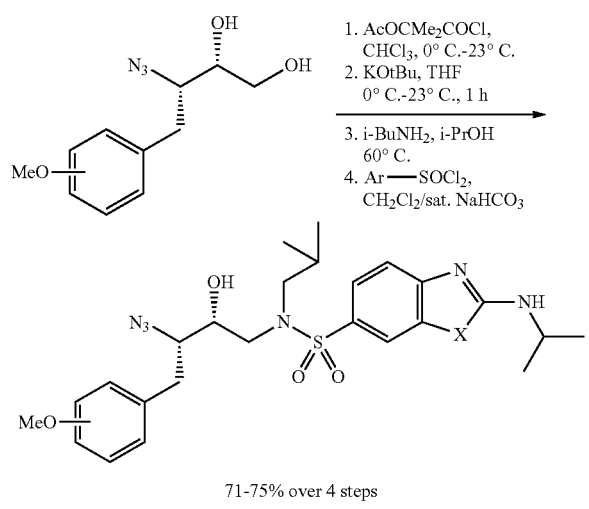

71-75% over 4 steps

X = O, S

The desired isosteres were obtained following the general procedures outlined by Ghosh et al. (J. Med. Chem. 1993, 36, 2300-2310) and Flentge et al. (US 2005-0131042). The desired isosteres were obtained in 71-75% yield over 4 steps.

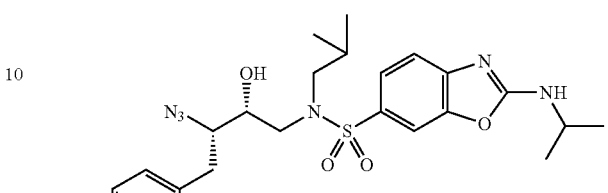

(18a): $^1$H NMR (400 MHz, Chloroform-d) δ 7.70 (d, J=1.5 Hz, 1H), 7.67-7.62 (d, J=8.1 Hz, 1H), 7.42 (d, J=8.3 Hz, 1H), 7.23 (t, J=7.7 Hz, 1H), 6.91-6.75 (m, 3H), 5.37 (d, J=7.7 Hz, 1H), 3.80-3.77 (s, 4H), 3.64-3.59 (m, 2H), 3.27 (dd, J=15.1, 9.4 Hz, 1H), 3.10-3.03 (m, 3H), 2.87-2.69 (m, 2H), 1.86-1.79 (m, 1H), 1.36 (d, J=6.5 Hz, 6H), 0.94 (d, J=6.6 Hz, 3H), 0.88 (d, J=6.6 Hz, 3H).

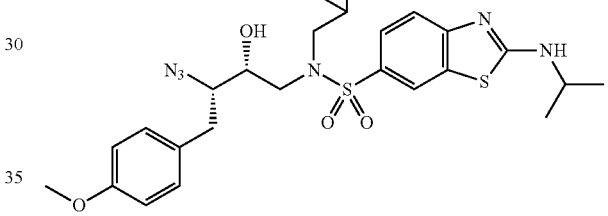

(18b): $^1$H NMR (400 MHz, Chloroform-d) δ 8.04 (d, J=1.7 Hz, 1H), 7.69 (dd, J=8.5, 1.9 Hz, 1H), 7.55 (d, J=8.5 Hz, 1H), 7.22 (t, J=8.1 Hz, 1H), 6.86-6.79 (m, 3H), 5.97 (bs, 1H), 3.93 (bs, 1H), 3.79 (m, 5H), 3.66-3.60 (m, 1H), 3.27 (dd, J=15.2, 9.1 Hz, 1H), 3.13-3.03 (m, 3H), 2.86-2.74 (m, 2H), 1.86-1.80 (m, 1H), 1.34 (d, J=6.4 Hz, 6H), 0.93 (d, J=6.6 Hz, 3H), 0.88 (d, J=6.6 Hz, 3H).

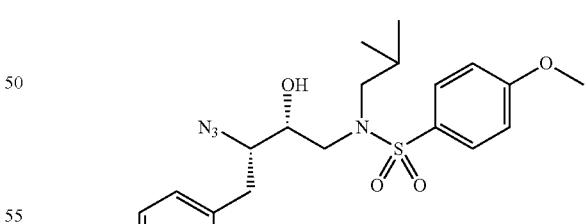

(18c): $^1$H NMR (400 MHz, Chloroform-d) δ 7.69 (s, 1H), 7.64 (dd, J=8.3, 1.7 Hz, 1H), 7.43 (d, J=8.3 Hz, 1H), 7.18 (d, J=8.6 Hz, 2H), 6.86 (d, J=8.6 Hz, 2H), 5.14 (d, J=7.9 Hz, 1H), 3.80 (s, 3H), 3.75 (d, J=7.2 Hz, 1H), 3.58-3.54 (m, 2H), 3.29-3.23 (dd, J=15.2, 9.3 Hz, 1H), 3.08-3.01 (m, 3H), 2.82-2.71 (m, 2H), 1.85-1.75 (m, 1H), 1.36 (d, J=6.5 Hz, 6H), 0.94 (d, J=6.6 Hz, 3H), 0.88 (d, J=6.6 Hz, 3H).

(18d): $^1$H NMR (400 MHz, Chloroform-d) δ 8.03 (d, J=1.7 Hz, 1H), 7.69 (dd, J=8.5, 1.9 Hz, 1H), 7.51 (d, J=8.5 Hz, 1H), 7.15 (d, J=8.6 Hz, 2H), 6.85 (d, J=8.6 Hz, 2H), 5.14 (d, J=7.9 Hz, 1H), 3.80 (s, 3H), 3.75 (d, J=7.2 Hz, 1H), 3.58-3.54 (m, 2H), 3.29-3.23 (dd, J=15.2, 9.3 Hz, 1H), 3.08-3.01 (m, 3H), 2.82-2.71 (m, 2H), 1.85-1.75 (m, 1H), 1.36 (d, J=6.5 Hz, 6H), 0.94 (d, J=6.6 Hz, 3H), 0.88 (d, J=6.6 Hz, 3H).

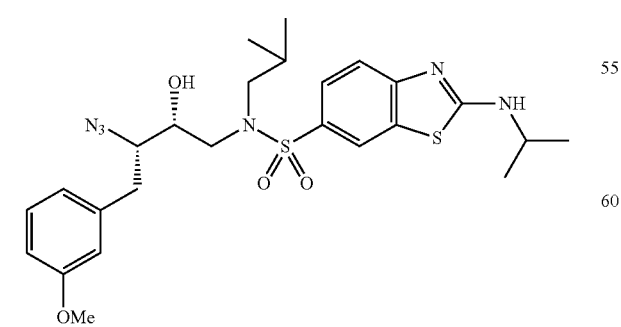

(18e):

General Procedure for the Reduction of Azides 18a-18e

Isosteres 18a-e were reduced following the Staudinger protocol (PPh$_3$, THF/H$_2$O, 23° C., 24 h) to give the corresponding amines 19a-19e, 19g (see 19g for NMR data.).

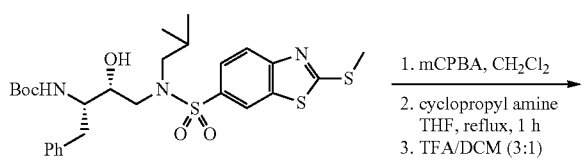

1. mCPBA, CH$_2$Cl$_2$
2. cyclopropyl amine THF, reflux, 1 h
3. TFA/DCM (3:1)

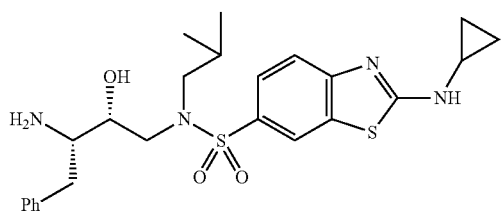

(19f): The above cyclopropyl amine isostere was obtained following the procedures outlined in J. Med. Chem. 2005, 48, 1965-1973. 84% yield over 3 steps. $^1$H NMR (400 MHz, Chloroform-d) δ 8.10 (s, 1H), 7.70 (d, J=8.5 Hz, 1H), 7.48 (d, J=8.5 Hz, 1H), 7.34-7.27 (m, 2H), 7.27-7.17 (m, 3H), 3.84-3.79 (m, 1H), 3.31-3.28 (m, 2H), 3.17-3.14 (m, 1H), 3.06 (dd, J=13.2, 8.2 Hz, 1H), 2.99-2.89 (m, 2H), 2.75-2.70 (m, 1H), 2.51 (dd, J=13.3, 10.1 Hz, 1H), 1.94-1.87 (m, 1H), 0.93 (d, J=6.6 Hz, 5H), 0.89 (d, J=6.6 Hz, 3H), 0.81-0.71 (m, 2H).

Synthesis of Fluorinated Isosteres

The desired azido epoxide was obtained following the general procedures outlined by Ghosh et al. (J. Med. Chem. 1993, 36, 2300-2310) (using the appropriate stating materials).

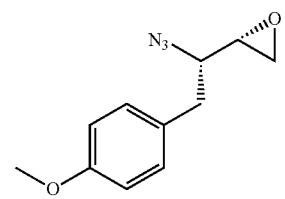 [SMILES: COc1ccc(C[C@H](N=[N+]=[N-])[C@H]2CO2)cc1]

(S)-2-((S)-1-azido-2-(4-methoxyphenyl)ethyl)oxirane (21): 84% over 2 steps. $^1$H NMR (400 MHz, Chloroform-d) δ 7.17 (d, J=8.4 Hz, 2H), 6.86 (d, J=8.4 Hz, 2H), 3.80 (s, 3H), 3.58-3.53 (m, 1H), 3.07-3.04 (m, 1H), 2.94 (dd, J=14.1, 4.6 Hz, 1H), 2.85-2.71 (m, 3H).

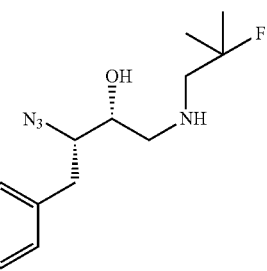

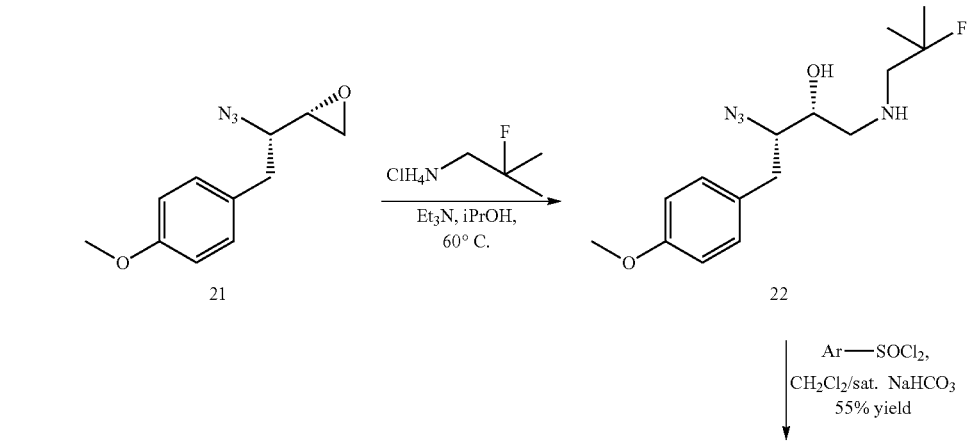

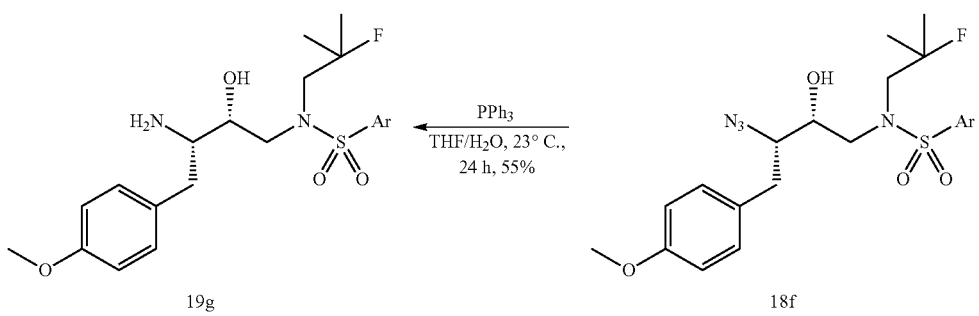

(2R,3S)-3-azido-1-(2-fluoro-2-methylpropylamino)-4-(4-methoxyphenyl)butan-2-ol (22)

To a solution of 2-fluoro-2-methylpropan-1-amine-HCl (2.0 eq) and triethyl amine (4.0 eq) in iPrOH was added an iPrOH solution of (S)-2-((S)-1-azido-2-(4-methoxy-phenyl)ethyl)oxirane. The mixture was heated at 60° C. for 6 h. Upon completion the reaction mixture was concentrated then dissolved in ethyl acetate and washed with H$_2$O. The organic layer was combined washed with brine, dried over sodium sulfate and concentrated under vacuum. The residue was purified by flash chromatography. 50% yield. $^1$H NMR (400 MHz, Chloroform-d) δ 7.4 (d, J=8.4 Hz, 2H), 6.89 (d, J=8.4 Hz, 2H), 3.80 (s, 3H), 3.64-3.57 (m, 2H), 2.96-2.88 (m, 2H), 2.78-2.68 (m, 4H), 1.42 (d, J=3.1 Hz, 3H), 1.37 (d, J=3.1 Hz, 3H).

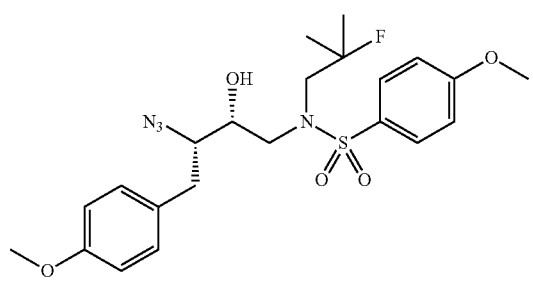

N-((2R,3S)-3-azido-2-hydroxy-4-(4-methoxyphenyl)butyl)-N-(2-fluoro-2-methylpropyl)-4-methoxybenzenesulfonamide (18f)

To a solution of amine 22 in dichloromethane was added 4-MeOPhSO$_2$Cl (1.2 eq) followed by a saturated solution of sodium bicarbonate (3.0 mL). The reaction was allowed to stir for 24 h. The reaction mixture was transferred to a separatory funnel and the organic layer was separated. The aqueous layer was washed with dichlormethane (2×). The organic layers were combined, dried over sodium sulfate, concentrated under vacuum and purified by flash chromatography. 55% yield. $^1$H NMR (400 MHz, Chloroform-d) δ 7.74 (d, J=8.9 Hz, 2H), 7.15 (d, J=8.6 Hz, 2H), 7.01 (d, J=8.9 Hz, 2H), 6.84 (d, J=8.6 Hz, 2H), 4.12-4.06 (m, 1H), 3.88 (s, 3H), 3.78 (s, 3H), 3.66-3.65 (m, 1H), 3.58-3.47 (m, 2H), 3.33 (dd, J=15.4, 9.1 Hz, 1H), 3.19-3.12 (m, 2H), 2.95 (dd, J=14.2, 3.4 Hz, 1H), 2.60 (dd, J=14.2, 10.0 Hz, 1H), 1.48 (d, J=21.7 Hz, 3H), 1.38 (d, J=21.4 Hz, 3H).

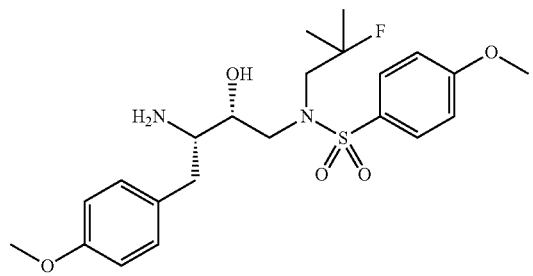

N-((2R,3S)-3-amino-2-hydroxy-4-(4-methoxyphenyl)butyl)-N-(2-fluoro-2-methylpropyl)-4-methoxybenzenesulfonamide (19g)

Azide 18f and triphenyl phosphine (1.2 eq) was dissolved in a solution of THF/H$_2$O (4:1). The reaction mixture was allowed to run for 24 h. Upon completion the reaction was diluted with ethyl acetate and extracted 3 times. The organic layers were combined and dried over anhydrous sodium sulfate. The solvent was removed under vacuum and the residue was purified using flash chromatography 60% ethylacetate/hexanes followed by 3% MeOH/CH$_2$Cl$_2$. 55% yield. $^1$H NMR (400 MHz, Chloroform-d) δ 7.74 (d, J=8.6 Hz, 2H), 7.09 (d, J=8.3 Hz, 2H), 6.98 (d, J=8.5 Hz, 2H), 6.82 (d, J=8.1 Hz, 2H), 3.93-3.90 (m, 1H), 3.85 (s, 3H), 3.77 (s, 3H), 3.51 (dd, J=27.4, 15.1 Hz, 1H), 3.41-3.20 (m, 3H), 3.04-3.01 (m, 1H), 2.88 (d, J=13.7 Hz, 1H), 2.33 (dd, J=13.4, 10.5 Hz, 1H), 1.46 (d, J=21.6 Hz, 3H), 1.37 (d, J=21.4 Hz, 3H).

General Procedure for the Synthesis of the HIV Protease Inhibitors

The desired isostere (19a-f) was taken up in CH$_3$CN and cooled to 0° C. DIPEA (5 eq, excess) was added, followed by the corresponding activated ligand (15a,b,c,d). The resulting solution was stirred at room temperature until the reaction was complete. The solution was concentrated and the crude residue purified by flash column chromatography on silica gel to obtain the desired inhibitor.

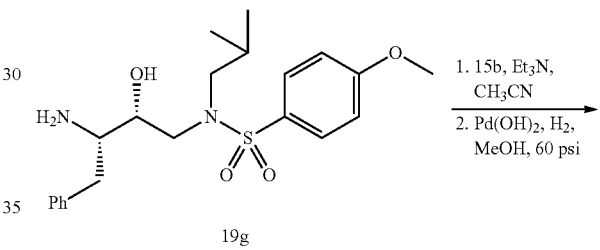

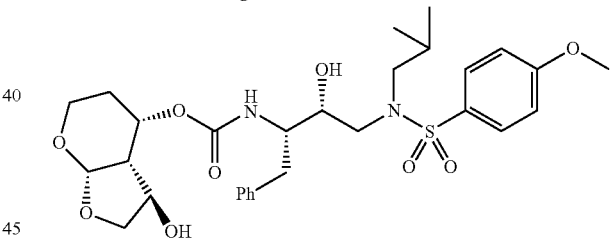

(3R,3aS,4S,7aS)-3-Hydroxyhexahydro-2H-furo[2,3-b]pyran-4-yl (2S,3R)-3-hydroxy-4-(N-isobutyl-4-methoxyphenylsulfonamido)-1-phenylbutan-2-ylcarbamate (20a)

The titled inhibitor was synthesized over 2 steps. 1. Using the general procedure outlined above. 2. The benzyl protected inhibitor was treated with Pd(OH)$_2$ (10 mol %) in methanol (2.0 mL) at 60 Psi for 12 h. Upon completion the reaction was filtered through a plug of celite and concentrated under vacuum. The crude product was purified on silica to give the desired product as a white solid. (38% yield, 2 steps). R$_f$=0.22, (50% ethyl acetate/hexanes). $^1$H NMR (300 MHz, Chloroform-d) δ 7.72 (d, J=7.1 Hz, 2H), 7.30-7.22 (m, 5H), 6.99 (d, J=8.9 Hz, 2H), 5.17 (s, 1H), 5.04 (d, J=3.7 Hz, 2H), 4.57 (s, 1H), 4.32 (t, J=8.4 Hz, 1H), 3.88 (s, 7H), 3.73 (dd, J=9.2 Hz, 5.0 Hz, 1H), 3.41-3.08 (m, 2H), 3.02-2.90 (m, 4H), 2.79 (dd, J=13.5 Hz, 6.8 Hz, 1H), 2.47 (s, 1H), 1.93-1.52 (m, 3H), 0.88 (dd, J=13.2 Hz, 6.4 Hz, 6H).

121

Mass: HRMS (ESI), Calcd for $C_{29}H_{40}N_2O_9S$: m/z 593.2532 (M+H) and 615.2352 (M+Na). found m/z 593.2520 (M+H) and 615.2330 (M+Na).

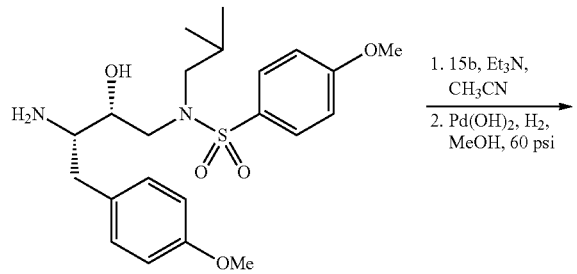

(3R,3aS,4S,7aS)-3-Hydroxyhexahydro-2H-furo[2,3-b]pyran-4-yl (2S,3R)-3-hydroxy-4-(N-isobutyl-4-methoxyphenylsulfonamido)-1-(4-methoxyphenyl)butan-2-ylcarbamate (30i)

The titled inhibitor was synthesized using the procedure for compound 30d. The crude product was purified on silica (70% ethyl acetate/hexanes) to give the desired product as a white solid. (25% yield, 2 steps). $R_f$=0.44, (70% ethyl acetate/hexanes). $^1$H NMR (400 MHz, Chloroform-d) δ 7.82-7.61 (m, 2H), 7.14 (d, J=8.3 Hz, 2H), 6.98 (d, J=8.9 Hz, 2H), 6.82 (d, J=8.6 Hz, 2H), 5.40-5.20 (m, 1H) 5.05 (s, 2H), 4.79 (d, J=6.3 Hz, 1H), 4.39-4.21 (m, 1H), 3.87 (s, 5H), 3.81-3.60 (m, 6H), 3.35-3.27 (m, 1H),), 2.97-2.91 (m, 5H), 2.54 (bs, 1H), 1.93-1.52 (m, 3H), 0.87 (dd, J=16.8 Hz, 5.4 Hz, 6H). Mass: LRMS: m/z 623.8 (M+H).

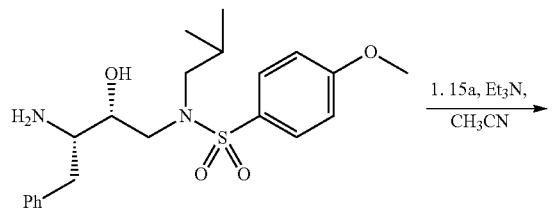

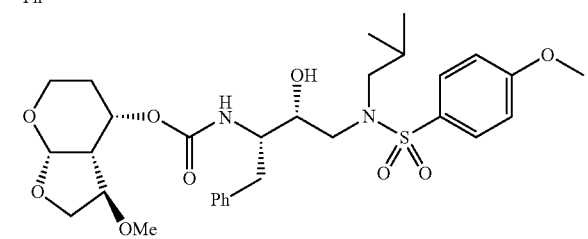

122

(3R,3aR,4S,7aS)-3-Methoxyhexahydro-2H-furo[2,3-b]pyran-4-yl (2S,3R)-3-hydroxy-4-(N-isobutyl-4-methoxyphenylsulfonamido)-1-phenylbutan-2-ylcarbamate (20b)

The titled inhibitor was synthesized using the general procedure outlined above. 61% yield. $R_f$=0.38 (60% ethyl acetate/hexanes). $^1$H NMR (300 MHz, Chloroform-d) δ 7.70 (d, J=8.6 Hz, 2H), 7.43-7.13 (m, 5H), 6.97 (d, J=8.7 Hz, 2H), 5.12 (d, J=3.7 Hz, 1H), 5.09-4.96 (m, 1H), 4.93 (d, J=8.5 Hz, 1H), 4.17-4.12 (m, 1H), 3.87 (s, 9H), 3.47-3.25 (m, 1H), 3.12 (s, 3H), 2.96 (dd, J=13.9 Hz, 7.4 Hz, 4H), 2.78 (dd, J=13.3 Hz, 6.7 Hz, 1H), 2.55 (d, J=4.5 Hz, 1H), 1.94-1.72 (m, 2H), 1.62 (dd, J=16.9 Hz, 7.9 Hz, 1H), 0.91 (d, J=6.5 Hz, 3H), 0.86 (d, J=6.6 Hz, 3H). Mass: HRMS (ESI), Calcd for $C_{30}H_{42}N_2O_9S$: m/z 629.2509 (M+Na). found m/z 629.2505 (M+Na).

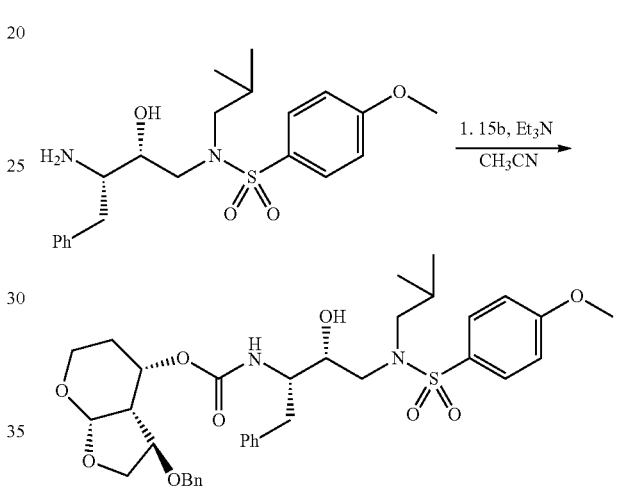

(3R,3aR,4S,7aS)-3-(Benzyloxy)hexahydro-2H-furo[2,3-b]pyran-4-yl (2S,3R)-3-hydroxy-4-(N-isobutyl-4-methoxyphenylsulfonamido)-1-phenylbutan-2-ylcarbamate (20c)

The titled inhibitor was synthesized using the general procedure outlined above. 82% yield. $R_f$=0.6, (50% ethyl acetate/hexanes). $^1$H NMR (300 MHz, Chloroform-d) δ 7.69 (d, J=8.9 Hz, 2H), 7.39-7.10 (m, 10H), 6.96 (d, J=8.9 Hz, 2H), 5.13 (d, J=3.7 Hz, 1H), 5.05 (d, J=4.3 Hz, 1H), 4.82 (d, J=8.4 Hz, 1H), 4.37 (s, 2H), 4.23-3.99 (m, 2H), 3.99-3.73 (m, 8H), 3.37 (t, J=10.2 Hz, 1H), 3.09 (dd, J=15.1 Hz, 8.4 Hz, 1H), 2.95-2.95 (m, 4H), 2.78 (dd, J=13.5 Hz, 6.7 Hz, 1H), 2.64-2.59 (m, 1H), 1.79 (d, J=7.4 Hz, 2H), 1.71-1.53 (m, 1H), 0.88 (dd, J=14.5 Hz, 7.0 Hz, 6H). Mass: LRMS: m/z 683.91 (M+H).

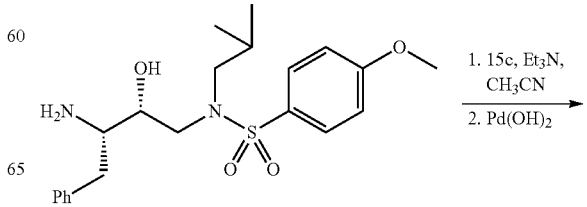

-continued

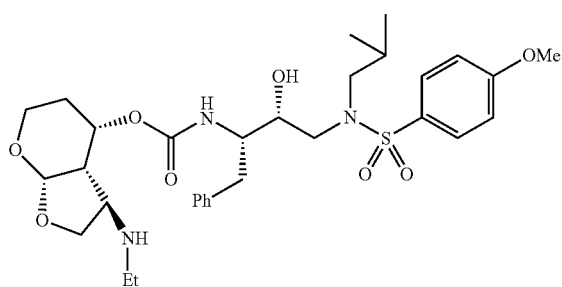

(3R,3aS,4S,7aS)-3-(Ethylamino)hexahydro-2H-furo[2,3-b]pyran-4-yl (2S,3R)-3-hydroxy-4-(N-isobutyl-4-methoxyphenylsulfonamido)-1-phenylbutan-2-ylcarbamate (20d)

The NH-ethyl inhibitor was synthesized over 2 steps. 1. Using the general procedure outlined above for the synthesis of HIV-protease inhibitors. 2. The N-Benzyl-N-ethyl inhibitor was treated with Pd(OH)$_2$ (10 mol %) in 5% ammonia/methanol (2.0 mL) at 1 atm for 4 h. Upon completion the reaction was filtered through a plug of celite and concentrated under vacuum. The crude product was purified on silica (5% methanol/dichloromethane) to give the desired product as a white solid. (50% yield, 2 steps). R$_f$=0.25 (10% methanol/DCM). $^1$H NMR (400 MHz, CD$_3$OD) δ 7.76 (d, J=8.8 Hz, 2H), 7.36-7.13 (m, 5H), 7.13-7.02 (d, J=9.2 Hz, 2H), 5.09 (d, J=3.8 Hz, 1H), 5.01 (dq, J=10.7 Hz, 5.3 Hz, 4.7 Hz, 1H), 4.25-4.14 (t, J=8.8 Hz, 1H), 3.87 (s, 3H), 3.86-3.79 (m, 3H), 3.78-3.72 (m, 1H), 3.70 (dd, J=8.7 Hz, 5.1 Hz, 1H), 3.50 (td, J=7.3 Hz, 5.3 Hz, 1H), 3.46-3.35 (m, 2H), 3.15 (dd, J=14.0 Hz, 3.7 Hz, 1H), 3.05 (dd, J=13.6 Hz, 8.1 Hz, 1H), 2.96 (dd, J=14.9 Hz, 8.3 Hz, 1H), 2.87 (dd, J=13.6 Hz, 6.9 Hz, 1H), 2.65-2.51 (m, 2H), 2.50-2.41 (m, 1H), 2.29 (td, J=6.8 Hz, 4.0 Hz, 1H), 2.07-1.96 (m, 1H), 1.82-1.60 (m, 2H), 1.10 (t, J=7.1 Hz, 3H), 0.91 (d, J=6.6 Hz, 3H), 0.86 (d, J=6.6 Hz, 3H). $^{13}$C NMR (100 MHz, CD$_3$OD) δ 164.5, 157.4, 140.2, 132.2, 130.6, 130.3, 129.3, 127.3, 115.4, 103.1, 74.3, 74.1, 70.4, 60.9, 58.8, 57.4, 57.2, 56.2, 53.9, 43.5, 36.7, 28.6, 28.1, 20.5, 15.0. Mass: HRMS (ESI), Calcd for C$_{31}$H$_{45}$N$_3$O$_8$S: m/z 620.3005 (M+Na). found m/z 620.3000 (M+Na).

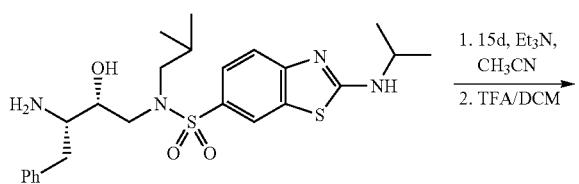

(3R,3aS,4S,7aS)-3-(ethylamino)hexahydro-2H-furo[2,3-b]pyran-4-yl (2S,3R)-3-hydroxy-4-(N-isobutyl-2-(isopropylamino)benzo[d]thiazole-6-sulfonamido)-1-phenylbutan-2-yl-carbamate (20e)

The desired inhibitor was obtained after 2 steps. 1. following the general procedure outlined above. 2. The N-Boc protected amine was treated with a solution of TFA/DCM (1:3) for 2 h. The reaction mixture was concentrated and the product was purified on silica (5% methanol/dichloromethane) to give the desired product as a white solid. (50% yield, 2 steps). $^1$H NMR (400 MHz, methanol-d) δ 8.07 (d, J=1.7 Hz, 1H), 7.68 (dd, J=8.5, 1.8 Hz, 1H), 7.49 (d, J=8.5 Hz, 1H), 7.27-7.25 (m, 4H), 7.20-7.17 (m, 1H), 5.22 (d, J=3.9 Hz, 1H), 5.06-5.00 (m, 1H), 4.30 (dd, J=10.1, 7.3 Hz, 1H), 4.13-4.06 (m, 1H), 3.93-3.85 (m, 3H), 3.81-3.74 (m, 2H), 3.50-3.40 (m, 2H), 3.17 (dd, J=14.1, 3.6 Hz, 1H), 3.10 (dd, J=13.7, 8.1 Hz, 1H), 3.00 (dd, J=14.8, 8.1 Hz, 1H), 2.92 (dd, J=13.7, 7.0 Hz, 1H), 2.85-2.81 (m, 2H), 2.66 (d, J=14.0 Hz, 1H), 2.56-2.52 (m, 1H), 2.07-2.00 (m, 1H), 1.80-1.78 (m, 1H), 1.62-1.53 (m, 1H), 1.30 (d, J=6.5 Hz, 6H), 1.19 (t, J=7.2 Hz, 3H), 0.93 (d, J=6.6 Hz, 3H), 0.87 (d, J=6.6 Hz, 3H).

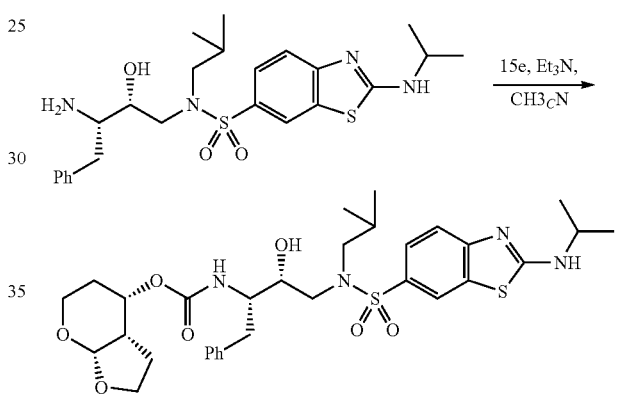

(3aS,4S,7aR)-hexahydro-2H-furo[2,3-b]pyran-4-yl (2S,3R)-3-hydroxy-4-(N-isobutyl-2-(isopropylamino)benzo[d]thiazole-6-sulfonamido)-1-phenylbutan-2-ylcarbamate (20f)

The above inhibitor was obtained following the general procedure outlined above. $^1$H NMR (400 MHz, methanol-d) δ 8.07 (s, 1H), 7.69 (d, J=8.5 Hz, 1H), 7.50 (d, J=8.5 Hz 1H), 7.23 (d, J=4.3 Hz, 4H), 7.22-7.05 (m, 1H), 4.93-4.90 (m, 2H), 4.11-4.03 (m, 2H), 3.81-3.73 (m, 5H), 3.42-3.34 (m, 2H), 3.20-3.07 (m, 2H), 2.97 (dd, J=15.1, 8.2 Hz, 1H), 2.89 (dd, J=13.6, 6.8 Hz, 1H), 2.54 (dd, J=13.7, 10.7 Hz, 1H), 2.33-2.27 (m, 1H), 2.04-2.01 (m, 1H), 1.87-1.81 (m, 1H), 1.71-1.60 (m, 2H), 1.30 (d, J=6.8 Hz, 6H), 0.94 (d, J=6.6 Hz, 3H), 0.89 (d, J=6.7 Hz, 3H). LRMS (ESI) m/z (M+H) 661.8.

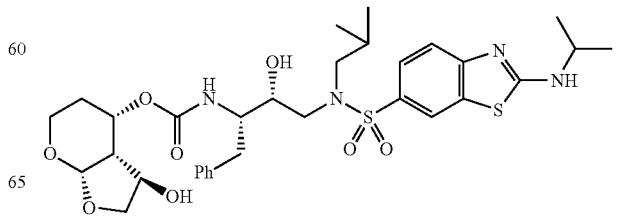

(3R,3aS,4S,7aS)-3-hydroxyhexahydro-2H-furo[2,3-b]pyran-4-yl (2S,3R)-3-hydroxy-4-(N-isobutyl-2-(isopropylamino)benzo[d]thiazole-6-sulfonamido)-1-phenylbutan-2-yl-carbamate (20g)

The above inhibitor was obtained over 2 steps. 1. Following the general procedure outlined above followed by deprotection of the C3-protected alcohol. ¹H NMR (400 MHz, methanol-d) δ 8.05 (d, J=1.8 Hz, 1H), 7.67 (dd, J=8.5, 1.9 Hz, 1H), 7.49 (d, J=8.5 Hz, 1H), 7.28-7.20 (m, 4H), 7.20-7.15 (m, 1H), 5.13 (d, J=3.8 Hz, 1H), 5.01-4.95 (m, 1H), 4.41-4.36 (m, 1H), 4.22 (dd, J=9.1, 6.9 Hz, 1H), 4.13-4.06 (m, 1H), 3.87-3.78 (m, 3H), 3.74-3.69 (m, 1H), 3.63 (dd, J=9.2, 3.9 Hz, 1H), 3.42-3.40 (m, 1H), 3.25-3.21 (m, 1H), 3.12-3.05 (m, 1H), 3.01-2.97 (m, 1H), 2.95-2.88 (m, 2H), 2.62 (dd, J=13.9, 10.0 Hz, 1H), 2.33-2.29 (m, 1H), 2.05-1.98 (m, 1H), 1.80-1.74 (m, 1H), 1.79-1.57 (m, 1H), 1.30 (d, J=6.5 Hz, 6H), 0.92 (d, J=6.6 Hz, 3H), 0.88 (d, J=6.7 Hz, 3H). LRMS (ESI) m/z (M+H) 677.8.

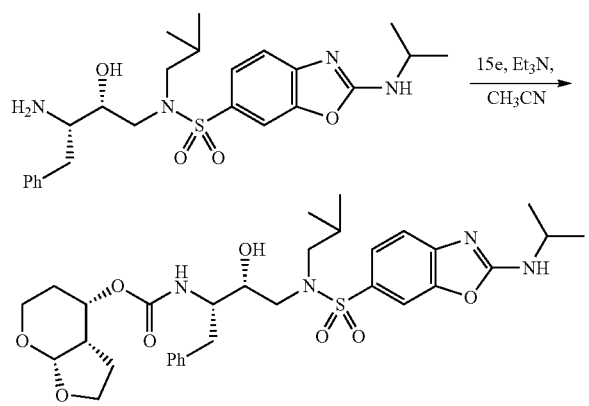

(3aS,4S,7aR)-hexahydro-2H-furo[2,3-b]pyran-4-yl (2S,3R)-3-hydroxy-4-(N-isobutyl-2-(isopropylamino)benzo[d]oxazole-6-sulfonamido)-1-phenylbutan-2-ylcarbamate (20h)

The above inhibitor was obtained following the general procedure outlined above. ¹H NMR (400 MHz, methanol-d) δ 7.71 (d, J=1.5 Hz, 1H), 7.66 (dd, J=8.3, 1.6 Hz, 1H), 7.34 (d, J=8.3 Hz, 1H), 7.23 (d, J=4.4 Hz, 4H), 7.18-7.11 (m, 1H), 4.92-4.89 (m, 2H), 4.07-3.96 (m, 2H), 3.81-3.72 (m, 5H), 3.42-3.33 (m, 1H), 3.16 (dd, J=14.0, 3.1 Hz, 1H), 3.10 (dd, J=13.6, 8.3 Hz, 1H), 2.97 (dd, J=15.0, 8.2 Hz, 1H), 2.88 (dd, J=14.2, 7.1 Hz, 1H), 2.54 (dd, J=13.8, 10.7 Hz, 1H), 2.34-2.27 (m, 1H), 2.05-2.00 (m, 1H), 1.90-1.80 (m, 1H), 1.72-1.59 (m, 2H), 1.45-1.38 (m, 1H), 1.31 (d, J=6.5 Hz, 6H), 0.94 (d, J=6.5 Hz, 3H), 0.91-0.86 (m, 3H). LRMS (ESI) m/z (M+H) 645.7.

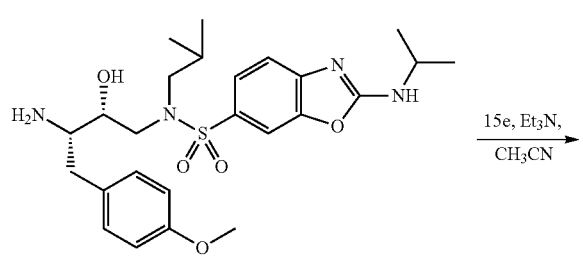

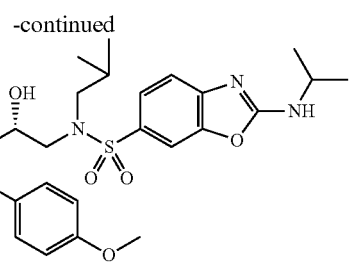

(3aS,4S,7aR)-hexahydro-2H-furo[2,3-b]pyran-4-yl (2S,3R)-3-hydroxy-4-(N-isobutyl-2-(isopropylamino)benzo[d]oxazole-6-sulfonamido)-1-(4-methoxyphenyl)butan-2-yl-carbamate (20i)

The above inhibitor was obtained following the general procedure outlined above. ¹H NMR (400 MHz, methanol-d) δ 7.71 (s, 1H), 7.66 (d, J=8.2 Hz, 1H), 7.34 (d, J=8.3 Hz, 1H), 7.14 (d, J=8.5 Hz, 2H), 6.79 (d, J=8.6 Hz, 2H), 4.93-4.90 (m, 2H), 4.08-4.03 (m, 1H), 4.01-3.96 (m, 1H), 3.82-3.68 (m, 7H), 3.39 (d, J=12.3 Hz, 2H), 3.12-3.07 (m, 2H), 2.96 (dd, J=14.4, 7.1 Hz, 1H), 2.89 (dd, J=13.5, 6.3 Hz, 1H), 2.47 (dd, J=14.0, 11.1 Hz, 1H), 2.36-2.29 (m, 1H), 2.08-1.98 (m, 1H), 1.90-1.82 (m, 1H), 1.73-1.61 (m, 2H), 1.43-1.36 (m, 1H), 1.31 (d, J=6.5 Hz, 6H), 0.94 (d, J=6.5 Hz, 3H), 0.91-0.86 (m, 3H). LRMS (ESI) m/z (M+Na) 697.8.

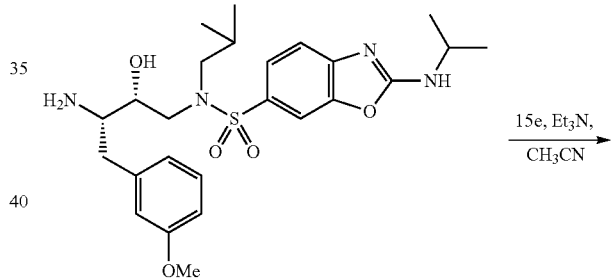

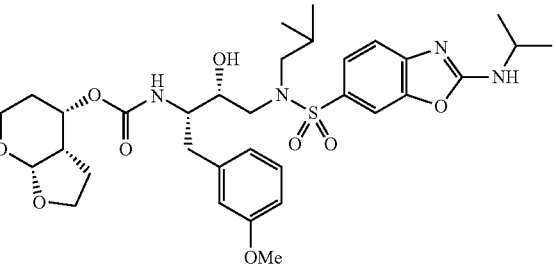

(3aS,4S,7aR)-hexahydro-2H-furo[2,3-b]pyran-4-yl (2S,3R)-3-hydroxy-4-(N-isobutyl-2-(isopropylamino)benzo[d]oxazole-6-sulfonamido)-1-(3-methoxyphenyl)butan-2-yl-carbamate (20j)

The above inhibitor was obtained following the general procedure outlined above. ¹H NMR (400 MHz, methanol-d) δ 7.71 (d, J=1.6 Hz, 1H), 7.66 (dd, J=8.3, 1.7 Hz, 1H), 7.34 (d, J=8.3 Hz, 1H), 7.14 (t, J=7.8 Hz, 1H), 6.81 (d, J=8.0 Hz, 2H), 6.73 (d, J=7.9 Hz, 1H), 4.96-4.89 (m, 2H), 4.08-3.96

(m, 2H), 3.76-3.71 (m, 8H), 3.42-3.37 (m, 1H), 3.16-3.07 (m, 2H), 2.96 (dd, J=15.0, 8.3 Hz, 1H), 2.89 (dd, J=13.6, 6.7 Hz, 1H), 2.51 (dd, J=14.0, 10.6 Hz, 1H), 2.38-2.30 (m, 1H), 2.05-1.98 (m, 1H), 1.91-1.83 (m, 2H), 1.73-1.60 (m, 1H), 1.47-1.43 (m, 1H), 1.31 (d, J=6.5 Hz, 6H), 0.94 (d, J=6.5 Hz, 3H), 0.89 (d, J=6.6 Hz, 3H). LRMS (ESI) m/z (M+H) 695.8.

J=13.7, 6.8 Hz, 1H), 2.52 (dd, J=13.8, 10.4 Hz, 1H), 2.37-2.31 (m, 1H), 2.05-1.99 (m, 1H), 1.90-1.87 (m, 1H), 1.76-1.68 (m, 1H), 1.64-1.59 (m, 1H), 1.46-1.42 (m, 1H), 1.30 (d, J=6.5 Hz, 6H), 0.93 (d, J=6.5 Hz, 3H), 0.88 (d, J=6.6 Hz, 3H). LRMS (ESI) m/z (M+H) 689.9.

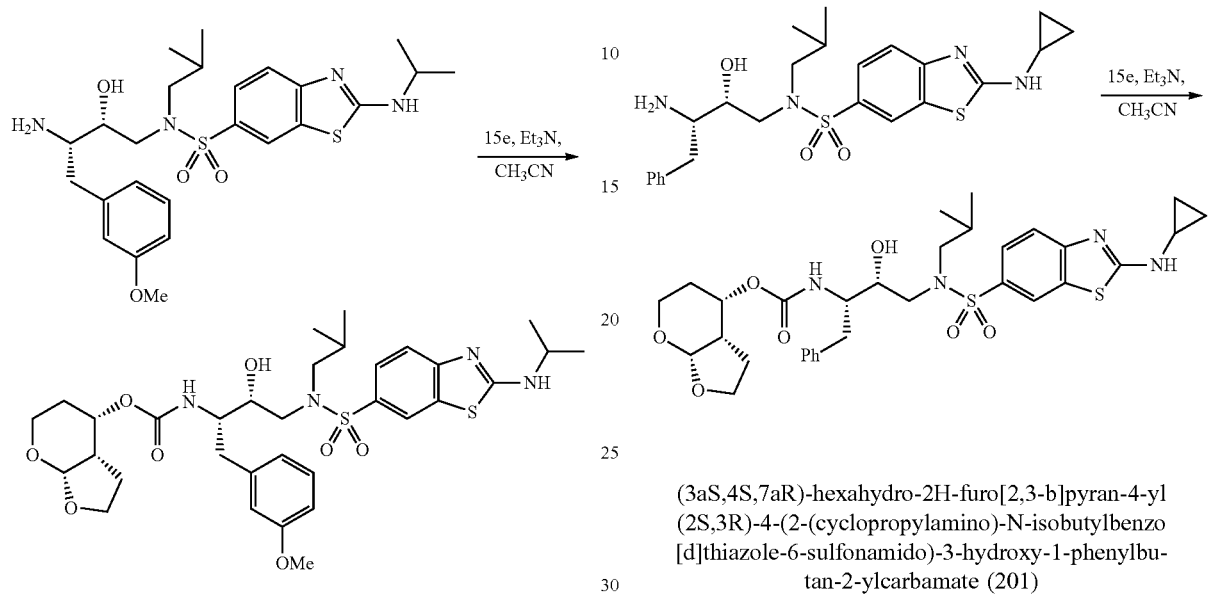

(3aS,4S,7aR)-hexahydro-2H-furo[2,3-b]pyran-4-yl (2S,3R)-3-hydroxy-4-(N-Isobutyl-2-(isopropylamino)benzo[d]thiazole-6-sulfonamido)-1-(3-methoxyphenyl)butan-2-yl-carbamate (20k)

The above inhibitor was obtained following the general procedure outlined above. ¹H NMR (400 MHz, methanol-d) δ 8.06 (d, J=1.8 Hz, 1H), 7.69 (dd, J=8.5, 1.9 Hz, 1H), 7.49 (d, J=8.5 Hz, 1H), 7.14 (t, J=7.8 Hz, 1H), 6.81 (d, J=8.7 Hz, 2H), 6.75-6.69 (m, 1H), 4.94-4.89 (m, 2H), 4.09-4.03 (m, 2H), 3.80-3.71 (m, 8H), 3.43-3.36 (m, 1H), 3.16-3.10 (m, 1H), 3.09-3.07 (m, 1H), 2.97 (dd, J=13.9, 7.1, 1H) 2.89 (dd, (3aS,4S,7aR)-hexahydro-2H-furo[2,3-b]pyran-4-yl (2S,3R)-4-(2-(cyclopropylamino)-N-isobutylbenzo[d]thiazole-6-sulfonamido)-3-hydroxy-1-phenylbutan-2-ylcarbamate (201)

The above inhibitor was obtained following the general procedure outlined above. ¹H NMR (400 MHz, methanol-d) δ 8.15 (d, J=1.8 Hz, 1H), 7.72 (dd, J=8.6, 1.9 Hz, 1H), 7.53 (d, J=8.5 Hz, 1H), 7.23 (d, J=4.4 Hz, 4H), 7.18-7.15 (m, 1H), 4.90 (d, J=3.6 Hz, 2H), 4.08-4.00 (m, 1H), 3.82-3.73 (m, 4H), 3.44-3.33 (m, 2H), 3.17 (dd, J=13.9, 3.1 Hz, 1H), 3.11 (dd, J=13.5, 8.2 Hz, 1H), 2.98 (dd, J=14.9, 8.2 Hz, 1H), 2.90 (dd, J=13.6, 6.8 Hz, 1H), 2.79-2.74 (m, 1H), 2.54 (dd, J=13.9, 10.7 Hz, 1H), 2.35-2.27 (m, 1H), 2.06-1.99 (m, 1H), 1.90-1.79 (m, 1H), 1.71-1.59 (m, 2H), 1.45-1.38 (m, 1H), 0.94 (d, J=6.6 Hz, 3H), 0.89-0.88 (m, 5H), 0.71-0.67 (m, 2H).

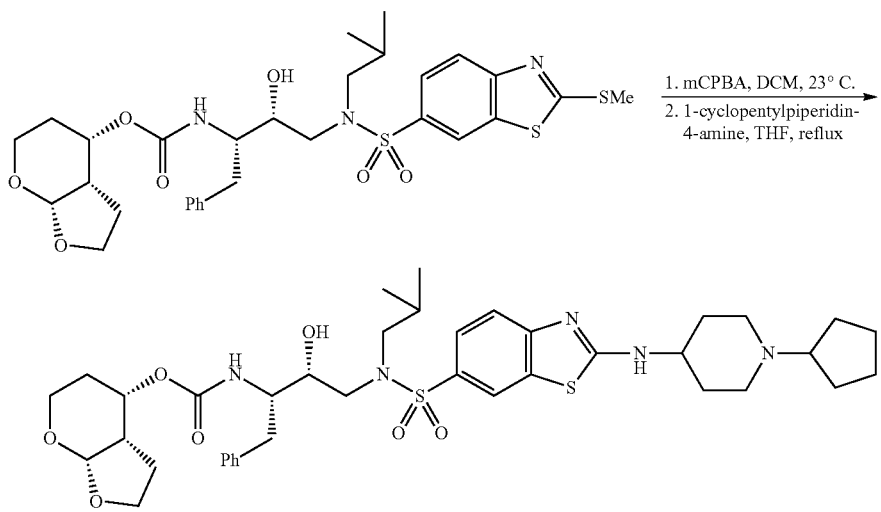

(3aS,4S,7aR)-hexahydro-2H-furo[2,3-b]pyran-4-yl (2S,3R)-4-(2-(1-cyclopentylpiperidin-4-ylamino)-N-Isobutylbenzo[d]thiazole-6-sulfonamido)-3-hydroxy-1-phenylbutan-2-yl-carbamate (20m)

The above inhibitor was obtained following the procedure outlined in J. Med. Chem. 2005, 48, 1965-1973. 60% yield over 2 steps. $^1$H NMR (400 MHz, methanol-d) δ 8.09 (d, J=1.8 Hz, 1H), 7.70 (dd, J=8.5, 1.9 Hz, 1H), 7.51 (d, J=8.5 Hz, 1H), 7.23 (d, J=4.0 Hz, 4H), 7.17-7.14 (m, 1H), 4.86-4.88 (m, 2H), 4.08-4.03 (m, 1H), 4.00-3.93 (m, 1H), 3.81-3.67 (m, 5H), 3.42-3.35 (m, 2H), 3.28-3.25 (m, 1H), 3.18 (dd, J=13.9, 3.2 Hz, 1H), 3.10 (dd, J=13.6, 8.3 Hz, 1H), 2.97 (dd, J=14.9, 8.3 Hz, 1H), 2.89 (dd, J=13.6, 6.7 Hz, 1H), 2.66-2.48 (m, 2H), 2.34-2.30 (m, 1H), 2.22 (d, J=12.0 Hz, 1H), 2.05-2.00 (m, 1H), 1.89-1.82 (m, 3H), 1.79-1.72 (m, 6H), 1.69-1.60 (m, 4H), 1.58-1.52 (m, 3H), 1.46-1.36 (m, 1H), 0.94 (d, J=6.6 Hz, 3H), 0.89 (d, J=6.6 Hz, 3H). LRMS (ESI) m/z (M+H) 770.8.

(3aS,4S,7aR)-hexahydro-2H-furo[2,3-b]pyran-4-yl (2S,3R)-4-(N-(2-fluoro-2-methyl-propyl)-4-methoxyphenylsulfonamido)-3-hydroxy-1-(4-methoxyphenyl)butan-2-yl-carbamate (20n)

The above inhibitor was obtained following the general procedure outlined above. $^1$H NMR (400 MHz, methanol-d) δ 7.79 (d, J=8.9 Hz, 2H), 7.14 (d, J=8.5 Hz, 2H), 7.07 (d, J=8.9 Hz, 2H), 6.79 (d, J=8.6 Hz, 2H), 4.89 (dd, J=7.6, 4.5 Hz, 2H), 4.07-4.03 (m, 1H), 3.87 (s, 4H), 3.82-3.77 (m, 3H), 3.74 (s, 4H), 3.55-3.34 (m, 4H), 3.29-3.23 (m, 1H), 3.04 (dd, J=14.1, 3.6 Hz, 1H), 2.46 (dd, J=13.9, 11.3 Hz, 1H), 2.34-2.26 (m, 1H), 1.89-1.78 (m, 1H), 1.73-1.62 (m, 1H), 1.41 (d, J=2.1 Hz, 3H), 1.36 (d, J=2.0 Hz, 3H).

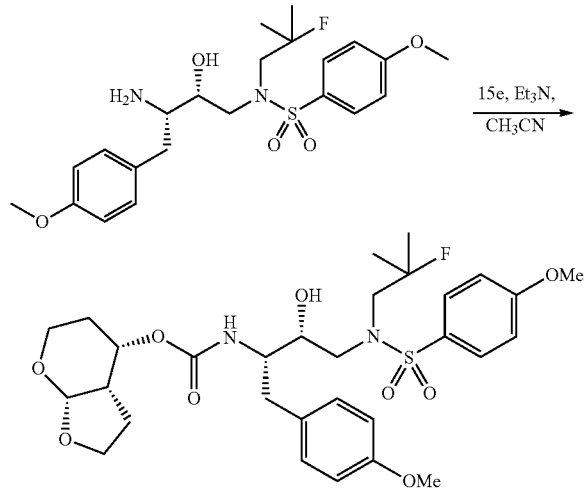

Examples Table 3

The scoring in the biological screens is as follows:

| HIV-1 Inhibitory Potency | | | |
|---|---|---|---|
| $K_i$: | | $IC_{50}$: | |
| >10 nM | − | >1000 nM | − |
| <10 nM | + | <1000 nM | + |
| <1 nM | ++ | <100 nM | ++ |
| <0.1 nM | +++ | <10 nM | +++ |
| | | <1 nM | +++ |

| Entry | Structure | Antiviral $K_i$ (nM) | $IC_{50}$, (nM) |
|---|---|---|---|
| 1 | 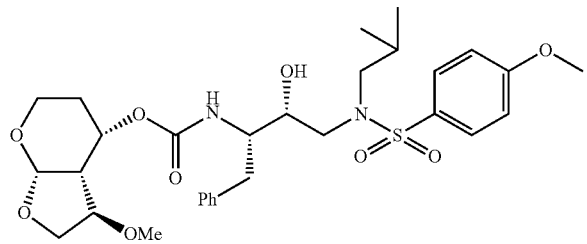 [SMILES: COc1ccc(S(=O)(=O)N(CC(C)C)C[C@@H](O)[C@H](Cc2ccccc2)NC(=O)O[C@H]2CCO[C@H]3OC[C@H](OC)[C@H]32)cc1] | +++ | ++++ |
| 2 | 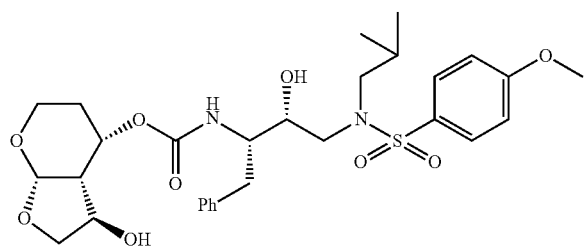 [SMILES: COc1ccc(S(=O)(=O)N(CC(C)C)C[C@@H](O)[C@H](Cc2ccccc2)NC(=O)O[C@H]2CCO[C@H]3OC[C@H](O)[C@H]32)cc1] | +++ | +++ |

-continued

| Entry | Structure | $K_i$ (nM) | Antiviral IC$_{50}$, (nM) |
|---|---|---|---|
| 3 | 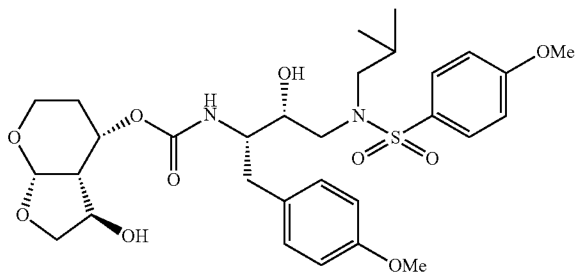 [SMILES: COc1ccc(C[C@H](NC(=O)O[C@H]2CCO[C@H]3OC[C@H](O)[C@H]32)[C@H](O)CN(CC(C)C)S(=O)(=O)c2ccc(OC)cc2)cc1] | +++ | +++ |
| 4 | 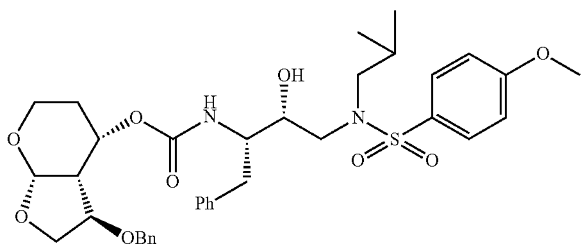 [SMILES: COc1ccc(S(=O)(=O)N(CC(C)C)C[C@@H](O)[C@H](Cc2ccccc2)NC(=O)O[C@H]2CCO[C@H]3OC[C@H](OCc4ccccc4)[C@H]32)cc1] | ++ | ++++ |
| 5 | (darunavir) | +++ | +++ |
| 6 | 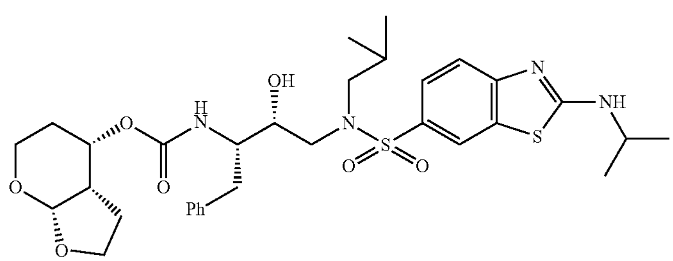 [SMILES: CC(C)CN(C[C@@H](O)[C@H](Cc1ccccc1)NC(=O)O[C@H]1CCO[C@H]2OCC[C@H]21)S(=O)(=O)c1ccc2nc(NC(C)C)sc2c1] | +++ | ++++ |
| 7 | 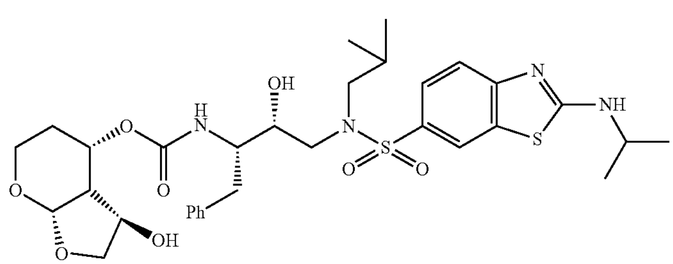 | +++ | +++ |

-continued

| Entry | Structure | $K_i$ (nM) | Antiviral $IC_{50}$, (nM) |
|---|---|---|---|
| 8 | 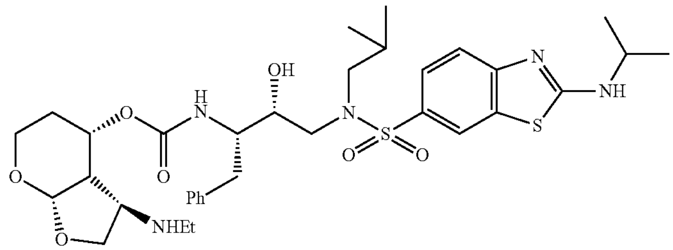 | +++ | +++ |
| 9 | 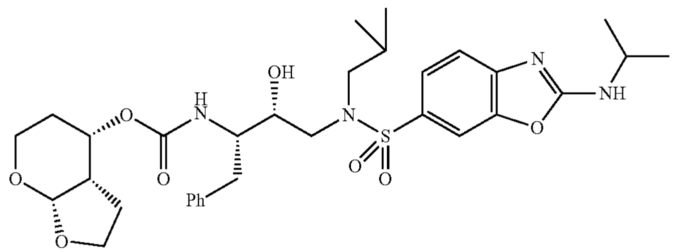 [SMILES: CC(C)CN(C[C@@H](O)[C@H](Cc1ccccc1)NC(=O)O[C@H]1CCO[C@H]2OCC[C@H]21)S(=O)(=O)c1ccc2nc(NC(C)C)oc2c1] | | +++ |
| 10 | 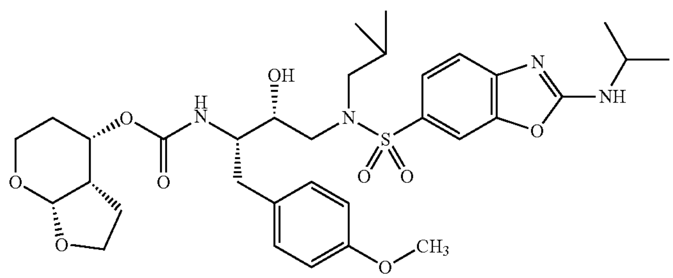 [SMILES: COc1ccc(C[C@H](NC(=O)O[C@H]2CCO[C@H]3OCC[C@H]32)[C@H](O)CN(CC(C)C)S(=O)(=O)c2ccc3nc(NC(C)C)oc3c2)cc1] | +++ | +++ |
| 11 | 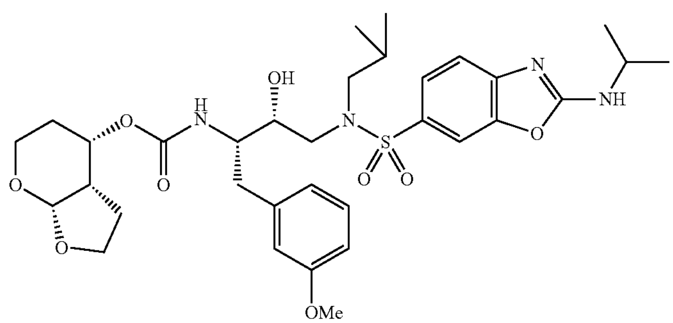 [SMILES: COc1cccc(C[C@H](NC(=O)O[C@H]2CCO[C@H]3OCC[C@H]32)[C@H](O)CN(CC(C)C)S(=O)(=O)c2ccc3nc(NC(C)C)oc3c2)c1] | +++ | +++ |
| 12 | 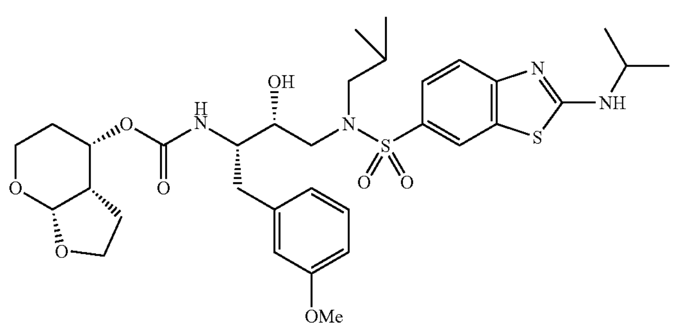 | +++ | ++++ |

Examples Table 4

Compounds of the following list were found to demonstrate potent activity in one or more of the biological screens.

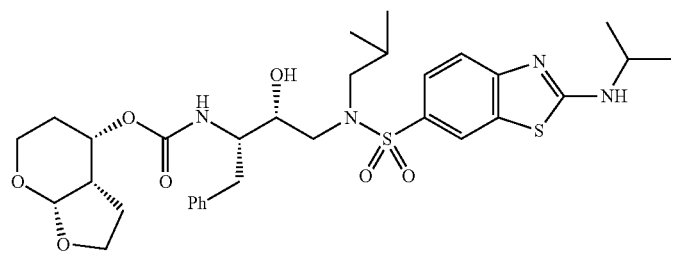
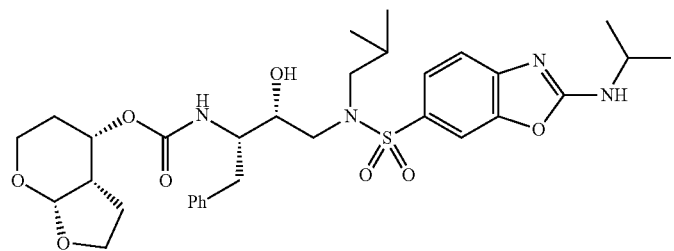
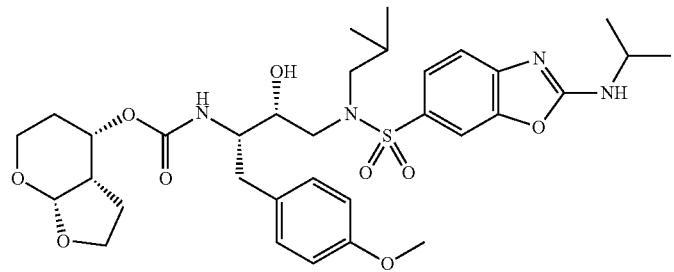
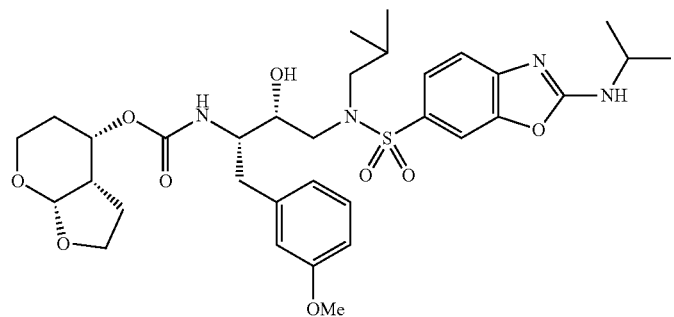
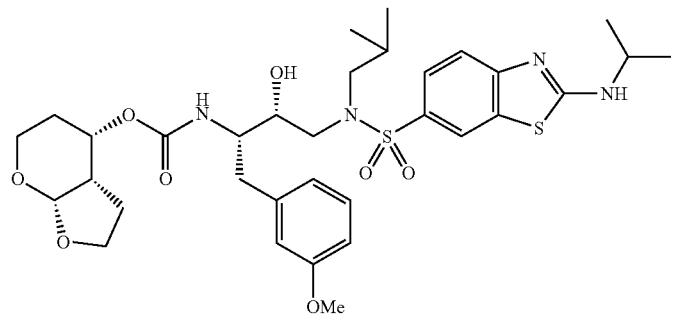
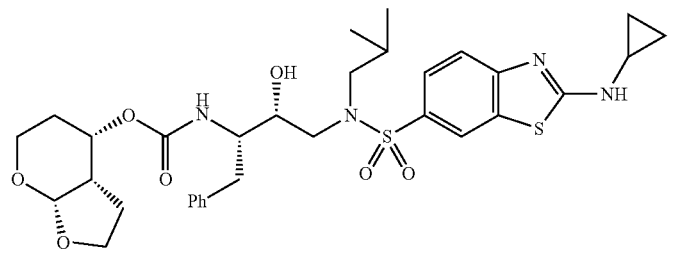

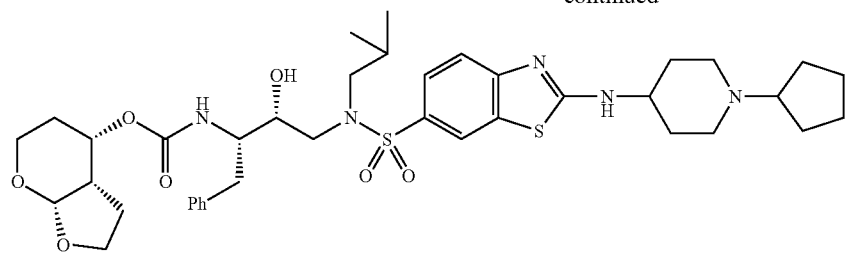
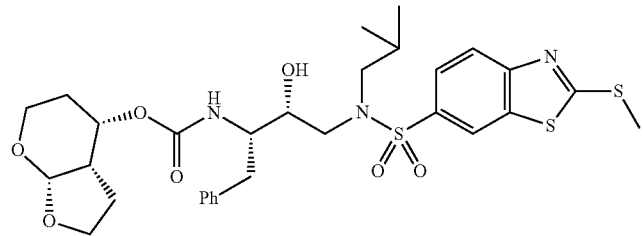
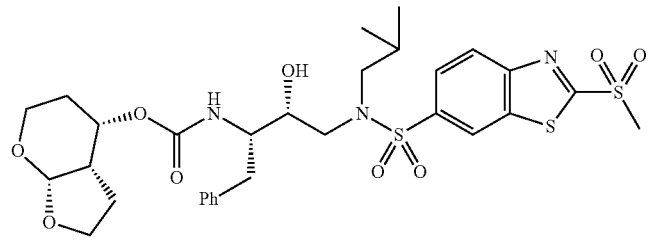
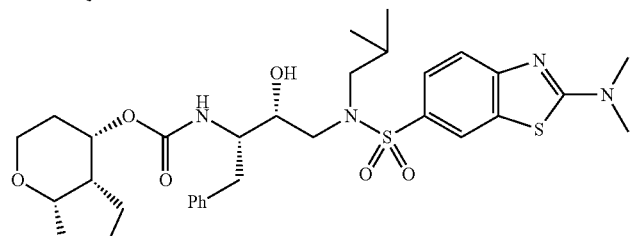
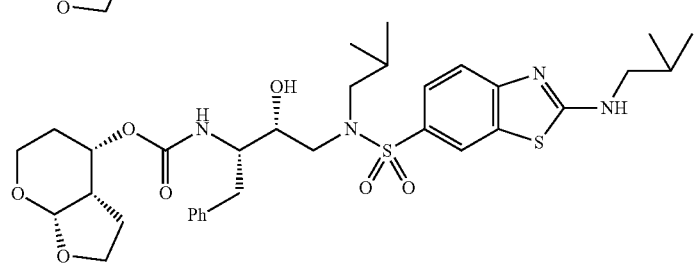
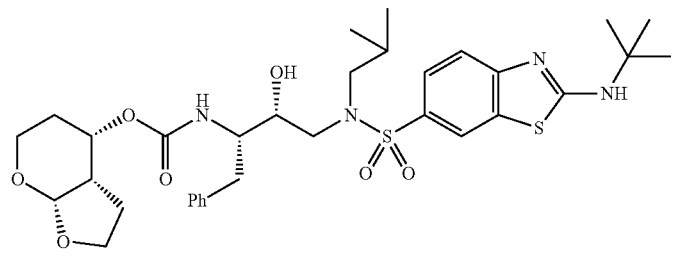
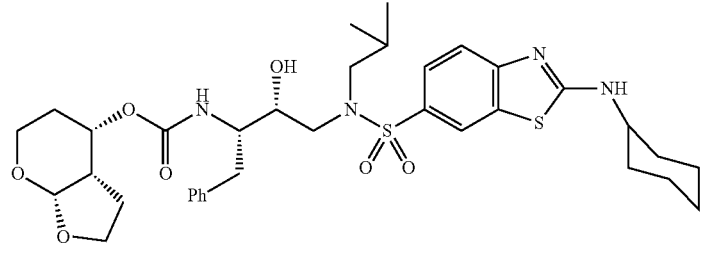

-continued
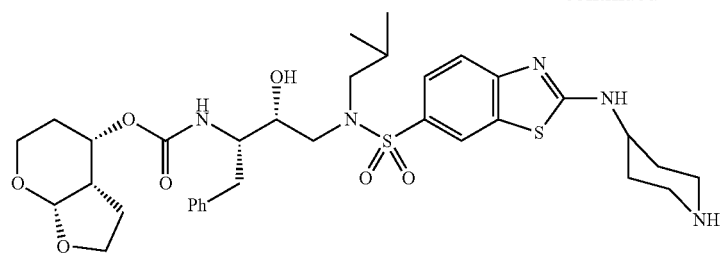
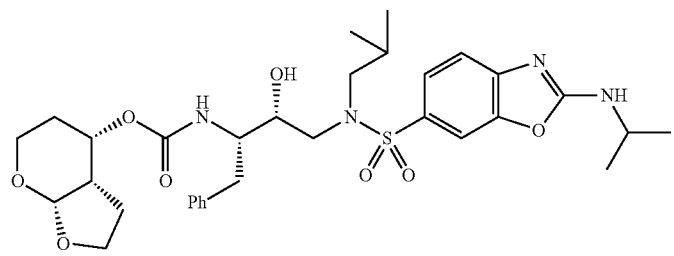
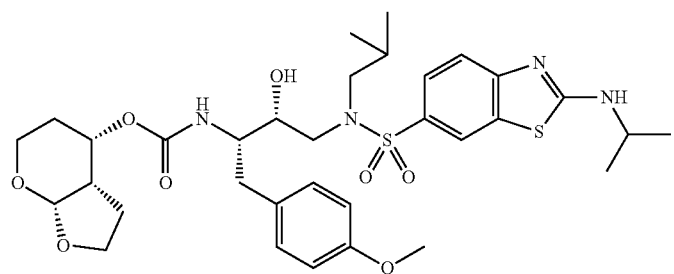
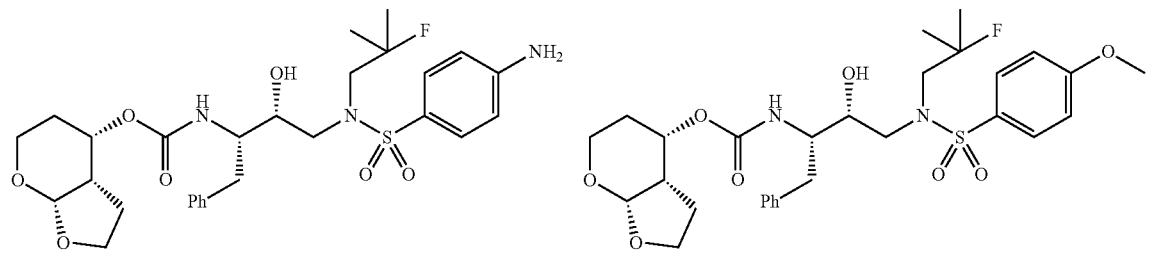
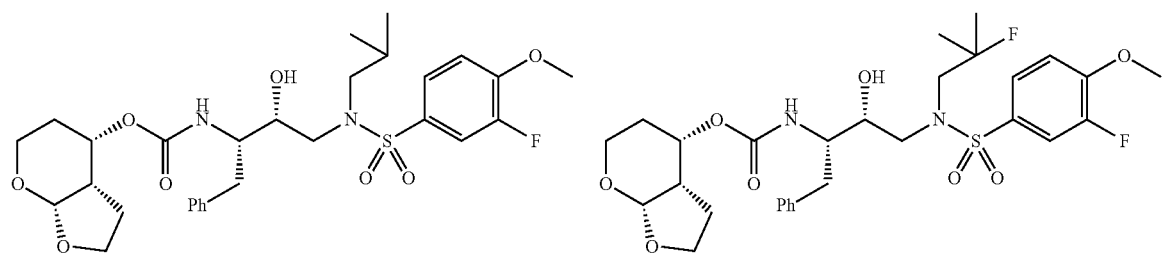
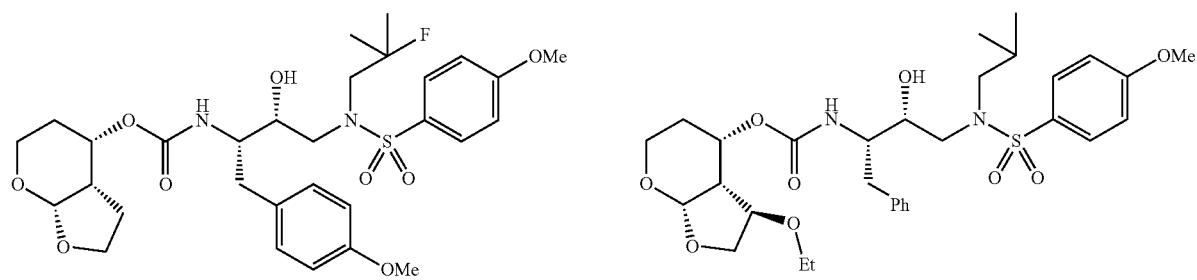

141
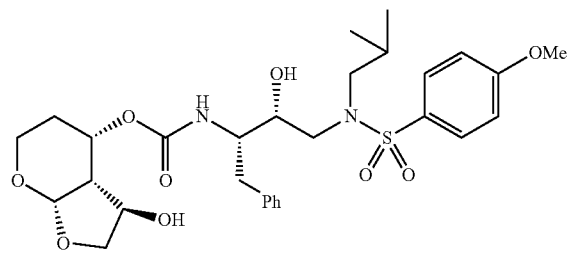
142
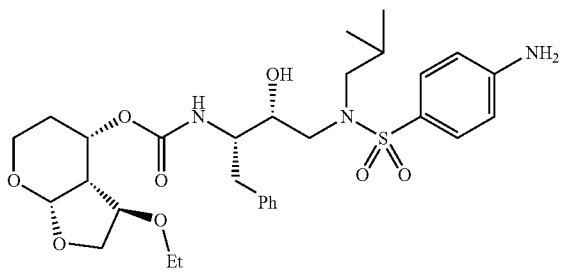
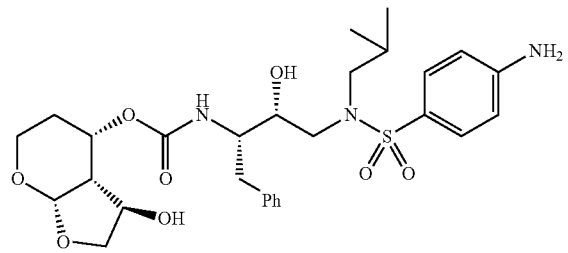
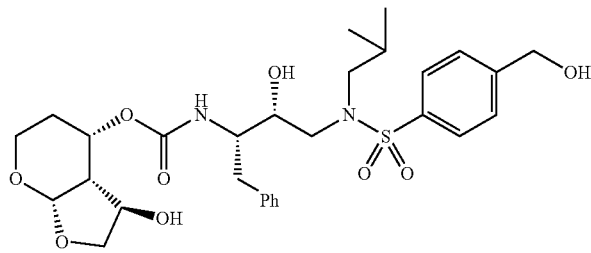
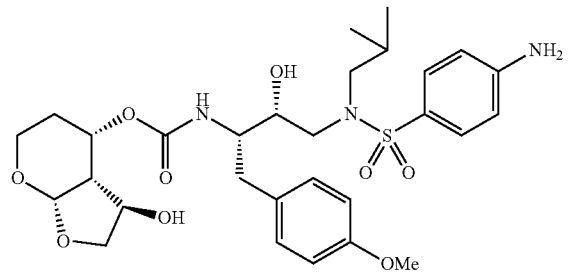
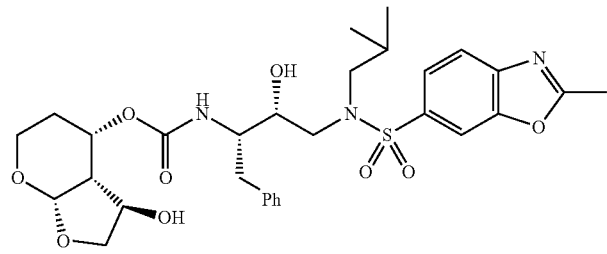
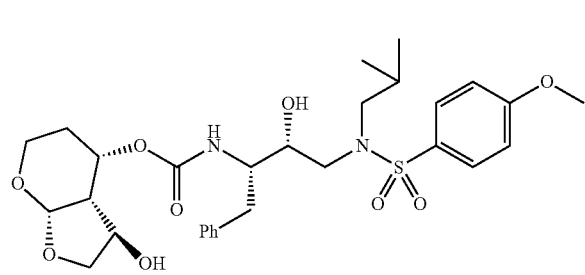
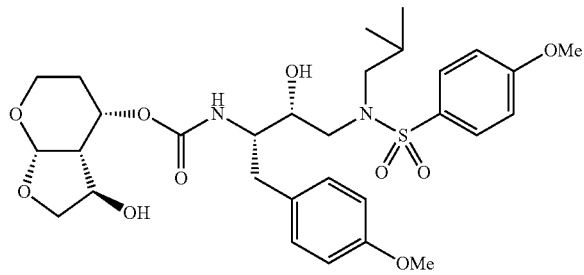
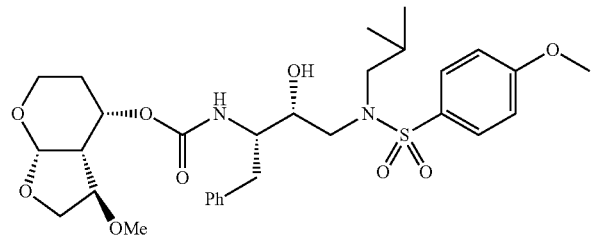
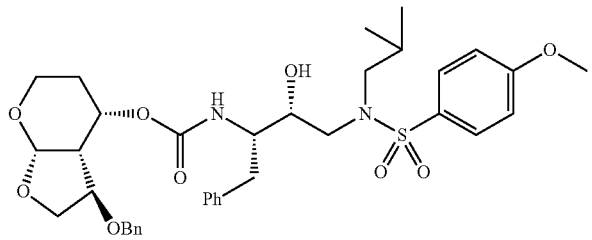

-continued
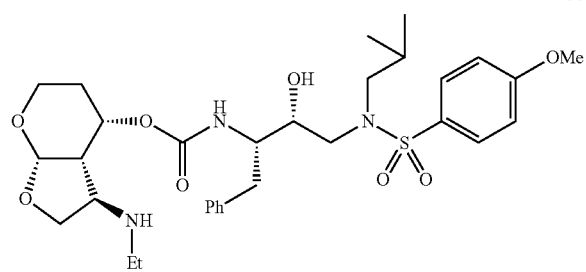
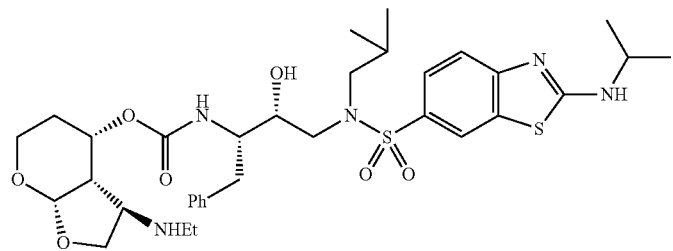
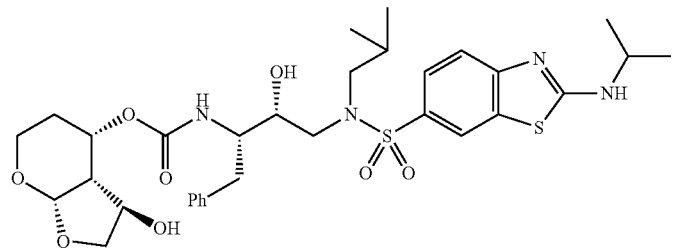
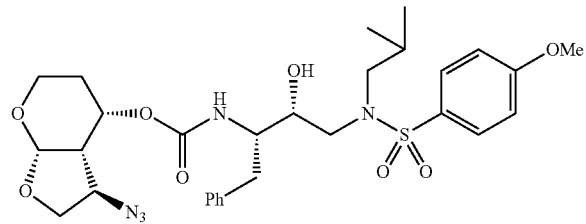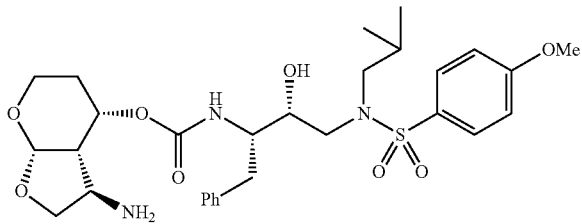
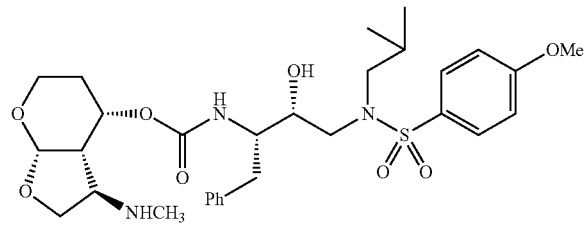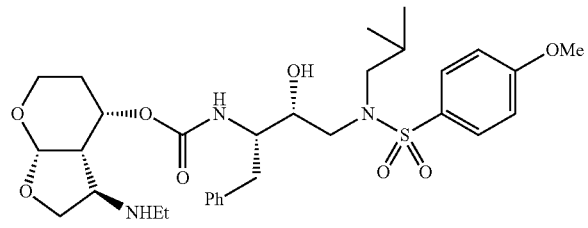
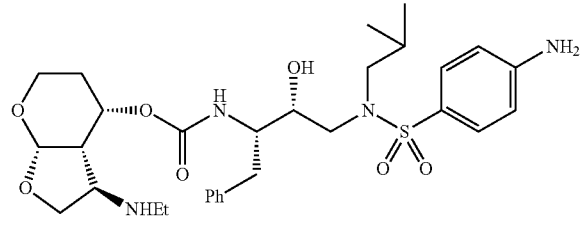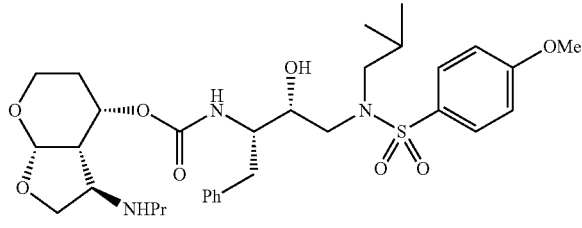
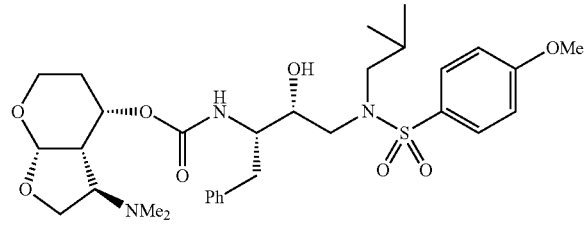

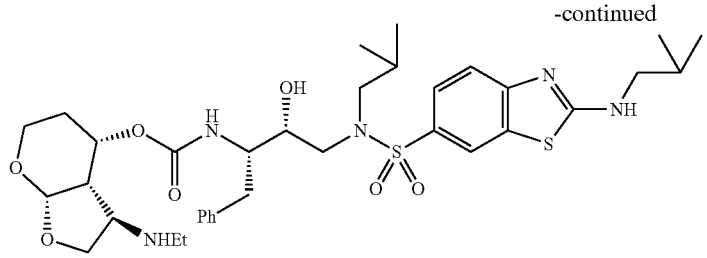

What is claimed is:

1. A compound of the formula (I)

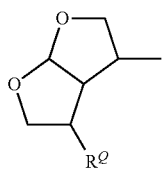

or a pharmaceutically acceptable salt thereof, wherein
A is a group of the formula

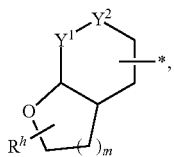

wherein (*) indicates the point of attachment; in which $R^Q$ is amino or alkylamino, which is optionally substituted; or
a group of the formula

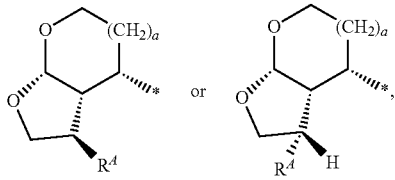

wherein (*) indicates the point of attachment; and wherein
m is an integer selected from 0, 1, 2 or 3;
$Y^1$ is oxygen and $Y^2$ is methylene; and $R^h$ amino or alkylamino, which is optionally substituted;
Q and W are each oxygen;
$R^1$ is hydrogen;
X is $C(R^aR^b)_n$, where n is 1, 2, or 3, and each of $R^a$ and $R^b$ is independently selected in each instance from the group consisting of hydrogen, alkyl, and alkoxy;
$R^2$ is phenyl substituted with one or more methoxy, isopropoxy, hydroxymethyl, methoxymethyl, methoxyethyl, halo or 2-(morpholino)ethoxy groups;
$R^3$ is hydrogen;
$R^4$ is alkyl, which is optionally substituted;
Z is $S(O)_2$;
$R^5$ is 4-aminophenyl, 4-methoxyphenyl, 4-isopropoxyphenyl, 4-hydroxymethylphenyl; 3-amino-4-methoxyphenyl, 3-amino-4-isopropoxyphenyl, 4-amino-3-fluorophenyl, 3-fluoro-4-methoxyphenyl, 3,4-methylenedioxyphenyl, or a group of the formula:

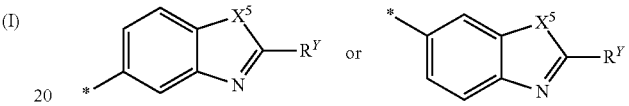

wherein (*) indicates the point of attachment; in which $X^5$ is O, S or NH; and $R^Y$ is (1-4C)alkylthio, (1-4C)alkylsulfinyl, (1-4C)alkylsulfonyl or $NHR^X$ or $NR^XR^Z$ and each of $R^X$ and $R^Z$ is independently methyl, isopropyl, cyclopropyl, isobutyl, tert-butyl, cyclohexyl, 4-piperidinyl 1-cyclopentylpiperidin-4-yl, or the group $NR^XR^Z$ is optionally substituted pyrrolidino, piperidino or piperazino.

2. The compound or salt of claim 1 wherein the phenyl is substituted with one or more methoxy, hydroxymethyl, fluoro or 2-(morpholino)ethoxy groups.

3. The compound or salt of claim 1 wherein $R^4$ is isobutyl.

4. The compound or salt of claim 1 wherein $X^5$ is O or S; and $R^Y$ is $NHR^X$; and $R^X$ is isopropyl, cyclopropyl or isobutyl.

5. The compound or salt of claim 1, wherein
the group A is a group of the formula

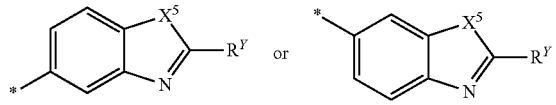

wherein a is 0 or 1; and $R^A$ amino or $NHR^B$ in which $R^B$ is alkyl;
$R^2$ is phenyl substituted with one or more methoxy, isopropoxy, hydroxymethyl, methoxymethyl, methoxyethyl, fluoro or 2-(morpholino)ethoxy groups;
$R^4$ is isobutyl; and
$R^5$ is 4-aminophenyl, 4-methoxyphenyl, 4-isopropoxyphenyl, 4-hydroxymethylphenyl; 3-amino-4-methoxyphenyl, 3-amino-4-isopropoxyphenyl, 4-amino-3-fluorophenyl, 3-fluoro-4-methoxyphenyl, 3,4-methylenedioxyphenyl, or a group of the formula

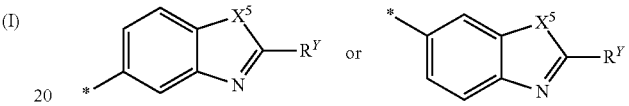

in which $X^5$ is O, S or NH; and $R^Y$ is (1-4C)alkylthio, (1-4C)alkylsulfinyl, (1-4C)alkylsulfonyl or $NHR^X$ or $NR^XR^Z$ and each of $R^X$ and $R^Z$ is independently isopropyl, cyclopropyl, isobutyl, tert-butyl, cyclohexyl, 4-piperidinyl or 1-cyclopentylpiperidin-4-yl, or the group $NR^XR^Z$ is optionally substituted pyrrolidino, piperidino or piperazino.

6. The compound or salt of claim 5 wherein $R^2$ is 3-methoxyphenyl, 4-methoxyphenyl, 3-isopropoxyphenyl, 4-isopropoxyphenyl, 3-hydroxymethylphenyl, 3-methoxymethylphenyl, 4-methoxymethylphenyl, 3-methoxyethylphenyl, 4-methoxyethylphenyl, 3-fluorophenyl, 4-fluorophenyl, 3-[2-(morpholino)ethoxy]phenyl, 4-[2-(morpholino)ethoxy]phenyl.

7. The compound or salt of claim 5 wherein $R^B$ is methyl, ethyl or isopropyl.

8. The compound or salt of claim 5 wherein $R^5$ is

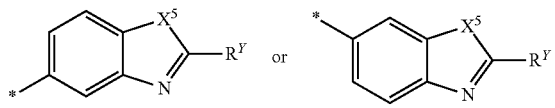

in which $X^5$ is O or S; and $R^Y$ is $NHR^X$ or $NR^X R^Z$ and each of $R^X$ and $R^Z$ is isopropyl or cyclopropyl or the group $NR^X R^Z$ is optionally substituted pyrrolidino, piperidino or piperazino.

9. The compound or salt of claim 5, wherein a is 1.

10. The compound or salt of claim 1 wherein $R^5$ is

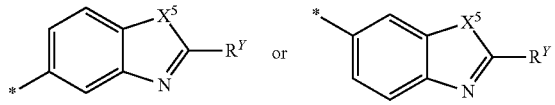

in which $X^5$ is O or S; and $R^Y$ is $NHR^X$; and $R^X$ is isopropyl or cyclopropyl.

11. A pharmaceutical composition comprising one or more compounds of claim 1 and one or more carriers, diluents, or excipients, or a combination thereof.

12. A method for treating a patient in need of relief from an HIV infection, the method comprising the step of administering to a patient in need of relief from the HIV infection a therapeutically effective amount of one or more compounds of claim 1.

13. A pharmaceutical composition comprising one or more compounds of claim 5 and one or more carriers, diluents, or excipients, or a combination thereof.

14. A method for treating a patient in need of relief from an HIV infection, the method comprising the step of administering to a patient in need of relief from the HIV infection a therapeutically effective amount of one or more compounds of claim 5.

15. The compound of claim 1, wherein A is a group of the formula:

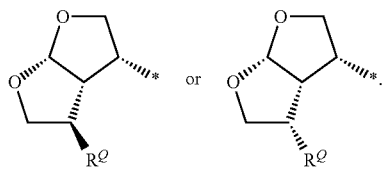

* * * * *